US012583910B2

(12) United States Patent
Jia et al.

(10) Patent No.: US 12,583,910 B2
(45) Date of Patent: Mar. 24, 2026

(54) T CELL ANTIGEN RECEPTOR, MULTIMERIC COMPLEX THEREOF, AND PREPARATION METHOD THEREFOR AND USE THEREOF

(71) Applicants: BRISTAR IMMUNOTECH LIMITED, Beijing (CN); TSINGHUA UNIVERSITY, Beijing (CN)

(72) Inventors: Lemei Jia, Beijing (CN); Hua Chen, Beijing (CN); Wenzhong Li, Beijing (CN); Jiasheng Wang, Beijing (CN); Lei Lei, Beijing (CN); Fang Liu, Beijing (CN); Xueqiang Zhao, Beijing (CN); Xin Lin, Beijing (CN)

(73) Assignees: TSINGHUA UNIVERSITY, Beijing (CN); BRISTAR IMMUNOTECH LIMITED, Beijing (CN)

( * ) Notice: Subject to any disclaimer, the term of this patent is extended or adjusted under 35 U.S.C. 154(b) by 711 days.

(21) Appl. No.: 17/923,522

(22) PCT Filed: Apr. 23, 2021

(86) PCT No.: PCT/CN2021/089237
§ 371 (c)(1),
(2) Date: Nov. 4, 2022

(87) PCT Pub. No.: WO2021/223604
PCT Pub. Date: Nov. 11, 2021

(65) Prior Publication Data
US 2023/0181639 A1 Jun. 15, 2023

(30) Foreign Application Priority Data
May 6, 2020 (CN) .......................... 202010373100.4

(51) Int. Cl.
| | |
|---|---|
| C07K 16/08 | (2006.01) |
| A61K 40/11 | (2025.01) |
| A61K 40/32 | (2025.01) |
| A61K 40/42 | (2025.01) |
| A61K 40/46 | (2025.01) |
| C07K 16/085 | (2026.01) |
| C12N 5/0783 | (2010.01) |

(52) U.S. Cl.
CPC ............ *C07K 16/085* (2013.01); *A61K 40/11* (2025.01); *A61K 40/32* (2025.01); *A61K 40/42* (2025.01); *A61K 40/46* (2025.01); *C12N 5/0636* (2013.01); *A61K 2239/31* (2023.05); *A61K 2239/38* (2023.05); *A61K 2239/48* (2023.05)

(58) Field of Classification Search
CPC .............. C07K 16/085; C07K 2319/03; C07K 14/7051; C07K 14/70539; C07K 2317/565; C07K 2317/622; A61K 40/11; A61K 40/32; A61K 40/42; A61K 40/46; A61K 2239/31; A61K 2239/38; A61K 2239/48; A61K 2039/585; A61K 2039/64; A61K 39/12; A61K 35/17; A61K 2039/5158; C12N 5/0636; C12N 2501/2302; C12N 2502/30; C12N 2510/00; C12N 15/86; C12N 2710/16234; C12N 2740/16043; A01K 2207/12; A01K 2227/105; A01K 2267/0331; A61P 31/20; A61P 31/22; A61P 35/00; G01N 33/56994; G01N 33/574
See application file for complete search history.

(56) References Cited

U.S. PATENT DOCUMENTS

| | | |
|---|---|---|
| 2004/0031072 A1 | 2/2004 | La Rosa et al. |
| 2016/0129094 A1 | 5/2016 | Heemskerk et al. |
| 2018/0282808 A1 | 10/2018 | Milla et al. |
| 2020/0115470 A1 | 4/2020 | Cheung et al. |

FOREIGN PATENT DOCUMENTS

| | | |
|---|---|---|
| CN | 1269804 | 10/2000 |
| CN | 1526072 | 9/2004 |
| CN | 109306005 | 3/2017 |
| CN | 108289950 | 7/2018 |
| CN | 110785432 | 2/2020 |
| CN | 110938136 | 3/2020 |
| EP | 1229043 | 8/2002 |
| EP | 3307319 | 4/2018 |
| EP | 3615565 | 3/2020 |
| EP | 3854802 | 7/2021 |
| WO | 1999002550 | 1/1999 |
| WO | 2004023973 | 3/2004 |
| WO | 2012038055 | 3/2012 |

(Continued)

OTHER PUBLICATIONS

Jokinen, et al., PLoS Comput Biol 2021 17(3): e1008814 (Year: 2021).*
Wong et al., Front. Immunol 2019 vol. 10 Article 2454 (Year: 2019).*
International Search Report for PCT/CN2021/089237 dated Jul. 22, 2021, 10 pages.
Written Opinion of the ISA for PCT/CN2021/089237 dated Jul. 22, 2021, 4 pages.

(Continued)

*Primary Examiner* — Julie Wu
*Assistant Examiner* — Sydney Van Druff
(74) *Attorney, Agent, or Firm* — NIXON & VANDERHYE, PC

(57) ABSTRACT

Provided is an antibody or an antigen-binding fragment thereof, a T cell antigen receptor, an immune cell expressing the T cell antigen receptor (TCR), and a preparation method therefor and the use thereof. The TCR can specifically recognize corresponding pMHC complexes, activate TCR T cells, and produce high-level cytokines IFNγ, IL2, TNFα, significantly kill target cells and prolong the life of tumor-bearing mice.

20 Claims, 16 Drawing Sheets
Specification includes a Sequence Listing.

(56) References Cited

FOREIGN PATENT DOCUMENTS

| WO | 2013039889 | 3/2013 |
|----|------------|--------|
| WO | 2014059489 | 4/2014 |
| WO | 2016095783 | 6/2016 |
| WO | 2017/085471 | 5/2017 |
| WO | 2017089766 | 6/2017 |
| WO | 2017120428 | 11/2017 |
| WO | 2018162563 | 9/2018 |
| WO | 2019036688 | 2/2019 |
| WO | 2019067242 | 4/2019 |
| WO | 2019129892 | 7/2019 |
| WO | 2019133853 | 7/2019 |
| WO | 2019180271 | 9/2019 |
| WO | 2020082130 | 4/2020 |
| WO | 2020089433 | 5/2020 |
| WO | 2020112815 | 6/2020 |
| WO | 2020154617 | 7/2020 |
| WO | 2020257288 | 12/2020 |
| WO | 2021011482 | 1/2021 |
| WO | 2021150804 | 7/2021 |

OTHER PUBLICATIONS

Xiao, Z., Ye, Z., Tadwal, V.S. et al. Dual non-contiguous peptide occupancy of HLA class I evoke antiviral human CD8 T cell response and form neo-epitopes with self-antigens. Sci Rep 7, 5072 (2017).

Cho HI, Kim UH, Shin AR, Won JN, Lee HJ, Sohn HJ, Kim TG. A novel Epstein-Barr virus-latent membrane protein-1- specific T-cell receptor for TCR gene therapy. Br J Cancer. Feb. 20, 2018;118(4):534-545. doi: 10.1038/bjc.2017.475. Epub Jan. 23, 2018. PMID: 29360818; Pmcid: PMC5830600.

Lorenz FKM, Ellinger C, Kieback E, Wilde S, Lietz M, Schendel DJ, Uckert W. Unbiased Identification of T-Cell Receptors Targeting Immunodominant Peptide-MHC Complexes for T-Cell Receptor Immunotherapy. Hum Gene Ther. Dec. 2017;28(12):1158-1168.

doi: 10.1089/hum.2017.122. Epub Sep. 26, 2017. PMID: 28950731; PMCID: PMC5737719.

Ge Y, Zhou Z, Wang X, Zhou Y, Liu W, Teng Z, Zeng Y. In vitro evaluation of the therapeutic effectiveness of EBV- LMP2 recombinant adenovirus vaccine in nasopharyngeal carcinoma. Biomed Pharmacother. Jan. 2020;121:109626. doi: 10.1016/j.biopha.2019. 109626. Epub Nov. 16, 2019. PMID: 31743878.

Zhu S, Chen J, Xiong Y, Kamara S, Gu M, Tang W, Chen S, Dong H, Xue X, Zheng ZM, Zhang L. Novel EBV LMP-2-affibody and affitoxin in molecular imaging and targeted therapy of nasopharyngeal carcinoma. PLoS Pathog. Jan. 6, 2020;16(1):e1008223. doi: 10.1371/journal.ppat.1008223. PMID: 31905218; PMCID: PMC6964910.

Xue SA, Chen Y, Voss RH, Kisan V, Wang B, Chen KK, He FQ, Cheng XX, Scolamiero L, Holler A, Gao L, Morris E, Stauss HJ. Enhancing the expression and function of an EBV-TCR on engineered T cells by combining Sc-TCR design with CRISPR editing to prevent mispairing. Cell Mol Immunol. Dec. 2020;17(12):1275-1277. doi: 10.1038/s41423-020-0396-9. Epub Mar. 17, 2020. PMID: 32203185; PMCID: PMC7784858.

Dudaniec K, Westendorf K, Nössner E, Uckert W. Generation of Epstein-Barr Virus Antigen-Specific T Cell Receptors Recognizing Immunodominant Epitopes of LMP1, LMP2A, and EBNA3C for Immunotherapy. Hum Gene Ther. Sep. 2021;32(17-18):919-935. doi: 10.1089/hum.2020.283. Epub May 14, 2021. PMID: 33798008.

Zhang C, Tan Q, Li S, Shen L, Zhang J, Liu Y, Yang W, Lu Z. Induction of EBV latent membrane protein-2A (LMP2A)-specific T cells and construction of individualized TCR-engineered T cells for EBV-associated malignancies. J Immunother Cancer. Jul. 2021;9(7):e002516. doi: 10.1136/jitc-2021-002516. PMID: 34210819; PMCID: PMC8252876.

Dojcinovic, D, Analysis of CD4+ and CD8+ T cells by defined MHC-peptide complexes; thesis published by Dojcinovic, D, in Sep. 2012, University of Lausanne.

Kishore R, Hicklin DJ, Dellaratta DV, Golde U, Kageshita T, Seliger B, Ferrone S. Development and characterization of mouse anti-human LMP2, LMP7, TAP1 and TAP2 monoclonal antibodies. Tissue Antigens. Feb. 1998;51(2):129-40. doi: 10.1111/j.1399-0039. 1998.tb02958.x. PMID: 9510369.

* cited by examiner

T CELL ANTIGEN RECEPTOR, MULTIMERIC COMPLEX THEREOF, AND PREPARATION METHOD THEREFOR AND USE THEREOF

CROSS-REFERENCE TO RELATED APPLICATIONS

This application is the U.S. national phase of International Application No. PCT/CN2021/089237 filed Apr. 23, 2021, which designated the U.S. and claims priority to CN 202010373100.4 filed May 6, 2020, the entire contents of each of which are hereby incorporated by reference.

Reference to Sequence Listing Submitted Electronically

The content of the electronically submitted sequence listing (Name: 8575-24_SEQUENCE_LISTING.txt; Size: 252,143 bytes; Date of Creation: Nov. 1, 2022) filed with the application is incorporated herein by reference in its entirety.

TECHNICAL FIELD

The present invention relates to the technical field of biomedicine, and particularly relates to an antibody or an antigen-binding fragment thereof, a T cell antigen receptor, a multimeric complex, and a preparation method therefor and use thereof.

BACKGROUND

EB virus (Epstein-Barr virus, EBV) is a γ herpes virus isolated from a sample of Burkitt's Lymphoma (BL) by Epstein and Barr in 1964, and is the first recognized onco-genic virus. Primary EBV infection mainly occurs in epi-thelial cells of the oropharynx of the human. Later, it was found that the positive rate of virus antibodies in serum of adults is more than 90% because EBV has remarkable B-lymphophilic characteristics and can infect B cells and can be latent in memory B cells for a long time, making infected individuals lifelong carriers. Although EBV infec-tion does not pose much of a threat to the vast majority of immunocompetent people, in people with congenital or acquired immunodeficiency, EBV can cause a variety of life-threatening diseases. In addition, the proteins expressed in latent EBV infection (6 nuclear proteins including EBNA1, 2, 3A, 3B and 3C and EBNA-LP, and 3 latent membrane proteins including LMP1, LMP2A and LMP2B) can stimulate the proliferation and transformation of cells, and have been shown to be directly related to the develop-ment, progression and clinical prognosis of various malig-nant tumors, including EBV related post-transplant lym-phoproliferative diseases (EBV-PTLDs), Burkitt's lymphoma, Hodgkin's Lymphoma (HL), Nasopharyngeal carcinoma (NPC), Gastric cancer, etc. The latent forms of EBV are classified into stages I, II, III based on differential expression of latent proteins in those diseases. At present, due to problems such as drug resistance and serious side effects, the effective control of various EBV-related diseases cannot be realized in the antiviral therapy targeting the EB virus.

It has been first found by Papadopounds et al. that PTLD patients could be cured by infusion of lymphocytes from healthy EBV carriers, and then the autologous EBV-CTLs cell therapy was developed clinically. To date, EBV-CTLs have been clinically applied in EBV-related lymphoma and nasopharyngeal carcinoma and found to have good safety and certain therapeutic efficacy in humans. However, their clinical efficacy was limited due to many defects of CTLs cultured in vitro. Firstly, the number of T cells specific for tumor-associated EBV antigens in CTLs is relatively low (<0.05%), and therefore multiple reinfusions (4-6) at high doses (greater than $10^{10}$) is typically required; secondly, the long preparation period results in relatively long waiting time for treatment, and the accompanying change of the differentiation subgroup of the T cells further results in weak in vivo functions; in addition, the prepared cells vary from person to person, and the efficacy is difficult to guarantee. Therefore, there is an urgent need to develop a cell immu-notherapy targeting EBV antigens with greater specificity, stronger in vivo tumor-killing ability, and higher durability for the treatment of EBV-related nasopharyngeal carcinoma or lymphoma.

T cells are an important part of the acquired immune system, and they mediate the clearance of pathogens, dis-eased cells and tumors, and are the protective force for maintaining the homeostasis of the body. T cell receptors (TCRs) are the identification of T cells. TCRs trigger T cell activation and a series of subsequent cell signaling and other physiological reactions through recognition of major histo-compatibility complexes (MHCs) of target cells and the presented antigen complexes, thus allowing antigen-specific T cells to exert immune effects on their target cells. The TCR-T cell therapy is a technology in which T cell receptors with high specificity and high affinity for an antigen peptide of a tumor/virus are cloned and introduced into autologous T cells of a patient by gene transduction, so that the autologous T cells can specifically recognize the antigen polypeptide of the tumor/virus, and thus clear the tumor or pathogen. Compared with CAR-T, the TCR-T therapy can recognize a broader range of tumor antigens (intracellular and membrane proteins), exhibit more enhanced killing effect with lower cytokine storm, and have greater potential for the treatment of solid tumors. To date, significant efficacy of the TCR-T therapy has been observed in clinical trials of a plurality of solid tumors such as lung cancer, colon cancer and synovial cell sarcoma. However, off-target effect and toxic and side effects were also found because the main targets were mostly tumor-associated antigens such as CEA, gp100, MART-1, MAGA-A3 and NY-ESO-1. For malignant diseases related to EBV infection, the EBV antigen, as a foreign antigen, has relatively strong immunogenicity and is not prone to the off-target effect, and thus is an ideal potential target.

The EBV latent membrane protein LMP2A can promote the proliferation, survival and migration of cells and assist the epithelial-mesenchymal transition, and is one of the major EBV genes expressed in all type II and type III diseases/malignant tumors. It is reported in the literatures that the proportion of LMP2-specific CTL cells in the reinfused EBV-CTL is closely related to the clinical efficacy. This evidence indicates that LMP2 can be used as a target for the treatment of the EBV infection-related type diseases such as nasopharyngeal carcinoma. For example: the patent CN1526072A discloses methods for the identification of extracellular domains of EBV tumor-associated latent mem-brane proteins and for the selection of antibody reagents reactive therewith, and specifically discloses amino acid sequences of the extracellular domain of EBV LMP2. The patent CN1269804A discloses numerous T-cell CTL epitopes of EBV. The patent CN108289950A discloses T cell receptor-like antibody agents specific for EBV LMP2 presented by human HLA, wherein the T cell receptor recognizes an antigen peptide epitope of CLGGLLTMV. The patent WO2017085471 discloses a TCR sequence specifically recognizing an antigen peptide as SSCSSCPLSK. Furthermore, the non-patent document "Dual non-contiguous peptide occupancy of HLA class I evoke antiviral human CD8 T cell response and form neo-epitopes with self-antigens" (Ziwei Xiao et al., *Sci Rep*, 2017) discloses that 7/8 of HLA-A*1101 individuals take the same TRBV4-1 fragment as the primary recognition specificity for SSC. The patent CN109306005A discloses an EB virus-specific T cell antigen receptor and its application. However, none of the prior art discloses the TCR described herein.

SUMMARY

The present invention finds that HLA-A*0201 limited peptide FLYALALLL, HLA-A*1101 limited peptide SSCSSCPLSK/SSCSSCPLTK and HLA-A*2402 limited peptides PYLFWLAAI and TYGPVFMSL/TYGPVFMCL of LMP2 protein are antigenic epitopes with stronger immunogenicity, and can trigger the production of specific T lymphocytes and corresponding immune responses in the body. Therefore, the present invention provides a plurality of T cell antigen receptors capable of specifically binding to an EBV latent membrane protein LMP2 peptide (comprising sequences FLYALALLL, PYLFWLAAI, TYGPVFMSL/TYGPVFMCL, SSCSSCPLSK/SSCSSCPLTK) and use thereof in preparing a pharmaceutical composition for the treatment of EBV-related diseases. The TCR described herein can specifically recognize corresponding pMHC complexes and activate TCR T cells, which in turn produce high levels of cytokines IFNγ, IL2, TNFα, thereby significantly killing target cells and prolonging the life of tumor-bearing mice. Specifically, in a first aspect of the present invention, provided is a complementarity determining region (CDR) binding to an EBV latent membrane protein LMP2, wherein the CDR is selected from one of or a combination of two or more of SEQ ID NOs: 35-117.

Preferably, the CDR comprises CDR1α-CDR3α and/or CDRs1β-CDR3β.

The CDR1α has an amino acid sequence set forth in any one of SEQ ID NOs: 35-44 or having at least 80% homology to any one of SEQ ID NOs: 35-44, the CDR2a has an amino acid sequence set forth in any one of SEQ ID NOs: 45-54 or having at least 80% homology to any one of SEQ ID NOs: 45-54, the CDR3α has an amino acid sequence set forth in any one of SEQ ID NOs: 55-73 or having at least 80% homology to any one of SEQ ID NOs: 55-73, the CDR1β has an amino acid sequence set forth in any one of SEQ ID NOs: 74-84 or having at least 80% homology to any one of SEQ ID NOs: 74-84, the CDR2β has an amino acid sequence set forth in any one of SEQ ID NOs: 85-96 or having at least 80% homology to any one of SEQ ID NOs: 85-96, the CDR3β has an amino acid sequence set forth in any one of SEQ ID NOs: 97-117 or having at least 80% homology to any one of SEQ ID NOs: 97-117.

In a specific embodiment of the present invention, the CDR is selected from any one of the following groups:

| CDR1α | CDR2α | CDR3α | CDR1β | CDR2β | CDR3β |
|---|---|---|---|---|---|
| TSINN (SEQ ID NO: 35) | IRSNERE (SEQ ID NO: 45) | ATEGDSGYS TLT (SEQ ID NO: 55) | MNHEY (SEQ ID NO: 74) | SVGAGI (SEQ ID NO: 85) | ASSYQGGSSGYT (SEQ ID NO: 97) |
| TSINN (SEQ ID NO: 35) | IRSNERE (SEQ ID NO: 45) | ATVGDSGYS TLT (SEQ ID NO: 56) | MNHEY (SEQ ID NO: 74) | SVGAGI (SEQ ID NO: 85) | ASSGQGGGYGYT (SEQ ID NO: 98) |
| SSNFYA (SEQ ID NO: 36) | MTLNGDE (SEQ ID NO: 46) | ASTNSNSGY ALN (SEQ ID NO: 57) | DFQATT (SEQ ID NO: 75) | SNEGSKA (SEQ ID NO: 86) | SARDTSGVNFYN EQF (SEQ ID NO: 99) |
| DSASNY (SEQ ID NO: 37) | IRSNVGE (SEQ ID NO: 47) | AARGGGYST LT (SEQ ID NO: 58) | LNHDA (SEQ ID NO: 76) | SQIVND (SEQ ID NO: 87) | ASAITGGTEAF (SEQ ID NO: 100) |
| NSAFQY (SEQ ID NO: 38) | TYSSGN (SEQ ID NO: 48) | AMFRSTLGR LY (SEQ ID NO: 59) | MNHEY (SEQ ID NO: 74) | SMNVEV (SEQ ID NO: 88) | ASTPLPTSSGRLG EQY (SEQ ID NO: 101) |
| DSVNN (SEQ ID NO: 39) | IPSGT (SEQ ID NO: 49) | AVLNNNDMR (SEQ ID NO: 60) | MGHRA (SEQ ID NO: 77) | YSYEKL (SEQ ID NO: 89) | ASSQGRWYEQY (SEQ ID NO: 102) |
| DSVNN (SEQ ID NO: 39) | IPSGT (SEQ ID NO: 49) | AVVDNNDM R (SEQ ID NO: 61) | MGHRA (SEQ ID NO: 77) | YSYEKL (SEQ ID NO: 89) | ASSPGRWYEQF (SEQ ID NO: 103) |
| TTSDR (SEQ ID NO: 40) | LLSNGAV (SEQ ID NO: 50) | AVAMNRDDKII (SEQ ID NO: 62) | SGHKS (SEQ ID NO: 78) | YYEKEE (SEQ ID NO: 90) | ASSLDRDRNDYG YT (SEQ ID NO: 104) |
| DSASNY (SEQ ID NO: 37) | IRSNVGE (SEQ ID NO: 47) | AAREGFYQT GANNLF (SEQ ID NO: 63) | KGHSH (SEQ ID NO: 79) | LQKENI (SEQ ID NO: 91) | ASSPAPRAGNQP QH (SEQ ID NO: 105) |
| DSASNY (SEQ ID NO: 37) | IRSNVGE (SEQ ID NO: 47) | AATAGGATN KLI (SEQ ID NO: 64) | MNHEY (SEQ ID NO: 74) | SMNVEV (SEQ ID NO: 88) | ASSLYPPGHSNQP QH (SEQ ID NO: 106) |

-continued

| CDR1α | CDR2α | CDR3α | CDR1β | CDR2β | CDR3β |
|---|---|---|---|---|---|
| TTSDR (SEQ ID NO: 40) | LLSNGAV (SEQ ID NO: 50) | AVELTGNQF Y (SEQ ID NO: 65) | SGHKS (SEQ ID NO: 78) | YYEKEE (SEQ ID NO: 90) | ASSLEPGWGDTQ Y (SEQ ID NO: 107) |
| DSVNN (SEQ ID NO: 39) | IPSGT (SEQ ID NO: 49) | AVLNNNDMR (SEQ ID NO: 60) | SGDLS (SEQ ID NO: 80) | YYNGEE (SEQ ID NO: 92) | ASSVGPWYEQY (SEQ ID NO: 108) |
| DSVNN (SEQ ID NO: 39) | IPSGT (SEQ ID NO: 49) | AVLNNNDMR (SEQ ID NO: 60) | MGHRA (SEQ ID NO: 77) | YSYEKL (SEQ ID NO: 89) | ASSPGRFYEQY (SEQ ID NO: 109) |
| DSVNN (SEQ ID NO: 39) | IPSGT (SEQ ID NO: 49) | AVVDNNDM R (SEQ ID NO: 61) | MGHRA (SEQ ID NO: 77) | YSYEKL (SEQ ID NO: 89) | ASSPGRWYEQY (SEQ ID NO: 110) |
| TTSDR (SEQ ID NO: 40) | LLSNGAV (SEQ ID NO: 50) | AVNTGFQKL V (SEQ ID NO: 66) | SNHLY (SEQ ID NO: 81) | FYNNEI (SEQ ID NO: 93) | ASSEGPTGTSYEQ Y (SEQ ID NO: 111) |
| TRDTTYY (SEQ ID NO: 41) | RNSFDEQN (SEQ ID NO: 51) | ALSEPPSGTY KYI (SEQ ID NO: 67) | SGHVS (SEQ ID NO: 82) | FQNEAQ (SEQ ID NO: 94) | ASSQESGGTDTQ Y (SEQ ID NO: 112) |
| DSVNN (SEQ ID NO: 39) | IPSGT (SEQ ID NO: 49) | AVLDNNDMR (SEQ ID NO: 68) | MGHRA (SEQ ID NO: 77) | YSYEKL (SEQ ID NO: 89) | ASSQGRWYEQY (SEQ ID NO: 102) |
| DSAIYN (SEQ ID NO: 42) | IQSSQRE (SEQ ID NO: 52) | AGKTSYDKVI (SEQ ID NO: 69) | SGHAT (SEQ ID NO: 83) | FQNNGV (SEQ ID NO: 95) | ASSVFPTSVEQY (SEQ ID NO: 113) |
| TSDQSYG (SEQ ID NO: 43) | QGSYDEQN (SEQ ID NO: 53) | AMVSGAGG GADGET (SEQ ID NO: 70) | LNHDA (SEQ ID NO: 76) | SQIVND (SEQ ID NO: 87) | ASSIGVGLSNTEA F (SEQ ID NO: 114) |
| NSASDY (SEQ ID NO: 44) | IRSNMDK (SEQ ID NO: 54) | AETPGGYQK VT (SEQ ID NO: 71) | MNHEY (SEQ ID NO: 74) | SMNVEV (SEQ ID NO: 88) | ASSLWTSNSPLH SEQ ID NO: (115) |
| DSASNY (SEQ ID NO: 37) | IRSNVGE (SEQ ID NO: 47) | AASNRDDKII (SEQ ID NO: 72) | SGHNS (SEQ ID NO: 84) | FNNNVP (SEQ ID NO: 96) | ASSLGAGHLWGY T (SEQ ID NO: 116) |
| TTSDR (SEQ ID NO: 40) | LLSNGAV (SEQ ID NO: 50) | AVDIGTEYG NKLV (SEQ ID NO: 73) | SGHVS (SEQ ID NO: 82) | FQNEAQ (SEQ ID NO: 94) | ASREGVGLYEQY (SEQ ID NO: 117) |

In a second aspect of the present invention, provided is an α-chain polypeptide binding to an EBV latent membrane protein LMP2, wherein the α-chain polypeptide comprises a CDR1α, a CDR2α and/or a CDR3α. The CDR1α has an amino acid sequence set forth in any one of SEQ ID NOs: 35-44 or having at least 80% homology to any one of SEQ ID NOs: 35-44, the CDR2α has an amino acid sequence set forth in any one of SEQ ID NOs: 45-54 or having at least 80% homology to any one of SEQ ID NOs: 45-54, the CDR3α has an amino acid sequence set forth in any one of SEQ ID NOs: 55-73 or having at least 80% homology to any one of SEQ ID NOs: 55-73.

Preferably, the α-chain polypeptide comprises CDR1α-CDR3α of any one of the following groups:

| CDR1α | CDR2α | CDR3α |
|---|---|---|
| TSINN (SEQ ID NO: 35) | IRSNERE (SEQ ID NO: 45) | ATEGDSGYSTLT (SEQ ID NO: 55) |
| TSINN (SEQ ID NO: 35) | IRSNERE (SEQ ID NO: 45) | ATVGDSGYSTLT (SEQ ID NO: 56) |
| SSNFYA (SEQ ID NO: 36) | MTLNGDE (SEQ ID NO: 46) | ASTNSNSGYALN (SEQ ID NO: 57) |
| DSASNY (SEQ ID NO: 37) | IRSNVGE (SEQ ID NO: 47) | AARGGGYSTLT (SEQ ID NO: 58) |
| NSAFQY (SEQ ID NO: 38) | TYSSGN (SEQ ID NO: 48) | AMFRSTLGRLY (SEQ ID NO: 59) |
| DSVNN (SEQ ID NO: 39) | IPSGT (SEQ ID NO: 49) | AVLNNNDMR (SEQ ID NO: 60) |
| DSVNN (SEQ ID NO: 39) | IPSGT (SEQ ID NO: 49) | AVVDNNDMR (SEQ ID NO: 61) |

-continued

| CDR1α | CDR2α | CDR3α |
|---|---|---|
| TTSDR (SEQ ID NO: 40) | LLSNGAV (SEQ ID NO: 50) | AVAMNRDDKII (SEQ ID NO: 62) |
| DSASNY (SEQ ID NO: 37) | IRSNVGE (SEQ ID NO: 47) | AAREGFYQTGANNLF (SEQ ID NO: 63) |
| DSASNY (SEQ ID NO: 37) | IRSNVGE (SEQ ID NO: 47) | AATAGGATNKLI (SEQ ID NO: 64) |
| TTSDR (SEQ ID NO: 40) | LLSNGAV (SEQ ID NO: 50) | AVELTGNQFY (SEQ ID NO: 65) |
| DSVNN (SEQ ID NO: 39) | IPSGT (SEQ ID NO: 49) | AVLNNNDMR (SEQ ID NO: 60) |
| DSVNN (SEQ ID NO: 39) | IPSGT (SEQ ID NO: 49) | AVLNNNDMR (SEQ ID NO: 60) |
| DSVNN (SEQ ID NO: 39) | IPSGT (SEQ ID NO: 49) | AVVDNNDMR (SEQ ID NO: 61) |
| TTSDR (SEQ ID NO: 40) | LLSNGAV (SEQ ID NO: 50) | AVNTGFQKLV (SEQ ID NO: 66) |
| TRDTTYY (SEQ ID NO: 41) | RNSFDEQN (SEQ ID NO: 51) | ALSEPPSGTYKYI (SEQ ID NO: 67) |
| DSVNN (SEQ ID NO: 39) | IPSGT (SEQ ID NO: 49) | AVLDNNDMR (SEQ ID NO: 68) |
| DSAIYN (SEQ ID NO: 42) | IQSSQRE (SEQ ID NO: 52) | AGKTSYDKVI (SEQ ID NO: 69) |
| TSDQSYG (SEQ ID NO: 43) | QGSYDEQN (SEQ ID NO: 53) | AMVSGAGGGADGLT (SEQ ID NO: 70) |
| NSASDY (SEQ ID NO: 44) | IRSNMDK (SEQ ID NO: 54) | AETPGGYQKVT (SEQ ID NO: 71) |
| DSASNY (SEQ ID NO: 37) | IRSNVGE (SEQ ID NO: 47) | AASNRDDKII (SEQ ID NO: 72) |
| TTSDR (SEQ ID NO: 40) | LLSNGAV (SEQ ID NO: 50) | AVDIGTEYGNKLV (SEQ ID NO: 73) |

In a third aspect of the present invention, provided is a β-chain polypeptide binding to an EBV latent membrane protein LMP2, wherein the β-chain polypeptide comprises a CDR1β, a CDR2β and/or a CDR3ƒ3.

The CDR1β has an amino acid sequence set forth in any one of SEQ ID NOs: 74-84 or having at least 80% homology to any one of SEQ ID NOs: 74-84, the CDR2β has an amino acid sequence set forth in SEQ ID NOs: 85-96 or having at least 80% homology to any one of SEQ ID NOs: 85-96, the CDR3β has an amino acid sequence set forth in SEQ ID NOs: 97-117 or having at least 80% homology to any one of SEQ ID NOs: 97-117.

In a specific embodiment of the present invention, the β-chain polypeptide comprises CDR1β-CDR3β of any one of the following groups:

| CDR1β | CDR2β | CDR3β |
|---|---|---|
| MNHEY (SEQ ID NO: 74) | SVGAGI (SEQ ID NO: 85) | ASSYQGGSSGYT (SEQ ID NO: 97) |
| MNHEY (SEQ ID NO: 74) | SVGAGI (SEQ ID NO: 85) | ASSGQGGGYGYT (SEQ ID NO: 98) |
| DFQATT (SEQ ID NO: 75) | SNEGSKA (SEQ ID NO: 86) | SARDTSGVNFYNEQF (SEQ ID NO: 99) |
| LNHDA (SEQ ID NO: 76) | SQIVND (SEQ ID NO: 87) | ASAITGGTEAF (SEQ ID NO: 100) |
| MNHEY (SEQ ID NO: 74) | SMNVEV (SEQ ID NO: 88) | ASTPLPTSSGRLGEQY (SEQ ID NO: 101) |
| MGHRA (SEQ ID NO: 77) | YSYEKL (SEQ ID NO: 89) | ASSQGRWYEQY (SEQ ID NO: 102) |
| MGHRA (SEQ ID NO: 77) | YSYEKL (SEQ ID NO: 89) | ASSPGRWYEQF (SEQ ID NO: 103) |
| SGHKS (SEQ ID NO: 78) | YYEKEE (SEQ ID NO: 90) | ASSLDRDRNDYGYT (SEQ ID NO: 104) |
| KGHSH (SEQ ID NO: 79) | LQKENI (SEQ ID NO: 91) | ASSPAPRAGNQPQH (SEQ ID NO: 105) |
| MNHEY (SEQ ID NO: 74) | SMNVEV (SEQ ID NO: 88) | ASSLYPPGHSNQPQH (SEQ ID NO: 106) |
| SGHKS (SEQ ID NO: 78) | YYEKEE (SEQ ID NO: 90) | ASSLEPGWGDTQY (SEQ ID NO: 107) |
| SGDLS (SEQ ID NO: 80) | YYNGEE (SEQ ID NO: 92) | ASSVGPWYEQY (SEQ ID NO: 108) |
| MGHRA (SEQ ID NO: 77) | YSYEKL (SEQ ID NO: 89) | ASSPGRFYEQY (SEQ ID NO: 109) |
| MGHRA (SEQ ID NO: 77) | YSYEKL (SEQ ID NO: 89) | ASSPGRWYEQY (SEQ ID NO: 110) |
| SNHLY (SEQ ID NO: 81) | FYNNEI (SEQ ID NO: 93) | ASSEGPTGTSYEQY (SEQ ID NO: 111) |

-continued

| CDR1β | CDR2β | CDR3β |
|---|---|---|
| SGHVS (SEQ ID NO: 82) | FQNEAQ (SEQ ID NO: 94) | ASSQESGGTDTQY (SEQ ID NO: 112) |
| MGHRA (SEQ ID NO: 77) | YSYEKL (SEQ ID NO: 89) | ASSQGRWYEQY (SEQ ID NO: 102) |
| SGHAT (SEQ ID NO: 83) | FQNNGV (SEQ ID NO: 95) | ASSVFPTSVEQY (SEQ ID NO: 113) |
| LNHDA (SEQ ID NO: 76) | SQIVND (SEQ ID NO: 87) | ASSIGVGLSNTEAF (SEQ ID NO: 114) |
| MNHEY (SEQ ID NO: 74) | SMNVEV (SEQ ID NO: 88) | ASSLWTSNSPLH SEQ ID NO: (115) |
| SGHNS (SEQ ID NO: 84) | FNNNVP (SEQ ID NO: 96) | ASSLGAGHLWGYT (SEQ ID NO: 116) |
| SGHVS (SEQ ID NO: 82) | FQNEAQ (SEQ ID NO: 94) | ASREGVGLYEQY (SEQ ID NO: 117) |

In a fourth aspect of the present invention, provided is a T cell antigen receptor specifically binding to an EBV latent membrane protein LMP2.

Preferably, the binding epitope comprises any one of or a combination of two or more of SEQ ID NOs: 29-34. Further preferably, the binding epitope comprises any one of or a combination of two or more of SEQ ID NO: 29, 30, 33 or 34.

Further preferably, the EBV latent membrane protein LMP2 comprises an amino acid sequence comprising SEQ ID NO: 27 and/or SEQ ID NO: 28, or an amino acid sequence having at least 80% homology to SEQ ID NO: 27 and/or SEQ ID NO: 28.

Preferably, the T cell antigen receptor specifically binds to a peptide derived from the EBV latent membrane protein LMP2 by presentation on the major histocompatibility complex (MHC).

Preferably, the T cell antigen receptor comprises at least one α-chain variable region and/or β-chain variable region.

Preferably, the T cell antigen receptor is an α-β heterodimer.

Preferably, the T cell antigen receptor comprises α-chain CDR1α-CDR3α and/or β-chain CDR1β-CDR3β. The CDR1α has an amino acid sequence set forth in any one of SEQ ID NOs: 35-44 or having at least 80% homology to any one of SEQ ID NOs: 35-44, the CDR2α has an amino acid sequence set forth in any one of SEQ ID NOs: 45-54 or having at least 80% homology to any one of SEQ ID NOs: 45-54, the CDR3α has an amino acid sequence set forth in any one of SEQ ID NOs: 55-73 or having at least 80% homology to any one of SEQ ID NOs: 55-73, the CDR1β has an amino acid sequence set forth in any one of SEQ ID NOs: 74-84 or having at least 80% homology to any one of SEQ ID NOs: 74-84, the CDR2β has an amino acid sequence set forth in any one of SEQ ID NOs: 85-96 or having at least 80% homology to any one of SEQ ID NOs: 85-96, and the CDR3β has an amino acid sequence set forth in any one of SEQ ID NOs: 97-117 or having at least 80% homology to any one of SEQ ID NOs: 97-117.

Preferably, the CDR1α-CDR3α and the CDR1β-CDR3β may be SEQ ID NOs: 35, 45, 55, 74, 85 and 97, respectively; or SEQ ID NOs: 35, 45, 56, 74, 85 and 98, respectively; or SEQ ID NOs: 36, 46, 57, 75, 86 and 99, respectively; or SEQ ID NOs: 37, 47, 58, 76, 87 and 100, respectively; or SEQ ID NOs: 38, 48, 59, 74, 88 and 101, respectively; or SEQ ID NOs: 39, 49, 60, 77, 89 and 102, respectively; or SEQ ID NOs: 39, 49, 61, 77, 89 and 103, respectively; or SEQ ID NOs: 40, 50, 62, 78, 90 and 104, respectively; or SEQ ID NOs: 37, 47, 63, 79, 91 and 105, respectively; or SEQ ID NOs: 37, 47, 64, 74, 88 and 106, respectively; or SEQ ID NOs: 40, 50, 65, 78, 90 and 107, respectively; or SEQ ID NOs: 39, 49, 60, 80, 92 and 108, respectively; or SEQ ID NOs: 39, 49, 60, 77, 89 and 109, respectively; or SEQ ID NOs: 39, 49, 61, 77, 89 and 110, respectively; or SEQ ID NOs: 40, 50, 66, 81, 93 and 111, respectively; or SEQ ID NOs: 41, 51, 67, 82, 94 and 112, respectively; or SEQ ID NOs: 39, 49, 68, 77, 89 and 102, respectively; or SEQ ID NOs: 42, 52, 69, 83, 95 and 113, respectively; or SEQ ID NOs: 43, 53, 70, 76, 87 and 114, respectively; or SEQ ID NOs: 44, 54, 71, 74, 88 and 115, respectively; or SEQ ID NOs: 37, 47, 72, 84, 96 and 116, respectively; or SEQ ID NOs: 40, 50, 73, 82, 94 and 117, respectively.

In a specific embodiment of the present invention, the CDR1α-CDR3α and the CDR1β-CDR3β are selected from any one of the following groups:

| TCR | Binding epitope | CDR1α | CDR2α | CDR3α | CDR1β | CDR2β | CDR3β |
|---|---|---|---|---|---|---|---|
| E23 | SEQ ID NO: 29 | TSINN (SEQ ID NO: 35) | IRSNERE (SEQ ID NO: 45) | ATEGDSGY STLT (SEQ ID NO: 55) | MNHEY (SEQ ID NO: 74) | SVGAGI (SEQ ID NO: 85) | ASSYQGGS SGYT (SEQ ID NO: 97) |
| E240 | SEQ ID NO: 29 | TSINN (SEQ ID NO: 35) | IRSNERE (SEQ ID NO: 45) | ATVGDSGY STLT (SEQ ID NO: 56) | MNHEY (SEQ ID NO: 74) | SVGAGI (SEQ ID NO: 85) | ASSGQGGG YGYT (SEQ ID NO: 98) |
| E29 | SEQ ID NO: 30 | SSNFYA (SEQ ID NO: 36) | MTLNGD E (SEQ ID NO: 46) | ASTNSNSG YALN (SEQ ID NO: 57) | DFQATT (SEQ ID NO: 75) | SNEGSKA (SEQ ID NO: 86) | SARDTSGV NFYNEQF (SEQ ID NO: 99) |

-continued

| TCR | Binding epitope | CDR1α | CDR2α | CDR3α | CDR1β | CDR2β | CDR3β |
|---|---|---|---|---|---|---|---|
| E180-1 | SEQ ID NO: 30 | DSASNY (SEQ ID NO: 37) | IRSNVGE (SEQ ID NO: 47) | AARGGGYS TLT (SEQ ID NO: 58) | LNHDA (SEQ ID NO: 76) | SQIVND (SEQ ID NO: 87) | ASAITGGTE AF (SEQ ID NO: 100) |
| E44 | SEQ ID NO: 31 or 32 | NSAFQY (SEQ ID NO: 38) | TYSSGN (SEQ ID NO: 48) | AMFRSTLG RLY (SEQ ID NO: 59) | MNHEY (SEQ ID NO: 74) | SMNVEV (SEQ ID NO: 88) | ASTPLPTSS GRLGEQY (SEQ ID NO: 101) |
| E141 | SEQ ID NO: 33 or 34 | DSVNN (SEQ ID NO: 39) | IPSGT (SEQ ID NO: 49) | AVLNNNDM R (SEQ ID NO: 60) | MGHRA (SEQ ID NO: 77) | YSYEKL (SEQ ID NO: 89) | ASSQGRWY EQY (SEQ ID NO: 102) |
| E149 | SEQ ID NO: 33 or 34 | DSVNN (SEQ ID NO: 39) | IPSGT (SEQ ID NO: 49) | AVVDNND MR (SEQ ID NO: 61) | MGHRA (SEQ ID NO: 77) | YSYEKL (SEQ ID NO: 89) | ASSPGRWY EQF (SEQ ID NO: 103) |
| E168 | SEQ ID NO: 33 or 34 | TTSDR (SEQ ID NO: 40) | LLSNGAV (SEQ ID NO: 50) | AVAMNRDD KII (SEQ ID NO: 62) | SGHKS (SEQ ID NO: 78) | YYEKEE (SEQ ID NO: 90) | ASSLDRDR NDYGYT (SEQ ID NO: 104) |
| E170 | SEQ ID NO: 33 or 34 | DSASNY (SEQ ID NO: 37) | IRSNVGE (SEQ ID NO: 47) | AAREGFYQ TGANNLF (SEQ ID NO: 63) | KGHSH (SEQ ID NO: 79) | LQKENI (SEQ ID NO: 91) | ASSPAPRAG NQPQH (SEQ ID NO: 105) |
| E244 | SEQ ID NO: 33 or 34 | DSASNY (SEQ ID NO: 37) | IRSNVGE (SEQ ID NO: 47) | AATAGGAT NKLI (SEQ ID NO: 64) | MNHEY (SEQ ID NO: 74) | SMNVEV (SEQ ID NO: 88) | ASSLYPPGH SNQPQH (SEQ ID NO: 106) |
| E245 | SEQ ID NO: 33 or 34 | TTSDR (SEQ ID NO: 40) | LLSNGAV (SEQ ID NO: 50) | AVELTGNQ FY (SEQ ID NO: 65) | SGHKS (SEQ ID NO: 78) | YYEKEE (SEQ ID NO: 90) | ASSLEPGW GDTQY (SEQ ID NO: 107) |
| E254 | SEQ ID NO: 33 or 34 | DSVNN (SEQ ID NO: 39) | IPSGT (SEQ ID NO: 49) | AVLNNNDM R (SEQ ID NO: 60) | SGDLS (SEQ ID NO: 80) | YYNGEE (SEQ ID NO: 92) | ASSVGPWY EQY (SEQ ID NO: 108) |
| E301 | SEQ ID NO: 33 or 34 | DSVNN (SEQ ID NO: 39) | IPSGT (SEQ ID NO: 49) | AVLNNNDM R (SEQ ID NO: 60) | MGHRA (SEQ ID NO: 77) | YSYEKL (SEQ ID NO: 89) | ASSPGRFYE QY (SEQ ID NO: 109) |
| E304 | SEQ ID NO: 33 or 34 | DSVNN (SEQ ID NO: 39) | IPSGT (SEQ ID NO: 49) | AVVDNND MR (SEQ ID NO: 61) | MGHRA (SEQ ID NO: 77) | YSYEKL (SEQ ID NO: 89) | ASSPGRWY EQY (SEQ ID NO: 110) |
| E305 | SEQ ID NO: 33 or 34 | TTSDR (SEQ ID NO: 40) | LLSNGAV (SEQ ID NO: 50) | AVNTGFQK LV (SEQ ID NO: 66) | SNHLY (SEQ ID NO: 81) | FYNNEI (SEQ ID NO: 93) | ASSEGPTGT SYEQY (SEQ ID NO: 111) |
| E307 | SEQ ID NO: 33 or 34 | TRDTTYY (SEQ ID NO: 41) | RNSFDEQ N (SEQ ID NO: 51) | ALSEPPSGT YKYI (SEQ ID NO: 67) | SGHVS (SEQ ID NO: 82) | FQNEAQ (SEQ ID NO: 94) | ASSQESGG TDTQY (SEQ ID NO: 112) |
| E314 | SEQ ID NO: 33 or 34 | DSVNN (SEQ ID NO: 39) | IPSGT (SEQ ID NO: 49) | AVLDNNDM R (SEQ ID NO: 68) | MGHRA (SEQ ID NO: 77) | YSYEKL (SEQ ID NO: 89) | ASSQGRWY EQY (SEQ ID NO: 102) |
| E315 | SEQ ID NO: 33 or 34 | DSAIYN (SEQ ID NO: 42) | IQSSQRE (SEQ ID NO: 52) | AGKTSYDK VI (SEQ ID NO: 69) | SGHAT (SEQ ID NO: 83) | FQNNGV (SEQ ID NO: 95) | ASSVFPTSV EQY (SEQ ID NO: 113) |
| E316 | SEQ ID NO: 33 or 34 | TSDQSYG (SEQ ID NO: 43) | QGSYDE QN (SEQ ID NO: 53) | AMVSGAG GGADGLT (SEQ ID NO: 70) | LNHDA (SEQ ID NO: 76) | SQIVND (SEQ ID NO: 87) | ASSIGVGLS NTEAF (SEQ ID NO: 114) |
| E317 | SEQ ID NO: 33 or 34 | NSASDY (SEQ ID NO: 44) | IRSNMDK (SEQ ID NO: 54) | AETPGGYQ KVT (SEQ ID NO: 71) | MNHEY (SEQ ID NO: 74) | SMNVEV (SEQ ID NO: 88) | ASSLWTSN SPLH SEQ ID NO: (115) |

-continued

| TCR | Binding epitope | CDR1α | CDR2α | CDR3α | CDR1β | CDR2β | CDR3β |
|-----|-----------------|-------|-------|-------|-------|-------|-------|
| E318 | SEQ ID NO: 33 or 34 | DSASNY (SEQ ID NO: 37) | IRSNVGE (SEQ ID NO: 47) | AASNRDDKII (SEQ ID NO: 72) | SGHNS (SEQ ID NO: 84) | FNNNVP (SEQ ID NO: 96) | ASSLGAGH LWGYT (SEQ ID NO: 116) |
| E320 | SEQ ID NO: 33 or 34 | TTSDR (SEQ ID NO: 40) | LLSNGAV (SEQ ID NO: 50) | AVDIGTEY GNKLV (SEQ ID NO: 73) | SGHVS (SEQ ID NO: 82) | FQNEAQ (SEQ ID NO: 94) | ASREGVGL YEQY (SEQ ID NO: 117) |

In a specific embodiment of the present invention, the T cell antigen receptor has an amino acid sequence selected from any one of SEQ ID NOs: 5-26 or having at least 80% homology to any one of SEQ ID NOs: 5-26.

Preferably, the α chain and β chain of the T cell antigen receptor are linked by a linker sequence, preferably a furin-SGSG-p2A sequence (abbreviated as fp2A below).

Preferably, the linking may be performed by the following order: an α chain, fp2A, a β chain, or a β chain, fp2A, an α chain.

In a specific embodiment of the present invention, the linking may be performed by the following order: a β chain, fp2A, an α chain.

Preferably, the T cell antigen receptor specifically binds to the EBV latent membrane protein LMP2 by presentation on MHC molecule or a multimeric complex. The multimeric complex comprises an antigen peptide comprising any one of or a combination of two or more of SEQ ID NOs: 29-34. Preferably, the multimeric complex further comprises a monomer, a biotin molecule, and a streptavidin or avidin molecule, wherein the monomer comprises an α-chain extracellular domain of an MHC molecule and a β2m chain, the monomer is conjugated to the biotin molecule binding to the streptavidin or avidin molecule.

In a fifth aspect of the present invention, provided is an antibody or an antigen-binding fragment thereof specifically binding to an EBV latent membrane protein LMP2.

Preferably, the LMP2 has a binding epitope comprising any one of or a combination of two or more of SEQ ID NOs: 29-34.

Further preferably, the binding epitope of LMP2 comprises any one of or a combination of two or more of SEQ ID NO: 29, 30, 33 or 34.

Preferably, the antibody or the antigen binding fragment thereof may further comprise a fragment such as a Fab, Fab', Fab'-SH, Fv, scFv, (Fab')₂, a single domain antibody, a diabody (dAb), or a linear antibody. Preferably, the antibody or the antigen-binding fragment thereof is a single domain antibody or a single chain antibody scFv.

Preferably, the antibody or the antigen-binding fragment thereof comprises α-chain CDR1α-CDR3α and/or β-chain CDR1β-CDR3β. In a specific embodiment of the present invention, the antibody or the antigen-binding fragment thereof has an amino acid sequence selected from any one of SEQ ID NOs: 5-26 or having at least 80% homology to any one of SEQ ID NOs: 5-26.

In a sixth aspect of the present invention, provided is a nucleic acid encoding the antibody or the antigen-binding fragment thereof described above, or the T cell antigen receptor described above, or the CDR described above, or the α-chain polypeptide described above, or the β-chain polypeptide described above.

In a specific embodiment of the present invention, the nucleotide sequence encoding the antibody or the antigen-binding fragment thereof or the T cell antigen receptor is selected from any one of SEQ ID NOs: 122-143, or has at least 80% homology to any one of SEQ ID NOs: 122-143.

Preferably, the nucleotide sequence may be codon-optimized. Further preferably, the codon optimization comprises changing a number of rare codons used by a virus or the like into corresponding mammalian codons, and/or removing mRNA unstable motifs and/or cryptic splicing sites.

In a seventh aspect of the present invention, provided is an expression vector comprising the nucleic acid described above.

Preferably, the expression vector can express in vivo or in vitro or ex vivo. Further preferably, the expression vector expresses at a high level continuously in a cell in vivo.

Preferably, the expression vector is a prokaryotic expression vector or a lentivirus expression vector.

Further preferably, the prokaryotic expression vector is of the *Escherichia coli* series. In a specific embodiment of the present invention, the expression vector is pET-26b or pET28a+.

In a specific embodiment of the present invention, the expression vector is pHAGE-IRES-RFP.

Further preferably, the β chain, the α chain and the vector backbone in the expression vector are linked by the following order: a promoter, the β chain, furin-p2A, the α chain, IRES and RFP sequences.

In an eighth aspect of the preset invention, provided is a host cell comprising the nucleic acid described above or the expression vector described above.

Preferably, the host cell may be eukaryotic or prokaryotic. More preferably, the host cell is a yeast cell, a 293 cell, a CHO cell, *Escherichia coli*, or the like.

In a specific embodiment of the present invention, the host cell is Stb13, BL21 or transetta.

In a ninth aspect of the present invention, provided is an immune cell expressing the CDR described above, the α-chain polypeptide described above, the β-chain polypeptide described above, the antibody or the antigen-binding fragment thereof described above, or the T cell antigen receptor described above.

Preferably, the immune cell includes, but is not limited to, lymphocytes (including T cells and B cells). Further, the immune cell is a B cell expressing the antibody or the antigen-binding fragment thereof described above.

The immune cell is a T cell having a T cell antigen receptor structure as defined above.

In a tenth aspect of the present invention, provided is a method for preparing an immune cell, which comprises transfecting an immune cell with a nucleic acid sequence encoding the CDR described above, the α-chain polypeptide described above, the β-chain polypeptide described above, the antibody or the antigen-binding fragment thereof described above, or the T cell antigen receptor for expression.

Preferably, the immune cell includes, but is not limited to, lymphocytes (including T cells and B cells). Further, the immune cell is a B cell expressing the antibody or the antigen-binding fragment thereof described above.

The immune cell is a T cell having a T cell antigen receptor structure as defined above.

Preferably, the method further comprises the step of knocking out an endogenous TCR of the cell. Specifically, a guide targeting the endogenous TCR can be constructed into a lentiviral vector, and co-transfected with a packaging plasmid and a transfection reagent into a T cell.

In an eleventh aspect of the present invention, provided is a method for preparing a recombinant T cell, which comprises the following steps:

1) obtaining a nucleic acid sequence encoding the T cell antigen receptor described above from a positive T cell clone;

2) separating and culturing a primary T cell;

3) delivering the nucleic acid sequence obtained in the step 1) to the primary T cell in the step 2) to obtain a recombinant T cell expressing the CDR described above, the α-chain polypeptide described above, the β-chain polypeptide described above or the T cell antigen receptor described above.

Preferably, the T cell is selected from hematopoietic stem cells or peripheral blood lymphocyte (PBL)-derived T cells.

In a twelfth aspect of the present invention, provided is a method for preparing an antibody or an antigen-binding fragment thereof or a T cell antigen receptor, which comprises the following steps:

(1) obtaining a nucleic acid sequence encoding the antibody or the antigen-binding fragment thereof described above, or the T cell antigen receptor described above, from a positive T cell clone;

(2) connecting the nucleic acid sequence obtained in the step (1) to a vector backbone to obtain an expression vector;

(3) transforming the expression vector obtained in the step (2) into a host cell, and then inducing the expression of the host cell;

(4) obtaining the antibody or the antigen-binding fragment thereof or the T cell antigen receptor.

Preferably, the positive T cell specifically binds to an MHC-presented EBV latent membrane protein LMP2 peptide. Further preferably, the MHC-presented EBV latent membrane protein LMP2 peptide is a monomer or multimeric complex.

In a thirteenth aspect of the present invention, provided is a multimeric complex comprising the T cell antigen receptor described in any one of the above embodiments.

Preferably, the multimeric complex further comprises a monomer, a biotin molecule and a fluorescently labeled streptavidin or avidin molecule, wherein the monomer comprises an antigen peptide, an α-chain extracellular domain of an MHC molecule and a β2m chain, and the monomer is conjugated with the biotin molecule binding to the streptavidin or avidin molecule.

Preferably, the α-chain extracellular domain of the MHC molecule is connected with an avi-tag sequence at the C-terminus.

Preferably, the α-chain extracellular domain of the MHC molecule does not contain a signal peptide sequence, with an amino acid M added before a mature peptide sequence.

Preferably, the β2m chain does not contain a signal peptide sequence, with two amino acids M and A added before a mature peptide sequence.

In a specific embodiment of the present invention, the β2m chain does not contain a signal peptide, with two amino acids, preferably M and A, added before a mature peptide sequence.

Preferably, the antigen peptide comprises any one of or a combination of two or more of SEQ ID NOs: 29-34. Further preferably, the antigen peptide comprises any one of or a combination of two or more of SEQ ID NO: 29, 30, 33 or 34.

In a specific embodiment of the present invention, the multimeric complex comprises:

(1) a T cell antigen receptor; wherein preferably, the T cell antigen receptor is any one of SEQ ID NOs: 5-26 or has at least 80% homology to an amino acid sequence set forth in any one of SEQ ID NOs: 5-26.

(3) a monomer, comprising an antigen peptide, an α-chain extracellular domain of an MHC molecule connected with an avi-tag sequence at the C terminus and a β2m chain without a signal peptide; wherein the antigen peptide is selected from any one of or a combination of two or more of SEQ ID NOs: 29-34;

(4) a biotin molecule; and (5) a streptavidin molecule or an avidin molecule; wherein the monomer is conjugated to the biotin molecule binding to the streptavidin or avidin.

Preferably, the MHC molecule is an MHC class I molecule or an MHC class II molecule. More preferably, the MHC molecule is an MHC class I molecule.

Preferably, the MHC molecule is selected from HLA-A*0201, HLA-A*2402 and HLA-A*1101.

In a specific embodiment of the present invention, the α chain of the MHC molecule has an amino acid sequence set forth in any one of SEQ ID NOs: 1-3 or having at least 80% homology to any one of SEQ ID NOs: 1-3.

In a specific embodiment of the present invention, the β2m chain of the MHC molecule is set forth in SEQ ID NO: 4 or has at least 80% homology to an amino acid sequence set forth in SEQ ID NO: 4.

To increase the specificity of binding of an antigen peptide-MHC molecule tetramer to a T cell antigen receptor, the monomer further comprises a chemical modification, mutation, insertion and/or deletion of at least one amino acid.

Preferably, the α-chain extracellular domain of the MHC molecule and the β2m chain are non-covalently bound.

Preferably, the multimeric complex comprises at least one monomer.

Preferably, each monomer is conjugated to at least one biotin molecule.

In a fourteenth aspect of the present invention, provided is a method for preparing the multimeric complex described above, which comprises the following steps:

I) expressing and purifying an α-chain extracellular domain of an MHC molecule connected with an avi-tag sequence at the C terminus and a β2m chain;

II) refolding an antigen peptide, the α-chain extracellular domain of the MHC molecule connected with the avi-tag sequence at the C terminus and the β2m chain obtained in the step I) to prepare a monomer;

III) biotinylating the monomer prepared in the step II) to obtain a biotinylated monomer;

IV) subjecting the biotinylated monomer obtained in the step III) to a reaction with fluorescently labeled streptavidin or avidin to prepare an antigen peptide-MHC molecule tetramer.

V) co-incubating the antigen peptide-MHC molecule tetramer obtained in the step IV) with T cells to form a complex of a T cell antigen receptor and the antigen peptide-MHC molecule tetramer to fish for a specific T cell antigen receptor.

Preferably, the step I) comprises separately cloning a nucleotide sequence encoding the α-chain extracellular domain of the MHC molecule connected with the avi-tag sequence at the C-terminus and a nucleotide sequence encoding the β2m chain of the MHC molecule, connecting the cloned sequences to a vector, transforming the vector into an expression strain, culturing the expression strain, adding an inducer, and extracting inclusion bodies.

Further preferably, the expression strain is cultured until the $OD_{600}$ value is between 0.2 and 0.4.

Further preferably, the final molar concentration of the inducer after addition is between 0.5 mM and 1 mM. Preferably, the expression is induced for 4-6 h.

Preferably, the step II) comprises refolding of the β2m chain, that is, sequentially adding the antigen peptide, the β2m chain of the MHC molecule, and the α-chain extracellular domain of the MHC molecule connected with the avi-tag sequence at the C-terminus into a dilution buffer for a water bath away from light, wherein the refolding of the β2m chain includes denaturation of inclusion bodies, addition of a protease inhibitor, and then dialysis.

Preferably, the antigen peptide, the β2m chain without the signal peptide and the α chain connected with the avi-tag sequence at the C-terminus are at a molar ratio of (30-50): (2-2.5):1, more preferably 40:2:1.

Preferably, the step II) further comprises a step of purifying the monomer.

Preferably, the biotinylation in the step III) is performed by binding the monomer to BiomixA and/or BiomixB under the catalysis of BirA enzyme.

Preferably, the step III) further comprises a step of purifying the biotinylated monomer.

Preferably, in the step IV), the monomer is reacted with streptavidin at a molar ratio of (4-7):1.

In a fifteenth aspect of the present invention, provided is use of the multimeric complex described above in preparing, screening or detecting the antibody or the antigen-binding fragment thereof or the T cell antigen receptor described herein.

In a sixteenth aspect of the present invention, provided is use of the CDR described above, the α-chain polypeptide described above, the β-chain polypeptide described above, the antibody or the antigen-binding fragment thereof described above, the T cell antigen receptor described above, the nucleic acid described above, the expression vector described above, the host cell described above, the immune cell described above, or the multimeric complex described above in preparing a product for the diagnosis or treatment of an EBV-related disease.

Preferably, the EBV-related disease is selected from infectious mononucleosis, linked lymphoproliferative syndrome, viral hemophagocytic syndrome, oral hairy leukoplakia, viral meningitis, peripheral neuritis, viral pneumonia, viral myocarditis, nasopharyngeal carcinoma, Hodgkin's lymphoma, Burkitt's lymphoma, gastric carcinoma, hepatocellular carcinoma, lymphoepithelioid sarcoma, salivary gland tumor, breast cancer, thymoma, primary effusion lymphoma, or B/T/NK cell lymphoma.

In a seventeenth aspect of the present invention, provided is use of the CDR described above, the α-chain polypeptide described above, the β-chain polypeptide described above, the antibody or the antigen-binding fragment thereof described above, the T cell antigen receptor described above, the nucleic acid described above, the expression vector described above, the host cell described above, the immune cell described above, or the multimeric complex described above in labeling, detection, cell sorting, or activation of T cells.

In an eighteenth aspect of the present invention, provided is a pharmaceutical composition comprising any one of the following groups:
   i) the CDR described herein;
   ii) the α-chain polypeptide described herein;
   iii) the β-chain polypeptide described herein;
   iv) the antibody or the antigen-binding fragment thereof described herein;
   v) the T cell antigen receptor described herein;
   vi) the nucleic acid described herein;
   vii) the expression vector described herein;
   viii) the host cell described herein;
   ix) the immune cell described herein; or
   x) the multimeric complex described herein.

Preferably, the pharmaceutical composition further comprises a pharmaceutically acceptable excipient.

Preferably, the pharmaceutical composition may also be used in combination with an additional therapeutic agent. Further preferably, the therapeutic agent may be an immunomodulator.

In a nineteenth aspect of the present invention, provided is a kit comprising any one of the following groups:
   i) the CDR described herein;
   ii) the α-chain polypeptide described herein;
   iii) the β-chain polypeptide described herein;
   iv) the antibody or the antigen-binding fragment thereof described herein;
   v) the T cell antigen receptor described herein;
   vi) the nucleic acid described herein;
   vii) the expression vector described herein;
   viii) the host cell described herein;
   ix) the immune cell described herein; or
   x) the multimeric complex described herein.

In a twentieth aspect of the present invention, involved is a method for detecting EBV LMP2, which comprises making a sample to be tested in contact with the antibody or the antigen-binding fragment thereof or the T cell antigen receptor described herein, and detecting a complex formed by EBV LMP2 and the antibody or the antigen-binding fragment thereof or the T-cell antigen receptor.

Preferably, the detecting EBV LMP2 is detecting presence or content of EBV LMP2. The presence indicates presence or absence, the content may be an expression level, or a protein concentration, or the like.

Preferably, the antibody or the antigen-binding fragment thereof or the T cell antigen receptor comprises a detectable marker.

In a specific embodiment of the present invention, the marker may be His and/or HA.

The method for detecting EBV LMP2 described herein is not a diagnostic method for the disease. Firstly, the sample to be tested is not an organism or an ex vivo tissue or cell thereof, and secondly, even if EBV LMP2 is present in an organism or an organism comprises a certain concentration or expression level of EBV LMP2, it cannot be determined that there is a disease, but only a possibility.

In a twenty-first aspect of the present invention, involved is a method for treating an EBV-related disease, which comprises administering to an individual an effective amount of the antibody or the antigen-binding fragment thereof, the T cell antigen receptor, the nucleic acid, the expression vector, the host cell, the immune cell or the pharmaceutical composition described herein.

Preferably, the method for treating an EBV-related disease comprises localizing the T cell antigen receptor described herein in the vicinity of the EBV-related disease (preferably a tumor or metastatic tumor) to increase the efficacy of a toxin or an immunostimulant.

Further, the EBV-related disease is selected from infectious mononucleosis, linked lymphoproliferative syndrome, viral hemophagocytic syndrome, oral hairy leukoplakia, viral meningitis, peripheral neuritis, viral pneumonia, viral myocarditis, nasopharyngeal carcinoma, Hodgkin's lymphoma, Burkitt's lymphoma, gastric carcinoma, hepatocellular carcinoma, lymphoepithelioid sarcoma, salivary gland tumor, breast cancer, thymoma, primary effusion lymphoma, or B/T/NK cell lymphoma.

In a twenty-second aspect of the present invention, involved is a method for diagnosing an EBV-related disease, which comprises sampling, making the sample in contact with the antibody or the antigen-binding fragment thereof or the T cell antigen receptor described herein and detecting a complex formed by EBV LMP2 and the antibody or the antigen-binding fragment thereof or the T cell antigen receptor. Preferably, the antibody or the antigen-binding fragment thereof or the T cell antigen receptor comprises a detectable marker.

The TCR described herein can specifically recognize corresponding EBV LMP2 antigen peptides or pMHC complexes and activate TCR T cells, which in turn produce high levels of cytokines IFNγ, IL2 and TNFα, thereby significantly killing target cells and prolonging the life of tumor-bearing mice.

"Antigen-binding fragment" described herein includes, but is not limited to: a Fab fragment, having VL, CL, VH and CH1 domains; a Fab' fragment, which is a Fab fragment having one or more cysteine residues at the C-terminus of the CH1 domain; an Fd fragment, having VH and CH1 domains; an Fd' fragment, having VH and CH1 domains and one or more cysteine residues at the C-terminus of the CH1 domain; an Fv fragment, having VL and VH domains of a single arm of an antibody; a dAb fragment, consisting of a VH domain or a VL domain; an isolated CDR region; an F(ab')₂ fragment, which is a bivalent fragment comprising two Fab' fragments connected by a disulfide bridge at the hinge region; a single chain antibody molecule (e.g., single chain Fv; scFv); a "diabody" with two antigen-binding sites, comprising a heavy chain variable domain (VH) linked to a light chain variable domain (VL) in the same polypeptide chain; a "linear antibody", comprising a pair of tandem Fd segments (VH-CH1-VH-CH1) that, together with a complementary light chain polypeptide, form a pair of antigen-binding regions; and a modified form of any of the foregoing, which retains antigen-binding activity.

The "CDR" described herein is a short fragment of an immunoglobulin (Ig) or a T cell antigen receptor (TCR) that binds to an antigen epitope alone or in combination with other CDR. The immunoglobulin may be an antibody, and the CDRs correspond to complementarity determining regions within the variable sequences of the antibody. For each variable region, there are three CDRs in each variable region of the heavy and light chains, which are referred to as heavy-chain or light-chain CDR1, CDR2 and CDR3, respectively. In the T cell antigen receptor (TCR), the CDRs are present in the α or chain, and there are three CDRs in each of the α or β chain, which are referred to as α-chain or β-chain CDR1, CDR2 and CDR3, respectively. The exact boundaries of these CDRs are defined differently according to different systems. The system described by Kabat et al. (Kabat et al, Sequences of Proteins of Immunological Interest (National Institutes of Health, Bethesda, Md. (1987) and (1991)) provides not only a clear residue numbering system applicable to antibody variable regions, but also residue boundaries defining the three CDRs. Those CDRs may be referred to as Kabat CDRs. Each complementarity determining region may comprise amino acid residues from a "complementarity determining region" as defined by Kabat. Chothia et al. (Chothia & Lesk, *J. mol. Biol*, 196: 901-917 (1987) and Chothia et al., *Nature* 342:877-883 (—1989)) found that certain sub-portions within the Kabat CDRs adopts almost identical peptide backbone conformation, although with large diversity at the amino acid sequence level. Those sub-portions are referred to as L1, L2 and L3, or H1, H2 and H3, respectively, where "L" and "H" represent the light and heavy chain regions, respectively. Those regions may be referred to as Chothia CDRs, which have boundaries that overlap with those of Kabat CDRs. There are some other CDRs whose boundaries may not be defined strictly following one of the above systems, but will still overlap with those of the Kabat CDRs. CDRs defined according to any of these systems may be used in the methods used herein, although CDRs defined by Kabat or Chothia are used in preferred embodiments. The residue boundaries of the CDRs in the TCR are as described above. "Antibody variable region" refers to the portion of the light and heavy chains of an antibody molecule that includes the amino acid sequences of the complementarity determining regions (CDRs, i.e., CDR1, CDR2 and CDR3) and the framework regions (FRs). VH refers to the variable domain of the heavy chain. VL refers to the variable domain of the light chain.

"LMP2" described herein comprises LMP2A and LMP2B. LMP2A differs from LPM2B in that there is an additional cytoplasmic domain of 119 amino acids at the N-terminus in LMP2A, otherwise LMP2A and LPM2B have identical structures. Meanwhile, either LMP2A or LMP2B comprises the T cell antigen receptor or the antibody-binding antigen peptide region described herein.

"Homology" described herein refers to that in the context of using an amino acid sequence or a nucleotide sequence, those skilled in the art can adjust the sequence according to as necessary for practice without changing the main structure or function of the original sequence, so as to obtain a sequence having (including but not limited to) 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% homology to the specific sequence described herein. For example, "having at least 80% homology to an amino acid sequence set forth in any one of SEQ ID NOs: 35-44" described herein refers to that SEQ ID NO: 35, 36, 37, 38, 39, 40, 41, 42, 43 or 44 can be adjusted as necessary for practice, for example, by substitution, deletion and/or insertion of one or more amino acids, while retaining the binding function to the EBV latent membrane protein LMP2 peptide epitope:MHC complex. "At least 80%" includes, but is not limited to, 80%, 81%, 82%, 83%, 84%, 85%, 86%, 87%, 88%, 89%, 90%, 91%, 92%, 93%, 94%, 95%, 96%, 97%, 98%, 99% or 100%.

"Individual" described herein includes, but is not limited to, a human or non-human mammal. Preferably, the non-human mammal includes, but is not limited to, a mouse, rat, monkey, pig or rabbit and so on.

"Effective amount" described herein refers to an amount or dose of the product described herein which provides the desired treatment or prevention after administration to a patient or organ in single or multiple doses.

"Diagnosis" or "diagnosing" described herein refers to the determination of whether a patient has suffered from, is suffering from, or will suffer from a disease or condition in the past, at the time of diagnosis, or in the future, or the determination of the progression or likely progression in the future of a disease, or the assessment of a patient's response to a therapy.

"Treatment" or "treating" described herein refers to slowing, interrupting, arresting, controlling, stopping, alleviating, or reversing the progression or severity of a sign, symptom, disorder, condition or disease, but does not necessarily involve the complete elimination of all disease-related signs, symptoms, conditions or disorders, and refers to therapeutic intervention that ameliorates the signs, symptoms, and the like of a disease or pathological state after the disease has begun to progress.

"Product" described herein includes, but is not limited to the antibody or the antigen binding fragment thereof, the T cell antigen receptor, the nucleic acid, the expression vector, the host cell, the immune cell or the multimeric complex described herein, and an additional agent that assists or cooperates with the above products.

"Product" described herein may be a pharmaceutical composition such as a kit, a chip, an antibody conjugate or a multifunctional antibody.

"And/or" described herein includes one listed item and any number of combinations of items.

"Comprise" or "comprising" described herein is an open-ended description that includes the specified component or step as described, as well as other specified components or steps that do not substantially affect the technical effect.

"TRBV" described herein refers to the T cell receptor variable region and "TRBC" refers to the T cell receptor β constant region.

BRIEF DESCRIPTION OF THE DRAWINGS

Hereinafter, embodiments of the present invention will be described in detail with reference to the accompanying drawings, in which:

FIG. 2: staining results of tetramers, wherein

FIG. 3: staining results of tetramers, wherein FIG. 3A shows staining results of A2402-TYGPVFMCL-tetramer and A2402-TYGPVFMSL-tetramer; FIG. 3B shows staining results of A1101-SSCSSCPLSK-tetramer, and staining results of A1101-SSCSSCPLTK-tetramer; and FIG. 3C shows staining results of A2402-PYLFWLAAI-tetramer.

FIG. 4: a schematic diagram of the linking of TCR β and α chains in a pHAGE vector, wherein the linking is performed by the following order: a promoter, the β chain, furin-p2A, the α chain, IRES and RFP sequences;

FIG. 5: the expression of HLA-A*A0201 FLYALALLL-specific TCRs (E23 and E240), HLA-A*A2402 TYGPVFMSL/TYGPVFMCL-specific TCR (E44) and PYLFWLAAI-specific TCRs (E29 and E180-1) on a membrane surface as assayed by flow cytometry, wherein BV421 is one of fluoresceins, and BV stands for Brilliant Violet;

DETAILED DESCRIPTION OF THE EMBODIMENTS

Figure 1:
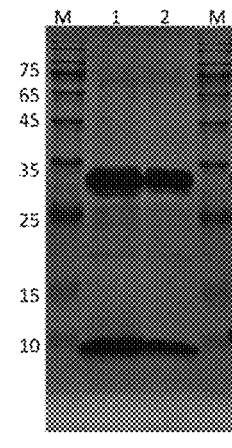
FIG. 1: SDS PAGE detection results of monomers, wherein M is protein Marker, and bands 1 and 2 are monomers.

Technical solutions in the embodiments of the present invention will be described clearly and completely below with reference to the drawings. It is apparent that the described embodiments are only a part of the embodiments of the present invention, but not all of them. Based on the embodiments of the present invention, all other embodiments obtained by those of ordinary skill in the art without making creative work shall fall within the protection scope of the present invention.

Example 1. Construction and Effect Assay on EBV Antigenic Epitope Tetramers

I. Construction of EBV Antigenic Epitope Tetramers

1) An α chain and a β2m chain (with the amino acid sequence set forth in SEQ ID NO: 4, and the nucleotide sequence set forth in SEQ ID NO: 121) of HLA-A*0201 (with the amino acid sequence set forth in SEQ ID NO: 1, and the nucleotide sequence set forth in SEQ ID NO: 118), HLA-A*2402 (with the amino acid sequence set forth in SEQ ID NO: 2, and the nucleotide sequence set forth in SEQ ID NO: 119) and HLA-A*1101 (with the amino acid sequence set forth in SEQ ID NO: 3, and the nucleotide sequence set forth in SEQ ID NO: 120) with optimized expression sequences were provided. The structure of the α chain was as follows: the extracellular domain sequence of the α chain of the corresponding HLA type was connected with an Avi-tag sequence, with a BamHI enzyme cutting site as a spacer to provide a biotinylation site. The β2m chain was depleted of the signal peptide sequence, with two amino acids (M and A) added before a mature peptide sequence. The expression vector was PET28a+, and the expression strain was transetta or BL21. IPTG was at a concentration of 0.5 mM, and the expression was induced for 4 h. The protein inclusion bodies of the α chain and β2m chain were extracted.

2) Selection of EBV epitopes (antigen peptides): HLA-A*0201 type corresponds to an antigenic epitope FLY-ALALLL (SEQ ID NO: 29); HLA-A*2402 type corresponds to antigenic epitopes PYLFWLAAI (SEQ ID NO: 30), TYGPVFMSL (SEQ ID NO: 31) and TYGPVFMCL (SEQ ID NO: 32); and HLA-A*1101 type corresponds to antigenic epitopes SSCSSCPLSK (SEQ ID NO: 33) and SSCSSCPLTK (SEQ ID NO: 34).

3) Folding and purification of pMHC I monomer: the antigen peptides in the step 2), and the corresponding β2m chain renaturation proteins and the α chain proteins in the step 1) were added into a reduction system in order according to the molar ratio of 40:2:1, and the folding reaction was performed for 72 h. The resulting products were purified on a Superdex75 10/300GL column. The purified products were collected, biotinylated using an avidity kit, and purified again to obtain biotinylated monomers, which were determined for the purity by gel electrophoresis.

4) The biotinylated monomers in the step 3) were subjected to a binding reaction with APC-labeled streptavidin to obtain corresponding tetramers, which were named as A0201-FLYALALLL-tetramer, A2402-PYLFWLAAI-tetramer, A2402-TYGPVFMSL-tetramer, A2402-TYGPVFMCL-tetramer, A1101-SSCSSCPLSK-tetramer and A1101-SSCSSCPLTK-tetramer, respectively.

II. Assay on the Effect of EBV Antigenic Epitope Tetramers

1. Human peripheral blood mononuclear cells (PBMCs) were isolated, and a cell suspension was prepared at a cell density of $1 \times 10^6$ cells/mL.
2. The cells were centrifuged at 3000 rpm for 5 min. The supernatant was removed and resuspended in 50 μL of PBS containing 1% serum.
3. 2 μL of tetramer was added, and the mixture was incubated at room temperature for 30 min.
4. 2 μL of CD8 antibody was added, and the mixture was incubated on ice for 20 min.
5. 1 mL of PBS was added, and the mixture was centrifuged at 3000 rpm for 5 min.
6. The supernatant was removed, 1 mL of PBS was added, and the mixture was centrifuged at 3000 rpm for 5 min.
7. The supernatant was removed, the cells were resuspended in 500 μL of 4% paraformaldehyde, and the cell suspension was filtered through a filter membrane.
8. Positive cells were detected by a flow cytometer.

III. Experimental Results

The SDS PAGE detection results of the monomers are shown in FIG. 1. As shown in the figure, after refolding and HPLC purification, for the resulting monomers, the proteins with sizes corresponding to those of the heavy chain (the α-chain extracellular domain connected with the Avi-tag sequence at the C-terminus) and the light chain (the β2m chain depleted of the signal peptide region), respectively, and having higher purity are clearly showed.

Figure 2A:
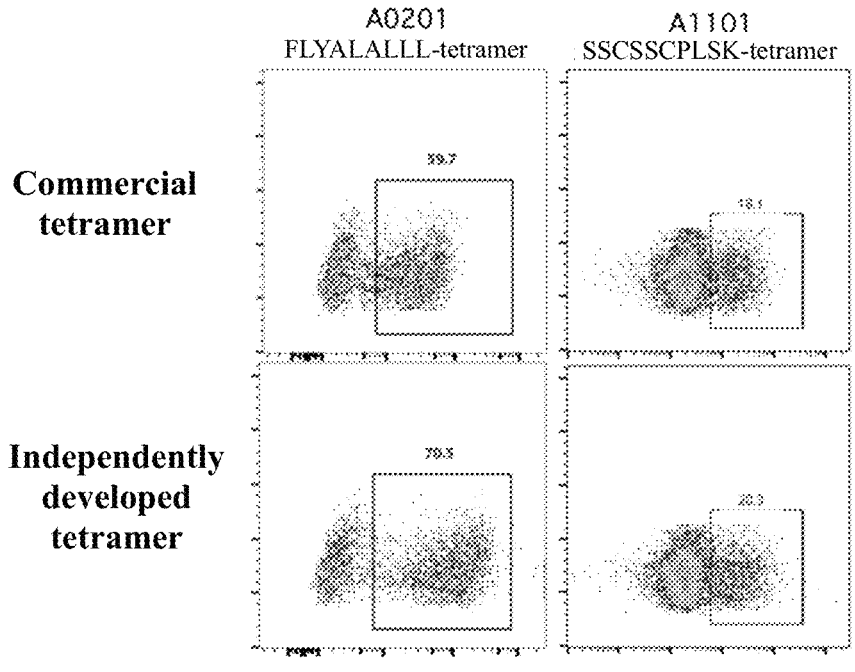
FIG. 2A shows staining results of A0201-FLYALALLL-tetramer and A1101-SSCSSCPLSK-tetramer.
Figure 2B:
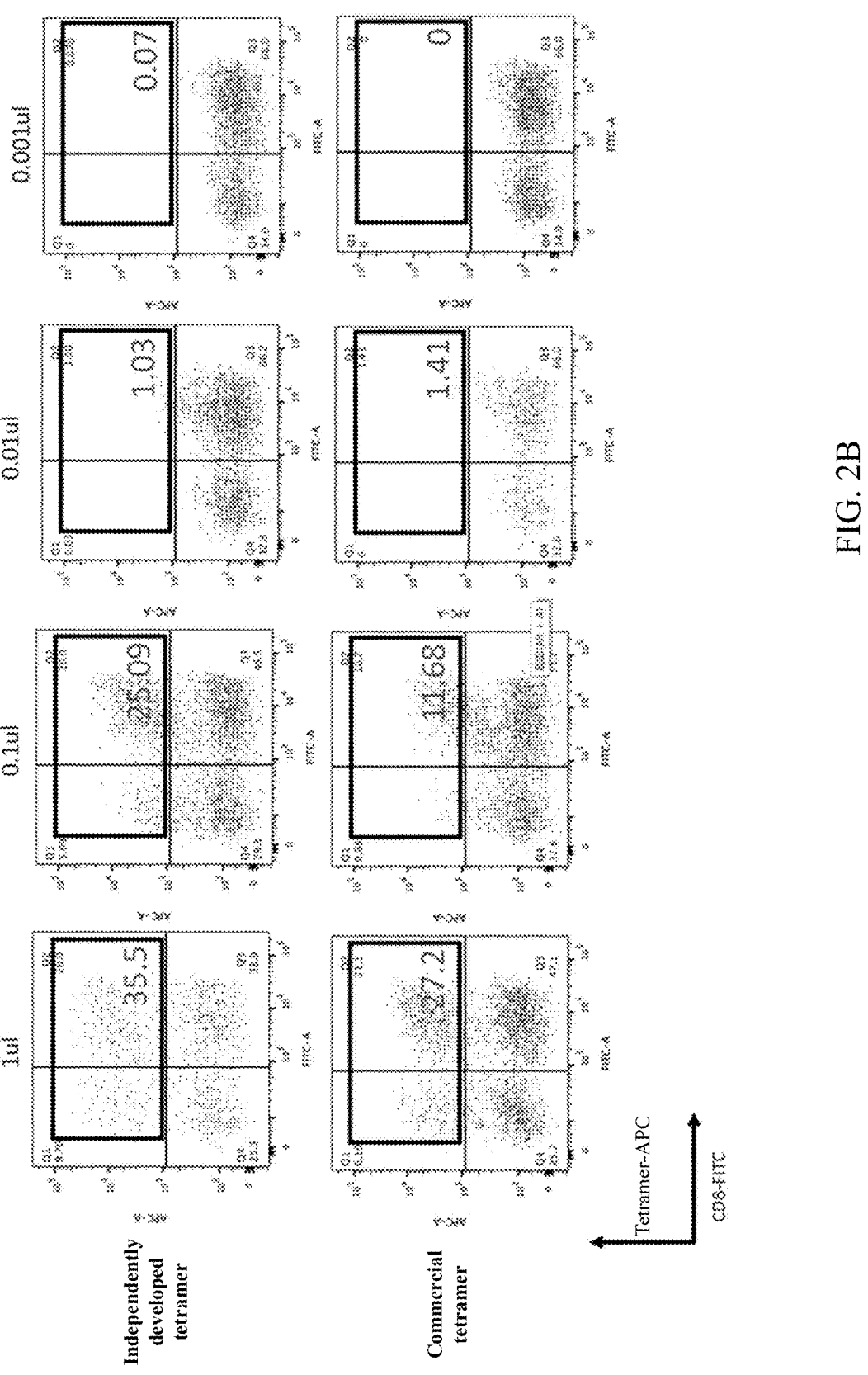
FIG. 2B shows the comparison of A2402-TYGPVFMSL-tetramer with commercial tetramer in volume gradient assays.

The constructed tetramers were separately co-incubated with cells infected with TCRs of corresponding HLA types. Illustratively, the constructed A0201-FLYALALLL-tetramer, A2402-TYGPVFMSL-tetramer, A2402-TYGPVFMCL-tetramer, A2402-PYLFWLAAI-tetramer, A1101-SSCSSCPLTK-tetramer, and A1101-SSCSSCPLSK-tetramer were separately co-incubated with cells infected with TCRs of corresponding HLA types (the LLL tetramer corresponds to TCR E23; the AAI tetramer corresponds to TCR E29; the MSL/MCL tetramer corresponds to TCR E44; and the LSK/LTK tetramer corresponds to TCR E141). By comparing with commercial tetramers from MBL, the percentage of positive cells detected for the A0201-FLY-ALALLL-tetramer was 70.5%, which was much higher than that of the commercial FLYALALLL tetramer (59.7%), and the percentage of positive cells detected for the A1101-SSCSSCPLSK-tetramer was 20.3%, which was significantly higher than that of the commercial SSCSSCPLSK-tetramer (18.1%), as shown in FIG. 2A. This fully suggests that the tetramers of the present invention exhibit a high degree of specificity and staining effect in detecting the positive rate of cells. In a further volume gradient assay, the independently developed A2402-TYGPVFMSL tetramer was found to have a specific binding effect much higher than the commercial tetramer (see FIG. 2B).

Figures 3, 4, 5:
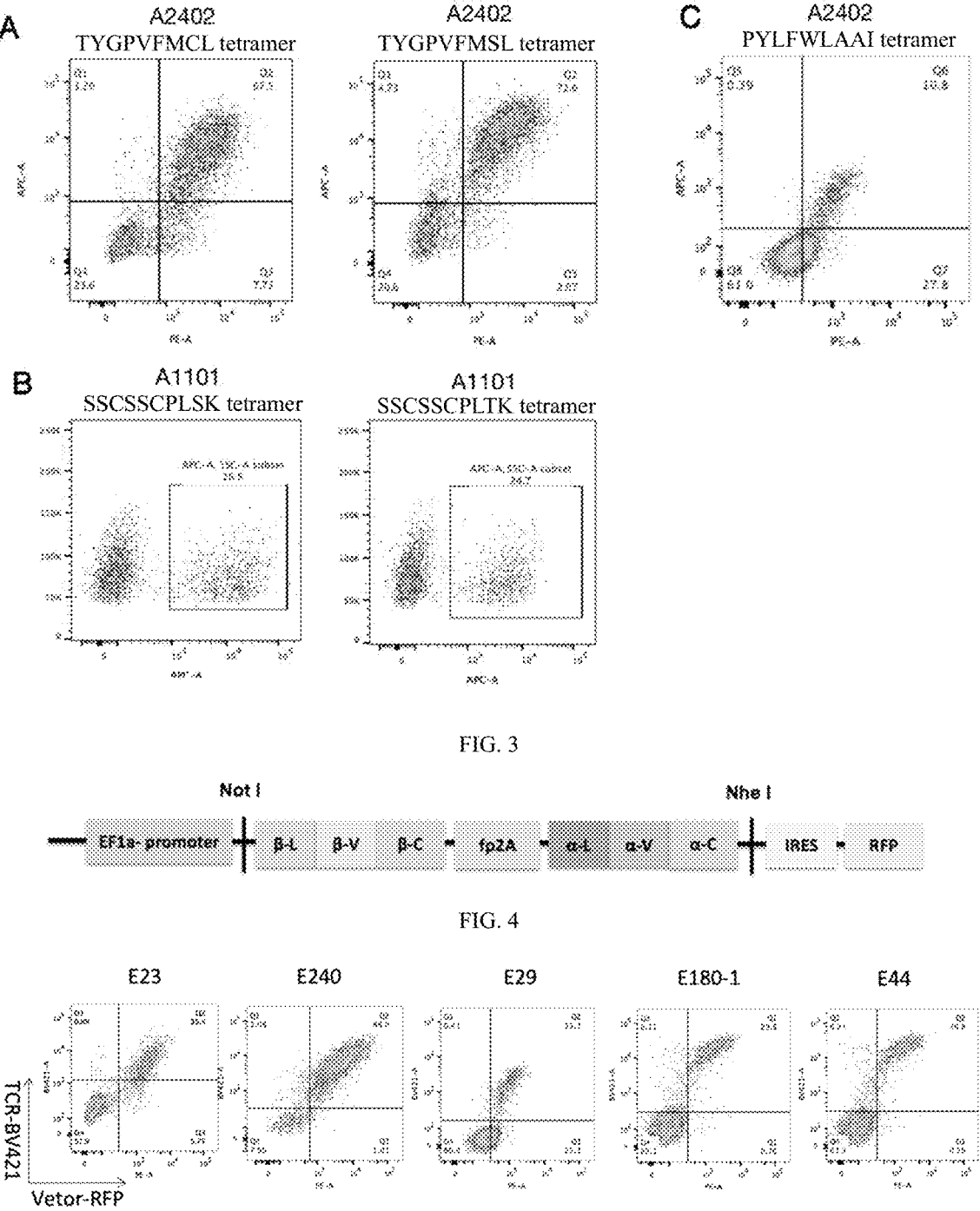

The TCRs fished by the tetramers constructed by the present invention can simultaneously recognize the wild-type antigenic epitope and the mutant-type antigenic epitope to prevent immune escape. As shown in FIG. 3-A, both A2402 HLA wild-type antigenic epitope (MCL) and mutant-type antigenic epitope (MSL) tetramers were able to be recognized by TCR E44, which was fished by the MSL tetramer. As shown in FIG. 3-B, both A1101 HLA wild-type antigenic epitope (LSK) and mutant-type antigenic epitope (LTK) tetramers were able to be recognized by TCR E141, which was fished by the LSK tetramer. The TCR with corresponding specificity can be fished by different antigenic epitope tetramers of the same HLA type. As shown in FIG. 3-C, positive cells corresponding to TCR E29 was able to be detected by the AAI tetramer.

Example 2. Construction of pHAGE-TCR-RFP Vector

I. Acquisition Off and a Gene Fragments of EBV LMP2 Epitope-Specific TCRs

1) The A0201-FLYALALLL-tetramer, A2402-PYLFW-LAAI-tetramer, A2402-TYGPVFMSL-tetramer, A2402-TYGPVFMCL-tetramer, A1101-SSCSSCPLSK-tetramer and A1101-SSCSSCPLTK-tetramer prepared in Example 1 were stained with peripheral blood, T cells positive for tetramer staining were sorted by flow cytometry to obtain single cells, and reverse transcription was performed to obtain cDNA (SuperScript® IV Reverse Transcriptase, Invitrogen). The variable region fragments of the TCRβ gene were obtained by amplification by two rounds of PCR (KOD-Plus-Neo, TOYOBO) based on the principle of multiplex PCR.

```
          Reverse transcription primer:
                              (SEQ ID NO: 144)
          TRBC1-TCAGGCAGTATCTGGAGTCATTG
```

PCR Amplification Primers:

```
          Upstream primer 1:
                    (see SEQ ID NOs: 147-185 and 366)
          TRBV_F1

Upstream primer 2:
                         (see SEQ ID NOs: 186-225)
          TRBV_F2

Downstream primer 1:
                              (SEQ ID NO: 145)
          TRBC2-GCACCTCCTTCCCATTCACC Downstream primer 2:
                              (SEQ ID NO: 146)
          TRBC3-GCTTCTGATGGCTCAAACACAG
```

Specifically, according to the product instructions of the PCR polymerase KOD-Plus-Neo, the PCR system of the first round was at 20 μL, the annealing temperature was 60° C., and the reaction was performed for 30 cycles. 1 μL of the product from the first round of PCR reaction was taken as a template of the second round of PCR, wherein the PCR system of the second round was at 30 μL, the annealing temperature was 60° C., and the reaction was performed for 30 cycles. The product from the second round of PCR was subjected to agarose gel electrophoresis, and the band with the corresponding size was extracted from gel (TIANGEN Gel Extraction Kit) and sent for sequencing, wherein the sequencing primer was the downstream primer 2. The TCRβ gene sequences were obtained, wherein the specific TCRβ gene sequences for E23, E240, E29, E180-1, E44, E141, E149, E168, E170, E244, E245, E254, E301, E304, E305, E307, E314, E315, E316, E317, E318 and E320 were shown as "double underlined" nucleotide sequences in SEQ ID NOs: 122-143, respectively.

2) As above, reverse transcription was performed on T cells positive for tetramer staining to obtain cDNA (Super-Script® IV Reverse Transcriptase, Invitrogen). The TCRα gene fragments were obtained by amplification by two rounds of PCR (KOD-Plus-Neo, TOYOBO) according to the product instructions.

```
          Reverse transcription primer:
                              (SEQ ID NO: 226)
          TRAC1-CGACCAGCTTGACATCACAG
```

PCR Amplification Primers:

```
          Upstream primer 3:
                         (see SEQ ID NOs: 229-273)
          TRAV_F1

Upstream primer 4:
                         (see SEQ ID NOs: 274-315)
          TRAV_F2

Downstream primer 3:
                              (SEQ ID NO: 227)
          TRAC2-GTTGCTCTTGAAGTCCATAGACCTC Downstream primer 4:
                              (SEQ ID NO: 228)
          TRAC3-CAGGGTCAGGGTTCTGGATA
```

Specifically, according to the product instructions of the PCR polymerase KOD-Plus-Neo, the PCR system of the first round was at 20 μL, the annealing temperature was 60° C., and the reaction was performed for 30 cycles. 1 μL of the product from the first round of PCR reaction was taken as a template of the second round of PCR, wherein the PCR system of the second round was at 30 μL, the annealing temperature was 60° C., and the reaction was performed for 30 cycles. The product from the second round of PCR was subjected to agarose gel electrophoresis, and the band with the corresponding size was extracted from gel (TIANGEN Gel Extraction Kit) and sent for sequencing, wherein the sequencing primer was the downstream primer 4. The TCRα gene sequences were obtained, wherein the specific TCRα gene sequences for E23, E240, E29, E180-1, E44, E141, E149, E168, E170, E244, E245, E254, E301, E304, E305, E307, E314, E315, E316, E317, E318 and E320 were shown as "wavy underlined" nucleotide sequences in SEQ ID NOs: 122-143, respectively.

II. Construction of pHAGE-TCR Vector

TCRβ, fp2A and TCRα were amplified by overlap-PCR (KOD-Plus-Neo, TOYOBO) with long primer (containing fp2A sequence) to obtain TCRβ-fp2A-TCRα fragments, which were named as pHAGE-TCR plasmids for E23, E240, E29, E180-1, E44, E141, E149, E168, E170, E244, E245, E254, E301, E304, E305, E307, E314, E315, E316, E317, E318 and E320, respectively.

Amplification Primers:

Upstream primer 5 is shown in Table 1.

TABLE 1

| TCR ID | Upstream primer 5 |
|---|---|
| E23 | atttcaggtgtcgtgaagcggccgcgccaccATGAGCATCGGCCTCCT (SEQ ID NO: 316) |
| E240 | atttcaggtgtcgtgaagcggccgcgccaccATGAGCATCGGCCTCCT (SEQ ID NO: 317) |
| E29 | atttcaggtgtcgtgaagcggccgcgccaccATGCTGCTGCTTCTGCT (SEQ ID NO: 318) |
| E180-1 | atttcaggtgtcgtgaagcggccgcgccaccATGAGCAACCAGGTGCT (SEQ ID NO: 319) |
| E44 | atttcaggtgtcgtgaagcggccgcgccaccATGGGCCCCCAGCTCCT (SEQ ID NO: 320) |
| E141 | atttcaggtgtcgtgaagcggccgcgccaccATGGGCTGCAGGCTGCTC (SEQ ID NO: 321) |
| E149 | atttcaggtgtcgtgaagcggccgcgccaccATGGGCTGCAGGCTGCTC (SEQ ID NO: 322) |
| E168 | atttcaggtgtcgtgaagcggccgcgccaccATGGGCCCTGGGCTCCT (SEQ ID NO: 323) |
| E170 | atttcaggtgtcgtgaagcggccgcgccaccATGGACACCAGAGTACTCTGCTG (SEQ ID NO: 324) |
| E244 | atttcaggtgtcgtgaagcggccgcgccaccATGGGCCCCCAGCTCC (SEQ ID NO: 325) |
| E245 | atttcaggtgtcgtgaagcggccgcgccaccATGGGCCCTGGGCTCCT (SEQ ID NO: 326) |
| E254 | atttcaggtgtcgtgaagcggccgcgccaccATGGGCTTCAGGCTCCTCTG (SEQ ID NO: 327) |
| E301 | atttcaggtgtcgtgaagcggccgcgccaccATGGGCTGCAGGCTGCTC (SEQ ID NO: 328) |
| E304 | atttcaggtgtcgtgaagcggccgcgccaccATGGGCTGCAGGCTGCTC (SEQ ID NO: 329) |
| E305 | atttcaggtgtcgtgaagcggccgcgccaccATGGATACCTGGCTCGTATGC (SEQ ID NO: 330) |
| E307 | atttcaggtgtcgtgaagcggccgcgccaccATGGGCACCAGGCTCCTC (SEQ ID NO: 331) |
| E314 | atttcaggtgtcgtgaagcggccgcgccaccATGGGCTGCAGGCTGCTC (SEQ ID NO: 332) |
| E315 | atttcaggtgtcgtgaagcggccgcgccaccATGGGCACCAGGCTCCTC (SEQ ID NO: 333) |
| E316 | atttcaggtgtcgtgaagcggccgcgccaccATGAGCAACCAGGTGCTCTG (SEQ ID NO: 334) |
| E317 | atttcaggtgtcgtgaagcggccgcgccaccATGGGCCCCCAGCTCC (SEQ ID NO: 335) |
| E318 | atttcaggtgtcgtgaagcggccgcgccaccATGGACTCCTGGACC (SEQ ID NO: 336) |
| E320 | atttcaggtgtcgtgaagcggccgcgccaccATGGGCACCAGGCTCCTC (SEQ ID NO: 337) |

Downstream primer 5:
TCTCCAGCCTGCTTCAGCAGGCTGAAGTTAGTAGCTCCGCTTCCGCTccgtttccgccgGAAATCCTTTC
TCTTGACCATG (SEQ ID NO: 338)

Upstream primer 6 is shown in Table 2.

TABLE 2

| TCR ID | Upstream primer 6 |
|---|---|
| E23 | TCAGCCTGCTGAAGCAGGCTGGAGACGTGGAGGAGAACCCTGGACC<br>T ATGGAAACTCTCCTGGGAGTGTCT (SEQ ID NO: 339) |
| E240 | TCAGCCTGCTGAAGCAGGCTGGAGACGTGGAGGAGAACCCTGGACC<br>T ATGGAAACTCTCCTGGGAGTGTCT (SEQ ID NO: 340) |
| E29 | TCAGCCTGCTGAAGCAGGCTGGAGACGTGGAGGAGAACCCTGGACC<br>T ATGGAGAAGAATCCTTTGGCAGCC (SEQ ID NO: 341) |
| E180-1 | TCAGCCTGCTGAAGCAGGCTGGAGACGTGGAGGAGAACCCTGGACC<br>T ATGACATCCATTCGAGCTGTATTT (SEQ ID NO: 342) |
| E44 | TCAGCCTGCTGAAGCAGGCTGGAGACGTGGAGGAGAACCCTGGACC<br>T ATGATGAAATCCTTGAGAGTTTTA (SEQ ID NO: 343) |
| E141 | TCAGCCTGCTGAAGCAGGCTGGAGACGTGGAGGAGAACCCTGGACC<br>TATGAAGAGGATATTGGGAGCTCTG (SEQ ID NO: 344) |
| E149 | TCAGCCTGCTGAAGCAGGCTGGAGACGTGGAGGAGAACCCTGGACC<br>TATGAAGAGGATATTGGGAGCTCTG (SEQ ID NO: 345) |

TABLE 2-continued

| TCR ID | Upstream primer 6 |
|--------|-------------------|
| E168 | TCAGCCTGCTGAAGCAGGCTGGAGACGTGGAGGAGAACCCTGGACC<br>TATGAAGAAGCTACTAGCAATGATTCTG (SEQ ID NO: 346) |
| E170 | TCAGCCTGCTGAAGCAGGCTGGAGACGTGGAGGAGAACCCTGGACC<br>TATGACATCCATTCGAGCTGTATTTAT (SEQ ID NO: 347) |
| E244 | TCAGCCTGCTGAAGCAGGCTGGAGACGTGGAGGAGAACCCTGGACC<br>TATGACATCCATTCGAGCTGTATTTAT (SEQ ID NO: 348) |
| E245 | TCAGCCTGCTGAAGCAGGCTGGAGACGTGGAGGAGAACCCTGGACC<br>TATGAAGAAGCTACTAGCAATGATTCTG (SEQ ID NO: 349) |
| E254 | TCAGCCTGCTGAAGCAGGCTGGAGACGTGGAGGAGAACCCTGGACC<br>TATGAAGAGGATATTGGGAGCTCTG (SEQ ID NO: 350) |
| E301 | TCAGCCTGCTGAAGCAGGCTGGAGACGTGGAGGAGAACCCTGGACC<br>TATGAAGAGGATATTGGGAGCTCTG (SEQ ID NO: 351) |
| E304 | TCAGCCTGCTGAAGCAGGCTGGAGACGTGGAGGAGAACCCTGGACC<br>TATGAAGAGGATATTGGGAGCTCTG (SEQ ID NO: 352) |
| E305 | TCAGCCTGCTGAAGCAGGCTGGAGACGTGGAGGAGAACCCTGGACC<br>TATGAAGAAGCTACTAGCAATGATTCTG (SEQ ID NO: 353) |
| E307 | TCAGCCTGCTGAAGCAGGCTGGAGACGTGGAGGAGAACCCTGGACC<br>TATGCTGACTGCCAGCCTGT (SEQ ID NO: 354) |
| E314 | TCAGCCTGCTGAAGCAGGCTGGAGACGTGGAGGAGAACCCTGGACC<br>TATGAAGAGGATATTGGGAGCTCTG (SEQ ID NO: 355) |
| E315 | TCAGCCTGCTGAAGCAGGCTGGAGACGTGGAGGAGAACCCTGGACC<br>TATGGAGACCCTCTTGGGCCT (SEQ ID NO: 356) |
| E316 | TCAGCCTGCTGAAGCAGGCTGGAGACGTGGAGGAGAACCCTGGACC<br>TATGTCACTTTCTAGCCTGCTGAAG (SEQ ID NO: 357) |
| E317 | TCAGCCTGCTGAAGCAGGCTGGAGACGTGGAGGAGAACCCTGGACC<br>TATGGCAGGCATTCGAGCTT (SEQ ID NO: 358) |
| E318 | TCAGCCTGCTGAAGCAGGCTGGAGACGTGGAGGAGAACCCTGGACC<br>TATGACATCCATTCGAGCTGTATTTAT (SEQ ID NO: 359) |
| E320 | TCAGCCTGCTGAAGCAGGCTGGAGACGTGGAGGAGAACCCTGGACC<br>TATGAAGAAGCTACTAGCAATGATTCTG (SEQ ID NO: 360) |

Downstream primer 6: agggatcctctagactcgagctagcTCAGCTGGACCACAGCCGCA (SEQ ID NO: 361)

Specifically, the TCRβ and the TCRα were firstly obtained by amplification by using a primer 5 and a primer 6, respectively, wherein the PCR system was at 50 μL, the annealing temperature was 60° C., and the reaction was performed for 30 cycles. The PCR products were subjected to gel electrophoresis and extracted (TIANGEN Gel Extraction Kit), and the extracted products were taken as templates, each at 1 μL, and subjected to overlap PCR by using an upstream primer 5 and a downstream primer 6, respectively, wherein the PCR system was at 50 μL, the annealing temperature was 60° C., and the reaction was performed for 30 cycles. The product was subjected to agarose gel electrophoresis to obtain a band of about 1800 bp, which was then extracted from gel. The lentiviral vector pHAGE-IRES-RFP was double digested with NotI and NheI, wherein the enzyme digestion system was at 40 μL, wherein the NotI and NheI were each at 1.5 μL, the plasmid was at 2-3 μg, and the enzyme digestion was performed at 37° C. for 6 h. Then 1 μL of alkaline phosphatase (NEB) was added into the system and treated for 1 h to reduce the self-ligation of the plasmid, and the plasmid after the enzyme digestion was subjected to gel electrophoresis and extracted, determined for the concentration using nanodrop, and used as a backbone for constructing the plasmid.

According to the product instructions of Clone Express II One Step Cloning kit, the TCR was connected with a linearized pHAGE-IRES-RFP vector after enzyme digestion through overlap (see FIG. 4), and transformed into Stb13 strain, which was then cultured in an ampicillin-containing LB plate for 12-16 h. The monoclonal strain was picked for sequencing, wherein the sequencing primers selected were primers seq-pHAGE-F and seq-pHAGE-R on the pHAGE vector and a downstream primer 4. Corresponding TCRs were obtained, abbreviated as E23, E240, E29, E180-1, E44, E141, E149, E168, E170, E244, E245, E254, E301, E304, E305, E307, E314, E315, E316, E317, E318 and E320, respectively.

Example 3. Assay on Membrane Expression and Affinity of TCRs by a pMHC Tetramer Staining Method 1. Construction of Endogenous TCR Knockout Jurkat T Cell Lines Based on the sequence characteristics of the Jurkat cell TCR, guide sequences (TRA_oligo1-CACCGTCTCTCA-GCTGGTACACGGC (SEQ ID NO: 362), TRA_oligo2-

AAACGCCGTGTACCAGCTGAGAGAC (SEQ ID NO: 363), TRB_oligo1-CACCGGGCTCAAACACAGCG-ACCTC (SEQ ID NO: 364), TRB_oligo2-AAACG-AGGTCGCTGTGTTTGAGCCC (SEQ ID NO: 365)) were designed in the constant regions of the α chain and the β chain.

The synthesized guide sequences of the α chain and the β chain were constructed into sgRNA-LentiCRISPR-puro and sgRNA-LentiCRISPR-BSD lentiviral vectors, respectively, and the vectors were co-transfected with packaging plasmids psPAX2 and pMD2.G and a PEI transfection reagent into 293T cells according to a certain ratio. The cell culture supernatants were harvested at 48 h and 72 h and concentrated, and the two viruses after concentration were simultaneously used to infect a human Jurkat T cell line. 48 h after the infection, killing was performed using puromycin and blasticidin at appropriate concentrations until all cells in the control group for each of the two drugs were dead. Surviving cells were sorted by flow cytometry to obtain single cells, which were added into a 96-well plate for culturing. For the obtained monoclonal cell line, its expression was separately identified using antibodies of the TCRα chain and the TCRβ chain, and the cell strain defective in both chains was the obtained endogenous TCR knockout Jurkat T cell, which was named as JC5.

2. Construction of JC5 Cell Line Stably Integrating EBV TCR

The pHAGE-TCR plasmids such as E23 and E240 constructed in Example 2 were separately mixed with packaging plasmids psPAX2 and pMD2.G and a PEI transfection reagent according to a certain ratio, and transfected into 293T cells. The cell culture supernatants were harvested at 48 h and 72 h and concentrated to infect JC5 cells in the logarithmic growth phase (MOI=0.3). 3 days after infection, cells were stained with anti-human CD3 and anti-human TCRαβ flow cytometry antibodies, and the cells with the same TCR expression level were sorted and cultured to obtain the JC5-TCR cell line.

3. Assay on Expression-On-Membrane and Affinity of TCRs $1 \times 10^6$ JC5-TCR cells were taken, stained with Brilliant Violet 421™ anti-human TCRαβ (Biolegend) and the corresponding EBV LMP2 pMHC tetramer-APC (tetramer-APC) and then analyzed by flow cytometry.

Figure 6:
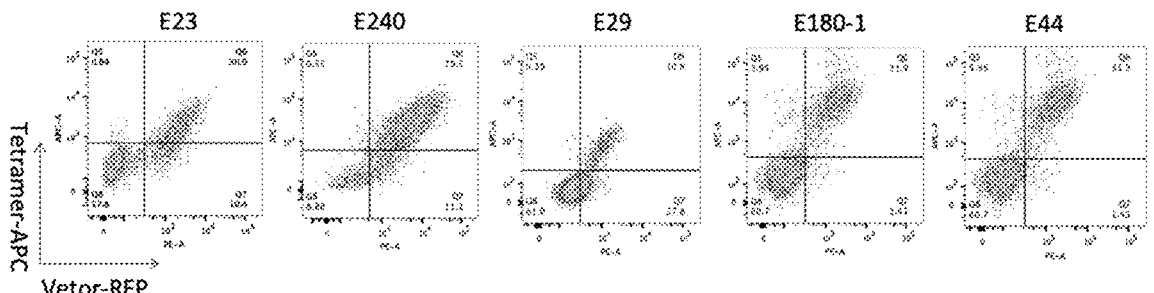
FIG. 6: the affinity of HLA-A*A0201 FLYALALLL-specific TCRs (E23 and E240), HLA-A*A2402 TYGPVFMSL/TYGPVFMCL-specific TCR (E44) and PYLFWLAAI-specific TCRs (E29 and E180-1) for binding to the EBV LMP2 tetramer probe as assayed by flow cytometry.

As can be seen from FIGS. 5 and 6, the prepared specific E23-TCR and E240-TCR for EBV LMP2 HLA-A*A0201 FLYALALLL, specific E29-TCR and E180-1-TCR for EBV LMP2HLA-A*A2402 PYLFWLAAI, and specific E44-TCR for EBV LMP2HLA-A*A2402 TYGPVFMSL/TYGPVFMCL were all able to be correctly expressed and displayed on the outer side of cell membrane, and had a certain affinity to the corresponding tetramer probes.

Figure 7:
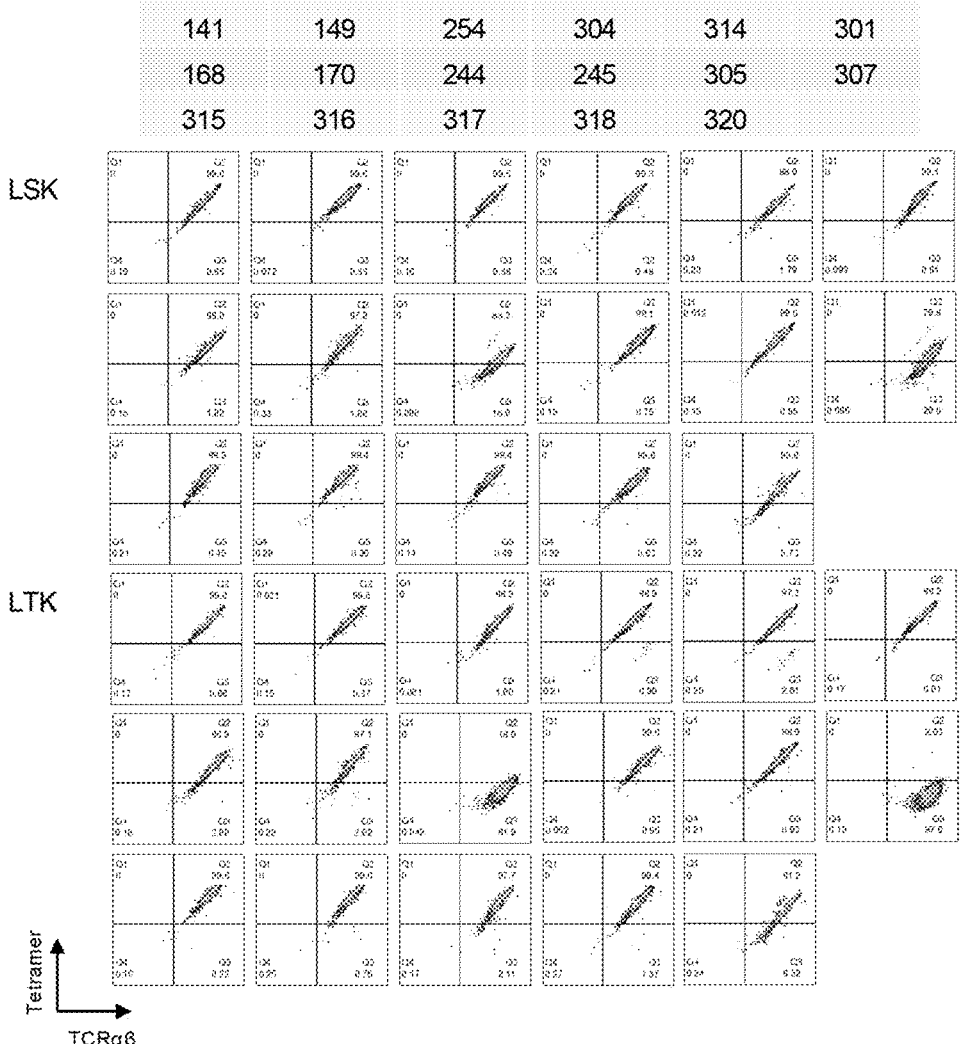
FIG. 7: the affinity of HLA-A*1101 epitope SSCSS-CPLSK (LSK)- and SSCSSCPLTK (LTK)-specific TCRs for binding to tetramer probes as assayed by flow cytometry.

As can be seen from FIG. 7, among the prepared specific TCRs for EBV LMP2 HLA-A*A1101 SSCSSCPLSK/SS-CSSCPLTK, all the constructed TCRs except E244-TCR and E307-TCR showed better binding to the SSCSSCPLSK/SSCSSCPLTK epitope. This result not only suggests that the self-made tetramers can be successfully used to identify specifically bound T cells, but also shows that the obtained TCRs have good affinity.

Example 4. Functional Activity and $EC_{50}$ of TCRs

It was taken into consideration that the pMHC tetramers in Example 3 were used to test the structural affinity of TCRs, and the tetramers binds tetravalently to the TCR on the surface of JC5. To further identify the activity of the TCRs, we stably integrated the HLA-A*1101 molecule in T2 cells and constructed a T2-HLA-A*1101 cell line for quantification of the half maximal effect antigen concentration ($EC_{50}$) of the TCRs, thus achieving the comparison of the functional activity of the TCRs.

1. Construction of T2 Cell Line Stably Integrating HLA-A*1101

The HLA-A*1101 molecule and β2m molecule (derived from human) were cloned, linked with fp2A, and constructed into a pHAGE-BSD vector, which was co-transfected with packaging plasmids psPAX2 and pMD2.G and a PEI transfection reagent into 293T cells according to a certain ratio for virus encapsulation, thereby infecting the T2 cell line. 48 h after infection, killing was performed on T2 cells using blasticidin at the appropriate concentration until all cells in the control group were dead, so that a T2-HLA-A*1101 cell line was obtained.

2. Determination of Functional Activity and $EC_{50}$ of TCR

Figure 8:
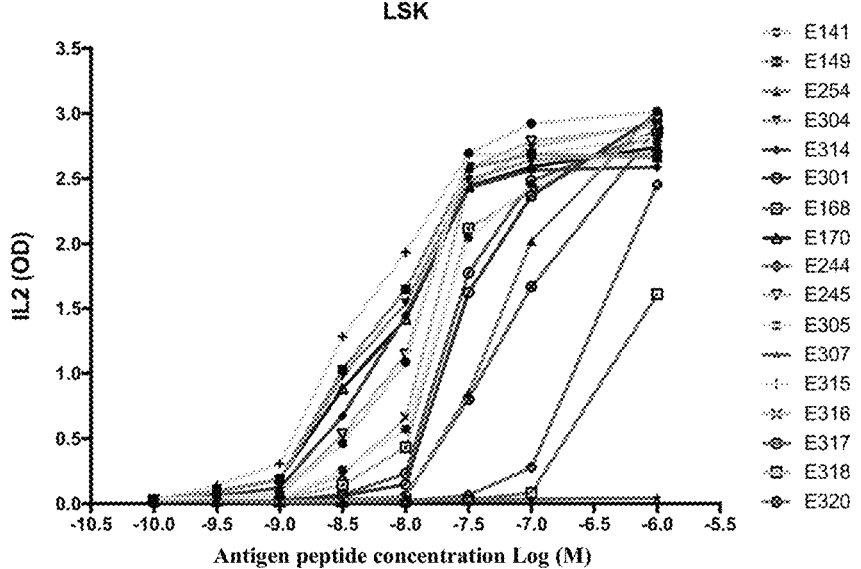
FIG. 8: IL-2 production by JC5-TCR cells stimulated by LSK peptide fragments at different concentrations.
Figure 9:
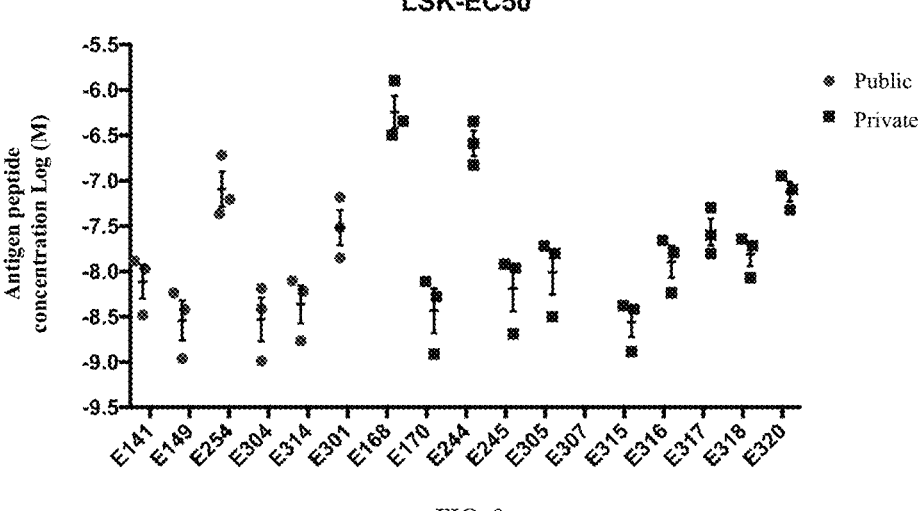
FIG. 9: $EC_{50}$ statistics for LSK epitope-specific TCRs, wherein public TCR represents the TCR conserved in the CDR3 motif and private TCR represents the TCR without conserved sequences in the CDR3 region.
Figure 10:
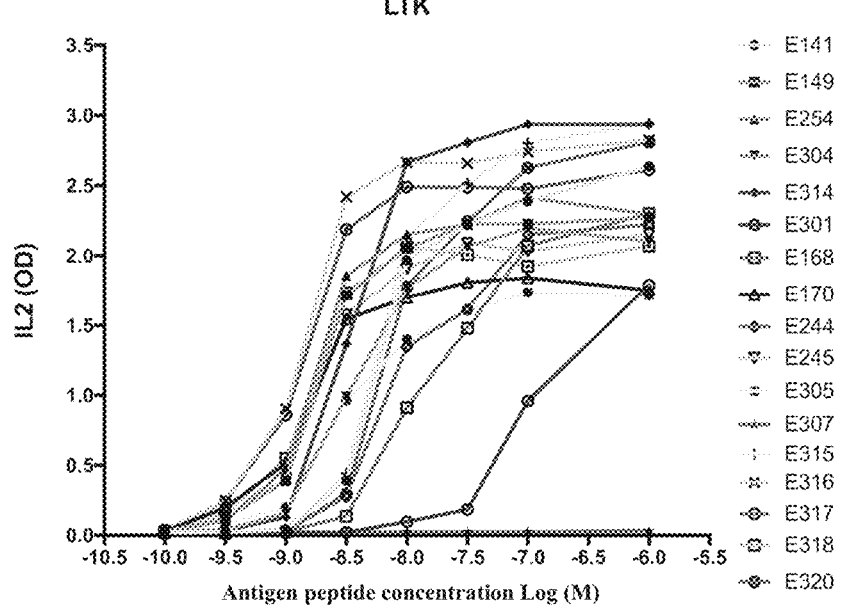
FIG. 10: IL-2 production by JC5-TCR cells stimulated by LTK peptide fragments at different concentrations.
Figure 11:
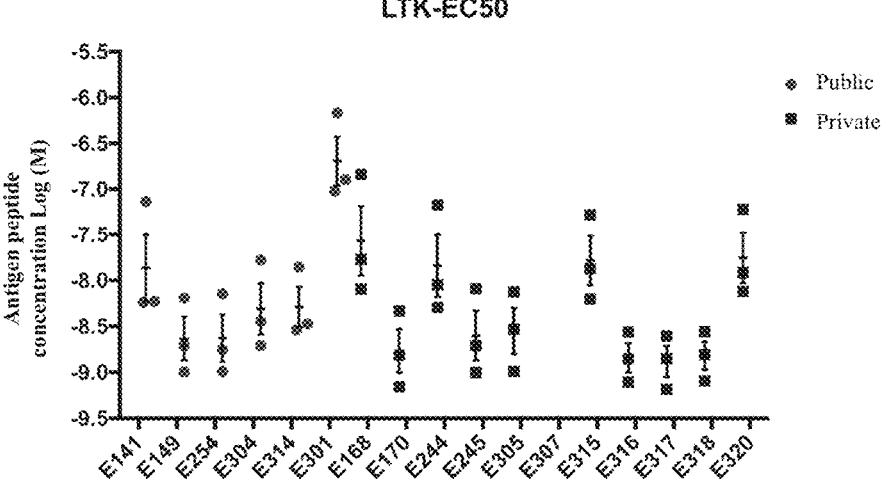
FIG. 11: $EC_{50}$ statistics for LTK epitope-specific TCRs, wherein public TCR represents the TCR conserved in the CDR3 motif and private TCR represents the TCR without conserved sequences in the CDR3 region.

The synthesized LMP2 antigenic epitopes were diluted with a DMSO solvent to a stock concentration of 4 mg/mL. Then peptide fragments of antigenic epitope were serially diluted at a gradient with a complete medium to obtain LSK and LTK peptide fragment solutions at $2 \times 10^{-8}$-$2 \times 10^{-4}$ M, each of which were added to a T2-HLA-A*1101 cell suspension at $1 \times 10^6$ cells/mL in a volume ratio of 1:100, and mixed uniformly. The cells were seeded in a 96-well plate at 100 μL/well, 100 μL of JC5-TCR cells at the concentration of $1 \times 10^6$ cells/mL were added, and mixed uniformly to obtain a T2 incubation system with the peptide fragment concentration of $1 \times 10^{-10}$-$1 \times 10^{-6}$ M. After 24 h of co-incubation, the culture supernatant was collected and assayed for IL2 production by an ELISA kit. The experiment was repeated three times. FIGS. 8 and 10 represent IL2 production by JC5-TCR cells stimulated by different concentrations of LSK and LTK peptides, respectively. Corresponding $EC_{50}$ values can be obtained by calculation with prism, and $EC_{50}$ values for triplicates were detailed in FIGS. 9 and 11. As can be seen from FIGS. 8-11, TCR E149, E304, E170 and E315 had excellent functional activity for the synthetic LSK antigenic epitope, while E149, E254, E170, E316, E317 and E318 all exhibited better functional activity for the LTK antigenic epitope. The results for E244 and E307 are consistent with the results of tetramer staining, that is, both E244 and E307 have weaker recognition ability for the SSCSSCPLSK/SSCSSCPLTK antigenic epitope.

Example 5. Construction of and In Vitro Functional Assay on Human Primary TCR T Cells 1. Isolation, Culture and Lentivirus Infection of Human Primary T Cells To further verify the recognition and killing function of the selected TCRs for the EBV LMP2 antigens, mononuclear cells (PBMCs) were isolated from peripheral blood of volunteers using the lymphocyte isolation solution Ficoll, then T cells were obtained from PBMCs by negative selection according to the product instructions of EasySep Human T cell isolation kit (stem cell technologies), resuspended to $1 \times 10^6$ cells/mL in a 1640 complete medium containing 100 U/mL IL2, and cultured in an anti-CD3/CD28 antibody coated culture dish for activation. After 48 h of activation, the T cells were infected with the TCR-loaded viral particles (prepared in Example 3) using a lentivirus system by centrifuging at 1500 rpm for 2 h at 32° C., culturing in a 37° C. cell incubator for 10 h and terminating the infection by media exchange, and then cultured in a 37° C. cell incubator. Three days after infection, TCR positive cells were sorted using a flow cytometer to obtain TCRT cells (including E23, E240, E29, E180-1, E44, E141, E149, E168, E170, E244, E245, E254, E301, E304, E305, E307, E314, E315, E316, E317, E318 and E320 described above).

2. Construction of Target Cells

Virus particles separately loaded with LMP2-RFP, HLA-A*0201-BSD/HLA-A*2402-BSD/HLA-A*1101-BSD and Luciferase-GFP were used to infect into Raji cells in the logarithmic growth phase using a lentivirus system. Raji cells simultaneously stably expressing LMP2, HLA-A molecules and Luciferas-GFP were obtained by drug screening and flow cytometry sorting, and named as Raji-HLA-A*A0201/2402/1101-LMP2-luciferase. In addition, virus particles of HLA-A*0201-BSD/HLA-A*2402-BSD/HLA-A*1101-BSD were used to infect EBV-LCL cells in the logarithmic growth phase. EBV-LCL cells stably expressing HLA-A molecules were obtained by drug screening, and named as EBV-LCL-HLA-A*0201, EBV-LCL-HLA-A*2402 and EBV-LCL-HLA-A*1101 cells, respectively.

3. In Vitro Functional Verification of TCRs in Human Primary T Cells

Figure 12:
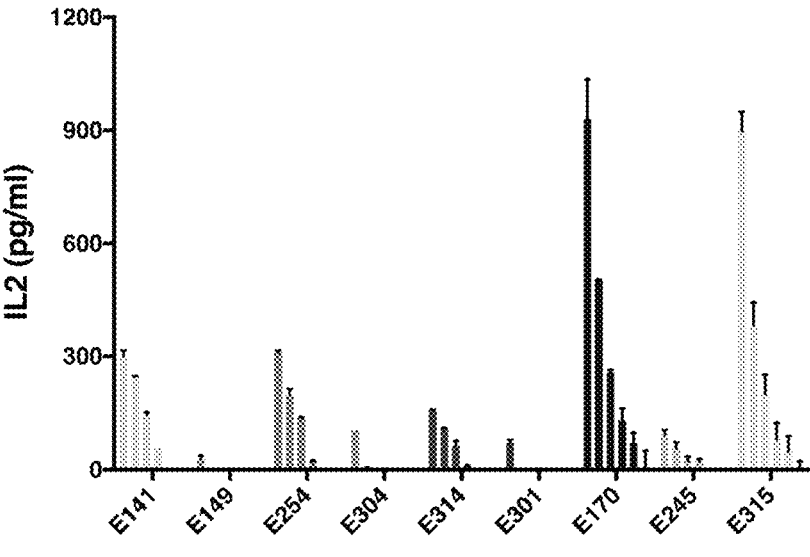
FIG. 12: IL2 release level after incubation of LSK-specific TCR T cells with EBV-LCL cells.
Figure 13:
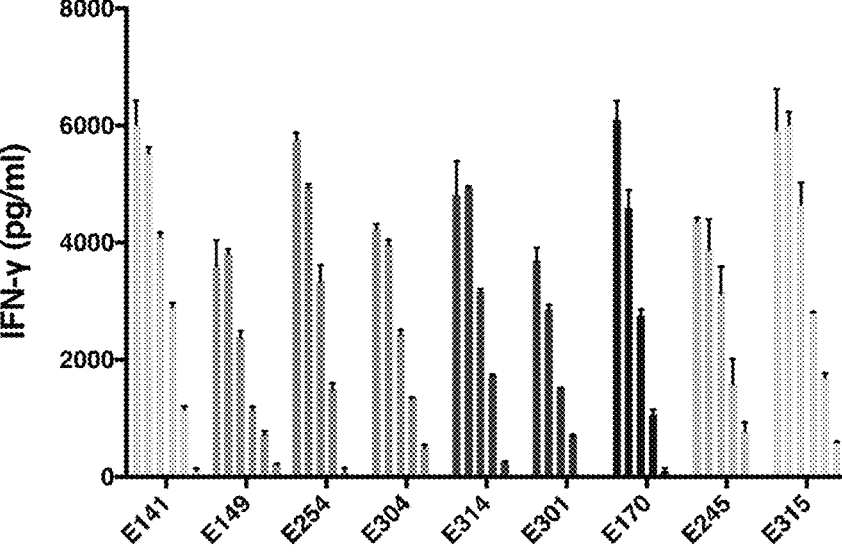
FIG. 13: IFNγ release level after incubation of LSK-specific TCR T cells and EBV-LCL cells.

1) Verification of the Recognition Ability of TCRs to Epitopes at an Endogenous Level The EBV-LCL is the immortalized human B cell infected with the EB virus, which more realistically simulates the antigen level in tumor cells in vivo. Thus, TCR T cells recognizing the SSCSSCPLSK/SSCSSCPLTK epitope and EBV-LCL-HLA-A*1101 cells were co-incubated at effector-to-target ratios of 8:1, 4:1, 2:1, 1:1, 0.5:1 and 0.25:1, with the target cells fixed at $1 \times 10^5$ cells. After 24 h of co-incubation, supernatants were collected for detection of secreted cytokines IL2 (FIG. 12) and IFN-γ (FIG. 13). In terms of the release level of cytokines, TCRs E141, E170, E254 and E315 can significantly activate T cells after binding to LSK at an endogenous level, particularly the E315 TCR T cell, which not only shows the best IFN-γ level at each effector-to-target ratio, but also has a higher corresponding IL2 value. The results suggest that the TCRs prepared by the present invention can effectively mediate the recognition of tumor endogenous antigens.

2) Verification of the Long-Term Killing Ability of TCR T Cells to Tumor Cells

Figure 14:
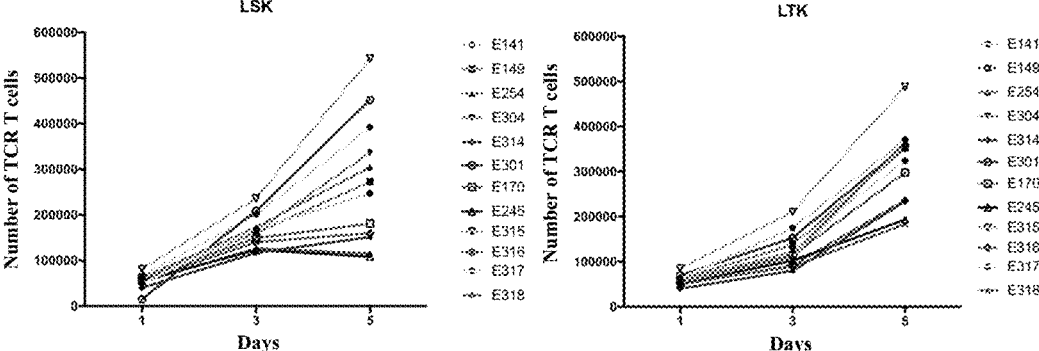
FIG. 14: proliferation results of TCR T cells under long-term stimulation by excess target cells in vitro.
Figures 15, 16:
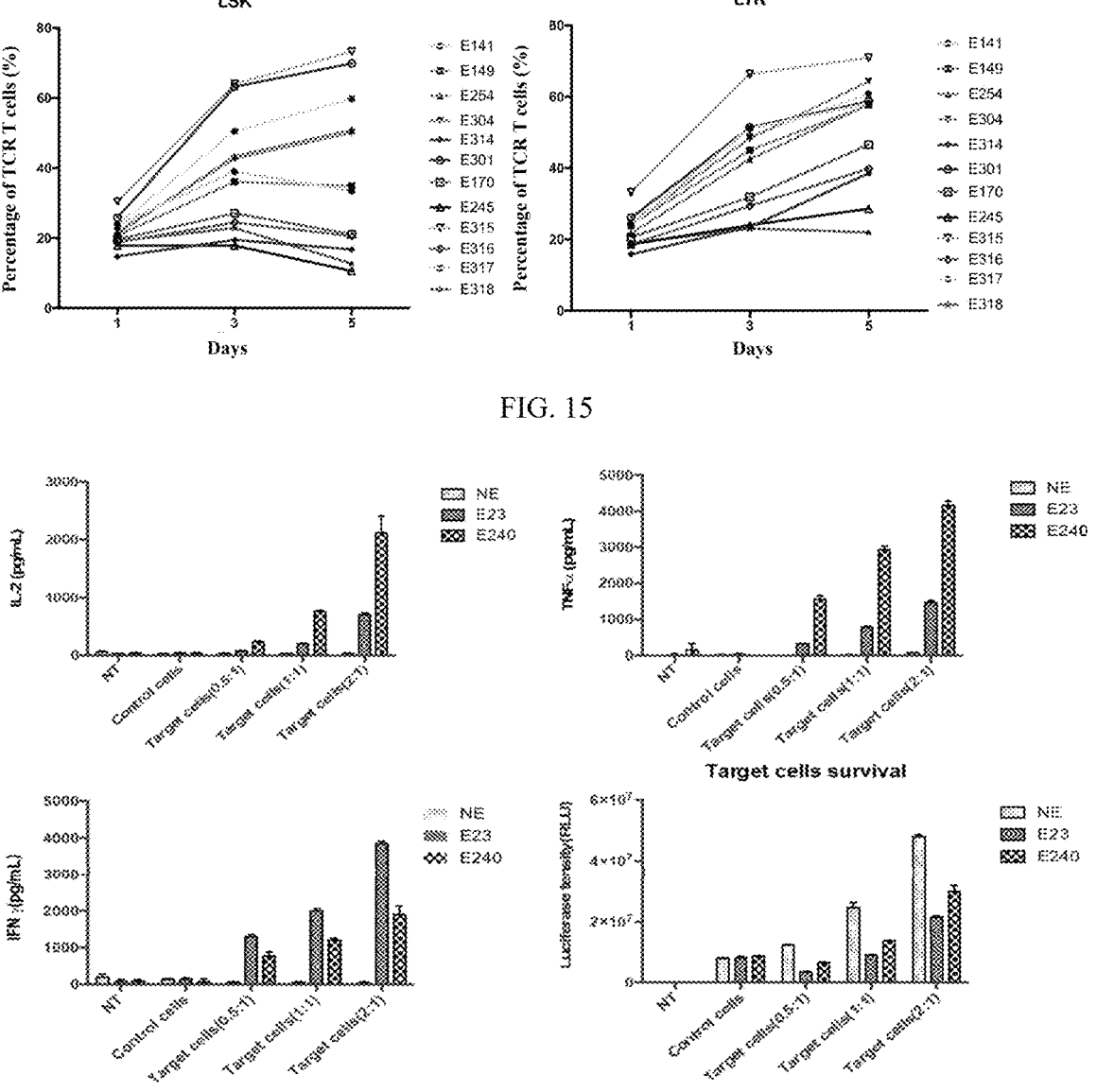
FIG. 15: assay results of killing ability of TCR T cells under long-term stimulation by excess target cells in vitro.
FIG. 16: assay results of the release levels of cytokines IL2, TNFα and IFNγ of E23-TCRT and E240-TCRT and the luciferase level of target cells, wherein E23 and E240 represent the TCRs prepared in Example 2, NE represents the blank control group, NT represents the T cell-only group, Ctrl is Raji cells untransfected with LMP2, and their effector-to-target ratios are 0.5:1, 1:1 and 2:1, respectively.

TCR T cells recognizing the SSCSSCPLSK/SSCSS-CPLTK epitope and Raji-HLA-A*1101-LMP2-luciferase cells were initially co-incubated at an effector-to-target of 1:3, recorded as day 0, and then cells were separately collected for flow cytometry analysis on day 1, day 3 and day 5. The culture medium used was a 1640 complete medium without IL2, the TCR T cells were initially at $1 \times 10^5$ cells, the samples at each time point were incubated independently, and the remaining co-incubated samples were separately subjected to half medium exchange on day 2 and day 4, and supplemented with target cells. Cells for flow cytometry analysis were firstly stained with the anti-human CD3 antibody, the cells with a specified volume were collected and recorded at the time of loading, and the number of T cells in the system was determined by conversion (see FIG. 14). As can be seen from the proliferation curves of absolute T cell numbers, E315-TCR T cells exhibited the best activation and proliferation after recognizing two antigenic epitopes. In addition, the effector-to-target ratio in the system was further analyzed (see FIG. 15), and E315-TCRT cells exhibited the strongest tumor-clearing ability, as with the proliferation results.

3) In Vitro Functional Verification of TCRs in Human Primary T Cells

Raji-HLA-A*0201-LMP2 and Raji cells untransfected with LMP2 were each separately co-incubated with E23-TCRT cells, E240-TCRT cells and 1G4 T cells according to the ratios of 1:0.5, 1:1 and 1:2. After 24 h of co-incubation, the cells and supernatant were separately collected, and the activation of E23-TCRT cells and E240-TCRT cells and the death of target cells were preliminarily determined. In terms of the release levels of the extracellular cytokines TNFα, IL2 and IFNγ (see FIG. 16), E240-TCRT and E23-TCRT, when co-incubated with target cells, were able to significantly cause the activation of T cells as compared to the control group 1G4 T. Moreover, the amount of luciferase released from the target cells after lysis reflects the death of the target cells (see FIG. 16). Experimental results show that the E23-TCRT cells and E240-TCRT cells constructed in the example of the present invention can be specifically activated by EBV LMP2 antigen peptide presenting cells, and can significantly kill target cells.

Figures 17, 18:
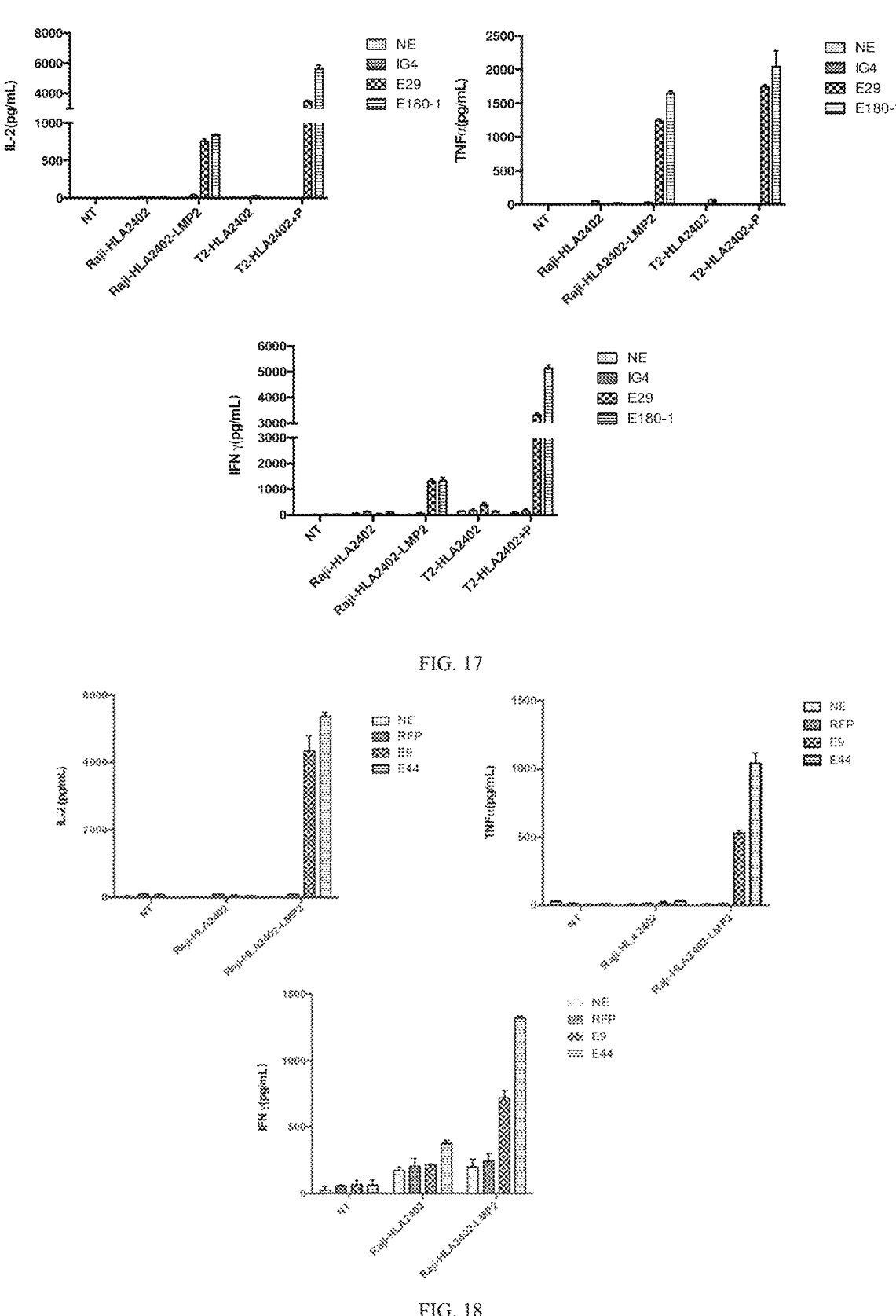
FIG. 17: assay results of the release levels of cytokines IL2, TNFα and IFNγ of E29-TCRT and E180-1-TCRT, wherein E29 and E180-1 represent the TCRs prepared in Example 2, 1G4 represents the control TCR capable of recognizing the antigen EY-ESO-1, NE represents the blank control group, and NT represents the T cell-only group.
FIG. 18: assay results of the release levels of cytokines IL2, TNFα and IFNγ of E44-TCRT, wherein E44 represents the TCR prepared in Example 2, E9 represents the positive control TCR capable of recognizing the antigen LMP2, RFP represents the negative control group, NE represents the blank control group, and NT represents the T cell-only group.

Raji-HLA-A*2402-antigen peptide, Raji cells untransfected with antigen peptide, T2-HLA2402 cells with antigen peptide and T2-HLA2402 cells without antigen peptide were each separately co-incubated with E29-TCRT cells, E180-1-TCRT cells and 1G4 T cells according to the ratio of 1:3. After 24 h of co-incubation, the cells and supernatant were separately collected, and the activation of the E29-TCRT cells and 180-1-TCRT cells were preliminarily determined. In terms of the release levels of the extracellular cytokines IL2 and IFNγ (see FIG. 17), E29-TCRT cells and 180-1-TCRT cells, when co-incubated with target cells, were able to significantly cause the activation of T cells as compared to the control group 1G4 T. In addition, in terms of the release levels of the extracellular cytokines (see FIG. 18), E44-TCRT cells, when co-incubated with target cells, were able to significantly cause the activation of T cells as compared to the control group RFP T. Experimental results show that the E29-TCRT cells, E180-1-TCRT cells and E44-TCRT cells constructed in the example of the present invention can be specifically activated by EBV LMP2 antigen peptide presenting cells, and can significantly kill target cells.

Example 6. Comparison of Function of TCRs Sharing CDR3 Motif

Since the identified E141, E149, E254, E301, E304 and E314 recognizing the SSCSSCPLSK/SSCSSCPLTK epitope, were very conserved in the CDR3 hypervariable region of both TCR α and β chains, and the sequences were highly similar with only one amino acid difference but were functionally far apart (FIGS. 9 and 11), TCRs with those conserved CDR3 motifs were defined as public TCRs, and TCRs without those conserved sequences were defined as private TCRs. Moreover, in this example, the structural affinity and function of the public TCRs were analyzed.

1. Determination of Structural Affinity of Public TCRs by a BFP Method

Red blood cells were fixed on one side of a micropipette, and beads specifically embedded with pMHC molecules were adsorbed on the surface of the red blood cell surface to form a hypersensitive biomembrane force probe (BFP). Meanwhile, JCR-TCR cells were fixed on the other side of the micropipette, and the contact between the two type of cells was controlled by a piezoelectric transducer, wherein the applied pressure was 10 pN and the contact time was 0.1 s when each cycle of contact was performed, then separated at the speed of 1000 pN/s for the next cycle of contact. The deformation of the red blood cell-bead surface was recorded by a microscope in the whole process, and whether a bond was formed or not and the duration were determined. As can be seen from the bonding duration in FIG. 19, the structural affinity for the LSK epitope varied among public TCRs, with E304 having better function, which was consistent with the results of T2 (FIG. 9).

Figures 19, 20:
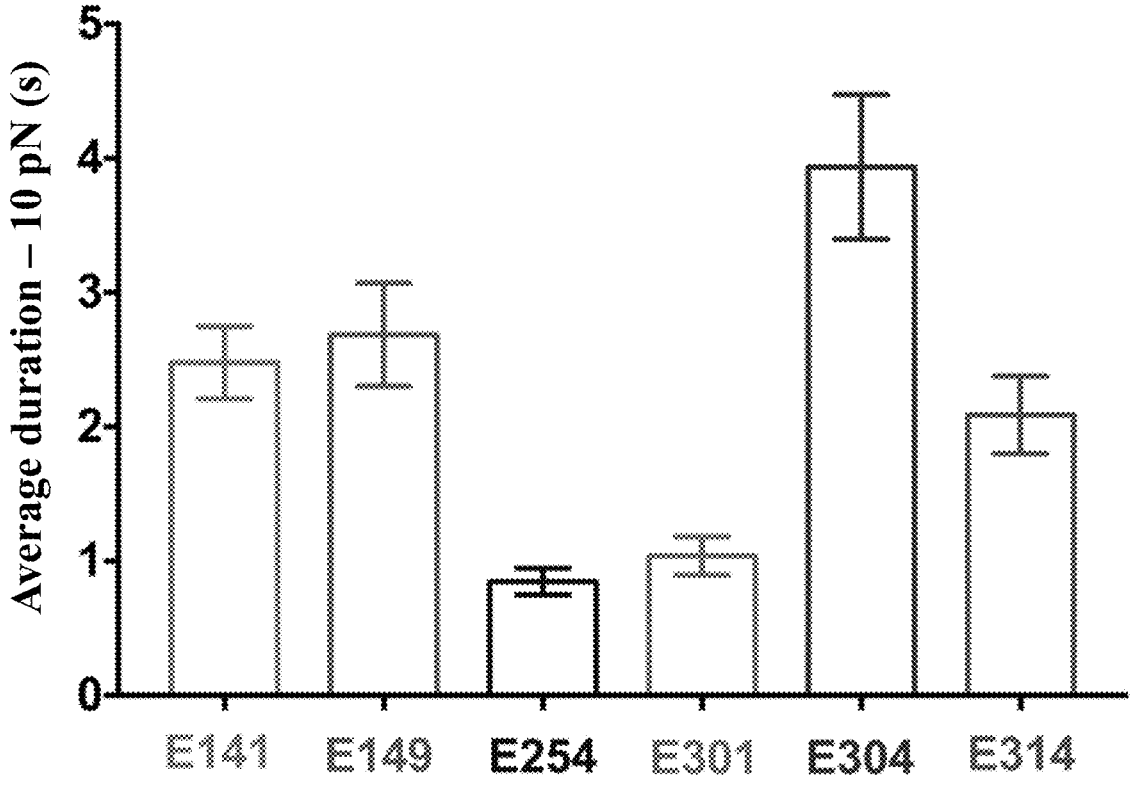
FIG. 19: structural affinity results of public TCRs as assayed by a BFP method.
FIG. 20: contribution of each amino acid in the E141-TCR CDR3 region to antigen recognition and target cell killing ability as analyzed by an Alanine Scanning method.
Figure 21:
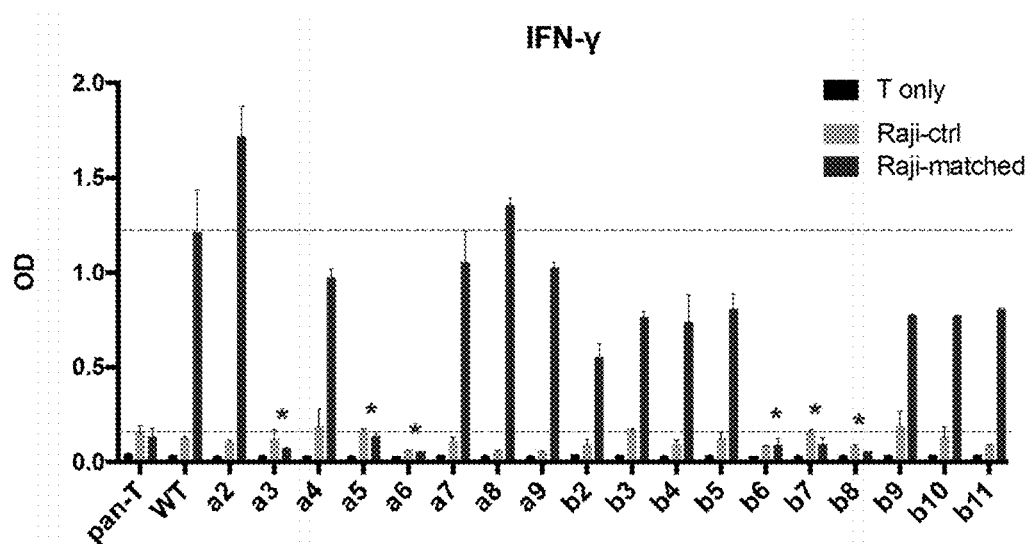
FIG. 21: contribution of each amino acid in the E141-TCR CDR3 region to antigen recognition and T cell activation ability as analyzed by an Alanine Scanning method.

2. Analysis of the Function of Conserved CDR3 Motif by an Alanine Screening Method The amino acids after the first position of CDR3 regions of TCR E141 α and β chains were mutated into alanine in sequence, named as a2-a9 and b2-b11, constructed into a pHAGE lentiviral vector, and used to infect human primary T cells (MOI=10) after virus encapsulation. After three days of infection, TCR positive cells could be sorted out by a flow cytometer. The sorted TCR T cells were co-incubated with Raji-LMP2-luciferase target cells according to the effector-to-target of 1:1, wherein the T cells were at $1\times10^5$ cells. After 24 h of co-incubation, the cells and supernatant were separately collected. The cells were used to determine the amount of luciferase released from the surviving target cells after lysis of the cell pellet (FIG. 20), and the supernatant was used to determine the cytokine IL2 secreted by TCR T cells (FIG. 21). As can be seen from FIGS. 20 and 21, compared with the background values of the control groups HLA unmatched-Raji cells, or HLA matched-Raji cells without TCR-T cells and with pan-T cells untransfected with TCRs, the unmutated E141 was able to efficiently clear the target cells when exposed to HLA matched-Raji and specifically produce a large amount of cytokine IL2. However, at the sites a3, a5 and a6 as well as b6, b7 and b8, a single amino acid mutation is sufficient to completely inactivate TCR T cells. Collectively, these experimental results suggest that although the public TCRs share the same conserved motif, their function may differ significantly from each other by one amino acid difference.

Example 7 Animal Model Construction and In Vivo Functional Assay on EBV TCRT EB virus mainly infects nasopharyngeal epithelial cells and B cells, and is closely related to development and progression of nasopharyngeal carcinoma and various B cell lymphomas. In this example, a mouse model of B-cell lymphoma and a solid tumor model of nasopharyngeal carcinoma were constructed to verify the in vivo function of the identified TCRs.

1. Lymphoma Model and In Vivo Functional Assay on TCRT

Figure 22:
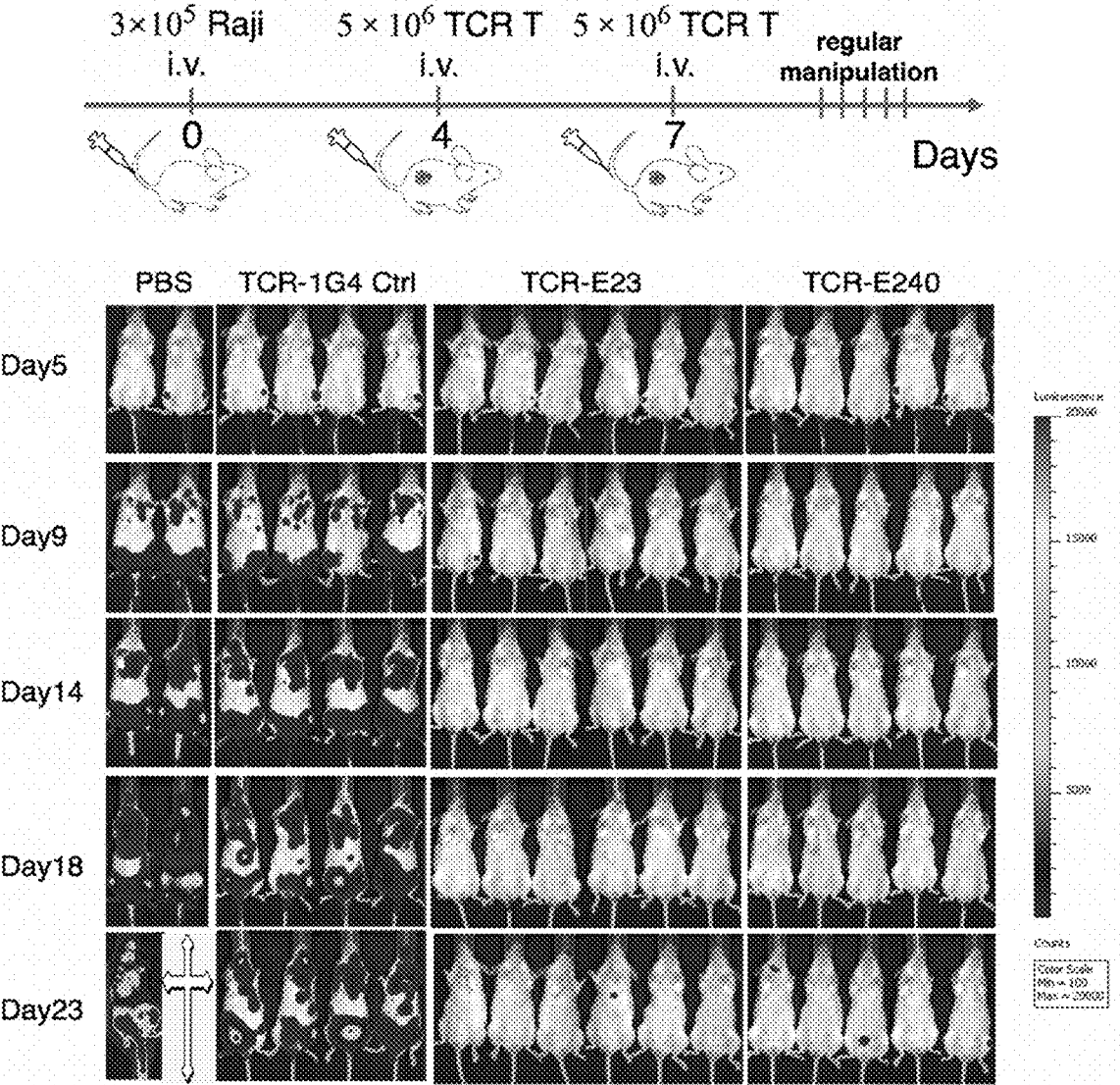
FIG. 22: evaluation of the inhibition of E23-TCR and E240-TCR on tumor growth in mice in a lymphoma animal model.
Figure 23:
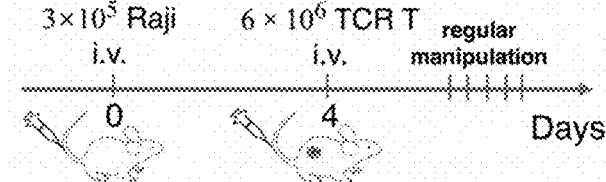
FIG. 23: evaluation of the inhibition of E29-TCR and E44-TCR on tumor growth in mice in a lymphoma animal model.
Figure 23:
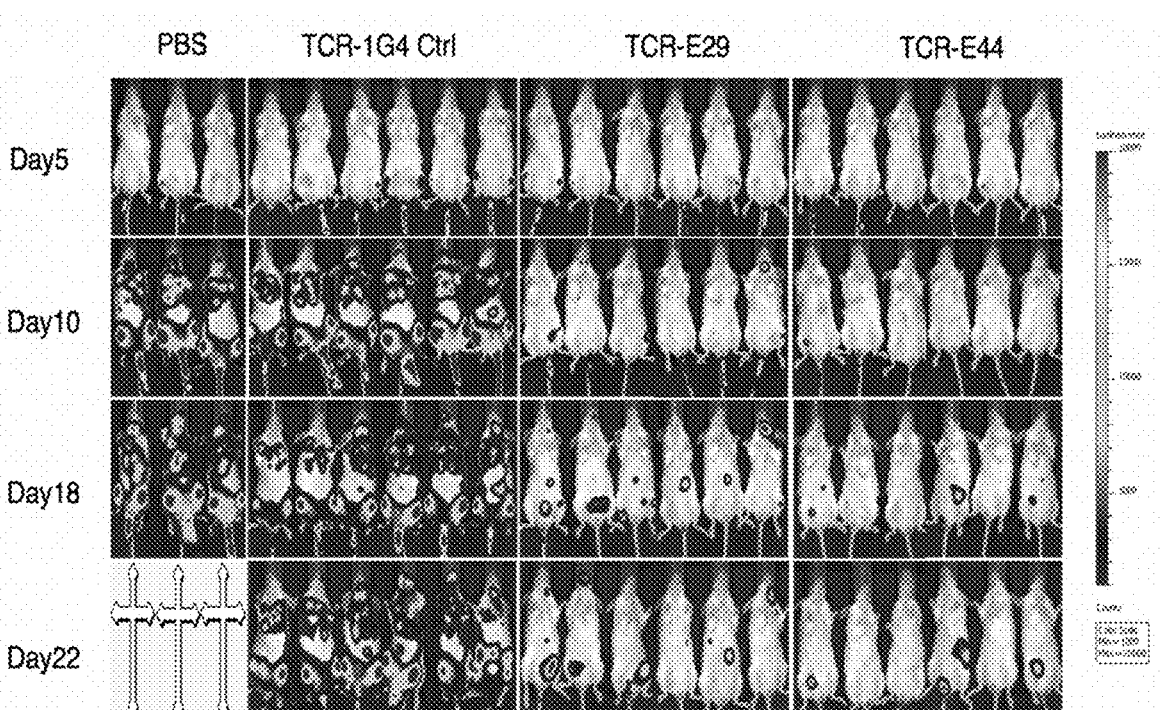
Figure 24:
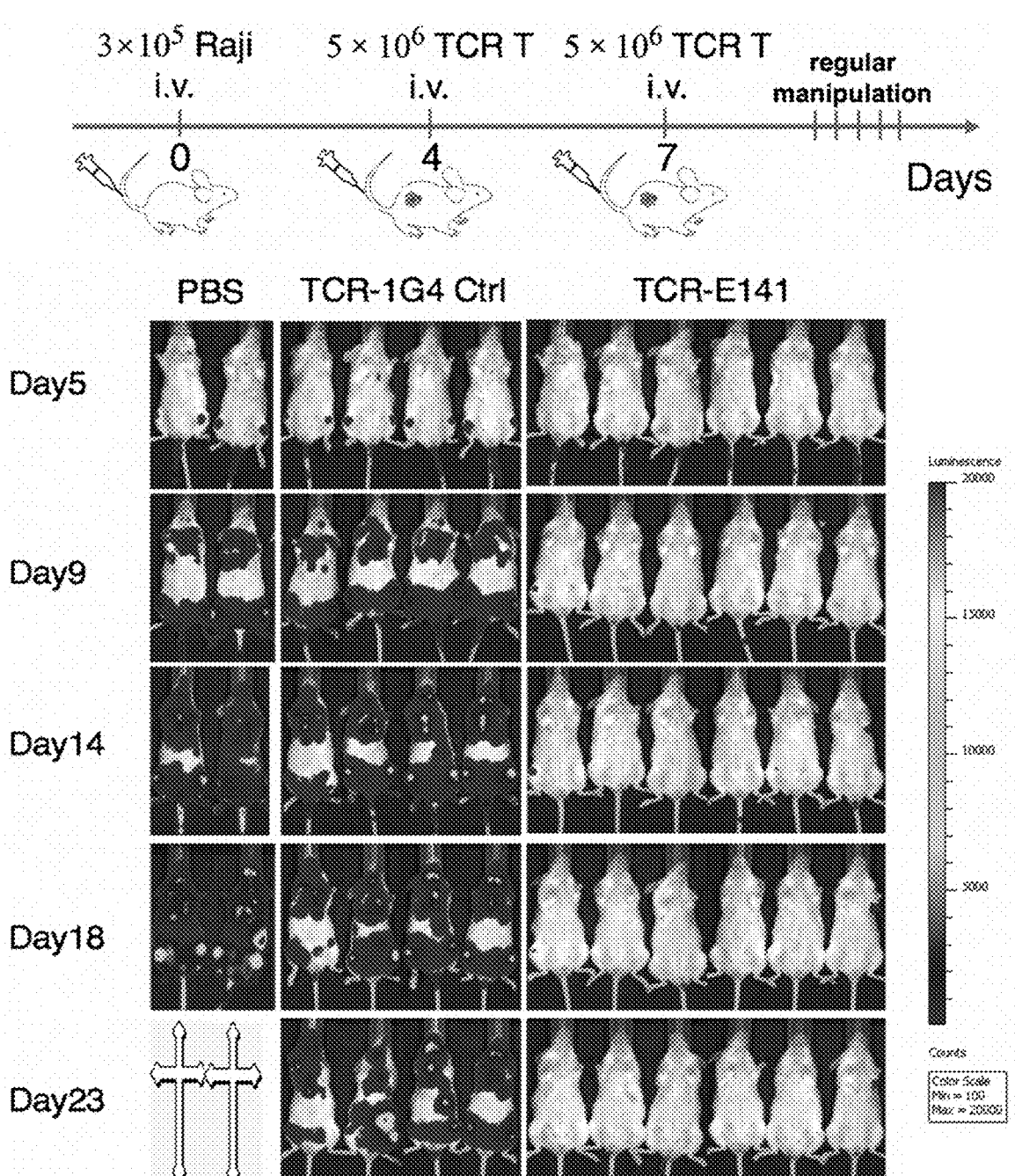
FIG. 24: evaluation of the inhibition of E141-TCR on tumor growth in mice in a lymphoma animal model.

NOD/Scid IL-2Rγ null (NCG) female mice aged 5-6 weeks were inoculated with $3\times10^5$ Raji-HLA-A*1101/0201/2402-LMP2-luciferase tumor cells via tail veins to construct a lymphoma model (see FIGS. 22, 23 and 24), which was recorded as day 1. On day 5, the mice were divided into 3 groups, i.e., A: a PBS injection group (with equal volume of PBS injected); B: a control TCRT cell injection group (TCR-1G4 T cells); and C: an EBV TCRT injection group (E141-TCRT cells), wherein the mice in group B/C were injected with $5\times10^6$ TCR T cells via tail veins, and the mice in group A were injected with equal volume (200 μL) of PBS. The second injection was given on day 8, and the procedure was identical to that on day 5. Specific reinfusion volume and reinfusion time points for other TCR T cells are shown in FIGS. 22 and 23. The mice were monitored for tumor cell growth, T cell proliferation and mouse survival over the next few weeks. As shown in FIG. 24, compared with the control group, the EBV-specific E141-TCRT cells constructed in the example of the present invention were able to significantly kill tumor cells in mice, and increase the survival rate of mice. In addition, as shown in FIGS. 22 and 23, compared with the control group, the EBV-specific E23-TCRT, E240-TCRT, E29-TCRT and E44-TCRT cells constructed in the example of the present invention were also able to significantly kill tumor cells in mice, and increase the survival rate of mice.

2. Solid Tumor Model

Figure 25:
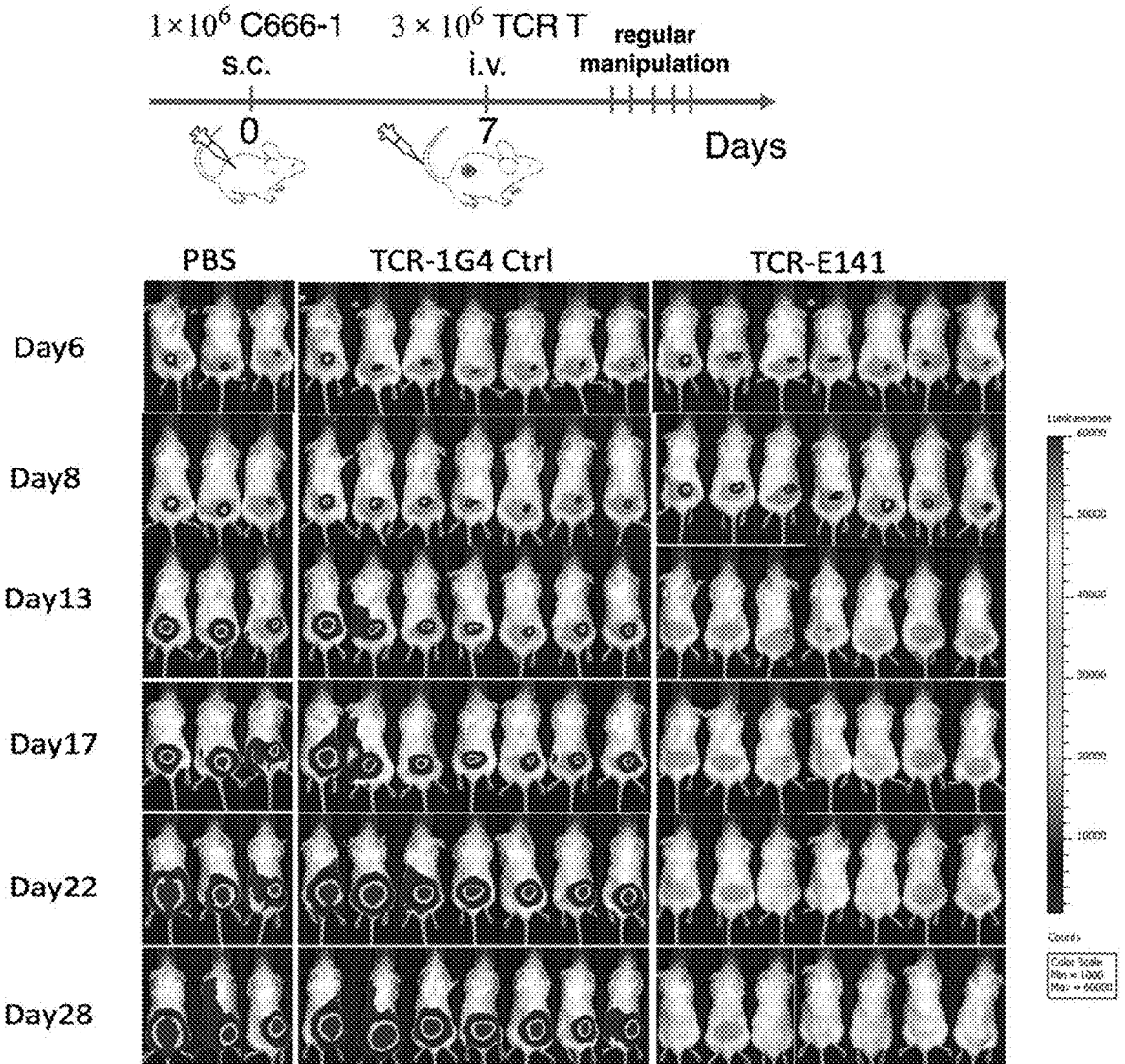
FIG. 25: evaluation of the inhibition of E141-TCR on tumor growth in mice in a solid tumor animal model.
Figure 26:
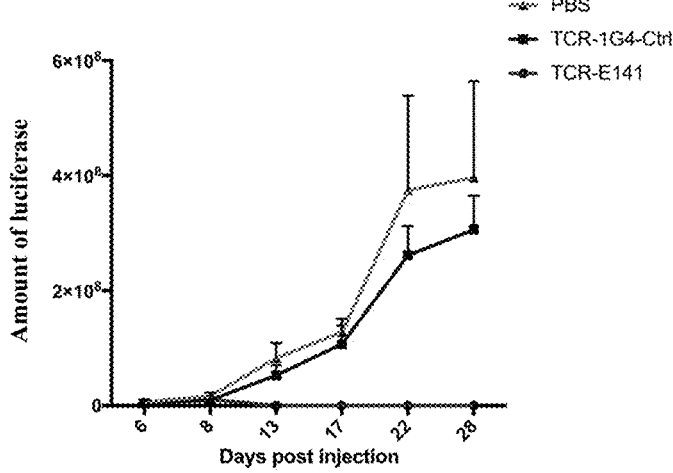
FIG. 26: statistics for tumor growth in mice in the solid tumor model, the T cell-free injection group (PBS), the control TCR-T cell injection group (TCR-1G4), and the EBV TCR-T injection group (E141-TCR)
Figure 27:
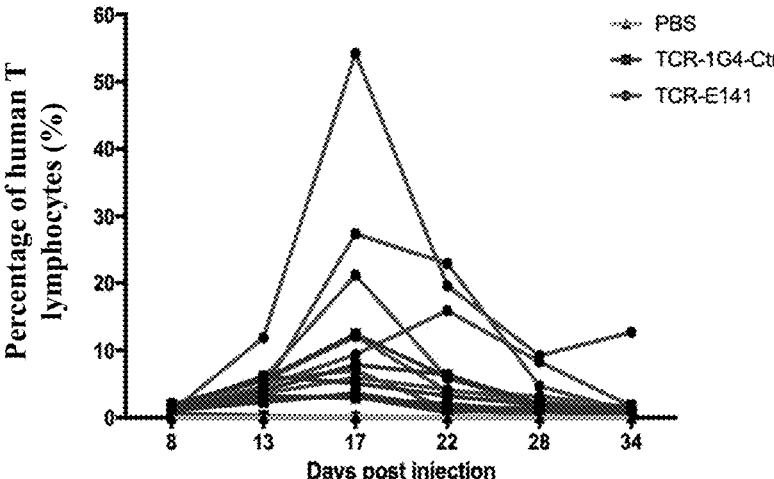
FIG. 27: statistics for TCR T cell-specific proliferation in mice in the solid tumor model, the T cell-free injection group (PBS), the control TCR-T cell injection group (TCR-1G4), and the EBV TCR-T injection group (E141-TCR).

NCG female mice aged 5-6 weeks were subcutaneously inoculated with $1\times10^6$ C666-1-HLA-A*1101-LMP2-luciferase tumor cells to construct a nasopharyngeal carcinoma solid tumor model (see FIG. 25), which was recorded as day 0. After 7 days, the mice were divided into 3 groups, i.e., A: a PBS injection group (with equal volume of PBS injected); B: a control TCR-T cell injection group (TCR-1G4 T cells); and C: an EBV TCR-T injection group (E141-TCRT cells), wherein the mice in group B/C were injected with $3\times10^6$ T cells via the tail vein, and the mice in group A were injected with equal volume (200 μL) of PBS. The mice were monitored for tumor cell growth, T cell proliferation and mouse survival over the next few weeks. As shown in FIGS. 25, 26 and 27, compared with the control group, the EBV-specific E141-TCRT cells constructed in the example of the present invention were able to significantly kill tumor cells in mice (FIGS. 25 and 26), and the returned TCR T cells proliferated specifically in vivo (FIG. 27).

The preferred embodiments of the present invention are described in detail above, which, however, are not intended to limit the present invention. Within the scope of the technical concept of the present invention, various simple modifications can be made to the technical solution of the present invention, all of which will fall within the protection scope of the present invention.

In addition, it should be noted that the various specific technical features described in the above specific embodiments can be combined in any suitable manner without contradiction. In order to avoid unnecessary repetition, such combinations will not be illustrated separately.

---

The invention claimed is:

1. A T cell antigen receptor, wherein the T cell antigen receptor specifically binding to an EBV latent membrane protein LMP2, wherein the T cell antigen receptor comprises α-chain CDR1α-CDR3α and β-chain CDR1β-CDR3β, wherein the CDR1α-CDR3α and the CDR1β-CDR3β are selected from any one of the following groups:

|  | Binding epitope | CDR1α | CDR2α |
|---|---|---|---|
| E23 | SEQ ID NO: 29 | TSINN (SEQ ID NO: 35) | IRSNERE (SEQ ID NO: 45) |
| E240 | SEQ ID NO: 29 | TSINN (SEQ ID NO: 35) | IRSNERE (SEQ ID NO: 45) |
| E29 | SEQ ID NO: 30 | SSNFYA (SEQ ID NO: 36) | MTLNGDE (SEQ ID NO: 46) |
| E180-1 | SEQ ID NO: 30 | DSASNY (SEQ ID NO: 37) | IRSNVGE (SEQ ID NO: 47) |
| E44 | SEQ ID NO: 31 or 32 | NSAFQY (SEQ ID NO: 38) | TYSSGN (SEQ ID NO: 48) |
| E141 | SEQ ID NO: 33 or 34 | DSVNN (SEQ ID NO: 39) | IPSGT (SEQ ID NO: 49) |
| E149 | SEQ ID NO: 33 or 34 | DSVNN (SEQ ID NO: 39) | IPSGT (SEQ ID NO: 49) |
| E168 | SEQ ID NO: 33 or 34 | TTSDR (SEQ ID NO: 40) | LLSNGAV (SEQ ID NO: 50) |
| E170 | SEQ ID NO: 33 or 34 | DSASNY (SEQ ID NO: 37) | IRSNVGE (SEQ ID NO: 47) |
| E244 | SEQ ID NO: 33 or 34 | DSASNY (SEQ ID NO: 37) | IRSNVGE (SEQ ID NO: 47) |

-continued

|  | Binding epitope | CDR1α | CDR2α |
|---|---|---|---|
| E245 | SEQ ID NO: 33 or 34 | TTSDR (SEQ ID NO: 40) | LLSNGAV (SEQ ID NO: 50) |
| E254 | SEQ ID NO: 33 or 34 | DSVNN (SEQ ID NO: 39) | IPSGT (SEQ ID NO: 49) |
| E301 | SEQ ID NO: 33 or 34 | DSVNN (SEQ ID NO: 39) | IPSGT (SEQ ID NO: 49) |
| E304 | SEQ ID NO: 33 or 34 | DSVNN (SEQ ID NO: 39) | IPSGT (SEQ ID NO: 49) |
| E305 | SEQ ID NO: 33 or 34 | TTSDR (SEQ ID NO: 40) | LLSNGAV (SEQ ID NO: 50) |
| E307 | SEQ ID NO: 33 or 34 | TRDTTYY (SEQ ID NO: 41) | RNSFDEQN (SEQ ID NO: 51) |
| E314 | SEQ ID NO: 33 or 34 | DSVNN (SEQ ID NO: 39) | IPSGT (SEQ ID NO: 49) |
| E315 | SEQ ID NO: 33 or 34 | DSAIYN (SEQ ID NO: 42) | IQSSQRE (SEQ ID NO: 52) |
| E316 | SEQ ID NO: 33 or 34 | TSDQSYG (SEQ ID NO: 43) | QGSYDEQ N (SEQ ID NO: 53) |
| E317 | SEQ ID NO: 33 or 34 | NSASDY (SEQ ID NO: 44) | IRSNMDK (SEQ ID NO: 54) |
| E318 | SEQ ID NO: 33 or 34 | DSASNY (SEQ ID NO: 37) | IRSNVGE (SEQ ID NO: 47) |
| E320 | SEQ ID NO: 33 or 34 | TTSDR (SEQ ID NO: 40) | LLSNGAV (SEQ ID NO: 50) |

| | 261 | | |
|---|---|---|---|
| | | -continued | |
| | CDR3α | CDR1β | CDR2β |
| E23 | ATEGDSGYST LT (SEQ ID NO: 55) | MNHEY (SEQ ID NO: 74) | SVGAGI (SEQ ID NO: 85) |
| E240 | ATVGDSGYST LT (SEQ ID NO: 56) | MNHEY (SEQ ID NO: 74) | SVGAGI (SEQ ID NO: 85) |
| E29 | ASTNSNSGYA LN (SEQ ID NO: 57) | DFQATT (SEQ ID NO: 75) | SNEGSKA (SEQ ID NO: 86) |
| E180-1 | AARGGGYST LT (SEQ ID NO: 58) | LNHDA (SEQ ID NO: 76) | SQIVND (SEQ ID NO: 87) |
| E44 | AMFRSTLGRL Y (SEQ ID NO: 59) | MNHEY (SEQ ID NO: 74) | SMNVEV (SEQ ID NO: 88) |
| E141 | AVLNNNDMR (SEQ ID NO: 60) | MGHRA (SEQ ID NO: 77) | YSYEKL (SEQ ID NO: 89) |
| E149 | AVVDNNDMR (SEQ ID NO: 61) | MGHRA (SEQ ID NO: 77) | YSYEKL (SEQ ID NO: 89) |
| E168 | AVAMNRDDKII (SEQ ID NO: 62) | SGHKS (SEQ ID NO: 78) | YYEKEE (SEQ ID NO: 90) |
| E170 | AAREGFYQT GANNLF (SEQ ID NO: 63) | KGHSH (SEQ ID NO: 79) | LQKENI (SEQ ID NO: 91) |
| E244 | AATAGGATN KLI (SEQ ID NO: 64) | MNHEY (SEQ ID NO: 74) | SMNVEV (SEQ ID NO: 88) |
| E245 | AVELTGNQF Y (SEQ ID NO: 65) | SGHKS (SEQ ID NO: 78) | YYEKEE (SEQ ID NO: 90) |
| E254 | AVLNNNDMR (SEQ ID NO: 60) | SGDLS (SEQ ID NO: 80) | YYNGEE (SEQ ID NO: 92) |
| E301 | AVLNNNDMR (SEQ ID NO: 60) | MGHRA (SEQ ID NO: 77) | YSYEKL (SEQ ID NO: 89) |
| E304 | AVVDNNDMR (SEQ ID NO: 61) | MGHRA (SEQ ID NO: 77) | YSYEKL (SEQ ID NO: 89) |
| E305 | AVNTGFQKL V (SEQ ID NO: 66) | SNHLY (SEQ ID NO: 81) | FYNNEI (SEQ ID NO: 93) |
| E307 | ALSEPPSGTY KYI (SEQ ID NO: 67) | SGHVS (SEQ ID NO: 82) | FQNEAQ (SEQ ID NO: 94) |
| E314 | AVLDNNDMR (SEQ ID NO: 68) | MGHRA (SEQ ID NO: 77) | YSYEKL (SEQ ID NO: 89) |
| E315 | AGKTSYDKVI (SEQ ID NO: 69) | SGHAT (SEQ ID NO: 83) | FQNNGV (SEQ ID NO: 95) |
| E316 | AMVSGAGGG ADGLT (SEQ ID NO: 70) | LNHDA (SEQ ID NO: 76) | SQIVND (SEQ ID NO: 87) |

| | 262 | | |
|---|---|---|---|
| | | -continued | |
| E317 | AETPGGYQK VT (SEQ ID NO: 71) | MNHEY (SEQ ID NO: 74) | SMNVEV (SEQ ID NO: 88) |
| E318 | AASNRDDKII (SEQ ID NO: 72) | SGHNS (SEQ ID NO: 84) | FNNNVP (SEQ ID NO: 96) |
| E320 | AVDIGTEYGN KLV (SEQ ID NO: 73) | SGHVS (SEQ ID NO: 82) | FQNEAQ (SEQ ID NO: 94) |

| | CDR3β |
|---|---|
| E23 | ASSYQGGSSG YT (SEQ ID NO: 97) |
| E240 | ASSGQGGGY GYT (SEQ ID NO: 98) |
| E29 | SARDTSGVNF YNEQF (SEQ ID NO: 99) |
| E180-1 | ASAITGGTEA F (SEQ ID NO: 100) |
| E44 | ASTPLPTSSG RLGEQY (SEQ ID NO: 101) |
| E141 | ASSQGRWYE QY (SEQ ID NO: 102) |
| E149 | ASSPGRWYE QF (SEQ ID NO: 103) |
| E168 | ASSLDRDRND YGYT (SEQ ID NO: 104) |
| E170 | ASSPAPRAGN QPQH (SEQ ID NO: 105) |
| E244 | ASSLYPPGHS NQPQH (SEQ ID NO: 106) |
| E245 | ASSLEPGWG DTQY (SEQ ID NO: 107) |
| E254 | ASSVGPWYE QY (SEQ ID NO: 108) |
| E301 | ASSPGRFYEQ Y (SEQ ID NO: 109) |
| E304 | ASSPGRWYE QY (SEQ ID NO: 110) |
| E305 | ASSEGPTGTS YEQY (SEQ ID NO: 111) |
| E307 | ASSQESGGTD TQY(SEQ ID NO: 112) |

-continued

| E314 | ASSQGRWYE QY (SEQ ID NO: 102) |
| E315 | ASSVFPTSVE QY (SEQ ID NO: 113) |
| E316 | ASSIGVGLSN TEAF (SEQ ID NO: 114) |
| E317 | ASSLWTSNSP LH SEQ ID NO: (115) |
| E318 | ASSLGAGHL WGYT (SEQ ID NO: 116) |
| E320 | ASREGVGLYE QY (SEQ ID NO: 117). |

2. The T cell antigen receptor according to claim 1, wherein the T cell antigen receptor has an amino acid sequence selected from any one of SEQ ID NOs: 5-26 or having at least 80% homology to any one of SEQ ID NOs: 5-26.

3. A nucleic acid encoding the T cell antigen receptor according to claim 1.

4. An immune cell expressing the T cell antigen receptor according to claim 1.

5. A method for preparing a recombinant T cell, comprising the following steps:
  1) obtaining a nucleic acid sequence encoding the T cell antigen receptor according to claim 1 from a positive T cell clone;
  2) separating and culturing a primary T cell;
  3) delivering the nucleic acid sequence obtained in the step 1) to the primary T cell in the step 2) to obtain a recombinant T cell expressing the T cell antigen receptor.

6. A method for preparing the T cell antigen receptor according to claim 1, comprising the following steps:
  (1) obtaining a nucleic acid sequence encoding the T cell antigen receptor according to claim 3 from a positive T cell clone;
  (2) connecting the nucleic acid sequence obtained in the step (1) to a vector backbone to obtain an expression vector;
  (3) transforming the expression vector obtained in the step (2) into a host cell, and then inducing the expression of the host cell;
  (4) obtaining the T cell antigen receptor.

7. A multimeric complex, wherein the multimeric complex comprises the T cell antigen receptor according to claim 1.

8. The multimeric complex according to claim 7, further comprising a monomer, a biotin molecule, and a streptavidin or avidin molecule, wherein the monomer comprises an α-chain extracellular domain of an MHC molecule, a β2m chain and an antigen peptide, the monomer is conjugated to the biotin molecule binding to the streptavidin or avidin molecule.

9. The multimeric complex according to claim 8, wherein the antigen peptide comprises any one of or a combination of two or more of SEQ ID NOs: 29-34.

10. The multimeric complex according to claim 8, wherein the MHC molecule is selected from HLA-A*0201, HLA-A*2402 and HLA-A*1101.

11. A method for treating an EBV-related disease, comprising administering to an individual an effective amount of the T cell antigen receptor according to claim 1, a nucleic acid encoding the T cell antigen receptor according to claim 1, or an immune cell expressing the T cell antigen receptor according to claim 1.

12. The method according to claim 11, wherein the EBV-related disease is selected from infectious mononucleosis, linked lymphoproliferative syndrome, viral hemophagocytic syndrome, oral hairy leukoplakia, viral meningitis, peripheral neuritis, viral pneumonia, viral myocarditis, nasopharyngeal carcinoma, Hodgkin's lymphoma, Burkitt's lymphoma, gastric carcinoma, hepatocellular carcinoma, lymphoepithelioid sarcoma, salivary gland tumor, breast cancer, thymoma, primary effusion lymphoma, or B/T/NK cell lymphoma.

13. A pharmaceutical composition or kit, wherein the pharmaceutical composition or kit comprises any one of the following groups:
  i) the T cell antigen receptor according to claim 1;
  ii) —a nucleic acid encoding the T cell antigen receptor according to claim 1; or
  iii) an immune cell expressing the T cell antigen receptor according to claim 1.

14. The T cell antigen receptor according to claim 1, wherein the T cell antigen receptor has an amino acid sequence selected from any one of SEQ ID NOs: 5-26.

15. The T cell antigen receptor according to claim 1, wherein the T cell antigen receptor has an amino acid sequence at least 90% homology to any one of SEQ ID NOs: 5-26.

16. The T cell antigen receptor according to claim 1, wherein the T cell antigen receptor has an amino acid sequence at least 95% homology to any one of SEQ ID NOs: 5-26.

17. The T cell antigen receptor according to claim 1, wherein the T cell antigen receptor has an amino acid sequence at least 98% homology to any one of SEQ ID NOs: 5-26.

18. A T cell expressing the T cell antigen receptor according to claim 1.

19. A T cell expressing the T cell antigen receptor according to claim 2.

20. A T cell expressing the T cell antigen receptor according to claim 14.

\* \* \* \* \*

SEQUENCE LISTING

<160> NUMBER OF SEQ ID NOS: 366

<210> SEQ ID NO 1
<211> LENGTH: 294
<212> TYPE: PRT
<213> ORGANISM: Artificial Sequence
<220> FEATURE:
<223> OTHER INFORMATION: A0201-aa

<400> SEQUENCE: 1

-continued

```
Met Gly Ser His Ser Met Arg Tyr Phe Phe Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Gly Glu
    50                  55                  60

Thr Arg Lys Val Lys Ala His Ser Gln Thr His Arg Val Asp Leu Gly
65                  70                  75                  80

Thr Leu Arg Gly Tyr Tyr Asn Gln Ser Glu Ala Gly Ser His Thr Val
                85                  90                  95

Gln Arg Met Tyr Gly Cys Asp Val Gly Ser Asp Trp Arg Phe Leu Arg
            100                 105                 110

Gly Tyr His Gln Tyr Ala Tyr Asp Gly Lys Asp Tyr Ile Ala Leu Lys
        115                 120                 125

Glu Asp Leu Arg Ser Trp Thr Ala Ala Asp Met Ala Ala Gln Thr Thr
    130                 135                 140

Lys His Lys Trp Glu Ala Ala His Val Ala Glu Gln Leu Arg Ala Tyr
145                 150                 155                 160

Leu Glu Gly Thr Cys Val Glu Trp Leu Arg Arg Tyr Leu Glu Asn Gly
                165                 170                 175

Lys Glu Thr Leu Gln Arg Thr Asp Ala Pro Lys Thr His Met Thr His
            180                 185                 190

His Ala Val Ser Asp His Glu Ala Thr Leu Arg Cys Trp Ala Leu Ser
            195                 200                 205

Phe Tyr Pro Ala Glu Ile Thr Leu Thr Trp Gln Arg Asp Gly Glu Asp
    210                 215                 220

Gln Thr Gln Asp Thr Glu Leu Val Glu Thr Arg Pro Ala Gly Asp Gly
225                 230                 235                 240

Thr Phe Gln Lys Trp Val Ala Val Val Val Pro Ser Gly Gln Glu Gln
                245                 250                 255

Arg Tyr Thr Cys His Val Gln His Glu Gly Leu Pro Lys Pro Leu Thr
            260                 265                 270

Leu Arg Trp Glu Pro Gly Ser Gly Leu Asn Asp Ile Phe Glu Ala Gln
            275                 280                 285

Lys Ile Glu Trp His Glu
    290
```

```
<210> SEQ ID NO 2
<211> LENGTH: 294
<212> TYPE: PRT
<213> ORGANISM: Artificial Sequence
<220> FEATURE:
<223> OTHER INFORMATION: A2402-aa

<400> SEQUENCE: 2
```

```
Met Gly Ser His Ser Met Arg Tyr Phe Ser Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Glu Glu
    50                  55                  60
```

-continued

```
Thr Gly Lys Val Lys Ala His Ser Gln Thr Asp Arg Glu Asn Leu Arg
65                  70                  75                  80

Ile Ala Leu Arg Tyr Tyr Asn Gln Ser Glu Ala Gly Ser His Thr Leu
                85                  90                  95

Gln Met Met Phe Gly Cys Asp Val Gly Ser Asp Gly Arg Phe Leu Arg
            100                 105                 110

Gly Tyr His Gln Tyr Ala Tyr Asp Gly Lys Asp Tyr Ile Ala Leu Lys
            115                 120                 125

Glu Asp Leu Arg Ser Trp Thr Ala Ala Asp Met Ala Ala Gln Ile Thr
        130                 135                 140

Lys Arg Lys Trp Glu Ala Ala His Val Ala Glu Gln Gln Arg Ala Tyr
145                 150                 155                 160

Leu Glu Gly Thr Cys Val Asp Gly Leu Arg Arg Tyr Leu Glu Asn Gly
                165                 170                 175

Lys Glu Thr Leu Gln Arg Thr Asp Pro Pro Lys Thr His Met Thr His
            180                 185                 190

His Pro Ile Ser Asp His Glu Ala Thr Leu Arg Cys Trp Ala Leu Gly
            195                 200                 205

Phe Tyr Pro Ala Glu Ile Thr Leu Thr Trp Gln Arg Asp Gly Glu Asp
        210                 215                 220

Gln Thr Gln Asp Thr Glu Leu Val Glu Thr Arg Pro Ala Gly Asp Gly
225                 230                 235                 240

Thr Phe Gln Lys Trp Val Ala Val Val Val Pro Ser Gly Glu Glu Gln
                245                 250                 255

Arg Tyr Thr Cys His Val Gln His Glu Gly Leu Pro Lys Pro Leu Thr
                260                 265                 270

Leu Arg Trp Glu Pro Gly Ser Gly Leu Asn Asp Ile Phe Glu Ala Gln
            275                 280                 285

Lys Ile Glu Trp His Glu
    290
```

```
<210> SEQ ID NO 3
<211> LENGTH: 294
<212> TYPE: PRT
<213> ORGANISM: Artificial Sequence
<220> FEATURE:
<223> OTHER INFORMATION: A1101-aa

<400> SEQUENCE: 3
```

```
Met Gly Ser His Ser Met Arg Tyr Phe Tyr Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Gln Glu
    50                  55                  60

Thr Arg Asn Val Lys Ala Gln Ser Gln Thr Asp Arg Val Asp Leu Gly
65                  70                  75                  80

Thr Leu Arg Gly Tyr Tyr Asn Gln Ser Glu Asp Gly Ser His Thr Ile
                85                  90                  95

Gln Ile Met Tyr Gly Cys Asp Val Gly Pro Asp Gly Arg Phe Leu Arg
            100                 105                 110

Gly Tyr Arg Gln Asp Ala Tyr Asp Gly Lys Asp Tyr Ile Ala Leu Asn
            115                 120                 125
```

```
Glu Asp Leu Arg Ser Trp Thr Ala Ala Asp Met Ala Ala Gln Ile Thr
    130             135             140

Lys Arg Lys Trp Glu Ala Ala His Ala Ala Glu Gln Gln Arg Ala Tyr
145             150             155             160

Leu Glu Gly Arg Cys Val Glu Trp Leu Arg Arg Tyr Leu Glu Asn Gly
                165             170             175

Lys Glu Thr Leu Gln Arg Thr Asp Pro Pro Lys Thr His Met Thr His
            180             185             190

His Pro Ile Ser Asp His Glu Ala Thr Leu Arg Cys Trp Ala Leu Gly
            195             200             205

Phe Tyr Pro Ala Glu Ile Thr Leu Thr Trp Gln Arg Asp Gly Glu Asp
    210             215             220

Gln Thr Gln Asp Thr Glu Leu Val Glu Thr Arg Pro Ala Gly Asp Gly
225             230             235             240

Thr Phe Gln Lys Trp Val Ala Val Val Val Pro Ser Gly Glu Glu Gln
            245             250             255

Arg Tyr Thr Cys His Val Gln His Glu Gly Leu Pro Lys Pro Leu Thr
            260             265             270

Leu Arg Trp Glu Leu Gly Ser Gly Leu Asn Asp Ile Phe Glu Ala Gln
            275             280             285

Lys Ile Glu Trp His Glu
    290
```

```
<210> SEQ ID NO 4
<211> LENGTH: 101
<212> TYPE: PRT
<213> ORGANISM: Artificial Sequence
<220> FEATURE:
<223> OTHER INFORMATION: b2m-aa

<400> SEQUENCE: 4

Met Ala Ile Gln Arg Thr Pro Lys Ile Gln Val Tyr Ser Arg His Pro
1               5               10              15

Ala Glu Asn Gly Lys Ser Asn Phe Leu Asn Cys Tyr Val Ser Gly Phe
                20              25              30

His Pro Ser Asp Ile Glu Val Asp Leu Leu Lys Asn Gly Glu Arg Ile
            35              40              45

Glu Lys Val Glu His Ser Asp Leu Ser Phe Ser Lys Asp Trp Ser Phe
    50              55              60

Tyr Leu Leu Tyr Tyr Thr Glu Phe Thr Pro Thr Glu Lys Asp Glu Tyr
65              70              75              80

Ala Cys Arg Val Asn His Val Thr Leu Ser Gln Pro Lys Ile Val Lys
                85              90              95

Trp Asp Arg Asp Met
            100
```

```
<210> SEQ ID NO 5
<211> LENGTH: 609
<212> TYPE: PRT
<213> ORGANISM: Artificial Sequence
<220> FEATURE:
<223> OTHER INFORMATION: E23 aa

<400> SEQUENCE: 5

Met Ser Ile Gly Leu Leu Cys Cys Ala Ala Leu Ser Leu Leu Trp Ala
1               5               10              15

Gly Pro Val Asn Ala Gly Val Thr Gln Thr Pro Lys Phe Gln Val Leu
```

```
                20              25              30

Lys Thr Gly Gln Ser Met Thr Leu Gln Cys Ala Gln Asp Met Asn His
            35              40              45

Glu Tyr Met Ser Trp Tyr Arg Gln Asp Pro Gly Met Gly Leu Arg Leu
        50              55              60

Ile His Tyr Ser Val Gly Ala Gly Ile Thr Asp Gln Gly Glu Val Pro
65              70              75              80

Asn Gly Tyr Asn Val Ser Arg Ser Thr Thr Glu Asp Phe Pro Leu Arg
                85              90              95

Leu Leu Ser Ala Ala Pro Ser Gln Thr Ser Val Tyr Phe Cys Ala Ser
            100             105             110

Ser Tyr Gln Gly Gly Ser Ser Gly Tyr Thr Phe Gly Ser Gly Thr Arg
            115             120             125

Leu Thr Val Val Glu Asp Leu Lys Asn Val Phe Pro Pro Glu Val Ala
            130             135             140

Val Phe Glu Pro Ser Glu Ala Glu Ile Ser His Thr Gln Lys Ala Thr
145             150             155             160

Leu Val Cys Leu Ala Thr Gly Phe Phe Pro Asp His Val Glu Leu Ser
            165             170             175

Trp Trp Val Asn Gly Lys Glu Val His Ser Gly Val Ser Thr Asp Pro
            180             185             190

Gln Pro Leu Lys Glu Gln Pro Ala Leu Asn Asp Ser Arg Tyr Cys Leu
            195             200             205

Ser Ser Arg Leu Arg Val Ser Ala Thr Phe Trp Gln Asn Pro Arg Asn
        210             215             220

His Phe Arg Cys Gln Val Gln Phe Tyr Gly Leu Ser Glu Asn Asp Glu
225             230             235             240

Trp Thr Gln Asp Arg Ala Lys Pro Val Thr Gln Ile Val Ser Ala Glu
            245             250             255

Ala Trp Gly Arg Ala Asp Cys Gly Phe Thr Ser Val Ser Tyr Gln Gln
            260             265             270

Gly Val Leu Ser Ala Thr Ile Leu Tyr Glu Ile Leu Leu Gly Lys Ala
            275             280             285

Thr Leu Tyr Ala Val Leu Val Ser Ala Leu Val Leu Met Ala Met Val
            290             295             300

Lys Arg Lys Asp Phe Arg Arg Lys Arg Ser Gly Ser Gly Ala Thr Asn
305             310             315             320

Phe Ser Leu Leu Lys Gln Ala Gly Asp Val Glu Glu Asn Pro Gly Pro
            325             330             335

Met Glu Thr Leu Leu Gly Val Ser Leu Val Ile Leu Trp Leu Gln Leu
            340             345             350

Ala Arg Val Asn Ser Gln Gln Gly Glu Glu Asp Pro Gln Ala Leu Ser
            355             360             365

Ile Gln Glu Gly Glu Asn Ala Thr Met Asn Cys Ser Tyr Lys Thr Ser
        370             375             380

Ile Asn Asn Leu Gln Trp Tyr Arg Gln Asn Ser Gly Arg Gly Leu Val
385             390             395             400

His Leu Ile Leu Ile Arg Ser Asn Glu Arg Glu Lys His Ser Gly Arg
            405             410             415

Leu Arg Val Thr Leu Asp Thr Ser Lys Lys Ser Ser Ser Leu Leu Ile
            420             425             430

Thr Ala Ser Arg Ala Ala Asp Thr Ala Ser Tyr Phe Cys Ala Thr Glu
            435             440             445
```

```
Gly Asp Ser Gly Tyr Ser Thr Leu Thr Phe Gly Lys Gly Thr Met Leu
    450                 455                 460

Leu Val Ser Pro Asp Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
                485                 490                 495

Asp Ser Gln Thr Asn Val Ser Gln Ser Lys Asp Ser Asp Val Tyr Ile
                500                 505                 510

Thr Asp Lys Thr Val Leu Asp Met Arg Ser Met Asp Phe Lys Ser Asn
            515                 520                 525

Ser Ala Val Ala Trp Ser Asn Lys Ser Asp Phe Ala Cys Ala Asn Ala
        530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
                565                 570                 575

Asn Leu Asn Phe Gln Asn Leu Ser Val Ile Gly Phe Arg Ile Leu Leu
                580                 585                 590

Leu Lys Val Ala Gly Phe Asn Leu Leu Met Thr Leu Arg Leu Trp Ser
            595                 600                 605

Ser
```

<210> SEQ ID NO 6
<211> LENGTH: 609
<212> TYPE: PRT
<213> ORGANISM: Artificial Sequence
<220> FEATURE:
<223> OTHER INFORMATION: E240 aa

<400> SEQUENCE: 6

```
Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
                100                 105                 110

Ser Gly Gln Gly Gly Gly Tyr Gly Tyr Thr Phe Gly Ser Gly Thr Arg
        115                 120                 125

Leu Thr Val Val Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190
```

```
Gln Pro Leu Lys Glu Gln Pro Ala Leu Asn Asp Ser Arg Tyr Cys Leu
        195             200             205

Ser Ser Arg Leu Arg Val Ser Ala Thr Phe Trp Gln Asn Pro Arg Asn
        210             215             220

His Phe Arg Cys Gln Val Gln Phe Tyr Gly Leu Ser Glu Asn Asp Glu
225             230             235             240

Trp Thr Gln Asp Arg Ala Lys Pro Val Thr Gln Ile Val Ser Ala Glu
                245             250             255

Ala Trp Gly Arg Ala Asp Cys Gly Phe Thr Ser Val Ser Tyr Gln Gln
                260             265             270

Gly Val Leu Ser Ala Thr Ile Leu Tyr Glu Ile Leu Leu Gly Lys Ala
        275             280             285

Thr Leu Tyr Ala Val Leu Val Ser Ala Leu Val Leu Met Ala Met Val
        290             295             300

Lys Arg Lys Asp Phe Arg Arg Lys Arg Ser Gly Ser Gly Ala Thr Asn
305             310             315             320

Phe Ser Leu Leu Lys Gln Ala Gly Asp Val Glu Glu Asn Pro Gly Pro
                325             330             335

Met Glu Thr Leu Leu Gly Val Ser Leu Val Ile Leu Trp Leu Gln Leu
                340             345             350

Ala Arg Val Asn Ser Gln Gln Gly Glu Glu Asp Pro Gln Ala Leu Ser
        355             360             365

Ile Gln Glu Gly Glu Asn Ala Thr Met Asn Cys Ser Tyr Lys Thr Ser
        370             375             380

Ile Asn Asn Leu Gln Trp Tyr Arg Gln Asn Ser Gly Arg Gly Leu Val
385             390             395             400

His Leu Ile Leu Ile Arg Ser Asn Glu Arg Glu Lys His Ser Gly Arg
                405             410             415

Leu Arg Val Thr Leu Asp Thr Ser Lys Lys Ser Ser Ser Leu Leu Ile
                420             425             430

Thr Ala Ser Arg Ala Ala Asp Thr Ala Ser Tyr Phe Cys Ala Thr Val
        435             440             445

Gly Asp Ser Gly Tyr Ser Thr Leu Thr Phe Gly Lys Gly Thr Met Leu
        450             455             460

Leu Val Ser Pro Asp Ile Gln Asn Pro Asp Pro Ala Val Tyr Gln Leu
465             470             475             480

Arg Asp Ser Lys Ser Ser Asp Lys Ser Val Cys Leu Phe Thr Asp Phe
                485             490             495

Asp Ser Gln Thr Asn Val Ser Gln Ser Lys Asp Ser Asp Val Tyr Ile
                500             505             510

Thr Asp Lys Thr Val Leu Asp Met Arg Ser Met Asp Phe Lys Ser Asn
        515             520             525

Ser Ala Val Ala Trp Ser Asn Lys Ser Asp Phe Ala Cys Ala Asn Ala
        530             535             540

Phe Asn Asn Ser Ile Ile Pro Glu Asp Thr Phe Phe Pro Ser Pro Glu
545             550             555             560

Ser Ser Cys Asp Val Lys Leu Val Glu Lys Ser Phe Glu Thr Asp Thr
                565             570             575

Asn Leu Asn Phe Gln Asn Leu Ser Val Ile Gly Phe Arg Ile Leu Leu
                580             585             590

Leu Lys Val Ala Gly Phe Asn Leu Leu Met Thr Leu Arg Leu Trp Ser
        595             600             605

Ser
```

-continued

<210> SEQ ID NO 7
<211> LENGTH: 613
<212> TYPE: PRT
<213> ORGANISM: Artificial Sequence
<220> FEATURE:
<223> OTHER INFORMATION: E29 aa

<400> SEQUENCE: 7

```
Met Leu Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
                20                  25                  30

Val Lys Ile Glu Cys Arg Ser Leu Asp Phe Gln Ala Thr Thr Met Phe
            35                  40                  45

Trp Tyr Arg Gln Phe Pro Lys Lys Ser Leu Met Leu Met Ala Thr Ser
        50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Arg Asp
            100                 105                 110

Thr Ser Gly Val Asn Phe Tyr Asn Glu Gln Phe Phe Gly Pro Gly Thr
            115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
        290                 295                 300

Val Lys Arg Lys Asp Phe Arg Arg Lys Arg Ser Gly Ser Gly Ala Thr
305                 310                 315                 320

Asn Phe Ser Leu Leu Lys Gln Ala Gly Asp Val Glu Glu Asn Pro Gly
                325                 330                 335

Pro Met Glu Lys Asn Pro Leu Ala Ala Pro Leu Leu Ile Leu Trp Phe
            340                 345                 350

His Leu Asp Cys Val Ser Ser Ile Leu Asn Val Glu Gln Ser Pro Gln
            355                 360                 365
```

-continued

```
Ser Leu His Val Gln Glu Gly Asp Ser Thr Asn Phe Thr Cys Ser Phe
    370             375             380

Pro Ser Ser Asn Phe Tyr Ala Leu His Trp Tyr Arg Trp Glu Thr Ala
385             390             395             400

Lys Ser Pro Glu Ala Leu Phe Val Met Thr Leu Asn Gly Asp Glu Lys
            405             410             415

Lys Lys Gly Arg Ile Ser Ala Thr Leu Asn Thr Lys Glu Gly Tyr Ser
            420             425             430

Tyr Leu Tyr Ile Lys Gly Ser Gln Pro Glu Asp Ser Ala Thr Tyr Leu
    435             440             445

Cys Ala Ser Thr Asn Ser Asn Ser Gly Tyr Ala Leu Asn Phe Gly Lys
    450             455             460

Gly Thr Ser Leu Leu Val Thr Pro His Ile Gln Asn Pro Asp Pro Ala
465             470             475             480

Val Tyr Gln Leu Arg Asp Ser Lys Ser Ser Asp Lys Ser Val Cys Leu
            485             490             495

Phe Thr Asp Phe Asp Ser Gln Thr Asn Val Ser Gln Ser Lys Asp Ser
            500             505             510

Asp Val Tyr Ile Thr Asp Lys Thr Val Leu Asp Met Arg Ser Met Asp
            515             520             525

Phe Lys Ser Asn Ser Ala Val Ala Trp Ser Asn Lys Ser Asp Phe Ala
    530             535             540

Cys Ala Asn Ala Phe Asn Asn Ser Ile Ile Pro Glu Asp Thr Phe Phe
545             550             555             560

Pro Ser Pro Glu Ser Ser Cys Asp Val Lys Leu Val Glu Lys Ser Phe
            565             570             575

Glu Thr Asp Thr Asn Leu Asn Phe Gln Asn Leu Ser Val Ile Gly Phe
            580             585             590

Arg Ile Leu Leu Leu Lys Val Ala Gly Phe Asn Leu Leu Met Thr Leu
    595             600             605

Arg Leu Trp Ser Ser
    610
```

```
<210> SEQ ID NO 8
<211> LENGTH: 607
<212> TYPE: PRT
<213> ORGANISM: Artificial Sequence
<220> FEATURE:
<223> OTHER INFORMATION: E180-1 aa

<400> SEQUENCE: 8

Met Ser Asn Gln Val Leu Cys Cys Val Val Leu Cys Phe Leu Gly Ala
1               5               10              15

Asn Thr Val Asp Gly Gly Ile Thr Gln Ser Pro Lys Tyr Leu Phe Arg
            20              25              30

Lys Glu Gly Gln Asn Val Thr Leu Ser Cys Glu Gln Asn Leu Asn His
        35              40              45

Asp Ala Met Tyr Trp Tyr Arg Gln Asp Pro Gly Gln Gly Leu Arg Leu
    50              55              60

Ile Tyr Tyr Ser Gln Ile Val Asn Asp Phe Gln Lys Gly Asp Ile Ala
65              70              75              80

Glu Gly Tyr Ser Val Ser Arg Glu Lys Lys Glu Ser Phe Pro Leu Thr
            85              90              95

Val Thr Ser Ala Gln Lys Asn Pro Thr Ala Phe Tyr Leu Cys Ala Ser
            100             105             110
```

-continued

```
Ala Ile Thr Gly Gly Thr Glu Ala Phe Phe Gly Gln Gly Thr Arg Leu
        115                 120                 125

Thr Val Val Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
                195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Ala Leu Val Leu Met Ala Met Val Lys
        290                 295                 300

Arg Lys Asp Phe Arg Arg Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Thr Ser Ile Arg Ala Val Phe Ile Phe Leu Trp Leu Gln Leu Asp Leu
                340                 345                 350

Val Asn Gly Glu Asn Val Glu Gln His Pro Ser Thr Leu Ser Val Gln
        355                 360                 365

Glu Gly Asp Ser Ala Val Ile Lys Cys Thr Tyr Ser Asp Ser Ala Ser
        370                 375                 380

Asn Tyr Phe Pro Trp Tyr Lys Gln Glu Leu Gly Lys Gly Pro Gln Leu
385                 390                 395                 400

Ile Ile Asp Ile Arg Ser Asn Val Gly Glu Lys Lys Asp Gln Arg Ile
                405                 410                 415

Ala Val Thr Leu Asn Lys Thr Ala Lys His Phe Ser Leu His Ile Thr
                420                 425                 430

Glu Thr Gln Pro Glu Asp Ser Ala Val Tyr Phe Cys Ala Ala Arg Gly
        435                 440                 445

Gly Gly Tyr Ser Thr Leu Thr Phe Gly Lys Gly Thr Met Leu Leu Val
        450                 455                 460

Ser Pro Asp Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
                485                 490                 495

Gln Thr Asn Val Ser Gln Ser Lys Asp Ser Asp Val Tyr Ile Thr Asp
                500                 505                 510

Lys Thr Val Leu Asp Met Arg Ser Met Asp Phe Lys Ser Asn Ser Ala
        515                 520                 525
```

-continued

```
Val Ala Trp Ser Asn Lys Ser Asp Phe Ala Cys Ala Asn Ala Phe Asn
    530             535             540

Asn Ser Ile Ile Pro Glu Asp Thr Phe Phe Pro Ser Pro Glu Ser Ser
545             550             555             560

Cys Asp Val Lys Leu Val Glu Lys Ser Phe Glu Thr Asp Thr Asn Leu
            565             570             575

Asn Phe Gln Asn Leu Ser Val Ile Gly Phe Arg Ile Leu Leu Leu Lys
            580             585             590

Val Ala Gly Phe Asn Leu Leu Met Thr Leu Arg Leu Trp Ser Ser
            595             600             605

<210> SEQ ID NO 9
<211> LENGTH: 614
<212> TYPE: PRT
<213> ORGANISM: Artificial Sequence
<220> FEATURE:
<223> OTHER INFORMATION: E44 aa

<400> SEQUENCE: 9

Met Gly Pro Gln Leu Leu Gly Tyr Val Val Leu Cys Leu Leu Gly Ala
1               5               10              15

Gly Pro Leu Glu Ala Gln Val Thr Gln Asn Pro Arg Tyr Leu Ile Thr
            20              25              30

Val Thr Gly Lys Lys Leu Thr Val Thr Cys Ser Gln Asn Met Asn His
            35              40              45

Glu Tyr Met Ser Trp Tyr Arg Gln Asp Pro Gly Leu Gly Leu Arg Gln
    50              55              60

Ile Tyr Tyr Ser Met Asn Val Glu Val Thr Asp Lys Gly Asp Val Pro
65              70              75              80

Glu Gly Tyr Lys Val Ser Arg Lys Glu Lys Arg Asn Phe Pro Leu Ile
            85              90              95

Leu Glu Ser Pro Ser Pro Asn Gln Thr Ser Leu Tyr Phe Cys Ala Ser
            100             105             110

Thr Pro Leu Pro Thr Ser Ser Gly Arg Leu Gly Glu Gln Tyr Phe Gly
            115             120             125

Pro Gly Thr Arg Leu Thr Val Thr Glu Asp Leu Lys Asn Val Phe Pro
            130             135             140

Pro Glu Val Ala Val Phe Glu Pro Ser Glu Ala Glu Ile Ser His Thr
145             150             155             160

Gln Lys Ala Thr Leu Val Cys Leu Ala Thr Gly Phe Phe Pro Asp His
            165             170             175

Val Glu Leu Ser Trp Trp Val Asn Gly Lys Glu Val His Ser Gly Val
            180             185             190

Ser Thr Asp Pro Gln Pro Leu Lys Glu Gln Pro Ala Leu Asn Asp Ser
            195             200             205

Arg Tyr Cys Leu Ser Ser Arg Leu Arg Val Ser Ala Thr Phe Trp Gln
    210             215             220

Asn Pro Arg Asn His Phe Arg Cys Gln Val Gln Phe Tyr Gly Leu Ser
225             230             235             240

Glu Asn Asp Glu Trp Thr Gln Asp Arg Ala Lys Pro Val Thr Gln Ile
            245             250             255

Val Ser Ala Glu Ala Trp Gly Arg Ala Asp Cys Gly Phe Thr Ser Val
            260             265             270

Ser Tyr Gln Gln Gly Val Leu Ser Ala Thr Ile Leu Tyr Glu Ile Leu
            275             280             285
```

```
Leu Gly Lys Ala Thr Leu Tyr Ala Val Leu Val Ser Ala Leu Val Leu
    290                 295                 300

Met Ala Met Val Lys Arg Lys Asp Phe Arg Arg Lys Arg Ser Gly Ser
305                 310                 315                 320

Gly Ala Thr Asn Phe Ser Leu Leu Lys Gln Ala Gly Asp Val Glu Glu
                325                 330                 335

Asn Pro Gly Pro Met Met Lys Ser Leu Arg Val Leu Leu Val Ile Leu
                340                 345                 350

Trp Leu Gln Leu Ser Trp Val Trp Ser Gln Gln Lys Glu Val Glu Gln
                355                 360                 365

Asp Pro Gly Pro Leu Ser Val Pro Glu Gly Ala Ile Val Ser Leu Asn
    370                 375                 380

Cys Thr Tyr Ser Asn Ser Ala Phe Gln Tyr Phe Met Trp Tyr Arg Gln
385                 390                 395                 400

Tyr Ser Arg Lys Gly Pro Glu Leu Leu Met Tyr Thr Tyr Ser Ser Gly
                405                 410                 415

Asn Lys Glu Asp Gly Arg Phe Thr Ala Gln Val Asp Lys Ser Ser Lys
                420                 425                 430

Tyr Ile Ser Leu Phe Ile Arg Asp Ser Gln Pro Ser Asp Ser Ala Thr
                435                 440                 445

Tyr Leu Cys Ala Met Phe Arg Ser Thr Leu Gly Arg Leu Tyr Phe Gly
    450                 455                 460

Arg Gly Thr Gln Leu Thr Val Trp Pro Asp Ile Gln Asn Pro Asp Pro
465                 470                 475                 480

Ala Val Tyr Gln Leu Arg Asp Ser Lys Ser Ser Asp Lys Ser Val Cys
                485                 490                 495

Leu Phe Thr Asp Phe Asp Ser Gln Thr Asn Val Ser Gln Ser Lys Asp
                500                 505                 510

Ser Asp Val Tyr Ile Thr Asp Lys Thr Val Leu Asp Met Arg Ser Met
                515                 520                 525

Asp Phe Lys Ser Asn Ser Ala Val Ala Trp Ser Asn Lys Ser Asp Phe
    530                 535                 540

Ala Cys Ala Asn Ala Phe Asn Asn Ser Ile Ile Pro Glu Asp Thr Phe
545                 550                 555                 560

Phe Pro Ser Pro Glu Ser Ser Cys Asp Val Lys Leu Val Glu Lys Ser
                565                 570                 575

Phe Glu Thr Asp Thr Asn Leu Asn Phe Gln Asn Leu Ser Val Ile Gly
                580                 585                 590

Phe Arg Ile Leu Leu Leu Lys Val Ala Gly Phe Asn Leu Leu Met Thr
                595                 600                 605

Leu Arg Leu Trp Ser Ser
    610
```

```
<210> SEQ ID NO 10
<211> LENGTH: 603
<212> TYPE: PRT
<213> ORGANISM: Artificial Sequence
<220> FEATURE:
<223> OTHER INFORMATION: E141 aa

<400> SEQUENCE: 10

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
                20                  25                  30
```

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
        50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Gln Gly Arg Trp Tyr Glu Gln Tyr Phe Gly Pro Gly Thr Arg Leu
            115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Phe Arg Arg Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Lys Arg Ile Leu Gly Ala Leu Leu Gly Leu Leu Ser Ala Gln Val Cys
            340                 345                 350

Cys Val Arg Gly Ile Gln Val Glu Gln Ser Pro Pro Asp Leu Ile Leu
            355                 360                 365

Gln Glu Gly Ala Asn Ser Thr Leu Arg Cys Asn Phe Ser Asp Ser Val
        370                 375                 380

Asn Asn Leu Gln Trp Phe His Gln Asn Pro Trp Gly Gln Leu Ile Asn
385                 390                 395                 400

Leu Phe Tyr Ile Pro Ser Gly Thr Lys Gln Asn Gly Arg Leu Ser Ala
                405                 410                 415

Thr Thr Val Ala Thr Glu Arg Tyr Ser Leu Leu Tyr Ile Ser Ser Ser
            420                 425                 430

Gln Thr Thr Asp Ser Gly Val Tyr Phe Cys Ala Val Leu Asn Asn Asn
            435                 440                 445

Asp Met Arg Phe Gly Ala Gly Thr Arg Leu Thr Val Lys Pro Asn Ile

-continued

```
        450              455              460

Gln Asn Pro Asp Pro Ala Val Tyr Gln Leu Arg Asp Ser Lys Ser Ser
465              470              475              480

Asp Lys Ser Val Cys Leu Phe Thr Asp Phe Asp Ser Gln Thr Asn Val
                485              490              495

Ser Gln Ser Lys Asp Ser Asp Val Tyr Ile Thr Asp Lys Thr Val Leu
            500              505              510

Asp Met Arg Ser Met Asp Phe Lys Ser Asn Ser Ala Val Ala Trp Ser
            515              520              525

Asn Lys Ser Asp Phe Ala Cys Ala Asn Ala Phe Asn Asn Ser Ile Ile
        530              535              540

Pro Glu Asp Thr Phe Phe Pro Ser Pro Glu Ser Ser Cys Asp Val Lys
545              550              555              560

Leu Val Glu Lys Ser Phe Glu Thr Asp Thr Asn Leu Asn Phe Gln Asn
                565              570              575

Leu Ser Val Ile Gly Phe Arg Ile Leu Leu Leu Lys Val Ala Gly Phe
            580              585              590

Asn Leu Leu Met Thr Leu Arg Leu Trp Ser Ser
        595              600

<210> SEQ ID NO 11
<211> LENGTH: 603
<212> TYPE: PRT
<213> ORGANISM: Artificial Sequence
<220> FEATURE:
<223> OTHER INFORMATION: E149 aa

<400> SEQUENCE: 11

Met Gly Cys Arg Leu Leu Cys Cys Ala Val Leu Cys Leu Leu Gly Ala
1              5              10              15

Val Pro Ile Asp Thr Glu Val Thr Gln Thr Pro Lys His Leu Val Met
                20              25              30

Gly Met Thr Asn Lys Lys Ser Leu Lys Cys Glu Gln His Met Gly His
            35              40              45

Arg Ala Met Tyr Trp Tyr Lys Gln Lys Ala Lys Lys Pro Pro Glu Leu
        50              55              60

Met Phe Val Tyr Ser Tyr Glu Lys Leu Ser Ile Asn Glu Ser Val Pro
65              70              75              80

Ser Arg Phe Ser Pro Glu Cys Pro Asn Ser Ser Leu Leu Asn Leu His
                85              90              95

Leu His Ala Leu Gln Pro Glu Asp Ser Ala Leu Tyr Leu Cys Ala Ser
            100              105              110

Ser Pro Gly Arg Trp Tyr Glu Gln Phe Phe Gly Pro Gly Thr Arg Leu
            115              120              125

Thr Val Leu Glu Asp Leu Lys Asn Val Phe Pro Pro Glu Val Ala Val
        130              135              140

Phe Glu Pro Ser Glu Ala Glu Ile Ser His Thr Gln Lys Ala Thr Leu
145              150              155              160

Val Cys Leu Ala Thr Gly Phe Phe Pro Asp His Val Glu Leu Ser Trp
            165              170              175

Trp Val Asn Gly Lys Glu Val His Ser Gly Val Ser Thr Asp Pro Gln
            180              185              190

Pro Leu Lys Glu Gln Pro Ala Leu Asn Asp Ser Arg Tyr Cys Leu Ser
        195              200              205

Ser Arg Leu Arg Val Ser Ala Thr Phe Trp Gln Asn Pro Arg Asn His
```

-continued

```
             210              215              220

Phe Arg Cys Gln Val Gln Phe Tyr Gly Leu Ser Glu Asn Asp Glu Trp
225              230              235              240

Thr Gln Asp Arg Ala Lys Pro Val Thr Gln Ile Val Ser Ala Glu Ala
             245              250              255

Trp Gly Arg Ala Asp Cys Gly Phe Thr Ser Val Ser Tyr Gln Gln Gly
             260              265              270

Val Leu Ser Ala Thr Ile Leu Tyr Glu Ile Leu Leu Gly Lys Ala Thr
             275              280              285

Leu Tyr Ala Val Leu Val Ser Ala Leu Val Leu Met Ala Met Val Lys
             290              295              300

Arg Lys Asp Phe Arg Arg Lys Arg Ser Gly Ser Gly Ala Thr Asn Phe
305              310              315              320

Ser Leu Leu Lys Gln Ala Gly Asp Val Glu Glu Asn Pro Gly Pro Met
             325              330              335

Lys Arg Ile Leu Gly Ala Leu Leu Gly Leu Leu Ser Ala Gln Val Cys
             340              345              350

Cys Val Arg Gly Ile Gln Val Glu Gln Ser Pro Pro Asp Leu Ile Leu
             355              360              365

Gln Glu Gly Ala Asn Ser Thr Leu Arg Cys Asn Phe Ser Asp Ser Val
370              375              380

Asn Asn Leu Gln Trp Phe His Gln Asn Pro Trp Gly Gln Leu Ile Asn
385              390              395              400

Leu Phe Tyr Ile Pro Ser Gly Thr Lys Gln Asn Gly Arg Leu Ser Ala
             405              410              415

Thr Thr Val Ala Thr Glu Arg Tyr Ser Leu Leu Tyr Ile Ser Ser Ser
             420              425              430

Gln Thr Thr Asp Ser Gly Val Tyr Phe Cys Ala Val Val Asp Asn Asn
             435              440              445

Asp Met Arg Phe Gly Ala Gly Thr Arg Leu Thr Val Lys Pro Asn Ile
             450              455              460

Gln Asn Pro Asp Pro Ala Val Tyr Gln Leu Arg Asp Ser Lys Ser Ser
465              470              475              480

Asp Lys Ser Val Cys Leu Phe Thr Asp Phe Asp Ser Gln Thr Asn Val
             485              490              495

Ser Gln Ser Lys Asp Ser Asp Val Tyr Ile Thr Asp Lys Thr Val Leu
             500              505              510

Asp Met Arg Ser Met Asp Phe Lys Ser Asn Ser Ala Val Ala Trp Ser
             515              520              525

Asn Lys Ser Asp Phe Ala Cys Ala Asn Ala Phe Asn Asn Ser Ile Ile
             530              535              540

Pro Glu Asp Thr Phe Phe Pro Ser Pro Glu Ser Ser Cys Asp Val Lys
545              550              555              560

Leu Val Glu Lys Ser Phe Glu Thr Asp Thr Asn Leu Asn Phe Gln Asn
             565              570              575

Leu Ser Val Ile Gly Phe Arg Ile Leu Leu Leu Lys Val Ala Gly Phe
             580              585              590

Asn Leu Leu Met Thr Leu Arg Leu Trp Ser Ser
             595              600

<210> SEQ ID NO 12
<211> LENGTH: 608
<212> TYPE: PRT
<213> ORGANISM: Artificial Sequence
```

```
<220> FEATURE:
<223> OTHER INFORMATION: E168 aa

<400> SEQUENCE: 12

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
                20                  25                  30

Thr Arg Gly Gln His Val Thr Leu Arg Cys Ser Pro Ile Ser Gly His
            35                  40                  45

Lys Ser Val Ser Trp Tyr Gln Gln Val Leu Gly Gln Gly Pro Gln Phe
        50                  55                  60

Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Asp Arg Asp Arg Asn Asp Tyr Gly Tyr Thr Phe Gly Ser Gly
        115                 120                 125

Thr Arg Leu Thr Val Val Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
        210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
        290                 295                 300

Met Val Lys Arg Lys Asp Phe Arg Arg Lys Arg Ser Gly Ser Gly Ala
305                 310                 315                 320

Thr Asn Phe Ser Leu Leu Lys Gln Ala Gly Asp Val Glu Glu Asn Pro
                325                 330                 335

Gly Pro Met Lys Lys Leu Leu Ala Met Ile Leu Trp Leu Gln Leu Asp
            340                 345                 350

Arg Leu Ser Gly Glu Leu Lys Val Glu Gln Asn Pro Leu Phe Leu Ser
        355                 360                 365

Met Gln Glu Gly Lys Asn Tyr Thr Ile Tyr Cys Asn Tyr Ser Thr Thr
        370                 375                 380

Ser Asp Arg Leu Tyr Trp Tyr Arg Gln Asp Pro Gly Lys Ser Leu Glu
385                 390                 395                 400
```

-continued

```
Ser Leu Phe Val Leu Leu Ser Asn Gly Ala Val Lys Gln Glu Gly Arg
            405                 410                 415

Leu Met Ala Ser Leu Asp Thr Lys Ala Arg Leu Ser Thr Leu His Ile
            420                 425                 430

Thr Ala Ala Val His Asp Leu Ser Ala Thr Tyr Phe Cys Ala Val Ala
            435                 440                 445

Met Asn Arg Asp Asp Lys Ile Ile Phe Gly Lys Gly Thr Arg Leu His
    450                 455                 460

Ile Leu Pro Asn Ile Gln Asn Pro Asp Pro Ala Val Tyr Gln Leu Arg
465                 470                 475                 480

Asp Ser Lys Ser Ser Asp Lys Ser Val Cys Leu Phe Thr Asp Phe Asp
            485                 490                 495

Ser Gln Thr Asn Val Ser Gln Ser Lys Asp Ser Asp Val Tyr Ile Thr
            500                 505                 510

Asp Lys Thr Val Leu Asp Met Arg Ser Met Asp Phe Lys Ser Asn Ser
            515                 520                 525

Ala Val Ala Trp Ser Asn Lys Ser Asp Phe Ala Cys Ala Asn Ala Phe
            530                 535                 540

Asn Asn Ser Ile Ile Pro Glu Asp Thr Phe Phe Pro Ser Pro Glu Ser
545                 550                 555                 560

Ser Cys Asp Val Lys Leu Val Glu Lys Ser Phe Glu Thr Asp Thr Asn
            565                 570                 575

Leu Asn Phe Gln Asn Leu Ser Val Ile Gly Phe Arg Ile Leu Leu Leu
            580                 585                 590

Lys Val Ala Gly Phe Asn Leu Leu Met Thr Leu Arg Leu Trp Ser Ser
            595                 600                 605

<210> SEQ ID NO 13
<211> LENGTH: 615
<212> TYPE: PRT
<213> ORGANISM: Artificial Sequence
<220> FEATURE:
<223> OTHER INFORMATION: E170 aa

<400> SEQUENCE: 13

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
            35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
            85                  90                  95

Arg Ile Gln Gln Val Val Arg Gly Asp Ser Ala Ala Tyr Phe Cys Ala
            100                 105                 110

Ser Ser Pro Ala Pro Arg Ala Gly Asn Gln Pro Gln His Phe Gly Asp
            115                 120                 125

Gly Thr Arg Leu Ser Ile Leu Glu Asp Leu Lys Asn Val Phe Pro Pro
            130                 135                 140

Glu Val Ala Val Phe Glu Pro Ser Glu Ala Glu Ile Ser His Thr Gln
145                 150                 155                 160
```

-continued

```
Lys Ala Thr Leu Val Cys Leu Ala Thr Gly Phe Phe Pro Asp His Val
            165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
    290                 295                 300

Ala Met Val Lys Arg Lys Asp Phe Arg Arg Lys Arg Ser Gly Ser Gly
305                 310                 315                 320

Ala Thr Asn Phe Ser Leu Leu Lys Gln Ala Gly Asp Val Glu Glu Asn
            325                 330                 335

Pro Gly Pro Met Thr Ser Ile Arg Ala Val Phe Ile Phe Leu Trp Leu
            340                 345                 350

Gln Leu Asp Leu Val Asn Gly Glu Asn Val Glu Gln His Pro Ser Thr
            355                 360                 365

Leu Ser Val Gln Glu Gly Asp Ser Ala Val Ile Lys Cys Thr Tyr Ser
    370                 375                 380

Asp Ser Ala Ser Asn Tyr Phe Pro Trp Tyr Lys Gln Glu Leu Gly Lys
385                 390                 395                 400

Arg Pro Gln Leu Ile Ile Asp Ile Arg Ser Asn Val Gly Glu Lys Lys
                405                 410                 415

Asp Gln Arg Ile Ala Val Thr Leu Asn Lys Thr Ala Lys His Phe Ser
            420                 425                 430

Leu His Ile Thr Glu Thr Gln Pro Glu Asp Ser Ala Val Tyr Phe Cys
            435                 440                 445

Ala Ala Arg Glu Gly Phe Tyr Gln Thr Gly Ala Asn Asn Leu Phe Phe
    450                 455                 460

Gly Thr Gly Thr Arg Leu Thr Val Ile Pro Tyr Ile Gln Asn Pro Asp
465                 470                 475                 480

Pro Ala Val Tyr Gln Leu Arg Asp Ser Lys Ser Ser Asp Lys Ser Val
            485                 490                 495

Cys Leu Phe Thr Asp Phe Asp Ser Gln Thr Asn Val Ser Gln Ser Lys
            500                 505                 510

Asp Ser Asp Val Tyr Ile Thr Asp Lys Thr Val Leu Asp Met Arg Ser
            515                 520                 525

Met Asp Phe Lys Ser Asn Ser Ala Val Ala Trp Ser Asn Lys Ser Asp
    530                 535                 540

Phe Ala Cys Ala Asn Ala Phe Asn Asn Ser Ile Ile Pro Glu Asp Thr
545                 550                 555                 560

Phe Phe Pro Ser Pro Glu Ser Ser Cys Asp Val Lys Leu Val Glu Lys
                565                 570                 575
```

-continued

```
Ser Phe Glu Thr Asp Thr Asn Leu Asn Phe Gln Asn Leu Ser Val Ile
            580                 585                 590

Gly Phe Arg Ile Leu Leu Leu Lys Val Ala Gly Phe Asn Leu Leu Met
        595                 600                 605

Thr Leu Arg Leu Trp Ser Ser
    610                 615

<210> SEQ ID NO 14
<211> LENGTH: 612
<212> TYPE: PRT
<213> ORGANISM: Artificial Sequence
<220> FEATURE:
<223> OTHER INFORMATION: E244/303 aa

<400> SEQUENCE: 14

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65              70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu Tyr Pro Pro Gly His Ser Asn Gln Pro Gln His Phe Gly Asp
        115                 120                 125

Gly Thr Arg Leu Ser Ile Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
            245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Phe Arg Arg Lys Arg Ser Gly Ser Gly
305                 310                 315                 320
```

```
Ala Thr Asn Phe Ser Leu Leu Lys Gln Ala Gly Asp Val Glu Glu Asn
            325                 330                 335

Pro Gly Pro Met Thr Ser Ile Arg Ala Val Phe Ile Phe Leu Trp Leu
            340                 345                 350

Gln Leu Asp Leu Val Asn Gly Glu Asn Val Glu Gln His Pro Ser Thr
            355                 360                 365

Leu Ser Val Gln Glu Gly Asp Ser Ala Val Ile Lys Cys Thr Tyr Ser
    370                 375                 380

Asp Ser Ala Ser Asn Tyr Phe Pro Trp Tyr Lys Gln Glu Leu Gly Lys
385                 390                 395                 400

Arg Pro Gln Leu Ile Ile Asp Ile Arg Ser Asn Val Gly Glu Lys Lys
                405                 410                 415

Asp Gln Arg Ile Ala Val Thr Leu Asn Lys Thr Ala Lys His Phe Ser
            420                 425                 430

Leu His Ile Thr Glu Thr Gln Pro Glu Asp Ser Ala Val Tyr Phe Cys
            435                 440                 445

Ala Ala Thr Ala Gly Gly Ala Thr Asn Lys Leu Ile Phe Gly Thr Gly
    450                 455                 460

Thr Leu Leu Ala Val Gln Pro Asn Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510

Val Tyr Ile Thr Asp Lys Thr Val Leu Asp Met Arg Ser Met Asp Phe
            515                 520                 525

Lys Ser Asn Ser Ala Val Ala Trp Ser Asn Lys Ser Asp Phe Ala Cys
    530                 535                 540

Ala Asn Ala Phe Asn Asn Ser Ile Ile Pro Glu Asp Thr Phe Phe Pro
545                 550                 555                 560

Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
            595                 600                 605

Leu Trp Ser Ser
    610
```

```
<210> SEQ ID NO 15
<211> LENGTH: 606
<212> TYPE: PRT
<213> ORGANISM: Artificial Sequence
<220> FEATURE:
<223> OTHER INFORMATION: E245 aa

<400> SEQUENCE: 15
```

```
Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln His Val Thr Leu Arg Cys Ser Pro Ile Ser Gly His
            35                  40                  45

Lys Ser Val Ser Trp Tyr Gln Gln Val Leu Gly Gln Gly Pro Gln Phe
    50                  55                  60
```

-continued

```
Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Glu Pro Gly Trp Gly Asp Thr Gln Tyr Phe Gly Pro Gly Thr
        115                 120                 125

Arg Leu Thr Val Leu Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
        290                 295                 300

Val Lys Arg Lys Asp Phe Arg Arg Lys Arg Ser Gly Ser Gly Ala Thr
305                 310                 315                 320

Asn Phe Ser Leu Leu Lys Gln Ala Gly Asp Val Glu Glu Asn Pro Gly
                325                 330                 335

Pro Met Lys Lys Leu Leu Ala Met Ile Leu Trp Leu Gln Leu Asp Arg
            340                 345                 350

Leu Ser Gly Glu Leu Lys Val Glu Gln Asn Pro Leu Phe Leu Ser Met
        355                 360                 365

Gln Glu Gly Lys Asn Tyr Thr Ile Tyr Cys Asn Tyr Ser Thr Thr Ser
        370                 375                 380

Asp Arg Leu Tyr Trp Tyr Arg Gln Asp Pro Gly Lys Ser Leu Glu Ser
385                 390                 395                 400

Leu Phe Val Leu Leu Ser Asn Gly Ala Val Lys Gln Glu Gly Arg Leu
                405                 410                 415

Met Ala Ser Leu Asp Thr Lys Ala Arg Leu Ser Thr Leu His Ile Thr
            420                 425                 430

Ala Ala Val His Asp Leu Ser Ala Thr Tyr Phe Cys Ala Val Glu Leu
            435                 440                 445

Thr Gly Asn Gln Phe Tyr Phe Gly Thr Gly Thr Ser Leu Thr Val Ile
        450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
```

-continued

```
              485              490              495
Thr Asn Val Ser Gln Ser Lys Asp Ser Asp Val Tyr Ile Thr Asp Lys
              500              505              510
Thr Val Leu Asp Met Arg Ser Met Asp Phe Lys Ser Asn Ser Ala Val
              515              520              525
Ala Trp Ser Asn Lys Ser Asp Phe Ala Cys Ala Asn Ala Phe Asn Asn
              530              535              540
Ser Ile Ile Pro Glu Asp Thr Phe Phe Pro Ser Pro Glu Ser Ser Cys
545              550              555              560
Asp Val Lys Leu Val Glu Lys Ser Phe Glu Thr Asp Thr Asn Leu Asn
              565              570              575
Phe Gln Asn Leu Ser Val Ile Gly Phe Arg Ile Leu Leu Leu Lys Val
              580              585              590
Ala Gly Phe Asn Leu Leu Met Thr Leu Arg Leu Trp Ser Ser
              595              600              605

<210> SEQ ID NO 16
<211> LENGTH: 603
<212> TYPE: PRT
<213> ORGANISM: Artificial Sequence
<220> FEATURE:
<223> OTHER INFORMATION: E254 aa

<400> SEQUENCE: 16

Met Gly Phe Arg Leu Leu Cys Cys Val Ala Phe Cys Leu Leu Gly Ala
1               5               10              15
Gly Pro Val Asp Ser Gly Val Thr Gln Thr Pro Lys His Leu Ile Thr
              20              25              30
Ala Thr Gly Gln Arg Val Thr Leu Arg Cys Ser Pro Arg Ser Gly Asp
              35              40              45
Leu Ser Val Tyr Trp Tyr Gln Gln Ser Leu Asp Gln Gly Leu Gln Phe
    50              55              60
Leu Ile Gln Tyr Tyr Asn Gly Glu Glu Arg Ala Lys Gly Asn Ile Leu
65              70              75              80
Glu Arg Phe Ser Ala Gln Gln Phe Pro Asp Leu His Ser Glu Leu Asn
              85              90              95
Leu Ser Ser Leu Glu Leu Gly Asp Ser Ala Leu Tyr Phe Cys Ala Ser
              100             105             110
Ser Val Gly Pro Trp Tyr Glu Gln Tyr Phe Gly Pro Gly Thr Arg Leu
              115             120             125
Thr Val Thr Glu Asp Leu Lys Asn Val Phe Pro Pro Glu Val Ala Val
              130             135             140
Phe Glu Pro Ser Glu Ala Glu Ile Ser His Thr Gln Lys Ala Thr Leu
145             150             155             160
Val Cys Leu Ala Thr Gly Phe Phe Pro Asp His Val Glu Leu Ser Trp
              165             170             175
Trp Val Asn Gly Lys Glu Val His Ser Gly Val Ser Thr Asp Pro Gln
              180             185             190
Pro Leu Lys Glu Gln Pro Ala Leu Asn Asp Ser Arg Tyr Cys Leu Ser
              195             200             205
Ser Arg Leu Arg Val Ser Ala Thr Phe Trp Gln Asn Pro Arg Asn His
              210             215             220
Phe Arg Cys Gln Val Gln Phe Tyr Gly Leu Ser Glu Asn Asp Glu Trp
225             230             235             240
Thr Gln Asp Arg Ala Lys Pro Val Thr Gln Ile Val Ser Ala Glu Ala
```

-continued

```
                    245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300

Arg Lys Asp Phe Arg Arg Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                    325                 330                 335

Lys Arg Ile Leu Gly Ala Leu Leu Gly Leu Leu Ser Ala Gln Val Cys
            340                 345                 350

Cys Val Arg Gly Ile Gln Val Glu Gln Ser Pro Pro Asp Leu Ile Leu
            355                 360                 365

Gln Glu Gly Ala Asn Ser Thr Leu Arg Cys Asn Phe Ser Asp Ser Val
            370                 375                 380

Asn Asn Leu Gln Trp Phe His Gln Asn Pro Trp Gly Gln Leu Ile Asn
385                 390                 395                 400

Leu Phe Tyr Ile Pro Ser Gly Thr Lys Gln Asn Gly Arg Leu Ser Ala
                    405                 410                 415

Thr Thr Val Ala Thr Glu Arg Tyr Ser Leu Leu Tyr Ile Ser Ser Ser
            420                 425                 430

Gln Thr Thr Asp Ser Gly Val Tyr Phe Cys Ala Val Leu Asn Asn Asn
            435                 440                 445

Asp Met Arg Phe Gly Ala Gly Thr Arg Leu Thr Val Lys Pro Asn Ile
            450                 455                 460

Gln Asn Pro Asp Pro Ala Val Tyr Gln Leu Arg Asp Ser Lys Ser Ser
465                 470                 475                 480

Asp Lys Ser Val Cys Leu Phe Thr Asp Phe Asp Ser Gln Thr Asn Val
                    485                 490                 495

Ser Gln Ser Lys Asp Ser Asp Val Tyr Ile Thr Asp Lys Thr Val Leu
            500                 505                 510

Asp Met Arg Ser Met Asp Phe Lys Ser Asn Ser Ala Val Ala Trp Ser
            515                 520                 525

Asn Lys Ser Asp Phe Ala Cys Ala Asn Ala Phe Asn Asn Ser Ile Ile
            530                 535                 540

Pro Glu Asp Thr Phe Phe Pro Ser Pro Glu Ser Ser Cys Asp Val Lys
545                 550                 555                 560

Leu Val Glu Lys Ser Phe Glu Thr Asp Thr Asn Leu Asn Phe Gln Asn
                    565                 570                 575

Leu Ser Val Ile Gly Phe Arg Ile Leu Leu Leu Lys Val Ala Gly Phe
            580                 585                 590

Asn Leu Leu Met Thr Leu Arg Leu Trp Ser Ser
            595                 600
```

<210> SEQ ID NO 17
<211> LENGTH: 603
<212> TYPE: PRT
<213> ORGANISM: Artificial Sequence
<220> FEATURE:
<223> OTHER INFORMATION: E301aa

<400> SEQUENCE: 17

Met Gly Cys Arg Leu Leu Cys Cys Ala Val Leu Cys Leu Leu Gly Ala

```
1                5                    10                   15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
            35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
            85                  90                  95

Leu His Ala Leu Gln Pro Glu Asp Ser Ala Leu Tyr Leu Cys Ala Ser
            100                 105                 110

Ser Pro Gly Arg Phe Tyr Glu Gln Tyr Phe Gly Pro Gly Thr Arg Leu
            115                 120                 125

Thr Val Thr Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
            165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
            210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
    290                 295                 300

Arg Lys Asp Phe Arg Arg Lys Arg Ser Gly Ser Gly Ala Thr Asn Phe
305                 310                 315                 320

Ser Leu Leu Lys Gln Ala Gly Asp Val Glu Glu Asn Pro Gly Pro Met
            325                 330                 335

Lys Arg Ile Leu Gly Ala Leu Leu Gly Leu Leu Ser Ala Gln Val Cys
            340                 345                 350

Cys Val Arg Gly Ile Gln Val Glu Gln Ser Pro Pro Asp Leu Ile Leu
            355                 360                 365

Gln Glu Gly Ala Asn Ser Thr Leu Arg Cys Asn Phe Ser Asp Ser Val
    370                 375                 380

Asn Asn Leu Gln Trp Phe His Gln Asn Pro Trp Gly Gln Leu Ile Asn
385                 390                 395                 400

Leu Phe Tyr Ile Pro Ser Gly Thr Lys Gln Asn Gly Arg Leu Ser Ala
            405                 410                 415

Thr Thr Val Ala Thr Glu Arg Tyr Ser Leu Leu Tyr Ile Ser Ser Ser
            420                 425                 430
```

-continued

```
Gln Thr Thr Asp Ser Gly Val Tyr Phe Cys Ala Val Leu Asn Asn Asn
        435             440             445

Asp Met Arg Phe Gly Ala Gly Thr Arg Leu Thr Val Lys Pro Asn Ile
    450             455             460

Gln Asn Pro Asp Pro Ala Val Tyr Gln Leu Arg Asp Ser Lys Ser Ser
465             470             475             480

Asp Lys Ser Val Cys Leu Phe Thr Asp Phe Asp Ser Gln Thr Asn Val
            485             490             495

Ser Gln Ser Lys Asp Ser Asp Val Tyr Ile Thr Asp Lys Thr Val Leu
            500             505             510

Asp Met Arg Ser Met Asp Phe Lys Ser Asn Ser Ala Val Ala Trp Ser
        515             520             525

Asn Lys Ser Asp Phe Ala Cys Ala Asn Ala Phe Asn Asn Ser Ile Ile
        530             535             540

Pro Glu Asp Thr Phe Phe Pro Ser Pro Glu Ser Ser Cys Asp Val Lys
545             550             555             560

Leu Val Glu Lys Ser Phe Glu Thr Asp Thr Asn Leu Asn Phe Gln Asn
            565             570             575

Leu Ser Val Ile Gly Phe Arg Ile Leu Leu Leu Lys Val Ala Gly Phe
        580             585             590

Asn Leu Leu Met Thr Leu Arg Leu Trp Ser Ser
        595             600
```

```
<210> SEQ ID NO 18
<211> LENGTH: 603
<212> TYPE: PRT
<213> ORGANISM: Artificial Sequence
<220> FEATURE:
<223> OTHER INFORMATION: E304 aa

<400> SEQUENCE: 18

Met Gly Cys Arg Leu Leu Cys Cys Ala Val Leu Cys Leu Leu Gly Ala
1               5               10              15

Val Pro Ile Asp Thr Glu Val Thr Gln Thr Pro Lys His Leu Val Met
            20              25              30

Gly Met Thr Asn Lys Lys Ser Leu Lys Cys Glu Gln His Met Gly His
        35              40              45

Arg Ala Met Tyr Trp Tyr Lys Gln Lys Ala Lys Lys Pro Pro Glu Leu
    50              55              60

Met Phe Val Tyr Ser Tyr Glu Lys Leu Ser Ile Asn Glu Ser Val Pro
65              70              75              80

Ser Arg Phe Ser Pro Glu Cys Pro Asn Ser Ser Leu Leu Asn Leu His
            85              90              95

Leu His Ala Leu Gln Pro Glu Asp Ser Ala Leu Tyr Leu Cys Ala Ser
        100             105             110

Ser Pro Gly Arg Trp Tyr Glu Gln Tyr Phe Gly Pro Gly Thr Arg Leu
        115             120             125

Thr Val Thr Glu Asp Leu Lys Asn Val Phe Pro Pro Glu Val Ala Val
        130             135             140

Phe Glu Pro Ser Glu Ala Glu Ile Ser His Thr Gln Lys Ala Thr Leu
145             150             155             160

Val Cys Leu Ala Thr Gly Phe Phe Pro Asp His Val Glu Leu Ser Trp
            165             170             175

Trp Val Asn Gly Lys Glu Val His Ser Gly Val Ser Thr Asp Pro Gln
        180             185             190
```

```
Pro Leu Lys Glu Gln Pro Ala Leu Asn Asp Ser Arg Tyr Cys Leu Ser
        195                 200             205

Ser Arg Leu Arg Val Ser Ala Thr Phe Trp Gln Asn Pro Arg Asn His
        210                 215             220

Phe Arg Cys Gln Val Gln Phe Tyr Gly Leu Ser Glu Asn Asp Glu Trp
225                 230             235                 240

Thr Gln Asp Arg Ala Lys Pro Val Thr Gln Ile Val Ser Ala Glu Ala
                245             250             255

Trp Gly Arg Ala Asp Cys Gly Phe Thr Ser Val Ser Tyr Gln Gln Gly
                260             265             270

Val Leu Ser Ala Thr Ile Leu Tyr Glu Ile Leu Leu Gly Lys Ala Thr
        275                 280             285

Leu Tyr Ala Val Leu Val Ser Ala Leu Val Leu Met Ala Met Val Lys
        290                 295             300

Arg Lys Asp Phe Arg Arg Lys Arg Ser Gly Ser Gly Ala Thr Asn Phe
305                 310             315                 320

Ser Leu Leu Lys Gln Ala Gly Asp Val Glu Glu Asn Pro Gly Pro Met
                325             330             335

Lys Arg Ile Leu Gly Ala Leu Leu Gly Leu Leu Ser Ala Gln Val Cys
                340             345             350

Cys Val Arg Gly Ile Gln Val Glu Gln Ser Pro Pro Asp Leu Ile Leu
        355             360             365

Gln Glu Gly Ala Asn Ser Thr Leu Arg Cys Asn Phe Ser Asp Ser Val
        370             375             380

Asn Asn Leu Gln Trp Phe His Gln Asn Pro Trp Gly Gln Leu Ile Asn
385             390             395                 400

Leu Phe Tyr Ile Pro Ser Gly Thr Lys Gln Asn Gly Arg Leu Ser Ala
                405             410             415

Thr Thr Val Ala Thr Glu Arg Tyr Ser Leu Leu Tyr Ile Ser Ser Ser
                420             425             430

Gln Thr Thr Asp Ser Gly Val Tyr Phe Cys Ala Val Val Asp Asn Asn
        435             440             445

Asp Met Arg Phe Gly Ala Gly Thr Arg Leu Thr Val Lys Pro Asn Ile
        450             455             460

Gln Asn Pro Asp Pro Ala Val Tyr Gln Leu Arg Asp Ser Lys Ser Ser
465             470             475                 480

Asp Lys Ser Val Cys Leu Phe Thr Asp Phe Asp Ser Gln Thr Asn Val
                485             490             495

Ser Gln Ser Lys Asp Ser Asp Val Tyr Ile Thr Asp Lys Thr Val Leu
                500             505             510

Asp Met Arg Ser Met Asp Phe Lys Ser Asn Ser Ala Val Ala Trp Ser
        515             520             525

Asn Lys Ser Asp Phe Ala Cys Ala Asn Ala Phe Asn Asn Ser Ile Ile
        530             535             540

Pro Glu Asp Thr Phe Phe Pro Ser Pro Glu Ser Ser Cys Asp Val Lys
545             550             555                 560

Leu Val Glu Lys Ser Phe Glu Thr Asp Thr Asn Leu Asn Phe Gln Asn
                565             570             575

Leu Ser Val Ile Gly Phe Arg Ile Leu Leu Leu Lys Val Ala Gly Phe
                580             585             590

Asn Leu Leu Met Thr Leu Arg Leu Trp Ser Ser
        595                 600
```

<210> SEQ ID NO 19
<211> LENGTH: 608
<212> TYPE: PRT
<213> ORGANISM: Artificial Sequence
<220> FEATURE:
<223> OTHER INFORMATION: E305 aa

<400> SEQUENCE: 19

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Gly Pro Thr Gly Thr Ser Tyr Glu Gln Tyr Phe Gly Pro
            115                 120                 125

Gly Thr Arg Leu Thr Val Thr Glu Asp Leu Lys Asn Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Phe Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Val Ser
            260                 265                 270

Tyr Gln Gln Gly Val Leu Ser Ala Thr Ile Leu Tyr Glu Ile Leu Leu
            275                 280                 285

Gly Lys Ala Thr Leu Tyr Ala Val Leu Val Ser Ala Leu Val Leu Met
        290                 295                 300

Ala Met Val Lys Arg Lys Asp Phe Arg Arg Lys Arg Ser Gly Ser Gly
305                 310                 315                 320

Ala Thr Asn Phe Ser Leu Leu Lys Gln Ala Gly Asp Val Glu Glu Asn
                325                 330                 335

Pro Gly Pro Met Lys Lys Leu Leu Ala Met Ile Leu Trp Leu Gln Leu
            340                 345                 350

Asp Arg Leu Ser Gly Glu Leu Lys Val Glu Gln Asn Pro Leu Phe Leu
        355                 360                 365

-continued

```
Ser Met Gln Glu Gly Lys Asn Tyr Thr Ile Tyr Cys Asn Tyr Ser Thr
    370             375             380

Thr Ser Asp Arg Leu Tyr Trp Tyr Arg Gln Asp Pro Gly Lys Ser Leu
385             390             395             400

Glu Ser Leu Phe Val Leu Leu Ser Asn Gly Ala Val Lys Gln Glu Gly
            405             410             415

Arg Leu Met Ala Ser Leu Asp Thr Lys Ala Arg Leu Ser Thr Leu His
            420             425             430

Ile Thr Ala Ala Val His Asp Leu Ser Ala Thr Tyr Phe Cys Ala Val
            435             440             445

Asn Thr Gly Phe Gln Lys Leu Val Phe Gly Thr Gly Thr Arg Leu Leu
    450             455             460

Val Ser Pro Asn Ile Gln Asn Pro Asp Pro Ala Val Tyr Gln Leu Arg
465             470             475             480

Asp Ser Lys Ser Ser Asp Lys Ser Val Cys Leu Phe Thr Asp Phe Asp
            485             490             495

Ser Gln Thr Asn Val Ser Gln Ser Lys Asp Ser Asp Val Tyr Ile Thr
            500             505             510

Asp Lys Thr Val Leu Asp Met Arg Ser Met Asp Phe Lys Ser Asn Ser
            515             520             525

Ala Val Ala Trp Ser Asn Lys Ser Asp Phe Ala Cys Ala Asn Ala Phe
            530             535             540

Asn Asn Ser Ile Ile Pro Glu Asp Thr Phe Phe Pro Ser Pro Glu Ser
545             550             555             560

Ser Cys Asp Val Lys Leu Val Glu Lys Ser Phe Glu Thr Asp Thr Asn
            565             570             575

Leu Asn Phe Gln Asn Leu Ser Val Ile Gly Phe Arg Ile Leu Leu Leu
            580             585             590

Lys Val Ala Gly Phe Asn Leu Leu Met Thr Leu Arg Leu Trp Ser Ser
            595             600             605
```

```
<210> SEQ ID NO 20
<211> LENGTH: 615
<212> TYPE: PRT
<213> ORGANISM: Artificial Sequence
<220> FEATURE:
<223> OTHER INFORMATION: E307 aa

<400> SEQUENCE: 20
```

```
Met Gly Thr Arg Leu Leu Cys Trp Val Val Leu Gly Phe Leu Gly Thr
1               5               10              15

Asp His Thr Gly Ala Gly Val Ser Gln Ser Pro Arg Tyr Lys Val Ala
            20              25              30

Lys Arg Gly Gln Asp Val Ala Leu Arg Cys Asp Pro Ile Ser Gly His
            35              40              45

Val Ser Leu Phe Trp Tyr Gln Gln Ala Leu Gly Gln Gly Pro Glu Phe
    50              55              60

Leu Thr Tyr Phe Gln Asn Glu Ala Gln Leu Asp Lys Ser Gly Leu Pro
65              70              75              80

Ser Asp Arg Phe Phe Ala Glu Arg Pro Glu Gly Ser Val Ser Thr Leu
            85              90              95

Lys Ile Gln Arg Thr Gln Gln Glu Asp Ser Ala Val Tyr Leu Cys Ala
            100             105             110

Ser Ser Gln Glu Ser Gly Gly Thr Asp Thr Gln Tyr Phe Gly Pro Gly
            115             120             125
```

```
Thr Arg Leu Thr Val Leu Glu Asp Leu Lys Asn Val Phe Pro Pro Glu
    130             135             140

Val Ala Val Phe Glu Pro Ser Glu Ala Glu Ile Ser His Thr Gln Lys
145             150             155             160

Ala Thr Leu Val Cys Leu Ala Thr Gly Phe Phe Pro Asp His Val Glu
        165             170             175

Leu Ser Trp Trp Val Asn Gly Lys Glu Val His Ser Gly Val Ser Thr
        180             185             190

Asp Pro Gln Pro Leu Lys Glu Gln Pro Ala Leu Asn Asp Ser Arg Tyr
        195             200             205

Cys Leu Ser Ser Arg Leu Arg Val Ser Ala Thr Phe Trp Gln Asn Pro
    210             215             220

Arg Asn His Phe Arg Cys Gln Val Gln Phe Tyr Gly Leu Ser Glu Asn
225             230             235             240

Asp Glu Trp Thr Gln Asp Arg Ala Lys Pro Val Thr Gln Ile Val Ser
            245             250             255

Ala Glu Ala Trp Gly Arg Ala Asp Cys Gly Phe Thr Ser Val Ser Tyr
            260             265             270

Gln Gln Gly Val Leu Ser Ala Thr Ile Leu Tyr Glu Ile Leu Leu Gly
        275             280             285

Lys Ala Thr Leu Tyr Ala Val Leu Val Ser Ala Leu Val Leu Met Ala
    290             295             300

Met Val Lys Arg Lys Asp Phe Arg Arg Lys Arg Ser Gly Ser Gly Ala
305             310             315             320

Thr Asn Phe Ser Leu Leu Lys Gln Ala Gly Asp Val Glu Glu Asn Pro
            325             330             335

Gly Pro Met Leu Thr Ala Ser Leu Leu Arg Ala Val Ile Ala Ser Ile
            340             345             350

Cys Val Val Ser Ser Met Ala Gln Lys Val Thr Gln Ala Gln Thr Glu
        355             360             365

Ile Ser Val Val Glu Lys Glu Asp Val Thr Leu Asp Cys Val Tyr Glu
    370             375             380

Thr Arg Asp Thr Thr Tyr Tyr Leu Phe Trp Tyr Lys Gln Pro Pro Ser
385             390             395             400

Gly Glu Leu Val Phe Leu Ile Arg Arg Asn Ser Phe Asp Glu Gln Asn
            405             410             415

Glu Ile Ser Gly Arg Tyr Ser Trp Asn Phe Gln Lys Ser Thr Ser Ser
        420             425             430

Phe Asn Phe Thr Ile Thr Ala Ser Gln Val Val Asp Ser Ala Val Tyr
        435             440             445

Phe Cys Ala Leu Ser Glu Pro Pro Ser Gly Thr Tyr Lys Tyr Ile Phe
    450             455             460

Gly Thr Gly Thr Arg Leu Lys Val Leu Ala Asn Ile Gln Asn Pro Asp
465             470             475             480

Pro Ala Val Tyr Gln Leu Arg Asp Ser Lys Ser Ser Asp Lys Ser Val
            485             490             495

Cys Leu Phe Thr Asp Phe Asp Ser Gln Thr Asn Val Ser Gln Ser Lys
        500             505             510

Asp Ser Asp Val Tyr Ile Thr Asp Lys Thr Val Leu Asp Met Arg Ser
        515             520             525

Met Asp Phe Lys Ser Asn Ser Ala Val Ala Trp Ser Asn Lys Ser Asp
    530             535             540

Phe Ala Cys Ala Asn Ala Phe Asn Asn Ser Ile Ile Pro Glu Asp Thr
```

-continued

```
545            550            555            560

Phe Phe Pro Ser Pro Glu Ser Ser Cys Asp Val Lys Leu Val Glu Lys
                565            570            575

Ser Phe Glu Thr Asp Thr Asn Leu Asn Phe Gln Asn Leu Ser Val Ile
            580            585            590

Gly Phe Arg Ile Leu Leu Leu Lys Val Ala Gly Phe Asn Leu Leu Met
            595            600            605

Thr Leu Arg Leu Trp Ser Ser
        610            615

<210> SEQ ID NO 21
<211> LENGTH: 603
<212> TYPE: PRT
<213> ORGANISM: Artificial Sequence
<220> FEATURE:
<223> OTHER INFORMATION: E314 aa

<400> SEQUENCE: 21

Met Gly Cys Arg Leu Leu Cys Cys Ala Val Leu Cys Leu Leu Gly Ala
1               5               10              15

Val Pro Ile Asp Thr Glu Val Thr Gln Thr Pro Lys His Leu Val Met
            20              25              30

Gly Met Thr Asn Lys Lys Ser Leu Lys Cys Glu Gln His Met Gly His
        35              40              45

Arg Ala Met Tyr Trp Tyr Lys Gln Lys Ala Lys Lys Pro Pro Glu Leu
    50              55              60

Met Phe Val Tyr Ser Tyr Glu Lys Leu Ser Ile Asn Glu Ser Val Pro
65              70              75              80

Ser Arg Phe Ser Pro Glu Cys Pro Asn Ser Ser Leu Leu Asn Leu His
            85              90              95

Leu His Ala Leu Gln Pro Glu Asp Ser Ala Leu Tyr Leu Cys Ala Ser
            100             105             110

Ser Gln Gly Arg Trp Tyr Glu Gln Tyr Phe Gly Pro Gly Thr Arg Leu
        115             120             125

Thr Val Thr Glu Asp Leu Lys Asn Val Phe Pro Pro Glu Val Ala Val
        130             135             140

Phe Glu Pro Ser Glu Ala Glu Ile Ser His Thr Gln Lys Ala Thr Leu
145             150             155             160

Val Cys Leu Ala Thr Gly Phe Phe Pro Asp His Val Glu Leu Ser Trp
            165             170             175

Trp Val Asn Gly Lys Glu Val His Ser Gly Val Ser Thr Asp Pro Gln
            180             185             190

Pro Leu Lys Glu Gln Pro Ala Leu Asn Asp Ser Arg Tyr Cys Leu Ser
        195             200             205

Ser Arg Leu Arg Val Ser Ala Thr Phe Trp Gln Asn Pro Arg Asn His
        210             215             220

Phe Arg Cys Gln Val Gln Phe Tyr Gly Leu Ser Glu Asn Asp Glu Trp
225             230             235             240

Thr Gln Asp Arg Ala Lys Pro Val Thr Gln Ile Val Ser Ala Glu Ala
            245             250             255

Trp Gly Arg Ala Asp Cys Gly Phe Thr Ser Val Ser Tyr Gln Gln Gly
            260             265             270

Val Leu Ser Ala Thr Ile Leu Tyr Glu Ile Leu Leu Gly Lys Ala Thr
        275             280             285

Leu Tyr Ala Val Leu Val Ser Ala Leu Val Leu Met Ala Met Val Lys
```

```
            290                 295                 300

Arg Lys Asp Phe Arg Arg Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Lys Arg Ile Leu Gly Ala Leu Leu Gly Leu Leu Ser Ala Gln Val Cys
                340                 345                 350

Cys Val Arg Gly Ile Gln Val Glu Gln Ser Pro Pro Asp Leu Ile Leu
            355                 360                 365

Gln Glu Gly Ala Asn Ser Thr Leu Arg Cys Asn Phe Ser Asp Ser Val
            370                 375                 380

Asn Asn Leu Gln Trp Phe His Gln Asn Pro Trp Gly Gln Leu Ile Asn
385                 390                 395                 400

Leu Phe Tyr Ile Pro Ser Gly Thr Lys Gln Asn Gly Arg Leu Ser Ala
                405                 410                 415

Thr Thr Val Ala Thr Glu Arg Tyr Ser Leu Leu Tyr Ile Ser Ser Ser
                420                 425                 430

Gln Thr Thr Asp Ser Gly Val Tyr Phe Cys Ala Val Leu Asp Asn Asn
            435                 440                 445

Asp Met Arg Phe Gly Ala Gly Thr Arg Leu Thr Val Lys Pro Asn Ile
            450                 455                 460

Gln Asn Pro Asp Pro Ala Val Tyr Gln Leu Arg Asp Ser Lys Ser Ser
465                 470                 475                 480

Asp Lys Ser Val Cys Leu Phe Thr Asp Phe Asp Ser Gln Thr Asn Val
                485                 490                 495

Ser Gln Ser Lys Asp Ser Asp Val Tyr Ile Thr Asp Lys Thr Val Leu
                500                 505                 510

Asp Met Arg Ser Met Asp Phe Lys Ser Asn Ser Ala Val Ala Trp Ser
            515                 520                 525

Asn Lys Ser Asp Phe Ala Cys Ala Asn Ala Phe Asn Asn Ser Ile Ile
            530                 535                 540

Pro Glu Asp Thr Phe Phe Pro Ser Pro Glu Ser Ser Cys Asp Val Lys
545                 550                 555                 560

Leu Val Glu Lys Ser Phe Glu Thr Asp Thr Asn Leu Asn Phe Gln Asn
                565                 570                 575

Leu Ser Val Ile Gly Phe Arg Ile Leu Leu Leu Lys Val Ala Gly Phe
                580                 585                 590

Asn Leu Leu Met Thr Leu Arg Leu Trp Ser Ser
            595                 600

<210> SEQ ID NO 22
<211> LENGTH: 608
<212> TYPE: PRT
<213> ORGANISM: Artificial Sequence
<220> FEATURE:
<223> OTHER INFORMATION: E315 aa

<400> SEQUENCE: 22

Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
                20                  25                  30

Glu Lys Arg Gln Ser Val Ala Phe Trp Cys Asn Pro Ile Ser Gly His
            35                  40                  45

Ala Thr Leu Tyr Trp Tyr Gln Gln Ile Leu Gly Gln Gly Pro Lys Leu
```

-continued

```
            50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
                100                 105                 110

Ser Ser Val Phe Pro Thr Ser Val Glu Gln Tyr Phe Gly Pro Gly Thr
                115                 120                 125

Arg Leu Thr Val Thr Glu Asp Leu Lys Asn Val Phe Pro Pro Glu Val
                130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
                195                 200                 205

Leu Ser Ser Arg Leu Arg Val Ser Ala Thr Phe Trp Gln Asn Pro Arg
                210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
                260                 265                 270

Gln Gly Val Leu Ser Ala Thr Ile Leu Tyr Glu Ile Leu Leu Gly Lys
                275                 280                 285

Ala Thr Leu Tyr Ala Val Leu Val Ser Ala Leu Val Leu Met Ala Met
                290                 295                 300

Val Lys Arg Lys Asp Phe Arg Arg Lys Arg Ser Gly Ser Gly Ala Thr
305                 310                 315                 320

Asn Phe Ser Leu Leu Lys Gln Ala Gly Asp Val Glu Glu Asn Pro Gly
                325                 330                 335

Pro Met Glu Thr Leu Leu Gly Leu Leu Ile Leu Trp Leu Gln Leu Gln
                340                 345                 350

Trp Val Ser Ser Lys Gln Glu Val Thr Gln Ile Pro Ala Ala Leu Ser
                355                 360                 365

Val Pro Glu Gly Glu Asn Leu Val Leu Asn Cys Ser Phe Thr Asp Ser
                370                 375                 380

Ala Ile Tyr Asn Leu Gln Trp Phe Arg Gln Asp Pro Gly Lys Gly Leu
385                 390                 395                 400

Thr Ser Leu Leu Leu Ile Gln Ser Ser Gln Arg Glu Gln Thr Ser Gly
                405                 410                 415

Arg Leu Asn Ala Ser Leu Asp Lys Ser Ser Gly Arg Ser Thr Leu Tyr
                420                 425                 430

Ile Ala Ala Ser Gln Pro Gly Asp Ser Ala Thr Tyr Leu Cys Ala Gly
                435                 440                 445

Lys Thr Ser Tyr Asp Lys Val Ile Phe Gly Pro Gly Thr Ser Leu Ser
                450                 455                 460

Val Ile Pro Asn Ile Gln Asn Pro Asp Pro Ala Val Tyr Gln Leu Arg
465                 470                 475                 480
```

-continued

```
Asp Ser Lys Ser Ser Asp Lys Ser Val Cys Leu Phe Thr Asp Phe Asp
            485             490             495

Ser Gln Thr Asn Val Ser Gln Ser Lys Asp Ser Asp Val Tyr Ile Thr
            500             505             510

Asp Lys Thr Val Leu Asp Met Arg Ser Met Asp Phe Lys Ser Asn Ser
            515             520             525

Ala Val Ala Trp Ser Asn Lys Ser Asp Phe Ala Cys Ala Asn Ala Phe
            530             535             540

Asn Asn Ser Ile Ile Pro Glu Asp Thr Phe Phe Pro Ser Pro Glu Ser
545             550             555             560

Ser Cys Asp Val Lys Leu Val Glu Lys Ser Phe Glu Thr Asp Thr Asn
            565             570             575

Leu Asn Phe Gln Asn Leu Ser Val Ile Gly Phe Arg Ile Leu Leu Leu
            580             585             590

Lys Val Ala Gly Phe Asn Leu Leu Met Thr Leu Arg Leu Trp Ser Ser
            595             600             605

<210> SEQ ID NO 23
<211> LENGTH: 616
<212> TYPE: PRT
<213> ORGANISM: Artificial Sequence
<220> FEATURE:
<223> OTHER INFORMATION: E316 aa

<400> SEQUENCE: 23

Met Ser Asn Gln Val Leu Cys Cys Val Val Leu Cys Leu Leu Gly Ala
1               5               10              15

Asn Thr Val Asp Gly Gly Ile Thr Gln Ser Pro Lys Tyr Leu Phe Arg
            20              25              30

Lys Glu Gly Gln Asn Val Thr Leu Ser Cys Glu Gln Asn Leu Asn His
            35              40              45

Asp Ala Met Tyr Trp Tyr Arg Gln Asp Pro Gly Gln Gly Leu Arg Leu
            50              55              60

Ile Tyr Tyr Ser Gln Ile Val Asn Asp Phe Gln Lys Gly Asp Ile Ala
65              70              75              80

Glu Gly Tyr Ser Val Ser Arg Glu Lys Lys Glu Ser Phe Pro Leu Thr
            85              90              95

Val Thr Ser Ala Gln Lys Asn Pro Thr Ala Phe Tyr Leu Cys Ala Ser
            100             105             110

Ser Ile Gly Val Gly Leu Ser Asn Thr Glu Ala Phe Phe Gly Gln Gly
            115             120             125

Thr Arg Leu Thr Val Val Glu Asp Leu Lys Asn Val Phe Pro Pro Glu
            130             135             140

Val Ala Val Phe Glu Pro Ser Glu Ala Glu Ile Ser His Thr Gln Lys
145             150             155             160

Ala Thr Leu Val Cys Leu Ala Thr Gly Phe Phe Pro Asp His Val Glu
            165             170             175

Leu Ser Trp Trp Val Asn Gly Lys Glu Val His Ser Gly Val Ser Thr
            180             185             190

Asp Pro Gln Pro Leu Lys Glu Gln Pro Ala Leu Asn Asp Ser Arg Tyr
            195             200             205

Cys Leu Ser Ser Arg Leu Arg Val Ser Ala Thr Phe Trp Gln Asn Pro
            210             215             220

Arg Asn His Phe Arg Cys Gln Val Gln Phe Tyr Gly Leu Ser Glu Asn
225             230             235             240
```

-continued

```
Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
            290                 295                 300

Met Val Lys Arg Lys Asp Phe Arg Arg Lys Arg Ser Gly Ser Gly Ala
305                 310                 315                 320

Thr Asn Phe Ser Leu Leu Lys Gln Ala Gly Asp Val Glu Glu Asn Pro
            325                 330                 335

Gly Pro Met Ser Leu Ser Ser Leu Leu Lys Val Val Thr Ala Ser Leu
            340                 345                 350

Trp Leu Gly Pro Gly Ile Ala Gln Lys Ile Thr Gln Thr Gln Pro Gly
            355                 360                 365

Met Phe Val Gln Glu Lys Glu Ala Val Thr Leu Asp Cys Thr Tyr Asp
    370                 375                 380

Thr Ser Asp Gln Ser Tyr Gly Leu Phe Trp Tyr Lys Gln Pro Ser Ser
385                 390                 395                 400

Gly Glu Met Ile Phe Leu Ile Tyr Gln Gly Ser Tyr Asp Glu Gln Asn
            405                 410                 415

Ala Thr Glu Gly Arg Tyr Ser Leu Asn Phe Gln Lys Ala Arg Lys Ser
            420                 425                 430

Ala Asn Leu Val Ile Ser Ala Ser Gln Leu Gly Asp Ser Ala Met Tyr
            435                 440                 445

Phe Cys Ala Met Val Ser Gly Ala Gly Gly Ala Asp Gly Leu Thr
    450                 455                 460

Phe Gly Lys Gly Thr His Leu Ile Ile Gln Pro Tyr Ile Gln Asn Pro
465                 470                 475                 480

Asp Pro Ala Val Tyr Gln Leu Arg Asp Ser Lys Ser Ser Asp Lys Ser
            485                 490                 495

Val Cys Leu Phe Thr Asp Phe Asp Ser Gln Thr Asn Val Ser Gln Ser
            500                 505                 510

Lys Asp Ser Asp Val Tyr Ile Thr Asp Lys Thr Val Leu Asp Met Arg
            515                 520                 525

Ser Met Asp Phe Lys Ser Asn Ser Ala Val Ala Trp Ser Asn Lys Ser
    530                 535                 540

Asp Phe Ala Cys Ala Asn Ala Phe Asn Asn Ser Ile Ile Pro Glu Asp
545                 550                 555                 560

Thr Phe Phe Pro Ser Pro Glu Ser Ser Cys Asp Val Lys Leu Val Glu
            565                 570                 575

Lys Ser Phe Glu Thr Asp Thr Asn Leu Asn Phe Gln Asn Leu Ser Val
            580                 585                 590

Ile Gly Phe Arg Ile Leu Leu Leu Lys Val Ala Gly Phe Asn Leu Leu
            595                 600                 605

Met Thr Leu Arg Leu Trp Ser Ser
    610                 615
```

<210> SEQ ID NO 24
<211> LENGTH: 609
<212> TYPE: PRT
<213> ORGANISM: Artificial Sequence
<220> FEATURE:

-continued

<223> OTHER INFORMATION: E317 aa

<400> SEQUENCE: 24

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
            85                  90                  95

Leu Glu Ser Pro Ser Pro Asn Gln Thr Ser Leu Tyr Phe Cys Ala Ser
            100                 105                 110

Ser Leu Trp Thr Ser Asn Ser Pro Leu His Phe Gly Asn Gly Thr Arg
            115                 120                 125

Leu Thr Val Thr Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
            165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
            245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Phe Arg Arg Lys Arg Ser Gly Ser Gly Ala Thr Asn
305                 310                 315                 320

Phe Ser Leu Leu Lys Gln Ala Gly Asp Val Glu Glu Asn Pro Gly Pro
            325                 330                 335

Met Ala Gly Ile Arg Ala Leu Phe Met Tyr Leu Trp Leu Gln Leu Asp
            340                 345                 350

Trp Val Ser Arg Gly Glu Ser Val Gly Leu His Leu Pro Thr Leu Ser
            355                 360                 365

Val Gln Glu Gly Asp Asn Ser Ile Ile Asn Cys Ala Tyr Ser Asn Ser
    370                 375                 380

Ala Ser Asp Tyr Phe Ile Trp Tyr Lys Gln Glu Ser Gly Lys Gly Pro
385                 390                 395                 400
```

-continued

```
Gln Phe Ile Ile Asp Ile Arg Ser Asn Met Asp Lys Arg Gln Gly Gln
            405             410             415

Arg Val Thr Val Leu Leu Asn Lys Thr Val Lys His Leu Ser Leu Gln
        420             425             430

Ile Ala Ala Thr Gln Pro Gly Asp Ser Ala Val Tyr Phe Cys Ala Glu
        435             440             445

Thr Pro Gly Gly Tyr Gln Lys Val Thr Phe Gly Thr Gly Thr Lys Leu
        450             455             460

Gln Val Ile Pro Asn Ile Gln Asn Pro Asp Pro Ala Val Tyr Gln Leu
465             470             475             480

Arg Asp Ser Lys Ser Ser Asp Lys Ser Val Cys Leu Phe Thr Asp Phe
            485             490             495

Asp Ser Gln Thr Asn Val Ser Gln Ser Lys Asp Ser Asp Val Tyr Ile
            500             505             510

Thr Asp Lys Thr Val Leu Asp Met Arg Ser Met Asp Phe Lys Ser Asn
            515             520             525

Ser Ala Val Ala Trp Ser Asn Lys Ser Asp Phe Ala Cys Ala Asn Ala
        530             535             540

Phe Asn Asn Ser Ile Ile Pro Glu Asp Thr Phe Phe Pro Ser Pro Glu
545             550             555             560

Ser Ser Cys Asp Val Lys Leu Val Glu Lys Ser Phe Glu Thr Asp Thr
            565             570             575

Asn Leu Asn Phe Gln Asn Leu Ser Val Ile Gly Phe Arg Ile Leu Leu
            580             585             590

Leu Lys Val Ala Gly Phe Asn Leu Leu Met Thr Leu Arg Leu Trp Ser
        595             600             605

Ser
```

```
<210> SEQ ID NO 25
<211> LENGTH: 609
<212> TYPE: PRT
<213> ORGANISM: Artificial Sequence
<220> FEATURE:
<223> OTHER INFORMATION: E318 aa

<400> SEQUENCE: 25
```

```
Met Asp Ser Trp Thr Phe Cys Cys Val Ser Leu Cys Ile Leu Val Ala
1               5               10              15

Lys His Thr Asp Ala Gly Val Ile Gln Ser Pro Arg His Glu Val Thr
            20              25              30

Glu Met Gly Gln Glu Val Thr Leu Arg Cys Lys Pro Ile Ser Gly His
        35              40              45

Asn Ser Leu Phe Trp Tyr Arg Gln Thr Met Met Arg Gly Leu Glu Leu
        50              55              60

Leu Ile Tyr Phe Asn Asn Asn Val Pro Ile Asp Asp Ser Gly Met Pro
65              70              75              80

Glu Asp Arg Phe Ser Ala Lys Met Pro Asn Ala Ser Phe Ser Thr Leu
            85              90              95

Lys Ile Gln Pro Ser Glu Pro Arg Asp Ser Ala Val Tyr Phe Cys Ala
            100             105             110

Ser Ser Leu Gly Ala Gly His Leu Trp Gly Tyr Thr Phe Gly Ser Gly
            115             120             125

Thr Arg Leu Thr Val Val Glu Asp Leu Lys Asn Val Phe Pro Pro Glu
        130             135             140

Val Ala Val Phe Glu Pro Ser Glu Ala Glu Ile Ser His Thr Gln Lys
```

```
145               150               155               160

Ala Thr Leu Val Cys Leu Ala Thr Gly Phe Phe Pro Asp His Val Glu
                165               170               175

Leu Ser Trp Trp Val Asn Gly Lys Glu Val His Ser Gly Val Ser Thr
                180               185               190

Asp Pro Gln Pro Leu Lys Glu Gln Pro Ala Leu Asn Asp Ser Arg Tyr
            195               200               205

Cys Leu Ser Ser Arg Leu Arg Val Ser Ala Thr Phe Trp Gln Asn Pro
        210               215               220

Arg Asn His Phe Arg Cys Gln Val Gln Phe Tyr Gly Leu Ser Glu Asn
225               230               235               240

Asp Glu Trp Thr Gln Asp Arg Ala Lys Pro Val Thr Gln Ile Val Ser
                245               250               255

Ala Glu Ala Trp Gly Arg Ala Asp Cys Gly Phe Thr Ser Val Ser Tyr
                260               265               270

Gln Gln Gly Val Leu Ser Ala Thr Ile Leu Tyr Glu Ile Leu Leu Gly
            275               280               285

Lys Ala Thr Leu Tyr Ala Val Leu Val Ser Ala Leu Val Leu Met Ala
        290               295               300

Met Val Lys Arg Lys Asp Phe Arg Arg Lys Arg Ser Gly Ser Gly Ala
305               310               315               320

Thr Asn Phe Ser Leu Leu Lys Gln Ala Gly Asp Val Glu Glu Asn Pro
            325               330               335

Gly Pro Met Thr Ser Ile Arg Ala Val Phe Ile Phe Leu Trp Leu Gln
            340               345               350

Leu Asp Leu Val Asn Gly Glu Asn Val Glu Gln His Pro Ser Thr Leu
        355               360               365

Ser Val Gln Glu Gly Asp Ser Ala Val Ile Lys Cys Thr Tyr Ser Asp
    370               375               380

Ser Ala Ser Asn Tyr Phe Pro Trp Tyr Lys Gln Glu Leu Gly Lys Arg
385               390               395               400

Pro Gln Leu Ile Ile Asp Ile Arg Ser Asn Val Gly Glu Lys Lys Asp
            405               410               415

Gln Arg Ile Ala Val Thr Leu Asn Lys Thr Ala Lys His Phe Ser Leu
            420               425               430

His Ile Thr Glu Thr Gln Pro Glu Asp Ser Ala Val Tyr Phe Cys Ala
        435               440               445

Ala Ser Asn Arg Asp Asp Lys Ile Ile Phe Gly Lys Gly Thr Arg Leu
    450               455               460

His Ile Leu Pro Asn Ile Gln Asn Pro Asp Pro Ala Val Tyr Gln Leu
465               470               475               480

Arg Asp Ser Lys Ser Ser Asp Lys Ser Val Cys Leu Phe Thr Asp Phe
            485               490               495

Asp Ser Gln Thr Asn Val Ser Gln Ser Lys Asp Ser Asp Val Tyr Ile
        500               505               510

Thr Asp Lys Thr Val Leu Asp Met Arg Ser Met Asp Phe Lys Ser Asn
        515               520               525

Ser Ala Val Ala Trp Ser Asn Lys Ser Asp Phe Ala Cys Ala Asn Ala
    530               535               540

Phe Asn Asn Ser Ile Ile Pro Glu Asp Thr Phe Phe Pro Ser Pro Glu
545               550               555               560

Ser Ser Cys Asp Val Lys Leu Val Glu Lys Ser Phe Glu Thr Asp Thr
            565               570               575
```

-continued

Asn Leu Asn Phe Gln Asn Leu Ser Val Ile Gly Phe Arg Ile Leu Leu
                580                585                590

Leu Lys Val Ala Gly Phe Asn Leu Leu Met Thr Leu Arg Leu Trp Ser
        595                600                605

Ser

<210> SEQ ID NO 26
<211> LENGTH: 609
<212> TYPE: PRT
<213> ORGANISM: Artificial Sequence
<220> FEATURE:
<223> OTHER INFORMATION: E320 aa

<400> SEQUENCE: 26

Met Gly Thr Arg Leu Leu Cys Trp Val Val Leu Gly Phe Leu Gly Thr
1                5                10                15

Asp His Thr Gly Ala Gly Val Ser Gln Ser Pro Arg Tyr Lys Val Ala
                20                25                30

Lys Arg Gly Gln Asp Val Ala Leu Arg Cys Asp Pro Ile Ser Gly His
        35                40                45

Val Ser Leu Phe Trp Tyr Gln Gln Ala Leu Gly Gln Gly Pro Glu Phe
    50                55                60

Leu Thr Tyr Phe Gln Asn Glu Ala Gln Leu Asp Lys Ser Gly Leu Pro
65                70                75                80

Ser Asp Arg Phe Phe Ala Glu Arg Pro Glu Gly Ser Val Ser Thr Leu
                85                90                95

Lys Ile Gln Arg Thr Gln Gln Glu Asp Ser Ala Val Tyr Leu Cys Ala
                100                105                110

Ser Arg Glu Gly Val Gly Leu Tyr Glu Gln Tyr Phe Gly Pro Gly Thr
        115                120                125

Arg Leu Thr Val Thr Glu Asp Leu Lys Asn Val Phe Pro Pro Glu Val
    130                135                140

Ala Val Phe Glu Pro Ser Glu Ala Glu Ile Ser His Thr Gln Lys Ala
145                150                155                160

Thr Leu Val Cys Leu Ala Thr Gly Phe Phe Pro Asp His Val Glu Leu
                165                170                175

Ser Trp Trp Val Asn Gly Lys Glu Val His Ser Gly Val Ser Thr Asp
                180                185                190

Pro Gln Pro Leu Lys Glu Gln Pro Ala Leu Asn Asp Ser Arg Tyr Cys
        195                200                205

Leu Ser Ser Arg Leu Arg Val Ser Ala Thr Phe Trp Gln Asn Pro Arg
    210                215                220

Asn His Phe Arg Cys Gln Val Gln Phe Tyr Gly Leu Ser Glu Asn Asp
225                230                235                240

Glu Trp Thr Gln Asp Arg Ala Lys Pro Val Thr Gln Ile Val Ser Ala
                245                250                255

Glu Ala Trp Gly Arg Ala Asp Cys Gly Phe Thr Ser Val Ser Tyr Gln
                260                265                270

Gln Gly Val Leu Ser Ala Thr Ile Leu Tyr Glu Ile Leu Leu Gly Lys
        275                280                285

Ala Thr Leu Tyr Ala Val Leu Val Ser Ala Leu Val Leu Met Ala Met
    290                295                300

Val Lys Arg Lys Asp Phe Arg Arg Lys Arg Ser Gly Ser Gly Ala Thr
305                310                315                320

```
Asn Phe Ser Leu Leu Lys Gln Ala Gly Asp Val Glu Glu Asn Pro Gly
            325                 330                 335

Pro Met Lys Lys Leu Leu Ala Met Ile Leu Trp Leu Gln Leu Asp Arg
            340                 345                 350

Leu Ser Gly Glu Leu Lys Val Glu Gln Asn Pro Leu Phe Leu Ser Met
            355                 360                 365

Gln Glu Gly Lys Asn Tyr Thr Ile Tyr Cys Asn Tyr Ser Thr Thr Ser
    370                 375                 380

Asp Arg Leu Tyr Trp Tyr Arg Gln Asp Pro Gly Lys Ser Leu Glu Ser
385                 390                 395                 400

Leu Phe Val Leu Leu Ser Asn Gly Ala Val Lys Gln Glu Gly Arg Leu
            405                 410                 415

Met Ala Ser Leu Asp Thr Lys Ala Arg Leu Ser Thr Leu His Ile Thr
            420                 425                 430

Ala Ala Val His Asp Leu Ser Ala Thr Tyr Phe Cys Ala Val Asp Ile
            435                 440                 445

Gly Thr Glu Tyr Gly Asn Lys Leu Val Phe Gly Ala Gly Thr Ile Leu
    450                 455                 460

Arg Val Lys Ser Tyr Ile Gln Asn Pro Asp Pro Ala Val Tyr Gln Leu
465                 470                 475                 480

Arg Asp Ser Lys Ser Ser Asp Lys Ser Val Cys Leu Phe Thr Asp Phe
            485                 490                 495

Asp Ser Gln Thr Asn Val Ser Gln Ser Lys Asp Ser Asp Val Tyr Ile
            500                 505                 510

Thr Asp Lys Thr Val Leu Asp Met Arg Ser Met Asp Phe Lys Ser Asn
            515                 520                 525

Ser Ala Val Ala Trp Ser Asn Lys Ser Asp Phe Ala Cys Ala Asn Ala
    530                 535                 540

Phe Asn Asn Ser Ile Ile Pro Glu Asp Thr Phe Phe Pro Ser Pro Glu
545                 550                 555                 560

Ser Ser Cys Asp Val Lys Leu Val Glu Lys Ser Phe Glu Thr Asp Thr
            565                 570                 575

Asn Leu Asn Phe Gln Asn Leu Ser Val Ile Gly Phe Arg Ile Leu Leu
            580                 585                 590

Leu Lys Val Ala Gly Phe Asn Leu Leu Met Thr Leu Arg Leu Trp Ser
    595                 600                 605

Ser
```

```
<210> SEQ ID NO 27
<211> LENGTH: 497
<212> TYPE: PRT
<213> ORGANISM: Artificial Sequence
<220> FEATURE:
<223> OTHER INFORMATION: LMP2 aa

<400> SEQUENCE: 27
```

```
Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
            35                  40                  45

Glu Arg Glu Ser Asn Glu Glu Pro Pro Pro Pro Tyr Glu Asp Pro Tyr
    50                  55                  60

Trp Gly Asn Gly Asp Arg His Ser Asp Tyr Gln Pro Leu Gly Thr Gln
```

```
65                      70                      75                      80

Asp Gln Ser Leu Tyr Leu Gly Leu Gln His Asp Gly Asn Asp Gly Leu
            85                      90                      95

Pro Pro Pro Pro Tyr Ser Pro Arg Asp Asp Ser Ser Gln His Ile Tyr
            100                     105                     110

Glu Glu Ala Gly Arg Gly Ser Met Asn Pro Val Cys Leu Pro Val Ile
            115                     120                     125

Val Ala Pro Tyr Leu Phe Trp Leu Ala Ala Ile Ala Ala Ser Cys Phe
            130                     135                     140

Thr Ala Ser Val Ser Thr Val Val Thr Ala Thr Gly Leu Ala Leu Ser
145                     150                     155                     160

Leu Leu Leu Leu Ala Ala Val Ala Ser Ser Tyr Ala Ala Ala Gln Arg
            165                     170                     175

Lys Leu Leu Thr Pro Val Thr Val Leu Thr Ala Val Val Thr Phe Phe
            180                     185                     190

Ala Ile Cys Leu Thr Trp Arg Ile Glu Asp Pro Pro Phe Asn Ser Leu
            195                     200                     205

Leu Phe Ala Leu Leu Ala Ala Ala Gly Gly Leu Gln Gly Ile Tyr Val
            210                     215                     220

Leu Val Met Leu Val Leu Leu Ile Leu Ala Tyr Arg Arg Arg Trp Arg
225                     230                     235                     240

Arg Leu Thr Val Cys Gly Gly Ile Met Phe Leu Ala Cys Val Leu Val
            245                     250                     255

Leu Ile Val Asp Ala Val Leu Gln Leu Ser Pro Leu Leu Gly Ala Val
            260                     265                     270

Thr Val Val Ser Met Thr Leu Leu Leu Ala Phe Val Leu Trp Leu
            275                     280                     285

Ser Ser Pro Gly Gly Leu Gly Thr Leu Gly Ala Ala Leu Leu Thr Leu
            290                     295                     300

Ala Ala Ala Leu Ala Leu Leu Ala Ser Leu Ile Leu Gly Thr Leu Asn
305                     310                     315                     320

Leu Thr Thr Met Phe Leu Leu Met Leu Leu Trp Thr Leu Val Val Leu
            325                     330                     335

Leu Ile Cys Ser Ser Cys Ser Ser Cys Pro Leu Ser Lys Ile Leu Leu
            340                     345                     350

Ala Arg Leu Phe Leu Tyr Ala Leu Ala Leu Leu Leu Ala Ser Ala
            355                     360                     365

Leu Ile Ala Gly Gly Ser Ile Leu Gln Thr Asn Phe Lys Ser Leu Ser
            370                     375                     380

Ser Thr Glu Phe Ile Pro Asn Leu Phe Cys Met Leu Leu Leu Ile Val
385                     390                     395                     400

Ala Gly Ile Leu Phe Ile Leu Ala Ile Leu Thr Glu Trp Gly Ser Gly
            405                     410                     415

Asn Arg Thr Tyr Gly Pro Val Phe Met Cys Leu Gly Gly Leu Leu Thr
            420                     425                     430

Met Val Ala Gly Ala Val Trp Leu Thr Val Met Ser Asn Thr Leu Leu
            435                     440                     445

Ser Ala Trp Ile Leu Thr Ala Gly Phe Leu Ile Phe Leu Ile Gly Phe
            450                     455                     460

Ala Leu Phe Gly Val Ile Arg Cys Cys Arg Tyr Cys Cys Tyr Tyr Cys
465                     470                     475                     480

Leu Thr Leu Glu Ser Glu Glu Arg Pro Pro Thr Pro Tyr Arg Asn Thr
            485                     490                     495
```

-continued

Val

<210> SEQ ID NO 28
<211> LENGTH: 497
<212> TYPE: PRT
<213> ORGANISM: Artificial Sequence
<220> FEATURE:
<223> OTHER INFORMATION: LMP2 aa

<400> SEQUENCE: 28

```
Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
            115                 120                 125

Val Ala Pro Tyr Leu Phe Trp Leu Ala Ala Ile Ala Ala Ser Cys Phe
            130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
            195                 200                 205

Leu Phe Ala Leu Leu Ala Ala Ala Gly Gly Leu Gln Gly Ile Tyr Val
        210                 215                 220

Leu Val Met Leu Val Leu Leu Ile Leu Ala Tyr Arg Arg Arg Trp Arg
225                 230                 235                 240

Arg Leu Thr Val Cys Gly Gly Ile Met Phe Leu Ala Cys Val Leu Val
                245                 250                 255

Leu Ile Val Asp Ala Val Leu Gln Leu Ser Pro Leu Leu Gly Ala Val
            260                 265                 270

Thr Val Val Ser Met Thr Leu Leu Leu Ala Phe Val Leu Trp Leu
            275                 280                 285

Ser Ser Pro Gly Gly Leu Gly Thr Leu Gly Ala Ala Leu Leu Thr Leu
    290                 295                 300

Ala Ala Ala Leu Ala Leu Leu Ala Ser Leu Ile Leu Gly Thr Leu Asn
305                 310                 315                 320

Leu Thr Thr Met Phe Leu Leu Met Leu Leu Trp Thr Leu Val Val Leu
                325                 330                 335

Leu Ile Cys Ser Ser Cys Ser Ser Cys Pro Leu Thr Lys Ile Leu Leu
            340                 345                 350
```

-continued

```
Ala Arg Leu Phe Leu Tyr Ala Leu Ala Leu Leu Leu Leu Ala Ser Ala
        355                 360                 365

Leu Ile Ala Gly Gly Ser Ile Leu Gln Thr Asn Phe Lys Ser Leu Ser
    370                 375                 380

Ser Thr Glu Phe Ile Pro Asn Leu Phe Cys Met Leu Leu Leu Ile Val
385                 390                 395                 400

Ala Gly Ile Leu Phe Ile Leu Ala Ile Leu Thr Glu Trp Gly Ser Gly
                405                 410                 415

Asn Arg Thr Tyr Gly Pro Val Phe Met Ser Leu Gly Gly Leu Leu Thr
                420                 425                 430

Met Val Ala Gly Ala Val Trp Leu Thr Val Met Ser Asn Thr Leu Leu
        435                 440                 445

Ser Ala Trp Ile Leu Thr Ala Gly Phe Leu Ile Phe Leu Ile Gly Phe
    450                 455                 460

Ala Leu Phe Gly Val Ile Arg Cys Cys Arg Tyr Cys Cys Tyr Tyr Cys
465                 470                 475                 480

Leu Thr Leu Glu Ser Glu Glu Arg Pro Pro Thr Pro Tyr Arg Asn Thr
                485                 490                 495

Val
```

```
<210> SEQ ID NO 29
<211> LENGTH: 9
<212> TYPE: PRT
<213> ORGANISM: Artificial Sequence
<220> FEATURE:
<223> OTHER INFORMATION: antigen

<400> SEQUENCE: 29

Phe Leu Tyr Ala Leu Ala Leu Leu Leu
1               5
```

```
<210> SEQ ID NO 30
<211> LENGTH: 9
<212> TYPE: PRT
<213> ORGANISM: Artificial Sequence
<220> FEATURE:
<223> OTHER INFORMATION: antigen

<400> SEQUENCE: 30

Pro Tyr Leu Phe Trp Leu Ala Ala Ile
1               5
```

```
<210> SEQ ID NO 31
<211> LENGTH: 9
<212> TYPE: PRT
<213> ORGANISM: Artificial Sequence
<220> FEATURE:
<223> OTHER INFORMATION: antigen

<400> SEQUENCE: 31

Thr Tyr Gly Pro Val Phe Met Ser Leu
1               5
```

```
<210> SEQ ID NO 32
<211> LENGTH: 9
<212> TYPE: PRT
<213> ORGANISM: Artificial Sequence
<220> FEATURE:
<223> OTHER INFORMATION: antigen

<400> SEQUENCE: 32

Thr Tyr Gly Pro Val Phe Met Cys Leu
```

-continued

```
1               5

<210> SEQ ID NO 33
<211> LENGTH: 10
<212> TYPE: PRT
<213> ORGANISM: Artificial Sequence
<220> FEATURE:
<223> OTHER INFORMATION: antigen

<400> SEQUENCE: 33

Ser Ser Cys Ser Ser Cys Pro Leu Ser Lys
1               5                   10

<210> SEQ ID NO 34
<211> LENGTH: 10
<212> TYPE: PRT
<213> ORGANISM: Artificial Sequence
<220> FEATURE:
<223> OTHER INFORMATION: antigen

<400> SEQUENCE: 34

Ser Ser Cys Ser Ser Cys Pro Leu Thr Lys
1               5                   10

<210> SEQ ID NO 35
<211> LENGTH: 5
<212> TYPE: PRT
<213> ORGANISM: Artificial Sequence
<220> FEATURE:
<223> OTHER INFORMATION: CDR

<400> SEQUENCE: 35

Thr Ser Ile Asn Asn
1               5

<210> SEQ ID NO 36
<211> LENGTH: 6
<212> TYPE: PRT
<213> ORGANISM: Artificial Sequence
<220> FEATURE:
<223> OTHER INFORMATION: CDR

<400> SEQUENCE: 36

Ser Ser Asn Phe Tyr Ala
1               5

<210> SEQ ID NO 37
<211> LENGTH: 6
<212> TYPE: PRT
<213> ORGANISM: Artificial Sequence
<220> FEATURE:
<223> OTHER INFORMATION: CDR

<400> SEQUENCE: 37

Asp Ser Ala Ser Asn Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: CDR

<400> SEQUENCE: 38

Asn Ser Ala Phe Gln Tyr
1               5
```

```
<210> SEQ ID NO 39
<211> LENGTH: 5
<212> TYPE: PRT
<213> ORGANISM: Artificial Sequence
<220> FEATURE:
<223> OTHER INFORMATION: CDR

<400> SEQUENCE: 39

Asp Ser Val Asn Asn
1               5

<210> SEQ ID NO 40
<211> LENGTH: 5
<212> TYPE: PRT
<213> ORGANISM: Artificial Sequence
<220> FEATURE:
<223> OTHER INFORMATION: CDR

<400> SEQUENCE: 40

Thr Thr Ser Asp Arg
1               5

<210> SEQ ID NO 41
<211> LENGTH: 7
<212> TYPE: PRT
<213> ORGANISM: Artificial Sequence
<220> FEATURE:
<223> OTHER INFORMATION: CDR

<400> SEQUENCE: 41

Thr Arg Asp Thr Thr Tyr Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: CDR

<400> SEQUENCE: 42

Asp Ser Ala Ile Tyr Asn
1               5

<210> SEQ ID NO 43
<211> LENGTH: 7
<212> TYPE: PRT
<213> ORGANISM: Artificial Sequence
<220> FEATURE:
<223> OTHER INFORMATION: CDR

<400> SEQUENCE: 43

Thr Ser Asp Gln Ser Tyr Gly
1               5

<210> SEQ ID NO 44
<211> LENGTH: 6
<212> TYPE: PRT
<213> ORGANISM: Artificial Sequence
<220> FEATURE:
<223> OTHER INFORMATION: CDR

<400> SEQUENCE: 44

Asn Ser Ala Ser Asp Tyr
1               5
```

-continued

```
<210> SEQ ID NO 45
<211> LENGTH: 7
<212> TYPE: PRT
<213> ORGANISM: Artificial Sequence
<220> FEATURE:
<223> OTHER INFORMATION: CDR

<400> SEQUENCE: 45

Ile Arg Ser Asn Glu Arg Glu
1               5

<210> SEQ ID NO 46
<211> LENGTH: 7
<212> TYPE: PRT
<213> ORGANISM: Artificial Sequence
<220> FEATURE:
<223> OTHER INFORMATION: CDR

<400> SEQUENCE: 46

Met Thr Leu Asn Gly Asp Glu
1               5

<210> SEQ ID NO 47
<211> LENGTH: 7
<212> TYPE: PRT
<213> ORGANISM: Artificial Sequence
<220> FEATURE:
<223> OTHER INFORMATION: CDR

<400> SEQUENCE: 47

Ile Arg Ser Asn Val Gly Glu
1               5

<210> SEQ ID NO 48
<211> LENGTH: 6
<212> TYPE: PRT
<213> ORGANISM: Artificial Sequence
<220> FEATURE:
<223> OTHER INFORMATION: CDR

<400> SEQUENCE: 48

Thr Tyr Ser Ser Gly Asn
1               5

<210> SEQ ID NO 49
<211> LENGTH: 5
<212> TYPE: PRT
<213> ORGANISM: Artificial Sequence
<220> FEATURE:
<223> OTHER INFORMATION: CDR

<400> SEQUENCE: 49

Ile Pro Ser Gly Thr
1               5

<210> SEQ ID NO 50
<211> LENGTH: 7
<212> TYPE: PRT
<213> ORGANISM: Artificial Sequence
<220> FEATURE:
<223> OTHER INFORMATION: CDR

<400> SEQUENCE: 50

Leu Leu Ser Asn Gly Ala Val
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: CDR

<400> SEQUENCE: 51

Arg Asn Ser Phe Asp Glu Gln Asn
1               5

<210> SEQ ID NO 52
<211> LENGTH: 7
<212> TYPE: PRT
<213> ORGANISM: Artificial Sequence
<220> FEATURE:
<223> OTHER INFORMATION: CDR

<400> SEQUENCE: 52

Ile Gln Ser Ser Gln Arg Glu
1               5

<210> SEQ ID NO 53
<211> LENGTH: 8
<212> TYPE: PRT
<213> ORGANISM: Artificial Sequence
<220> FEATURE:
<223> OTHER INFORMATION: CDR

<400> SEQUENCE: 53

Gln Gly Ser Tyr Asp Glu Gln Asn
1               5

<210> SEQ ID NO 54
<211> LENGTH: 7
<212> TYPE: PRT
<213> ORGANISM: Artificial Sequence
<220> FEATURE:
<223> OTHER INFORMATION: CDR

<400> SEQUENCE: 54

Ile Arg Ser Asn Met Asp Lys
1               5

<210> SEQ ID NO 55
<211> LENGTH: 12
<212> TYPE: PRT
<213> ORGANISM: Artificial Sequence
<220> FEATURE:
<223> OTHER INFORMATION: CDR

<400> SEQUENCE: 55

Ala Thr Glu Gly Asp Ser Gly Tyr Ser Thr Leu Thr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: CDR

<400> SEQUENCE: 56

Ala Thr Val Gly Asp Ser Gly Tyr Ser Thr Leu Thr
1               5                   10

<210> SEQ ID NO 57
```

```
<211> LENGTH: 12
<212> TYPE: PRT
<213> ORGANISM: Artificial Sequence
<220> FEATURE:
<223> OTHER INFORMATION: CDR

<400> SEQUENCE: 57

Ala Ser Thr Asn Ser Asn Ser Gly Tyr Ala Leu Asn
1               5                   10

<210> SEQ ID NO 58
<211> LENGTH: 11
<212> TYPE: PRT
<213> ORGANISM: Artificial Sequence
<220> FEATURE:
<223> OTHER INFORMATION: CDR

<400> SEQUENCE: 58

Ala Ala Arg Gly Gly Gly Tyr Ser Thr Leu Thr
1               5                   10

<210> SEQ ID NO 59
<211> LENGTH: 11
<212> TYPE: PRT
<213> ORGANISM: Artificial Sequence
<220> FEATURE:
<223> OTHER INFORMATION: CDR

<400> SEQUENCE: 59

Ala Met Phe Arg Ser Thr Leu Gly Arg Leu Tyr
1               5                   10

<210> SEQ ID NO 60
<211> LENGTH: 9
<212> TYPE: PRT
<213> ORGANISM: Artificial Sequence
<220> FEATURE:
<223> OTHER INFORMATION: CDR

<400> SEQUENCE: 60

Ala Val Leu Asn Asn Asn Asp Met Arg
1               5

<210> SEQ ID NO 61
<211> LENGTH: 9
<212> TYPE: PRT
<213> ORGANISM: Artificial Sequence
<220> FEATURE:
<223> OTHER INFORMATION: CDR

<400> SEQUENCE: 61

Ala Val Val Asp Asn Asn Asp Met Arg
1               5

<210> SEQ ID NO 62
<211> LENGTH: 11
<212> TYPE: PRT
<213> ORGANISM: Artificial Sequence
<220> FEATURE:
<223> OTHER INFORMATION: CDR

<400> SEQUENCE: 62

Ala Val Ala Met Asn Arg Asp Asp Lys Ile Ile
1               5                   10

<210> SEQ ID NO 63
<211> LENGTH: 15
```

```
<212> TYPE: PRT
<213> ORGANISM: Artificial Sequence
<220> FEATURE:
<223> OTHER INFORMATION: CDR

<400> SEQUENCE: 63

Ala Ala Arg Glu Gly Phe Tyr Gln Thr Gly Ala Asn Asn Leu Phe
1               5                   10                  15

<210> SEQ ID NO 64
<211> LENGTH: 12
<212> TYPE: PRT
<213> ORGANISM: Artificial Sequence
<220> FEATURE:
<223> OTHER INFORMATION: CDR

<400> SEQUENCE: 64

Ala Ala Thr Ala Gly Gly Ala Thr Asn Lys Leu Ile
1               5                   10

<210> SEQ ID NO 65
<211> LENGTH: 10
<212> TYPE: PRT
<213> ORGANISM: Artificial Sequence
<220> FEATURE:
<223> OTHER INFORMATION: CDR

<400> SEQUENCE: 65

Ala Val Glu Leu Thr Gly Asn Gln Phe Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: CDR

<400> SEQUENCE: 66

Ala Val Asn Thr Gly Phe Gln Lys Leu Val
1               5                   10

<210> SEQ ID NO 67
<211> LENGTH: 13
<212> TYPE: PRT
<213> ORGANISM: Artificial Sequence
<220> FEATURE:
<223> OTHER INFORMATION: CDR

<400> SEQUENCE: 67

Ala Leu Ser Glu Pro Pro Ser Gly Thr Tyr Lys Tyr Ile
1               5                   10

<210> SEQ ID NO 68
<211> LENGTH: 9
<212> TYPE: PRT
<213> ORGANISM: Artificial Sequence
<220> FEATURE:
<223> OTHER INFORMATION: CDR

<400> SEQUENCE: 68

Ala Val Leu Asp Asn Asn Asp Met Arg
1               5

<210> SEQ ID NO 69
<211> LENGTH: 10
<212> TYPE: PRT
```

<213> ORGANISM: Artificial Sequence
<220> FEATURE:
<223> OTHER INFORMATION: CDR

<400> SEQUENCE: 69

Ala Gly Lys Thr Ser Tyr Asp Lys Val Ile
1               5                   10

<210> SEQ ID NO 70
<211> LENGTH: 14
<212> TYPE: PRT
<213> ORGANISM: Artificial Sequence
<220> FEATURE:
<223> OTHER INFORMATION: CDR

<400> SEQUENCE: 70

Ala Met Val Ser Gly Ala Gly Gly Gly Ala Asp Gly Leu Thr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: CDR

<400> SEQUENCE: 71

Ala Glu Thr Pro Gly Gly Tyr Gln Lys Val Thr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: CDR

<400> SEQUENCE: 72

Ala Ala Ser Asn Arg Asp Asp Lys Ile Ile
1               5                   10

<210> SEQ ID NO 73
<211> LENGTH: 13
<212> TYPE: PRT
<213> ORGANISM: Artificial Sequence
<220> FEATURE:
<223> OTHER INFORMATION: CDR

<400> SEQUENCE: 73

Ala Val Asp Ile Gly Thr Glu Tyr Gly Asn Lys Leu Val
1               5                   10

<210> SEQ ID NO 74
<211> LENGTH: 5
<212> TYPE: PRT
<213> ORGANISM: Artificial Sequence
<220> FEATURE:
<223> OTHER INFORMATION: CDR

<400> SEQUENCE: 74

Met Asn His Glu Tyr
1               5

<210> SEQ ID NO 75
<211> LENGTH: 6
<212> TYPE: PRT
<213> ORGANISM: Artificial Sequence

```
<220> FEATURE:
<223> OTHER INFORMATION: CDR

<400> SEQUENCE: 75

Asp Phe Gln Ala Thr Thr
1               5

<210> SEQ ID NO 76
<211> LENGTH: 5
<212> TYPE: PRT
<213> ORGANISM: Artificial Sequence
<220> FEATURE:
<223> OTHER INFORMATION: CDR

<400> SEQUENCE: 76

Leu Asn His Asp Ala
1               5

<210> SEQ ID NO 77
<211> LENGTH: 5
<212> TYPE: PRT
<213> ORGANISM: Artificial Sequence
<220> FEATURE:
<223> OTHER INFORMATION: CDR

<400> SEQUENCE: 77

Met Gly His Arg Ala
1               5

<210> SEQ ID NO 78
<211> LENGTH: 5
<212> TYPE: PRT
<213> ORGANISM: Artificial Sequence
<220> FEATURE:
<223> OTHER INFORMATION: CDR

<400> SEQUENCE: 78

Ser Gly His Lys Ser
1               5

<210> SEQ ID NO 79
<211> LENGTH: 5
<212> TYPE: PRT
<213> ORGANISM: Artificial Sequence
<220> FEATURE:
<223> OTHER INFORMATION: CDR

<400> SEQUENCE: 79

Lys Gly His Ser His
1               5

<210> SEQ ID NO 80
<211> LENGTH: 5
<212> TYPE: PRT
<213> ORGANISM: Artificial Sequence
<220> FEATURE:
<223> OTHER INFORMATION: CDR

<400> SEQUENCE: 80

Ser Gly Asp Leu Ser
1               5

<210> SEQ ID NO 81
<211> LENGTH: 5
<212> TYPE: PRT
<213> ORGANISM: Artificial Sequence
<220> FEATURE:
```

```
<223> OTHER INFORMATION: CDR

<400> SEQUENCE: 81

Ser Asn His Leu Tyr
1               5

<210> SEQ ID NO 82
<211> LENGTH: 5
<212> TYPE: PRT
<213> ORGANISM: Artificial Sequence
<220> FEATURE:
<223> OTHER INFORMATION: CDR

<400> SEQUENCE: 82

Ser Gly His Val Ser
1               5

<210> SEQ ID NO 83
<211> LENGTH: 5
<212> TYPE: PRT
<213> ORGANISM: Artificial Sequence
<220> FEATURE:
<223> OTHER INFORMATION: CDR

<400> SEQUENCE: 83

Ser Gly His Ala Thr
1               5

<210> SEQ ID NO 84
<211> LENGTH: 5
<212> TYPE: PRT
<213> ORGANISM: Artificial Sequence
<220> FEATURE:
<223> OTHER INFORMATION: CDR

<400> SEQUENCE: 84

Ser Gly His Asn Ser
1               5

<210> SEQ ID NO 85
<211> LENGTH: 6
<212> TYPE: PRT
<213> ORGANISM: Artificial Sequence
<220> FEATURE:
<223> OTHER INFORMATION: CDR

<400> SEQUENCE: 85

Ser Val Gly Ala Gly Ile
1               5

<210> SEQ ID NO 86
<211> LENGTH: 7
<212> TYPE: PRT
<213> ORGANISM: Artificial Sequence
<220> FEATURE:
<223> OTHER INFORMATION: CDR

<400> SEQUENCE: 86

Ser Asn Glu Gly Ser Lys Ala
1               5

<210> SEQ ID NO 87
<211> LENGTH: 6
<212> TYPE: PRT
<213> ORGANISM: Artificial Sequence
<220> FEATURE:
<223> OTHER INFORMATION: CDR
```

```
<400> SEQUENCE: 87

Ser Gln Ile Val Asn Asp
1               5

<210> SEQ ID NO 88
<211> LENGTH: 6
<212> TYPE: PRT
<213> ORGANISM: Artificial Sequence
<220> FEATURE:
<223> OTHER INFORMATION: CDR

<400> SEQUENCE: 88

Ser Met Asn Val Glu Val
1               5

<210> SEQ ID NO 89
<211> LENGTH: 6
<212> TYPE: PRT
<213> ORGANISM: Artificial Sequence
<220> FEATURE:
<223> OTHER INFORMATION: CDR

<400> SEQUENCE: 89

Tyr Ser Tyr Glu Lys Leu
1               5

<210> SEQ ID NO 90
<211> LENGTH: 6
<212> TYPE: PRT
<213> ORGANISM: Artificial Sequence
<220> FEATURE:
<223> OTHER INFORMATION: CDR

<400> SEQUENCE: 90

Tyr Tyr Glu Lys Glu Glu
1               5

<210> SEQ ID NO 91
<211> LENGTH: 6
<212> TYPE: PRT
<213> ORGANISM: Artificial Sequence
<220> FEATURE:
<223> OTHER INFORMATION: CDR

<400> SEQUENCE: 91

Leu Gln Lys Glu Asn Ile
1               5

<210> SEQ ID NO 92
<211> LENGTH: 6
<212> TYPE: PRT
<213> ORGANISM: Artificial Sequence
<220> FEATURE:
<223> OTHER INFORMATION: CDR

<400> SEQUENCE: 92

Tyr Tyr Asn Gly Glu Glu
1               5

<210> SEQ ID NO 93
<211> LENGTH: 6
<212> TYPE: PRT
<213> ORGANISM: Artificial Sequence
<220> FEATURE:
<223> OTHER INFORMATION: CDR
```

```
<400> SEQUENCE: 93

Phe Tyr Asn Asn Glu Ile
1               5

<210> SEQ ID NO 94
<211> LENGTH: 6
<212> TYPE: PRT
<213> ORGANISM: Artificial Sequence
<220> FEATURE:
<223> OTHER INFORMATION: CDR

<400> SEQUENCE: 94

Phe Gln Asn Glu Ala Gln
1               5

<210> SEQ ID NO 95
<211> LENGTH: 6
<212> TYPE: PRT
<213> ORGANISM: Artificial Sequence
<220> FEATURE:
<223> OTHER INFORMATION: CDR

<400> SEQUENCE: 95

Phe Gln Asn Asn Gly Val
1               5

<210> SEQ ID NO 96
<211> LENGTH: 6
<212> TYPE: PRT
<213> ORGANISM: Artificial Sequence
<220> FEATURE:
<223> OTHER INFORMATION: CDR

<400> SEQUENCE: 96

Phe Asn Asn Asn Val Pro
1               5

<210> SEQ ID NO 97
<211> LENGTH: 12
<212> TYPE: PRT
<213> ORGANISM: Artificial Sequence
<220> FEATURE:
<223> OTHER INFORMATION: CDR

<400> SEQUENCE: 97

Ala Ser Ser Tyr Gln Gly Gly Ser Ser Gly Tyr Thr
1               5                   10

<210> SEQ ID NO 98
<211> LENGTH: 12
<212> TYPE: PRT
<213> ORGANISM: Artificial Sequence
<220> FEATURE:
<223> OTHER INFORMATION: CDR

<400> SEQUENCE: 98

Ala Ser Ser Gly Gln Gly Gly Gly Tyr Gly Tyr Thr
1               5                   10

<210> SEQ ID NO 99
<211> LENGTH: 15
<212> TYPE: PRT
<213> ORGANISM: Artificial Sequence
<220> FEATURE:
<223> OTHER INFORMATION: CDR

<400> SEQUENCE: 99
```

```
Ser Ala Arg Asp Thr Ser Gly Val Asn Phe Tyr Asn Glu Gln Phe
1               5               10              15
```

```
<210> SEQ ID NO 100
<211> LENGTH: 11
<212> TYPE: PRT
<213> ORGANISM: Artificial Sequence
<220> FEATURE:
<223> OTHER INFORMATION: CDR

<400> SEQUENCE: 100
```

```
Ala Ser Ala Ile Thr Gly Gly Thr Glu Ala Phe
1               5               10
```

```
<210> SEQ ID NO 101
<211> LENGTH: 16
<212> TYPE: PRT
<213> ORGANISM: Artificial Sequence
<220> FEATURE:
<223> OTHER INFORMATION: CDR

<400> SEQUENCE: 101
```

```
Ala Ser Thr Pro Leu Pro Thr Ser Ser Gly Arg Leu Gly Glu Gln Tyr
1               5               10              15
```

```
<210> SEQ ID NO 102
<211> LENGTH: 11
<212> TYPE: PRT
<213> ORGANISM: Artificial Sequence
<220> FEATURE:
<223> OTHER INFORMATION: CDR

<400> SEQUENCE: 102
```

```
Ala Ser Ser Gln Gly Arg Trp Tyr Glu Gln Tyr
1               5               10
```

```
<210> SEQ ID NO 103
<211> LENGTH: 11
<212> TYPE: PRT
<213> ORGANISM: Artificial Sequence
<220> FEATURE:
<223> OTHER INFORMATION: CDR

<400> SEQUENCE: 103
```

```
Ala Ser Ser Pro Gly Arg Trp Tyr Glu Gln Phe
1               5               10
```

```
<210> SEQ ID NO 104
<211> LENGTH: 14
<212> TYPE: PRT
<213> ORGANISM: Artificial Sequence
<220> FEATURE:
<223> OTHER INFORMATION: CDR

<400> SEQUENCE: 104
```

```
Ala Ser Ser Leu Asp Arg Asp Arg Asn Asp Tyr Gly Tyr Thr
1               5               10
```

```
<210> SEQ ID NO 105
<211> LENGTH: 14
<212> TYPE: PRT
<213> ORGANISM: Artificial Sequence
<220> FEATURE:
<223> OTHER INFORMATION: CDR

<400> SEQUENCE: 105
```

```
Ala Ser Ser Pro Ala Pro Arg Ala Gly Asn Gln Pro Gln His
1               5               10

<210> SEQ ID NO 106
<211> LENGTH: 15
<212> TYPE: PRT
<213> ORGANISM: Artificial Sequence
<220> FEATURE:
<223> OTHER INFORMATION: CDR

<400> SEQUENCE: 106

Ala Ser Ser Leu Tyr Pro Pro Gly His Ser Asn Gln Pro Gln His
1               5               10                  15

<210> SEQ ID NO 107
<211> LENGTH: 13
<212> TYPE: PRT
<213> ORGANISM: Artificial Sequence
<220> FEATURE:
<223> OTHER INFORMATION: CDR

<400> SEQUENCE: 107

Ala Ser Ser Leu Glu Pro Gly Trp Gly Asp Thr Gln Tyr
1               5               10

<210> SEQ ID NO 108
<211> LENGTH: 11
<212> TYPE: PRT
<213> ORGANISM: Artificial Sequence
<220> FEATURE:
<223> OTHER INFORMATION: CDR

<400> SEQUENCE: 108

Ala Ser Ser Val Gly Pro Trp Tyr Glu Gln Tyr
1               5               10

<210> SEQ ID NO 109
<211> LENGTH: 11
<212> TYPE: PRT
<213> ORGANISM: Artificial Sequence
<220> FEATURE:
<223> OTHER INFORMATION: CDR

<400> SEQUENCE: 109

Ala Ser Ser Pro Gly Arg Phe Tyr Glu Gln Tyr
1               5               10

<210> SEQ ID NO 110
<211> LENGTH: 11
<212> TYPE: PRT
<213> ORGANISM: Artificial Sequence
<220> FEATURE:
<223> OTHER INFORMATION: CDR

<400> SEQUENCE: 110

Ala Ser Ser Pro Gly Arg Trp Tyr Glu Gln Tyr
1               5               10

<210> SEQ ID NO 111
<211> LENGTH: 14
<212> TYPE: PRT
<213> ORGANISM: Artificial Sequence
<220> FEATURE:
<223> OTHER INFORMATION: CDR

<400> SEQUENCE: 111

Ala Ser Ser Glu Gly Pro Thr Gly Thr Ser Tyr Glu Gln Tyr
```

-continued

```
1               5                   10

<210> SEQ ID NO 112
<211> LENGTH: 13
<212> TYPE: PRT
<213> ORGANISM: Artificial Sequence
<220> FEATURE:
<223> OTHER INFORMATION: CDR

<400> SEQUENCE: 112

Ala Ser Ser Gln Glu Ser Gly Gly Thr Asp Thr Gln Tyr
1               5                   10

<210> SEQ ID NO 113
<211> LENGTH: 12
<212> TYPE: PRT
<213> ORGANISM: Artificial Sequence
<220> FEATURE:
<223> OTHER INFORMATION: CDR

<400> SEQUENCE: 113

Ala Ser Ser Val Phe Pro Thr Ser Val Glu Gln Tyr
1               5                   10

<210> SEQ ID NO 114
<211> LENGTH: 14
<212> TYPE: PRT
<213> ORGANISM: Artificial Sequence
<220> FEATURE:
<223> OTHER INFORMATION: CDR

<400> SEQUENCE: 114

Ala Ser Ser Ile Gly Val Gly Leu Ser Asn Thr Glu Ala Phe
1               5                   10

<210> SEQ ID NO 115
<211> LENGTH: 12
<212> TYPE: PRT
<213> ORGANISM: Artificial Sequence
<220> FEATURE:
<223> OTHER INFORMATION: CDR

<400> SEQUENCE: 115

Ala Ser Ser Leu Trp Thr Ser Asn Ser Pro Leu His
1               5                   10

<210> SEQ ID NO 116
<211> LENGTH: 13
<212> TYPE: PRT
<213> ORGANISM: Artificial Sequence
<220> FEATURE:
<223> OTHER INFORMATION: CDR

<400> SEQUENCE: 116

Ala Ser Ser Leu Gly Ala Gly His Leu Trp Gly Tyr Thr
1               5                   10

<210> SEQ ID NO 117
<211> LENGTH: 12
<212> TYPE: PRT
<213> ORGANISM: Artificial Sequence
<220> FEATURE:
<223> OTHER INFORMATION: CDR

<400> SEQUENCE: 117

Ala Ser Arg Glu Gly Val Gly Leu Tyr Glu Gln Tyr
1               5                   10
```

-continued

```
<210> SEQ ID NO 118
<211> LENGTH: 885
<212> TYPE: DNA
<213> ORGANISM: Artificial Sequence
<220> FEATURE:
<223> OTHER INFORMATION: A0201 NT

<400> SEQUENCE: 118
atgggcagcc atagcatgcg ttacttcttc accagcgtta gtcgccccgg tcgcggtgaa      60
ccgcgcttta tcgcagtggg ttacgttgac gacacccagt ttgtgcgttt tgacagcgat     120
gccgcaagcc agcgtatgga accgcgtgcc ccgtggattg aacaagaagg cccggaatac     180
tgggatggcg aaacccgcaa agttaaagcc cacagccaga cccatcgcgt ggatctgggt     240
actttacgtg gctactataa ccagagcgaa gccggtagcc ataccgtgca gcgcatgtat     300
ggctgtgatg tgggcagtga ttggcgcttt ctgcgcggct atcatcagta cgcctatgac     360
ggcaaggact acatcgcttt aaaagaagat ttacgtagtt ggaccgccgc cgatatggca     420
gcccagacca ccaaacataa atgggaagcc gcccatgtgg cagagcagct gcgcgcatat     480
ctggaaggca catgcgtgga atggctgcgt cgctatctgg agaacggcaa agaaacttta     540
cagcgcaccg acgcaccgaa aacccatatg acccaccatg ccgtgagtga ccatgaagcc     600
actttacgct gttgggcttt aagcttctat ccggccgaaa ttactttaac ttggcagcgc     660
gatggtgaag accagaccca agataccgag ctggtggaaa cccgtccggc tggtgatggc     720
acctttcaga aatgggtggc cgttgtggtg ccgagcggtc aagaacagcg ctatacttgt     780
catgtgcagc atgagggctt accgaaaccg ctgactttac gctgggaacc gggatccggt     840
ttgaacgaca tcttcgaagc tcagaaaatc gaatggcacg aataa                     885

<210> SEQ ID NO 119
<211> LENGTH: 885
<212> TYPE: DNA
<213> ORGANISM: Artificial Sequence
<220> FEATURE:
<223> OTHER INFORMATION: A2402 NT

<400> SEQUENCE: 119
atgggcagcc acagtatgcg ctacttcagc accagcgtta gtcgcccggg tcgtggtgaa      60
ccgcgtttta tcgcagtggg ctatgtggac gatacccagt cgttcgctt cgacagtgat     120 gccgcaagtc agcgcatgga accgcgtgcc ccgtggatcg aacaggaagg cccggaatac     180
tgggatgagg aaaccggcaa ggtgaaagca cacagccaga ccgaccgtga aaacctgcgc     240
attgccctgc gctattacaa tcagagcgaa gccggcagcc acaccctgca gatgatgttt     300
ggttgcgatg tgggcagtga tggtcgcttt ctgcgcggct atcaccagta cgcctacgac     360
ggcaaggatt atatcgccct gaaagaagac ctgcgtagct ggaccgcagc cgatatggcc     420
gcccagatta ccaaacgcaa atgggaggcc gcacatgttg ccgaacaaca gcgcgcatat     480
ctggaaggta cctgtgtgga tggtctgcgt cgctatctgg aaaacggcaa agaaaccctg     540
cagcgcaccg atcctccgaa aacccacatg acccaccacc cgatcagcga ccatgaagcc     600
acactgcgtt gctgggccct gggctttac ccggccgaaa tcaccctgac ctggcagcgc     660
gatggcgaag atcagaccca ggacaccgaa ctggtggaaa cccgtccggc aggtgatggc     720
acctttcaga aatgggtggc agtggttgtg ccgagcggcg aagaacagcg ttataccgc      780 catgtgcagc acgaaggtct gccgaaaccg ctgaccctgc gctgggaacc tggatccggt     840
```

```
ttgaacgaca tcttcgaagc tcagaaaatc gaatggcacg aataa                      885
```

```
<210> SEQ ID NO 120
<211> LENGTH: 885
<212> TYPE: DNA
<213> ORGANISM: Artificial Sequence
<220> FEATURE:
<223> OTHER INFORMATION: A1101 NT

<400> SEQUENCE: 120
atgggtagcc atagcatgcg ctacttctat accagcgtga gtcgtccggg ccgtggtgaa       60
cctcgcttta ttgccgtggg ctatgtggat gacacccagt tcgtgcgctt tgatagcgat      120
gccgcaagtc agcgcatgga accgcgtgcc ccgtggattg aacaagaagg cccggaatat      180
tgggaccaag aaacacgcaa cgttaaggcc cagagccaga cagatcgtgt ggatctgggt      240
acactgcgcg gctattacaa tcagagcgag gatggcagcc acaccattca gatcatgtac      300
ggctgcgatg ttggtccgga cggtcgcttt ttacgtggct accgtcaaga tgcctatgat      360
ggcaaggact atatcgcttt aaacgaggat ctgcgcagtt ggaccgcagc cgatatggcc      420
gcacagatca ccaaacgcaa atgggaagca gcacacgccg ccgagcagca acgtgcatat      480
ttagaaggtc gttgcgtgga atggctgcgc cgctatctgg agaatggcaa agaaacttta      540
cagcgtaccg atccgccgaa aacccatatg acccatcacc cgatcagcga tcatgaggcc      600
actttacgtt gttgggcact gggcttttat ccggcagaaa tcactttaac ttggcagcgc      660
gatggtgaag atcagaccca agataccgaa ctggtggaaa cccgccccgc tggtgatggc      720
acctttcaga aatgggttgc agtggttgtg ccgagcggcg aggaacagcg ttacacttgt      780
cacgttcagc atgaaggttt accgaaaccg ctgactttac gttgggaact gggatccggt      840
ttgaacgaca tcttcgaagc tcagaaaatc gaatggcacg aataa                      885
```

```
<210> SEQ ID NO 121
<211> LENGTH: 306
<212> TYPE: DNA
<213> ORGANISM: Artificial Sequence
<220> FEATURE:
<223> OTHER INFORMATION: b2m NT

<400> SEQUENCE: 121
atggcaatcc agcgtactcc aaagattcag gtttactcac gtcatccagc agagaatgga       60
aagtcaaatt tcctgaattg ctatgtgtct gggtttcatc catccgacat tgaagttgac      120
ttactgaaga atggagagag aattgaaaaa gtggagcatt cagacttgtc tttcagcaag      180
gactggtctt tctatctctt gtactacact gaattcaccc ccactgaaaa agatgagtat      240
gcctgccgtg tgaaccatgt gactttgtca cagcccaaga tagttaagtg ggatcgagac      300
atgtaa                                                                 306
```

```
<210> SEQ ID NO 122
<211> LENGTH: 1830
<212> TYPE: DNA
<213> ORGANISM: Artificial Sequence
<220> FEATURE:
<223> OTHER INFORMATION: E23 NT

<400> SEQUENCE: 122
atgagcatcg gcctcctgtg ctgtgcagcc ttgtctctcc tgtgggcagg tccagtgaat       60
gctggtgtca ctcagacccc aaaattccag gtcctgaaga caggacagag catgacactg      120
cagtgtgccc aggatatgaa ccatgaatac atgtcctggt atcgacaaga cccaggcatg      180
```

```
gggctgaggc tgattcatta ctcagttggt gctggtatca ctgaccaagg agaagtcccc      240
aatggctaca atgtctccag atcaaccaca gaggatttcc cgctcaggct gctgtcggct      300
gctccctccc agacatctgt gtacttctgt gccagcagtt accaaggggg tagtagtggc      360
tacaccttcg gttcggggac caggttaacc gttgtagagg acctgaaaaa cgtgttccca      420
cccgaggtcg ctgtgtttga gccatcagaa gcagagatct cccacaccca aaaggccaca      480
ctggtgtgcc tggccacagg cttcttcccc gaccacgtgg agctgagctg gtgggtgaat      540
gggaaggagg tgcacagtgg ggtcagcaca gacccgcagc ccctcaagga gcagcccgcc      600
ctcaatgact ccagatactg cctgagcagc cgcctgaggg tctcggccac cttctggcag      660
aacccccgca accacttccg ctgtcaagtc cagttctacg ggctctcgga gaatgacgag      720
tggacccagg atagggccaa acccgtcacc cagatcgtca gcgccgaggc ctggggtaga      780
gcagactgtg gctttaccctc ggtgtcctac cagcaagggg tcctgtctgc caccatcctc      840
tatgagatcc tgctagggaa ggccaccctg tatgctgtgc tggtcagcgc ccttgtgttg      900
atggccatgg tcaagagaaa ggatttccgg cggaaacgga gcggaagcgg agctactaac      960
ttcagcctgc tgaagcaggc tggagacgtg gaggagaacc ctggacctat ggaaactctc     1020
ctgggagtgt ctttggtgat tctatggctt caactggcta gggtgaacag tcaacaggga     1080
gaagaggatc ctcaggcctt gagcatccag gagggtgaaa atgccaccat gaactgcagt     1140
tacaaaacta gtataaacaa tttacagtgg tatagacaaa attcaggtag aggccttgtc     1200
cacctaattt taatacgttc aaatgaaaga gagaaacaca gtggaagatt aagagtcacg     1260
cttgacactt ccaagaaaag cagttccttg ttgatcacgg cttcccgggc agcagacact     1320
gcttcttact tctgtgctac ggaaggggat tcaggataca gcaccctcac ctttgggaag     1380
gggactatgc ttctagtctc tccagatatc cagaaccctg accctgccgt gtaccagctg     1440
agagactcta aatccagtga caagtctgtc tgcctattca ccgatttttga ttctcaaaca     1500 aatgtgtcac aaagtaagga ttctgatgtg tatatcacag acaaaactgt gctagacatg     1560
aggtctatgg acttcaagag caacagtgct gtggcctgga gcaacaaatc tgactttgca     1620
tgtgcaaacg ccttcaacaa cagcattatt ccagaagaca ccttcttccc cagcccagaa     1680
agttcctgtg atgtcaagct ggtcgagaaa agctttgaaa cagatacgaa cctaaacttt     1740
caaaacctgt cagtgattgg gttccgaatc ctcctcctga aagtggccgg gtttaatctg     1800
ctcatgacgc tgcggctgtg gtccagctga                                      1830
```

```
<210> SEQ ID NO 123
<211> LENGTH: 1830
<212> TYPE: DNA
<213> ORGANISM: Artificial Sequence
<220> FEATURE:
<223> OTHER INFORMATION: E240 NT

<400> SEQUENCE: 123
```

```
atgagcatcg gcctcctgtg ctgtgcagcc ttgtctctcc tgtgggcagg tccagtgaat       60
gctggtgtca ctcagacccc aaaattccag gtcctgaaga caggacagag catgacactg      120
cagtgtgccc aggatatgaa ccatgaatac atgtcctggt atcgacaaga cccaggcatg      180
gggctgaggc tgattcatta ctcagttggt gctggtatca ctgaccaagg agaagtcccc      240
aatggctaca atgtctccag atcaaccaca gaggatttcc cgctcaggct gctgtcggct      300
gctccctccc agacatctgt gtacttctgt gccagcagcg gacagggcgg ggggtatggc      360
```

-continued

```
tacaccttcg gttcggggac caggttaacc gttgtagagg acctgaaaaa cgtgttccca      420
cccgaggtcg ctgtgtttga gccatcagaa gcagagatct cccacaccca aaaggccaca      480
ctggtgtgcc tggccacagg cttcttcccc gaccacgtgg agctgagctg gtgggtgaat      540
gggaaggagg tgcacagtgg ggtcagcaca gacccgcagc ccctcaagga gcagcccgcc      600
ctcaatgact ccagatactg cctgagcagc cgcctgaggg tctcggccac cttctggcag      660
aacccccgca accacttccg ctgtcaagtc cagttctacg ggctctcgga gaatgacgag      720
tggacccagg atagggccaa acccgtcacc cagatcgtca gcgccgaggc ctgggtaga      780 gcagactgtg gctttacctc ggtgtcctac cagcaagggg tcctgtctgc caccatcctc      840
tatgagatcc tgctagggaa ggccaccctg tatgctgtgc tggtcagcgc ccttgtgttg      900
atggccatgg tcaagagaaa ggatttccgg cggaaacgga gcggaagcgg agctactaac      960
ttcagcctgc tgaagcaggc tggagacgtg gaggagaacc ctggacctat ggaaactctc     1020
ctgggagtgt ctttggtgat ctatggctt caactggcta gggtgaacag tcaacaggga     1080
gaagaggatc ctcaggcctt gagcatccag gagggtgaaa atgccaccat gaactgcagt     1140
tacaaaacta gtataaacaa tttacagtgg tatagacaaa attcaggtag aggccttgtc     1200
cacctaattt taatacgttc aaatgaaaga gagaaacaca gtggaagatt aagagtcacg     1260
cttgacactt ccaagaaaag cagttccttg ttgatcacgg cttcccgggc agcagacact     1320
gcttcttact tctgtgctac ggtcgggggat tcaggataca gcaccctcac ctttgggaag     1380
gggactatgc ttctagtctc tccagatatc cagaaccctg accctgccgt gtaccagctg     1440
agagactcta aatccagtga caagtctgtc tgcctattca ccgattttga ttctcaaaca     1500
aatgtgtcac aaagtaagga ttctgatgtg tatatcacag acaaaactgt gctagacatg     1560
aggtctatgg acttcaagag caacagtgct gtggcctgga gcaacaaatc tgactttgca     1620
tgtgcaaacg ccttcaacaa cagcattatt ccagaagaca ccttcttccc cagcccagaa     1680
agttcctgtg atgtcaagct ggtcgagaaa agctttgaaa cagatacgaa cctaaacttt     1740
caaaacctgt cagtgattgg gttccgaatc ctcctcctga aagtggccgg gtttaatctg     1800
ctcatgacgc tgcggctgtg gtccagctga                                      1830
```

```
<210> SEQ ID NO 124
<211> LENGTH: 1842
<212> TYPE: DNA
<213> ORGANISM: Artificial Sequence
<220> FEATURE:
<223> OTHER INFORMATION: E29 NT

<400> SEQUENCE: 124
```

```
atgctgctgc ttctgctgct tctggggcca ggctccgggc ttggtgctgt cgtctctcaa       60
catccgagca gggttatctg taagagtgga acctctgtga agatcgagtg ccgttccctg      120
gactttcagg ccacaactat gttttggtat cgtcagttcc cgaaaaagag tctcatgctg      180
atggcaactt ccaatgaggg ctccaaggcc acatacgagc aaggcgtcga gaaggacaag      240
tttctcatca accatgcaag cctgaccttg tccactctga cagtgaccag tgcccatcct      300
gaagacagca gcttctacat ctgcagtgct agagatacta gcggggttaa cttttacaat      360
gagcagttct tcgggccagg gacacggctc accgtgctag aggacctgaa aaacgtgttc      420
ccacccgagg tcgctgtgtt tgagccatca gaagcagaga tctcccacac ccaaaaggcc      480
acactggtgt gcctggccac aggcttcttc cccgaccacg tggagctgag ctggtgggtg      540
aatgggaagg aggtgcacag tggggtcagc acagacccgc agcccctcaa ggagcagccc      600
```

-continued

```
gccctcaatg actccagata ctgcctgagc agccgcctga gggtctcggc caccttctgg       660
cagaaccccc gcaaccactt ccgctgtcaa gtccagttct acgggctctc ggagaatgac       720
gagtggaccc aggatagggc caaacccgtc acccagatcg tcagcgccga ggcctggggt       780
agagcagact gtggctttac ctcggtgtcc taccagcaag gggtcctgtc tgccaccatc       840
ctctatgaga tcctgctagg gaaggccacc ctgtatgctg tgctggtcag cgcccttgtg       900
ttgatggcca tggtcaagag aaaggatttc cggcggaaac ggagcggaag cggagctact       960
aacttcagcc tgctgaagca ggctggagac gtggaggaga accctggacc tatggagaag      1020
aatcctttgg cagccccatt actaatcctc tggtttcatc ttgactgcgt gagcagcata      1080
ctgaacgtgg aacaaagtcc tcagtcactg catgttcagg agggagacag caccaatttc      1140
acctgcagct tcccttccag caattttttat gccttacact ggtacagatg ggaaactgca      1200
aaaagccccg aggccttgtt tgtaatgact ttaaatgggg atgaaaagaa gaaaggacga      1260
ataagtgcca ctcttaatac caaggagggt tacagctatt tgtacatcaa aggatcccag      1320
cctgaagact cagccacata cctctgtgcc tccacgaact caaattccgg gtatgcactc      1380
aacttcggca aaggcacctc gctgttggtc acaccccata tccagaaccc tgaccctgcc      1440
gtgtaccagc tgagagactc taaatccagt gacaagtctg tctgcctatt caccgatttt      1500
gattctcaaa caaatgtgtc acaaagtaag gattctgatg tgtatatcac agacaaaact      1560
gtgctagaca tgaggtctat ggacttcaag agcaacagtg ctgtggcctg gagcaacaaa      1620
tctgactttg catgtgcaaa cgccttcaac aacagcatta ttccagaaga caccttcttc      1680
cccagcccag aaagttcctg tgatgtcaag ctggtcgaga aaagctttga aacagatacg      1740
aacctaaact ttcaaaacct gtcagtgatt gggttccgaa tcctcctcct gaaagtggcc      1800
gggtttaatc tgctcatgac gctgcggctg tggtccagct ga                        1842
```

<210> SEQ ID NO 125
<211> LENGTH: 1824
<212> TYPE: DNA
<213> ORGANISM: Artificial Sequence
<220> FEATURE:
<223> OTHER INFORMATION: E180-1 NT

<400> SEQUENCE: 125

```
atgagcaacc aggtgctctg ctgtgtggtc ctttgtttcc tgggagcaaa caccgtggat        60
ggtggaatca ctcagtcccc aaagtacctg ttcagaaagg aaggacagaa tgtgaccctg       120
agttgtgaac agaatttgaa ccacgatgcc atgtactggt accgcacagga cccagggcaa       180 gggctgagat tgatctacta ctcacagata gtaaatgact ttcagaaagg agatatagct       240
gaagggtaca cgctctctcg ggagaagaag gaatcctttc ctctcactgt gacatcggcc       300
caaaagaacc cgacagcttt ctatctctgt gccagtgcga ttacgggggg cactgaagct       360
ttctttggac aaggcaccag actcacagtt gtagaggacc tgaaaaacgt gttcccaccc       420
gaggtcgctg tgtttgagcc atcagaagca gagatctccc acacccaaaa ggccacactg       480
gtgtgcctgg ccacaggctt cttccccgac cacgtggagc tgagctggtg ggtgaatggg       540
aaggaggtgc acagtggggt cagcacagac ccgcagcccc tcaaggagca gcccgccctc       600
aatgactcca gatactgcct gagcagccgc ctgagggtct cggccacctt ctggcagaac       660
ccccgcaacc acttccgctg tcaagtccag ttctacgggc tctcggagaa tgacgagtgg       720
acccaggata gggccaaacc cgtcacccag atcgtcagcg ccgaggcctg gggtagagca       780
```

-continued

```
gactgtggct ttacctcggt gtcctaccag caaggggtcc tgtctgccac catcctctat      840
gagatcctgc tagggaaggc caccctgtat gctgtgctgg tcagcgccct tgtgttgatg      900
gccatggtca agagaaagga tttccggcgg aaacggagcg gaagcggagc tactaacttc      960
agcctgctga agcaggctgg agacgtggag gagaaccctg gacctatgac atccattcga     1020
gctgtattta tattcctgtg gctgcagctg gacttggtga atggagagaa tgtggagcag     1080
catccttcaa ccctgagtgt ccaggaggga gacagcgctg ttatcaagtg tacttattca     1140
gacagtgcct caaactactt cccttggtat aagcaagaac ttggaaaagg acctcagctt     1200
attatagaca ttcgttcaaa tgtgggcgaa aagaaagacc aacgaattgc tgttacattg     1260
aacaagacag ccaaacattt ctccctgcac atcacagaga cccaacctga agactcggct     1320
gtctacttct gtgcagcccg cgggggagga tacagcaccc tcacctttgg aaggggact      1380 atgcttctag tctctccaga tatccagaac cctgaccctg ccgtgtacca gctgagagac     1440
tctaaatcca gtgacaagtc tgtctgccta ttcaccgatt ttgattctca aacaaatgtg     1500
tcacaaagta aggattctga tgtgtatatc acagacaaaa ctgtgctaga catgaggtct     1560
atggacttca gagcaacag tgctgtggcc tggagcaaca atctgacttg tgcatgtgca      1620
aacgccttca caacagcat tattccagaa gacaccttct tccccagccc agaaagttcc      1680
tgtgatgtca gctggtcga gaaaagcttt gaaacagata cgaacctaaa ctttcaaaac      1740
ctgtcagtga ttgggttccg aatcctcctc ctgaaagtgg ccgggtttaa tctgctcatg     1800
acgctgcggc tgtggtccag ctga                                            1824
```

<210> SEQ ID NO 126
<211> LENGTH: 1845
<212> TYPE: DNA
<213> ORGANISM: Artificial Sequence
<220> FEATURE:
<223> OTHER INFORMATION: E44 NT

<400> SEQUENCE: 126

```
atgggccccc agctccttgg ctatgtggtc ctttgccttc taggagcagg cccccctggaa      60 gcccaagtga cccagaaccc aagatacctc atcacagtga ctggaaagaa gttaacagtg      120
acttgttctc agaatatgaa ccatgagtat atgtcctggt atcgacaaga cccagggctg      180
ggcttaaggc agatctacta ttcaatgaat gttgaggtga ctgataaggg agatgttcct      240
gaagggtaca aagtctctcg aaaagagaag aggaatttcc ccctgatcct ggagtcgccc      300
agccccaacc agacctctct gtacttctgt gccagcactc ccctacccac tctagcggga      360
agacttggtg agcagtactt cgggccgggc accaggctca cggtcacaga ggacctgaaa      420
aacgtgttcc cacccgaggt cgctgtgttt gagccatcag aagcagagat ctcccacacc      480
caaaaggcca cactggtgtg cctggccaca ggcttcttcc ccgaccacgt ggagctgagc      540
tggtgggtga atgggaagga ggtgcacagt ggggtcagca cagacccgca gcccctcaag      600
gagcagcccg ccctcaatga ctccagatac tgcctgagca gccgcctgag ggtctcggcc      660
accttctggc agaaccccg caaccacttc cgctgtcaag tccagttcta cgggctctcg      720
gagaatgacg agtggaccca ggatagggcc aaacccgtca cccagatcgt cagcgccgag      780
gcctggggta gagcagactg tggctttacc tcggtgtcct accagcaagg ggtcctgtct      840
gccaccatcc tctatgagat cctgctaggg aaggccaccc tgtatgctgt gctggtcagc      900
gcccttgtgt tgatggccat ggtcaagaga aaggatttcc ggcggaaacg gagcggaagc      960
ggagctacta acttcagcct gctgaagcag gctggagacg tggaggagaa ccctggacct    1020
```

-continued

```
atgatgaaat ccttgagagt tttactggtg atcctgtggc ttcagttaag ctgggtttgg      1080
agccaacaga aggaggtgga gcaggatcct ggaccactca gtgttccaga gggagccatt      1140
gtttctctca actgcactta cagcaacagt gcttttcaat acttcatgtg gtacagacag      1200
tattccagaa aaggccctga gttgctgatg tacacatact ccagtggtaa caaagaagat      1260
ggaaggttta cagcacaggt cgataaatcc agcaagtata tctccttgtt catcagagac      1320 tcacagcccca gtgattcagc cacctacctc tgtgcaatgt tccgctcaac cctggggagg      1380
ctatactttg aagaggaac tcagttgact gtctggcctg atatccagaa ccctgaccct      1440
gccgtgtacc agctgagaga ctctaaatcc agtgacaag ctgtctgcct attcaccgat      1500
tttgattctc aaacaaatgt gtcacaaagt aaggattctg atgtgtatat cacagacaaa      1560
actgtgctag acatgaggtc tatggacttc aagagcaaca gtgctgtggc ctggagcaac      1620
aaatctgact ttgcatgtgc aaacgccttc aacaacagca ttattccaga agacaccttc      1680
ttccccagcc cagaaagttc ctgtgatgtc aagctggtcg agaaaagctt tgaaacagat      1740
acgaacctaa actttcaaaa cctgtcagtg attgggttcc gaatcctcct cctgaaagtg      1800
gccgggttta atctgctcat gacgctgcgg ctgtggtcca gctga              1845
```

```
<210> SEQ ID NO 127
<211> LENGTH: 1812
<212> TYPE: DNA
<213> ORGANISM: Artificial Sequence
<220> FEATURE:
<223> OTHER INFORMATION: E141 NT

<400> SEQUENCE: 127
atgggctgca ggctgctctg ctgtgcggtt ctctgtctcc tgggagcagt tcccatagac       60
actgaagtta cccagacacc aaaacacctg gtcatgggaa tgacaaataa gaagtctttg      120
aaatgtgaac aacatatggg gcacagggct atgtattggt acaagcagaa agctaagaag      180
ccaccggagc tcatgtttgt ctacagctat gagaaactct ctataaatga aagtgtgcca      240
agtcgcttct cacctgaatg ccccaacagc tctctcttaa accttcacct acacgcctg       300 cagccagaag actcagccct gtatctctgc gccagcagcc aggggcgatg gtacgagcag      360
tacttcgggc cgggcaccag gctcacggtc acagaggacc tgaaaaacgt gttcccaccc      420
gaggtcgctg tgtttgagcc atcagaagca gagatctccc acacccaaaa ggccacactg      480
gtgtgcctgg ccacaggctt cttccccgac cacgtggagc tgagctggtg ggtgaatggg      540
aaggaggtgc acagtggggt cagcacagac ccgcagcccc tcaaggagca gcccgccctc      600
aatgactcca gatactgcct gagcagccgc ctgagggtct cggccacctt ctggcagaac      660
ccccgcaacc acttccgctg tcaagtccag ttctacgggc tctcggagaa tgacgagtgg      720
acccaggata gggccaaacc cgtcacccag atcgtcagcg ccgaggcctg gggtagagca      780
gactgtggct ttacctcggt gtcctaccag caagggtcc tgtctgccac catcctctat      840
gagatcctgc tagggaaggc caccctgtat gctgtgctgg tcagcgccct tgtgttgatg      900
gccatggtca agagaaagga tttccggcgg aaacggagcg gaagcggagc tactaacttc      960
agcctgctga agcaggctgg agacgtggag gagaaccctg acctatgaa gaggatattg     1020 ggagctctgc tggggctctt gagtgcccag gtttgctgtg tgagaggaat acaagtggag     1080
cagagtcctc cagacctgat tctccaggag ggagccaatt ccacgctgcg gtgcaatttt     1140
tctgactctg tgaacaattt gcagtggttt catcaaaacc cttggggaca gctcatcaac     1200
```

-continued

```
ctgtttttaca ttccctcagg gacaaaacag aatggaagat taagcgccac gactgtcgct    1260
acggaacgct acagcttatt gtacatttcc tcttcccaga ccacagactc aggcgtttat    1320
ttctgtgctg ttctaaataa caatgacatg cgctttggag cagggaccag actgacagta    1380
aaaccaaata tccagaaccc tgaccctgcc gtgtaccagc tgagagactc taaatccagt    1440
gacaagtctg tctgcctatt caccgatttt gattctcaaa caaatgtgtc acaaagtaag    1500
gattctgatg tgtatatcac agacaaaact gtgctagaca tgaggtctat ggacttcaag    1560
agcaacagtg ctgtggcctg gagcaacaaa tctgactttg catgtgcaaa cgccttcaac    1620
aacagcatta ttccagaaga caccttcttc cccagcccag aaagttcctg tgatgtcaag    1680
ctggtcgaga aaagctttga aacagatacg aacctaaact ttcaaaacct gtcagtgatt    1740
gggttccgaa tcctcctcct gaaagtggcc gggtttaatc tgctcatgac gctgcggctg    1800
tggtccagct ga                                                       1812
```

<210> SEQ ID NO 128
<211> LENGTH: 1812
<212> TYPE: DNA
<213> ORGANISM: Artificial Sequence
<220> FEATURE:
<223> OTHER INFORMATION: E149 NT

<400> SEQUENCE: 128

```
atgggctgca ggctgctctg ctgtgcggtt ctctgtctcc tgggagcagt tcccatagac      60
actgaagtta cccagacacc aaaacacctg gtcatgggaa tgacaaataa gaagtctttg     120
aaatgtgaac aacatatggg gcacagggct atgtattggt acaagcagaa agctaagaag     180
ccaccggagc tcatgtttgt ctacagctat gagaaactct ctataaatga aagtgtgcca     240
agtcgcttct cacctgaatg ccccaacagc tctctcttaa accttcacct acacgccctg     300
cagccagaag actcagccct gtatctctgc gccagcagcc ccgggaggtg gtatgagcag     360
ttcttcgggc cagggacacg gctcaccgtg ctagaggacc tgaaaaacgt gttcccaccc     420
gaggtcgctg tgtttgagcc atcagaagca gagatctccc acacccaaaa ggccacactg     480
gtgtgcctgg ccacaggctt cttccccgac cacgtggagc tgagctggtg ggtgaatggg     540
aaggaggtgc acagtggggt cagcacagac ccgcagcccc tcaaggagca gcccgccctc     600
aatgactcca gatactgcct gagcagccgc ctgagggtct cggccacctt ctggcagaac     660
ccccgcaacc acttccgctg tcaagtccag ttctacgggc tctcggagaa tgacgagtgg     720
acccaggata gggccaaacc cgtcacccag atcgtcagcg ccgaggcctg gggtagagca     780
gactgtggct ttacctcggt gtcctaccag caaggggtcc tgtctgccac catcctctat     840
gagatcctgc tagggaaggc caccctgtat gctgtgctgg tcagcgccct tgtgttgatg     900
gccatggtca agagaaagga tttccggcgg aaacggagcg aagcggagc tactaacttc     960 agcctgctga gcaggctgg agacgtggag gagaaccctg acctatgaa gaggatattg    1020 ggagctctgc tgggctctt gagtgcccag gtttgctgtg tgagaggaat acaagtggag    1080
cagagtcctc cagacctgat tctccaggag ggagccaatt ccacgctgcg gtgcaatttt    1140
tctgactctg tgaacaattt gcagtggttt catcaaaacc cttggggaca gctcatcaac    1200 ctgtttttaca ttccctcagg gacaaaacag aatggaagat taagcgccac gactgtcgct    1260
acggaacgct acagcttatt gtacatttcc tcttcccaga ccacagactc aggcgtttat    1320
ttctgtgctg tggtcgataa caatgacatg cgctttggag cagggaccag actgacagta    1380
aaaccaaata tccagaaccc tgaccctgcc gtgtaccagc tgagagactc taaatccagt    1440
```

-continued

```
gacaagtctg tctgcctatt caccgatttt gattctcaaa caaatgtgtc acaaagtaag      1500
gattctgatg tgtatatcac agacaaaact gtgctagaca tgaggtctat ggacttcaag      1560
agcaacagtg ctgtggcctg gagcaacaaa tctgactttg catgtgcaaa cgccttcaac      1620
aacagcatta ttccagaaga caccttcttc cccagcccag aaagttcctg tgatgtcaag      1680
ctggtcgaga aaagctttga aacagatacg aacctaaact ttcaaaacct gtcagtgatt      1740
gggttccgaa tcctcctcct gaaagtggcc gggtttaatc tgctcatgac gctgcggctg      1800
tggtccagct ga                                                          1812
```

<210> SEQ ID NO 129
<211> LENGTH: 1827
<212> TYPE: DNA
<213> ORGANISM: Artificial Sequence
<220> FEATURE:
<223> OTHER INFORMATION: E168 NT

<400> SEQUENCE: 129

```
atgggccctg ggctcctctg ctgggtgctg ctttgtctcc tgggagcagg cccagtggac       60
gctggagtca cccaaagtcc cacacacctg atcaaaacga gaggacagca cgtgactctg      120
agatgctctc ctatctctgg gcacaagagt gtgtcctggt accaacaggt cctgggtcag      180
gggccccagt ttatctttca gtattatgag aaagaagaga gaggaagagg aaacttccct      240
gatcgattct cagctcgcca gttccctaac tatagctctg agctgaatgt gaacgccttg      300
ttgctggggg actcggccct gtatctctgt gccagcagct tggatcggga caggaatgac      360
tatggctaca ccttcggttc ggggaccagg ttaaccgttg tagaggacct gaaaaacgtg      420
ttcccacccg aggtcgctgt gtttgagcca tcagaagcag agatctccca cacccaaaag      480
gccacactgg tgtgcctggc cacaggcttc ttccccgacc acgtggagct gagctggtgg      540
gtgaatggga aggaggtgca cagtggggtc agcacagacc cgcagcccct caaggagcag      600
cccgccctca tgactccag atactgcctg agcagccgcc tgagggtctc ggccaccttc      660
tggcagaacc cccgcaacca cttccgctgt caagtccagt tctacgggct ctcggagaat      720
gacgagtgga cccaggatag ggccaaaccc gtcacccaga tcgtcagcgc cgaggcctgg      780
ggtagagcag actgtggctt tacctcggtg tcctaccagc aaggggtcct gtctgccacc      840
atcctctatg agatcctgct agggaaggcc accctgtatg ctgtgctggt cagcgccctt      900
gtgttgatgg ccatggtcaa gagaaaggat ttccggcgga acggagcgg aagcggagct      960 actaacttca gcctgctgaa gcaggctgga gacgtggagg agaaccctgg acctatgaag     1020
aagctactag caatgattct gtggcttcaa ctagaccgat taagtggaga gctgaaagtg     1080
gaacaaaacc ctctgttcct gagcatgcag gagggaaaaa actataccat ctactgcaat     1140
tattcaacca cttcagacag actgtattgg tacaggcagg atcctgggaa aagtctggaa     1200
tctctgtttg tgttgctatc aaatggagca gtgaagcagg agggacgatt aatggcctca     1260
cttgatacca aagcccgtct cagcaccctc cacatcacag ctgccgtgca tgacctctct     1320
gccacctact tctgtgccgt agccatgaac agagatgaca agatcatctt tggaaaaggg     1380
acacgacttc atattctccc caatatccag aaccctgacc ctgccgtgta ccagctgaga     1440
gactctaaat ccagtgacaa gtctgtctgc ctattcaccg attttgattc tcaaacaaat     1500
gtgtcacaaa gtaaggattc tgatgtgtat atcacagaca aaactgtgct agacatgagg     1560
tctatggact tcaagagcaa cagtgctgtg gcctggagca acaaatctga ctttgcatgt     1620
```

-continued

```
gcaaacgcct tcaacaacag cattattcca gaagacacct tcttccccag cccagaaagt    1680
tcctgtgatg tcaagctggt cgagaaaagc tttgaaacag atacgaacct aaactttcaa    1740
aacctgtcag tgattgggtt ccgaatcctc ctcctgaaag tggccgggtt taatctgctc    1800
atgacgctgc ggctgtggtc cagctga                                        1827

<210> SEQ ID NO 130
<211> LENGTH: 1848
<212> TYPE: DNA
<213> ORGANISM: Artificial Sequence
<220> FEATURE:
<223> OTHER INFORMATION: E170 NT

<400> SEQUENCE: 130
atggacacca gagtactctg ctgtgcggtc atctgtcttc tgggggcagg tctctcaaat      60
gccggcgtca tgcagaaccc aagacacctg gtcaggagga ggggacagga ggcaagactg     120
agatgcagcc caatgaaagg acacagtcat gtttactggt atcggcagct cccagaggaa     180
ggtctgaaat tcatggttta tctccagaaa gaaaatatca tagatgagtc aggaatgcca     240
aaggaacgat tttctgctga atttcccaaa gagggcccca gcatcctgag gatccagcag     300
gtagtgcgag gagattcggc agcttatttc tgtgccagct cacccgcccc cagggcgggc     360
aatcagcccc agcattttgg tgatgggact cgactctcca tcctagagga cctgaaaaac     420
gtgttcccac ccgaggtcgc tgtgtttgag ccatcagaag cagagatctc ccacacccaa     480
aaggccacac tggtgtgcct ggccacaggc ttcttccccg accacgtgga gctgagctgg     540
tgggtgaatg ggaaggaggt gcacagtggg gtcagcacag acccgcagcc cctcaaggag     600
cagcccgccc tcaatgactc cagatactgc ctgagcagcc gcctgagggt ctcggccacc     660
ttctggcaga accccgcaa ccacttccgc tgtcaagtcc agttctacgg gctctcggag     720
aatgacgagt ggaccaggga tagggccaaa cccgtcaccc agatcgtcag cgccgaggcc     780
tggggtagag cagactgtgg ctttacctcg gtgtcctacc agcaagggg cctgtctgcc     840 accatcctct atgagatcct gctagggaag gccaccctgt atgctgtgct ggtcagcgcc     900
cttgtgttga tggccatggt caagagaaag gatttccggc ggaaacggag cggaagcgga     960
gctactaact tcagcctgct gaagcaggct ggagacgtgg aggagaaccc tggacctatg    1020
acatccattc gagctgtatt tatattcctg tggctgcagc tggacttggt gaatggagag    1080
aatgtggagc agcatccttc aaccctgagt gtccaggagg gagacagcgc tgttatcaag    1140
tgtacttatt cagacagtgc ctcaaactac ttcccttggt ataagcaaga acttggaaaa    1200
agacctcagc ttattataga cattcgttca aatgtgggcg aaaagaaaga ccaacgaatt    1260
gctgttacat tgaacaagac agccaaacat ttctccctgc acatcacaga cacccaacct    1320
gaagactcgg ctgtctactt ctgtgcagca agggagggt tttatcaaac tggggcaaac    1380
aacctcttct ttgggactgg aacgagactc accgttattc cctatatcca gaaccctgac    1440
cctgccgtgt accagctgag agactctaaa tccagtgaca agtctgtctg cctattcacc    1500
gattttgatt ctcaaacaaa tgtgtcacaa agtaaggatt ctgatgtgta tatcacagac    1560
aaaactgtgc tagacatgag gtctatggac ttcaagagca cagtgctgt ggcctggagc    1620 aacaaatctg actttgcatg tgcaaacgcc ttcaacaaca gcattattcc agaagacacc    1680
ttcttcccca gcccagaaag ttcctgtgat gtcaagctgg tcgagaaaag ctttgaaaca    1740
gatacgaacc taaactttca aaacctgtca gtgattgggt tccgaatcct cctcctgaaa    1800
gtggccgggt ttaatctgct catgacgctg cggctgtggt ccagctga                 1848
```

-continued

```
<210> SEQ ID NO 131
<211> LENGTH: 1839
<212> TYPE: DNA
<213> ORGANISM: Artificial Sequence
<220> FEATURE:
<223> OTHER INFORMATION: E244/303 NT

<400> SEQUENCE: 131
atgggccccc agctccttgg ctatgtggtc ctttgccttc taggagcagg ccccctggaa        60
gcccaagtga cccagaaccc aagatacctc atcacagtga ctggaaagaa gttaacagtg       120
acttgttctc agaatatgaa ccatgagtat atgtcctggt atcgacaaga cccagggctg       180
ggcttaaggc agatctacta ttcaatgaat gttgaggtga ctgataaggg agatgttcct       240
gaagggtaca aagtctctcg aaaagagaag aggaatttcc ccctgatcct ggagtcgccc       300
agccccaacc agacctctct gtacttctgt gccagcagtc tatatccgcc cggacactcc       360
aatcagcccc agcattttgg tgatgggact cgactctcca tcctagagga cctgaaaaac       420
gtgttcccac ccgaggtcgc tgtgtttgag ccatcagaag cagagatctc ccacacccaa       480
aaggccacac tggtgtgcct ggccacaggc ttcttccccg accacgtgga gctgagctgg       540
tgggtgaatg ggaaggaggt gcacagtggg gtcagcacag acccgcagcc cctcaaggag       600
cagcccgccc tcaatgactc cagatactgc ctgagcagcc gcctgagggt ctcggccacc       660
ttctggcaga accccgcaa ccacttccgc tgtcaagtcc agttctacgg gctctcggag        720
aatgacgagt ggacccagga tagggccaaa cccgtcaccc agatcgtcag cgccgaggcc       780
tggggtagag cagactgtgg ctttacctcg gtgtcctacc agcaaggggt cctgtctgcc       840
accatcctct atgagatcct gctagggaag gccaccctgt atgctgtgct ggtcagcgcc       900
cttgtgttga tggccatggt caagagaaag gatttccggc ggaaacggag cggaagcgga       960
gctactaact tcagcctgct gaagcaggct ggagacgtgg aggagaaccc tggacctatg      1020
acatccattc gagctgtatt tatattcctg tggctgcagc tggacttggt gaatggagag      1080
aatgtggagc agcatccttc aaccctgagt gtccaggagg agacagcgc tgttatcaag       1140 tgtacttatt cagacagtgc ctcaaactac ttcccttggt ataagcaaga acttggaaaa      1200
agacctcagc ttattataga cattcgttca aatgtgggcg aaaagaaaga ccaacgaatt      1260
gctgttacat tgaacaagac agccaaacat ttctccctgc acatcacaga cccccaacct      1320
gaagactcgg ctgtctactt ctgtgcagca accgccggtg gtgctacaaa caagctcatc      1380
tttggaactg gcactctgct tgctgtccag ccaaatatcc agaaccctga ccctgccgtg      1440
taccagctga gagactctaa atccagtgac aagtctgtct gcctattcac cgattttgat      1500
tctcaaacaa atgtgtcaca aagtaaggat tctgatgtgt atatcacaga caaaactgtg      1560
ctagacatga ggtctatgga cttcaagagc aacagtgctg tggcctggag caacaaatct      1620
gactttgcat gtgcaaacgc cttcaacaac agcattattc agaagacac cttcttcccc       1680 agcccagaaa gttcctgtga tgtcaagctg gtcgagaaaa gctttgaaac agatacgaac      1740
ctaaactttc aaaacctgtc agtgattggg ttccgaatcc tcctcctgaa agtggccggg      1800
tttaatctgc tcatgacgct gcggctgtgg tccagctga                           1839

<210> SEQ ID NO 132
<211> LENGTH: 1821
<212> TYPE: DNA
<213> ORGANISM: Artificial Sequence
<220> FEATURE:
```

<223> OTHER INFORMATION: E245 NT

<400> SEQUENCE: 132

```
atgggccctg ggctcctctg ctgggtgctg ctttgtctcc tgggagcagg cccagtggac        60
gctggagtca cccaaagtcc cacacacctg atcaaaacga gaggacagca cgtgactctg       120
agatgctctc ctatctctgg gcacaagagt gtgtcctggt accaacaggt cctgggtcag       180
gggccccagt ttatctttca gtattatgag aaagaagaga gaggaagagg aaacttccct       240
gatcgattct cagctcgcca gttccctaac tatagctctg agctgaatgt gaacgccttg       300
ttgctggggg actcggccct gtatctctgt gccagcagct tggagccggg atggggggat       360
acgcagtatt ttggcccagg caccggctg acagtgctcg aggacctgaa aaacgtgttc       420
ccacccgagg tcgctgtgtt tgagccatca gaagcagaga tctcccacac ccaaaaggcc       480
acactggtgt gcctggccac aggcttcttc cccgaccacg tggagctgag ctggtgggtg       540
aatgggaagg aggtgcacag tggggtcagc acagacccgc agcccctcaa ggagcagccc       600
gccctcaatg actccagata ctgcctgagc agccgcctga gggtctcggc caccttctgg       660
cagaaccccc gcaaccactt ccgctgtcaa gtccagttct acgggctctc ggagaatgac       720
gagtggaccc aggataggc caaacccgtc acccagatcg tcagcgccga ggcctggggt       780
agagcagact gtggctttac ctcggtgtcc taccagcaag gggtcctgtc tgccaccatc       840
ctctatgaga tcctgctagg gaaggccacc ctgtatgctg tgctggtcag cgcccttgtg       900
ttgatggcca tggtcaagag aaaggatttc cggcggaaac ggagcggaag cggagctact       960
aacttcagcc tgctgaagca ggctggagac gtggaggaga accctggacc tatgaagaag      1020
ctactagcaa tgattctgtg gcttcaacta gaccggttaa gtggagagct gaaagtggaa      1080
caaaaccctc tgttcctgag catgcaggag ggaaaaaact ataccatcta ctgcaattat      1140
tcaaccactt cagacagact gtattggtac aggcaggatc ctgggaaaag tctggaatct      1200
ctgtttgtgt tgctatcaaa tggagcagtg aagcaggagg gacgattaat ggcctcactt      1260
gataccaaag cccgtctcag caccctccac atcacagctg ccgtgcatga cctctctgcc      1320
acctacttct gtgccgtgga acttaccggt aaccagttct attttgggac agggacaagt      1380
ttgacggtca ttccaaatat ccagaaccct gaccctgccg tgtaccagct gagagactct      1440
aaatccagtg acaagtctgt ctgcctattc accgattttg attctcaaac aaatgtgtca      1500
caaagtaagg attctgatgt gtatatcaca gacaaaactg tgctagacat gaggtctatg      1560
gacttcaaga gcaacagtgc tgtggcctgg agcaacaaat ctgactttgc atgtgcaaac      1620
gccttcaaca acagcattat tccagaagac accttcttcc ccagcccaga aagttcctgt      1680
gatgtcaagc tggtcgagaa aagctttgaa acagatacga acctaaactt tcaaaacctg      1740
tcagtgattg ggttccgaat cctcctcctg aaagtggccg ggtttaatct gctcatgacg      1800
ctgcggctgt ggtccagctg a                                               1821
```

<210> SEQ ID NO 133
<211> LENGTH: 1812
<212> TYPE: DNA
<213> ORGANISM: Artificial Sequence
<220> FEATURE:
<223> OTHER INFORMATION: E254 NT

<400> SEQUENCE: 133

```
atgggcttca ggctcctctg ctgtgtggcc ttttgtctcc tgggagcagg cccagtggat        60
tctggagtca cacaaacccc aaagcacctg atcacagcaa ctggacagcg agtgacgctg       120
```

```
agatgctccc ctaggtctgg agacctctct gtgtactggt accaacagag cctggaccag        180
ggcctccagt tcctcattca gtattataat ggagaagaga gagcaaaagg aaacattctt        240
gaacgattct ccgcacaaca gttccctgac ttgcactctg aactaaacct gagctctctg        300
gagctggggg actcagcttt gtatttctgt gccagcagcg taggtccatg gtacgagcag        360
tacttcgggc cgggcaccag gctcacggtc acagaggacc tgaaaaacgt gttcccaccc        420
gaggtcgctg tgtttgagcc atcagaagca gagatctccc acacccaaaa ggccacactg        480
gtgtgcctgg ccacaggctt cttccccgac cacgtggagc tgagctggtg ggtgaatggg        540
aaggaggtgc acagtggggt cagcacagac ccgcagcccc tcaaggagca gcccgccctc        600
aatgactcca gatactgcct gagcagccgc ctgagggtct cggccacctt ctggcagaac        660
ccccgcaacc acttccgctg tcaagtccag ttctacgggc tctcggagaa tgacgagtgg        720
acccaggata gggccaaacc cgtcacccag atcgtcagcg ccgaggcctg gggtagagca        780
gactgtggct ttacctcggt gtcctaccag caaggggtcc tgtctgccac catcctctat        840
gagatcctgc tagggaaggc caccctgtat gctgtgctgg tcagcgccct tgtgttgatg        900
gccatggtca agagaaagga tttccggcgg aaacggagcg gaagcggagc tactaacttc        960
agcctgctga agcaggctgg agacgtggag gagaaccctg acctatgaa gaggatattg       1020 ggagctctgc tggggctctt gagtgcccag gtttgctgtg tgagaggaat acaagtggag       1080
cagagtcctc cagacctgat tctccaggag ggagccaatt ccacgctgcg gtgcaatttt       1140
tctgactctg tgaacaattt gcagtggttt catcaaaacc cttggggaca gctcatcaac       1200 ctgtttaca ttccctcagg gacaaaacag aatggaagat taagcgccac gactgtcgct       1260
acggaacgct acagcttatt gtacatttcc tcttcccaga ccacagactc aggcgtttat       1320
ttctgtgctg tgctaaataa caatgacatg cgctttggag cagggaccag actgacagta       1380
aaaccaaata tccagaaccc tgaccctgcc gtgtaccagc tgagagactc taaatccagt       1440
gacaagtctg tctgcctatt caccgatttt gattctcaaa caaatgtgtc acaaagtaag       1500
gattctgatg tgtatatcac agacaaaact gtgctagaca tgaggtctat ggacttcaag       1560
agcaacagtg ctgtggcctg gagcaacaaa tctgactttg catgtgcaaa cgccttcaac       1620
aacagcatta ttccagaaga caccttcttc cccagcccag aaagttcctg tgatgtcaag       1680
ctggtcgaga aaagctttga aacagatacg aacctaaact ttcaaaacct gtcagtgatt       1740
gggttccgaa tcctcctcct gaaagtggcc gggtttaatc tgctcatgac gctgcggctg       1800
tggtccagct ga                                                            1812
```

```
<210> SEQ ID NO 134
<211> LENGTH: 1812
<212> TYPE: DNA
<213> ORGANISM: Artificial Sequence
<220> FEATURE:
<223> OTHER INFORMATION: E301 NT

<400> SEQUENCE: 134
atgggctgca ggctgctctg ctgtgcggtt ctctgtctcc tgggagcagt tcccatagac         60
actgaagtta cccagacacc aaaacacctg gtcatgggaa tgacaaataa gaagtctttg        120
aaatgtgaac aacatatggg gcacagggct atgtattggt acaagcagaa agctaagaag        180
ccaccggagc tcatgtttgt ctacagctat gagaaactct ctataaatga agtgtgcca         240 agtcgcttct cacctgaatg ccccaacagc tctctcttaa accttcacct acacgccctg        300
```

```
cagccagaag actcagccct gtatctctgc gccagcagcc ccgggcgatt ctacgagcag      360
tacttcgggc cgggcaccag gctcacggtc acagaggacc tgaaaaacgt gttcccaccc      420
gaggtcgctg tgtttgagcc atcagaagca gagatctccc acacccaaaa ggccacactg      480
gtgtgcctgg ccacaggctt cttccccgac cacgtggagc tgagctggtg ggtgaatggg      540
aaggaggtgc acagtggggt cagcacagac ccgcagcccc tcaaggagca gcccgccctc      600
aatgactcca gatactgcct gagcagccgc ctgagggtct cggccacctt ctggcagaac      660
ccccgcaacc acttccgctg tcaagtccag ttctacgggc tctcggagaa tgacgagtgg      720
acccaggata gggccaaacc cgtcacccag atcgtcagcg ccgaggcctg gggtagagca      780
gactgtggct ttacctcggt gtcctaccag caaggggtcc tgtctgccac catcctctat      840
gagatcctgc tagggaaggc caccctgtat gctgtgctgg tcagcgccct tgtgttgatg      900
gccatggtca agagaaagga tttccggcgg aaacggagcg gaagcggagc tactaacttc      960
agcctgctga gcaggctgga gacgtggag gagaaccctg gacctatgaa gaggatattg     1020
ggagctctgc tggggctctt gagtgcccag gtttgctgtg tgagaggaat acaagtggag     1080
cagagtcctc cagacctgat tctccaggag ggagccaatt ccacgctgcg gtgcaatttt     1140
tctgactctg tgaacaattt gcagtggttt catcaaaacc cttggggaca gctcatcaac     1200 ctgtttaca ttccctcagg dacaaaacag aatggaagat taagcgccac gactgtcgct     1260
acggaacgct acagcttatt gtacatttcc tcttcccaga ccacagactc aggcgtttat     1320
ttctgtgctg tccttaataa caatgacatg cgctttggag cagggaccag actgacagta     1380
aaaccaaata tccagaaccc tgaccctgcc gtgtaccagc tgagagactc taaatccagt     1440
gacaagtctg tctgcctatt caccgatttt gattctcaaa caaatgtgtc acaaagtaag     1500
gattctgatg tgtatatcac agacaaaact gtgctagaca tgaggtctat ggacttcaag     1560
agcaacagtg ctgtggcctg gagcaacaaa tctgactttg catgtgcaaa cgccttcaac     1620
aacagcatta ttccagaaga caccttcttc cccagcccag aaagttcctg tgatgtcaag     1680
ctggtcgaga aaagctttga aacagatacg aacctaaact ttcaaaacct gtcagtgatt     1740
gggttccgaa tcctcctcct gaaagtggcc gggtttaatc tgctcatgac gctgcggctg     1800
tggtccagct ga                                                         1812
```

<210> SEQ ID NO 135
<211> LENGTH: 1812
<212> TYPE: DNA
<213> ORGANISM: Artificial Sequence
<220> FEATURE:
<223> OTHER INFORMATION: E304 NT

<400> SEQUENCE: 135

```
atgggctgca ggctgctctg ctgtgcggtt ctctgtctcc tgggagcagt tcccatagac       60
actgaagtta cccagacacc aaaacacctg gtcatgggaa tgacaaataa gaagtctttg      120
aaatgtgaac aacatatggg gcacagggct atgtattggt acaagcagaa agctaagaag      180
ccaccggagc tcatgtttgt ctacagctat gagaaactct ctataaatga aagtgtgcca      240
agtcgcttct cacctgaatg ccccaacagc tctctcttaa accttcacct acacgccctg      300
cagccagaag actcagccct gtatctctgc gccagcagcc cggggcggtg gtacgagcag      360
tacttcgggc cgggcaccag gctcacggtc acagaggacc tgaaaaacgt gttcccaccc      420
gaggtcgctg tgtttgagcc atcagaagca gagatctccc acacccaaaa ggccacactg      480
gtgtgcctgg ccacaggctt cttccccgac cacgtggagc tgagctggtg ggtgaatggg      540
```

```
aaggaggtgc acagtggggt cagcacagac ccgcagcccc tcaaggagca gcccgccctc        600
aatgactcca gatactgcct gagcagccgc ctgagggtct cggccacctt ctggcagaac        660
ccccgcaacc acttccgctg tcaagtccag ttctacgggc tctcggagaa tgacgagtgg        720
acccaggata gggccaaacc cgtcacccag atcgtcagcg ccgaggcctg gggtagagca        780
gactgtggct ttacctcggt gtcctaccag caaggggtcc tgtctgccac catcctctat        840
gagatcctgc tagggaaggc caccctgtat gctgtgctgg tcagcgccct tgtgttgatg        900
gccatggtca agagaaagga tttccggcgg aaacggagcg gaagcggagc tactaacttc        960
agcctgctga agcaggctgg agacgtggag gagaaccctg gacctatgaa gaggatattg       1020
ggagctctgc tggggctctt gagtgcccag gtttgctgtg tgagaggaat acaagtggag       1080
cagagtcctc cagacctgat tctccaggag ggagccaatt ccacgctgcg gtgcaatttt       1140
tctgactctg tgaacaattt gcagtggttt catcaaaacc cttggggaca gctcatcaac       1200 ctgtttttaca ttccctcagg acaaaacag aatggaagat taagcgccac gactgtcgct       1260
acggaacgct acagcttatt gtacatttcc tcttcccaga ccacagactc aggcgtttat       1320
ttctgtgctg tggtcgataa caatgacatg cgctttggag cagggaccag actgacagta       1380
aaaccaaata tccagaaccc tgaccctgcc gtgtaccagc tgagagactc taaatccagt       1440
gacaagtctg tctgcctatt caccgatttt gattctcaaa caaatgtgtc acaaagtaag       1500
gattctgatg tgtatatcac agacaaaact gtgctagaca tgaggtctat ggacttcaag       1560
agcaacagtg ctgtggcctg gagcaacaaa tctgactttg catgtgcaaa cgccttcaac       1620
aacagcatta ttccagaaga caccttcttc cccagcccag aaagttcctg tgatgtcaag       1680
ctggtcgaga aaagctttga aacagatacg aacctaaact ttcaaaacct gtcagtgatt       1740
gggttccgaa tcctcctcct gaaagtggcc gggtttaatc tgctcatgac gctgcggctg       1800
tggtccagct ga                                                          1812
```

<210> SEQ ID NO 136
<211> LENGTH: 1827
<212> TYPE: DNA
<213> ORGANISM: Artificial Sequence
<220> FEATURE:
<223> OTHER INFORMATION: E305 NT
<400> SEQUENCE: 136

```
atggatacct ggctcgtatg ctgggcaatt tttagtctct tgaaagcagg actcacagaa         60
cctgaagtca cccagactcc cagccatcag gtcacacaga tgggacagga agtgatcttg        120
cgctgtgtcc ccatctctaa tcacttatac ttctattggt acagacaaat cttggggcag        180
aaagtcgagt ttctggtttc cttttataat aatgaaatct cagagaagtc tgaaatattc        240
gatgatcaat ctcagttga aaggcctgat ggatcaaatt tcactctgaa gatccggtcc        300
acaaagctgg aggactcagc catgtacttc tgtgccagca gtgaaggtcc gacaggtact        360
tcctacgagc agtacttcgg gccgggcacc aggctcacgg tcacagagga cctgaaaaac        420
gtgttcccac ccgaggtcgc tgtgtttgag ccatcagaag cagagatctc ccacacccaa        480
aaggccacac tggtgtgcct ggccacaggc ttcttcccg accacgtgga gctgagctgg        540
tgggtgaatg ggaaggaggt gcacagtggg gtcagcacag accccgcagcc cctcaaggag        600 cagcccgccc tcaatgactc cagatactgc ctgagcagcc gcctgagggt ctcggccacc        660
ttctggcaga accccgcaa ccacttccgc tgtcaagtcc agttctacgg gctctcggag        720
```

```
aatgacgagt ggacccagga tagggccaaa cccgtcaccc agatcgtcag cgccgaggcc      780
tggggtagag cagactgtgg ctttacctcg gtgtcctacc agcaaggggt cctgtctgcc      840
accatcctct atgagatcct gctagggaag gccaccctgt atgctgtgct ggtcagcgcc      900
cttgtgttga tggccatggt caagagaaag gatttccggc ggaaacggag cggaagcgga      960
gctactaact tcagcctgct gaagcaggct ggagacgtgg aggagaaccc tggacctatg     1020
aagaagctac tagcaatgat tctgtggctt caactagacc ggttaagtgg agagctgaaa     1080
gtggaacaaa accctctgtt cctgagcatg caggagggaa aaaactatac catctactgc     1140
aattattcaa ccacttcaga cagactgtat tggtacaggc aggatcctgg gaaaagtctg     1200
gaatctctgt ttgtgttgct atcaaatgga gcagtgaagc aggagggacg attaatggcc     1260
tcacttgata ccaaagcccg tctcagcacc ctccacatca cagctgccgt gcatgacctc     1320
tctgccacct acttctgtgc cgtgaacaca ggctttcaga aacttgtatt tggaactggc     1380
acccgacttc tggtcagtcc aaatatccag aaccctgacc ctgccgtgta ccagctgaga     1440
gactctaaat ccagtgacaa gtctgtctgc ctattcaccg attttgattc tcaaacaaat     1500
gtgtcacaaa gtaaggattc tgatgtgtat atcacagaca aaactgtgct agacatgagg     1560
tctatggact tcaagagcaa cagtgctgtg gcctggagca caaatctga ctttgcatgt      1620 gcaaacgcct tcaacaacag cattattcca gaagacacct tcttccccag cccagaaagt     1680
tcctgtgatg tcaagctggt cgagaaaagc tttgaaacag atacgaacct aaactttcaa     1740
aacctgtcag tgattgggtt ccgaatcctc ctcctgaaag tggccgggtt taatctgctc     1800
atgacgctgc ggctgtggtc cagctga                                        1827
```

```
<210> SEQ ID NO 137
<211> LENGTH: 1848
<212> TYPE: DNA
<213> ORGANISM: Artificial Sequence
<220> FEATURE:
<223> OTHER INFORMATION: E307 NT

<400> SEQUENCE: 137
```

```
atgggcacca ggctcctctg ctgggtggtc ctgggtttcc tagggacaga tcacacaggt       60
gctggagtct cccagtcccc taggtacaaa gtcgcaaaga gaggacagga tgtagctctc      120
aggtgtgatc caatttcggg tcatgtatcc cttttttggt accaacaggc cctggggcag      180
gggccagagt ttctgactta tttccagaat gaagctcaac tagacaaatc ggggctgccc      240
agtgatcgct tctttgcaga aaggcctgag ggatccgtct ccactctgaa gatccagcgc      300
acacagcagg aggactccgc cgtgtatctc tgtgccagca gccaggagag cggggggaca      360
gatacgcagt attttggccc aggcaccccg ctgacagtgc tcgaggacct gaaaaacgtg      420
ttcccacccg aggtcgctgt gtttgagcca tcagaagcag agatctccca cacccaaaag      480
gccacactgg tgtgcctggc cacaggcttc ttccccgacc acgtggagct gagctggtgg      540
gtgaatggga aggaggtgca cagtggggtc agcacagacc cgcagcccct caaggagcag      600
cccgccctca tgactccag atactgcctg agcagccgcc tgagggtctc ggccaccttc      660
tggcagaacc cccgcaacca cttccgctgt caagtccagt ctacgggct ctcggagaat      720 gacgagtgga cccaggatag ggccaaaccc gtcacccaga tcgtcagcgc cgaggcctgg      780
ggtagagcag actgtggctt tacctcggtg tcctaccagc aagggtcct gtctgccacc      840 atcctctatg agatcctgct agggaaggcc accctgtatg ctgtgctggt cagcgccctt      900
gtgttgatgg ccatggtcaa gagaaaggat ttccggcgga aacggagcgg aagcggagct      960
```

```
actaacttca gcctgctgaa gcaggctgga gacgtggagg agaaccctgg acctatgctg    1020
actgccagcc tgttgagggc agtcatagcc tccatctgtg ttgtatccag catggctcag    1080
aaggtaactc aagcgcagac tgaaatttct gtggtggaga aggaggatgt gaccttggac    1140
tgtgtgtatg aaacccgtga tactacttat tacttattct ggtacaagca accaccaagt    1200
ggagaattgg ttttccttat tcgtcggaac tcttttgatg agcaaaatga aataagtggt    1260
cggtattctt ggaacttcca gaaatccacc agttccttca acttcaccat cacagcctca    1320
caagtcgtgg actcagcagt atacttctgt gctctgagtg agccgccctc aggaacctac    1380
aaatacatct ttggaacagg caccaggctg aaggttttag caaatatcca gaaccctgac    1440
cctgccgtgt accagctgag agactctaaa tccagtgaca agtctgtctg cctattcacc    1500
gattttgatt ctcaaacaaa tgtgtcacaa agtaaggatt ctgatgtgta tatcacagac    1560
aaaactgtgc tagacatgag gtctatggac ttcaagagca acagtgctgt ggcctggagc    1620
aacaaatctg actttgcatg tgcaaacgcc ttcaacaaca gcattattcc agaagacacc    1680
ttcttcccca gcccagaaag ttcctgtgat gtcaagctgg tcgagaaaag ctttgaaaca    1740
gatacgaacc taaactttca aaacctgtca gtgattgggt ccgaatcct cctcctgaaa    1800 gtggccgggt ttaatctgct catgacgctg cggctgtggt ccagctga    1848
```

```
<210> SEQ ID NO 138
<211> LENGTH: 1812
<212> TYPE: DNA
<213> ORGANISM: Artificial Sequence
<220> FEATURE:
<223> OTHER INFORMATION: E314 NT

<400> SEQUENCE: 138
```

```
atgggctgca ggctgctctg ctgtgcggtt ctctgtctcc tgggagcagt tcccatagac     60
actgaagtta cccagacacc aaaacacctg gtcatgggaa tgacaaataa gaagtctttg    120
aaatgtgaac aacatatggg gcacagggct atgtattggt acaagcagaa agctaagaag    180
ccaccggagc tcatgtttgt ctacagctat gagaaactct ctataaatga aagtgtgcca    240
agtcgcttct cacctgaatg ccccaacagc tctctcttaa accttcacct cacgccctg    300 cagccagaag actcagccct gtatctctgc gccagcagcc aagggcggtg gtacgagcag    360
tacttcgggc cgggcaccag gctcacggtc acagaggacc tgaaaaacgt gttcccaccc    420
gaggtcgctg tgtttgagcc atcagaagca gagatctccc acacccaaaa ggccacactg    480
gtgtgcctgg ccacaggctt cttccccgac acgtggagc tgagctggtg ggtgaatggg    540
aaggaggtgc acagtggggt cagcacagac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc cgtcacccag atcgtcagcg ccgaggcctg ggtagagca    780 gactgtggct ttacctcggt gtcctaccag caaggggtcc tgtctgccac catcctctat    840
gagatcctgc tagggaaggc caccctgtat gctgtgctgg tcagcgccct tgtgttgatg    900
gccatggtca agagaaagga tttccggcgg aaacggagcg aagcggagc tactaacttc    960 agcctgctga gcaggctgg agacgtggag gagaaccctg acctatgaa gaggatattg    1020 ggagctctgc tggggctctt gagtgcccag gtttgctgtg tgagaggaat acaagtggag    1080
cagagtcctc cagacctgat tctccaggag ggagccaatt ccacgctgcg gtgcaatttt    1140
```

```
tctgactctg tgaacaattt gcagtggttt catcaaaacc cttggggaca gctcatcaac       1200 ctgtttttaca ttccctcagg gacaaaacag aatggaagat taagcgccac gactgtcgct       1260
acggaacgct acagcttatt gtacatttcc tcttcccaga ccacagactc aggcgtttat       1320
ttctgtgctg tgctagataa caatgacatg cgctttggag cagggaccag actgacagta       1380
aaaccaaata tccagaaccc tgaccctgcc gtgtaccagc tgagagactc taaatccagt       1440
gacaagtctg tctgcctatt caccgatttt gattctcaaa caaatgtgtc acaaagtaag       1500
gattctgatg tgtatatcac agacaaaact gtgctagaca tgaggtctat ggacttcaag       1560
agcaacagtg ctgtggcctg gagcaacaaa tctgactttg catgtgcaaa cgccttcaac       1620
aacagcatta ttccagaaga caccttcttc cccagcccag aaagttcctg tgatgtcaag       1680
ctggtcgaga aaagctttga aacagatacg aacctaaact ttcaaaacct gtcagtgatt       1740
gggttccgaa tcctcctcct gaaagtggcc gggtttaatc tgctcatgac gctgcggctg       1800
tggtccagct ga                                                            1812
```

<210> SEQ ID NO 139
<211> LENGTH: 1827
<212> TYPE: DNA
<213> ORGANISM: Artificial Sequence
<220> FEATURE:
<223> OTHER INFORMATION: E315 NT

<400> SEQUENCE: 139

```
atgggcacca ggctcctctg ctgggcggcc ctctgtctcc tgggagcaga actcacagaa        60
gctggagttg cccagtctcc cagatataag attatagaga aaaggcagag tgtggctttt       120
tggtgcaatc ctatatctgg ccatgctacc ctttactggt accagcagat cctgggacag       180
ggcccaaagc ttctgattca gtttcagaat aacggtgtag tggatgattc acagttgcct       240
aaggatcgat tttctgcaga gaggctcaaa ggagtagact ccactctcaa gatccagcct       300
gcaaagcttg aggactcggc cgtgtatctc tgtgccagca gcgtcttccc tactagcgtc       360
gagcagtact tcgggccggg caccaggctc acggtcacag aggacctgaa aaacgtgttc       420
ccacccgagt cgctgtgtgtt tgagccatca gaagcagaga tctcccacac ccaaaaggcc       480
acactggtgt gcctggccac aggcttcttc cccgaccacg tggagctgag ctggtgggtg       540
aatgggaagg aggtgcacag tggggtcagc acagacccgc agcccctcaa ggagcagccc       600
gccctcaatg actccagata ctgcctgagc agccgcctga gggtctcggc caccttctgg       660 cagaacccccc gcaaccactt ccgctgtcaa gtccagttct acgggctctc ggagaatgac       720
gagtggaccc aggataggc caaacccgtc acccagatcg tcagcgccga ggcctggggt       780
agagcagact gtggctttac ctcggtgtcc taccagcaag gggtcctgtc tgccaccatc       840
ctctatgaga tcctgctagg gaaggccacc ctgtatgctg tgctggtcag cgcccttgtg       900
ttgatggcca tggtcaagag aaaggatttc cggcggaaac ggagcggaag cggagctact       960
aacttcagcc tgctgaagca ggctggagac gtggaggaga accctggacc tatggagacc      1020
ctcttgggcc tgcttatcct ttggctgcag ctgcaatggg tgagcagcaa acaggaggtg      1080
acgcagattc ctgcagctct gagtgtccca gaaggagaaa acttggttct caactgcagt      1140
ttcactgata gcgctatttta caacctccag tggtttaggc aggaccctgg gaaaggtctc      1200
acatctctgt tgcttattca gtcaagtcag agagagcaaa caagtggaag acttaatgcc      1260
tcgctggata aatcatcagg acgtagtact ttatacattg cagcttctca gcctggtgac      1320
tcagccacct acctctgtgc tggtaaaacc tcctacgaca aggtgatatt tgggccaggg      1380
```

-continued

```
acaagcttat cagtcattcc aaatatccag aaccctgacc ctgccgtgta ccagctgaga   1440
gactctaaat ccagtgacaa gtctgtctgc ctattcaccg attttgattc tcaaacaaat   1500
gtgtcacaaa gtaaggattc tgatgtgtat atcacagaca aaactgtgct agacatgagg   1560
tctatggact tcaagagcaa cagtgctgtg gcctggagca caaatctgat ctttgcatgt   1620
gcaaacgcct tcaacaacag cattattcca gaagacacct tcttccccag cccagaaagt   1680
tcctgtgatg tcaagctggt cgagaaaagc tttgaaacag atacgaacct aaactttcaa   1740
aacctgtcag tgattgggtt ccgaatcctc ctcctgaaag tggccgggtt taatctgctc   1800
atgacgctgc ggctgtggtc cagctga                                       1827
```

```
<210> SEQ ID NO 140
<211> LENGTH: 1851
<212> TYPE: DNA
<213> ORGANISM: Artificial Sequence
<220> FEATURE:
<223> OTHER INFORMATION: E316 NT

<400> SEQUENCE: 140
atgagcaacc aggtgctctg ctgtgtggtc ctttgtctcc tgggagcaaa caccgtggat     60
ggtggaatca ctcagtcccc gaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact ttcagaaagg agatatagct    240
gaagggtaca gcgtctctcg ggagaagaag gaatcctttc ctctcactgt gacatcggcc    300
caaaagaacc cgacagcttt ctatctctgt gccagtagta tcggtgtggg gttatctaac    360
actgaagctt tctttggaca aggcaccaga ctcacagttg tagaggacct gaaaaacgtg    420
ttcccacccg aggtcgctgt gtttgagcca tcagaagcag agatctccca cacccaaaag    480
gccacactgg tgtgcctggc cacaggcttc ttccccgacc acgtggagct gagctggtgg    540
gtgaatggga aggaggtgca cagtgggggtc agcacagacc cgcagcccct caaggagcag    600
cccgccctca atgactccag atactgcctg agcagccgcc tgagggtctc ggccaccttc    660
tggcagaacc cccgcaacca cttccgctgt caagtccagt tctacgggct ctcggagaat    720
gacgagtgga cccaggatag ggccaaaccc gtcacccaga tcgtcagcgc cgaggcctgg    780
ggtagagcag actgtggctt tacctcggtg tcctaccagc aaggggtcct gtctgccacc    840
atcctctatg agatcctgct agggaaggcc accctgtatg ctgtgctggt cagcgccctt    900
gtgttgatgg ccatggtcaa gagaaaggat ttccggcgga acggagcgg aagcggagct    960 actaacttca gcctgctgaa gcaggctgga cgtggagg agaaccctgg acctatgtca   1020
ctttctagcc tgctgaaggt ggtcacagct tcactgtggc taggacctgg cattgcccag   1080
aagataactc aaacccaacc aggaatgttc gtgcaggaaa aggaggctgt gactctggac   1140
tgcacatatg acaccagtga tcaaagttat ggtctattct ggtacaagca gcccagcagt   1200
ggggaaatga ttttttcttat ttatcagggg tcttatgacg agcaaaatgc aacagaaggt   1260
cgctactcat tgaatttcca gaaggcaaga aaatccgcca accttgtcat ctccgcttca   1320
caactggggg actcagcaat gtatttctgt gcatggtct cgggggcagg aggaggtgct   1380
gacggactca cctttggcaa agggactcat ctaatcatcc agccctatat ccagaaccct   1440
gaccctgccg tgtaccagct gagagactct aaatccagtg acaagtctgt ctgcctattc   1500
accgattttg attctcaaac aaatgtgtca caaagtaagg attctgatgt gtatatcaca   1560
```

-continued

```
gacaaaactg tgctagacat gaggtctatg gacttcaaga gcaacagtgc tgtggcctgg    1620
agcaacaaat ctgactttgc atgtgcaaac gccttcaaca acagcattat tccagaagac    1680
accttcttcc ccagcccaga aagttcctgt gatgtcaagc tggtcgagaa aagctttgaa    1740
acagatacga acctaaactt tcaaaacctg tcagtgattg ggttccgaat cctcctcctg    1800
aaagtggccg ggtttaatct gctcatgacg ctgcggctgt ggtccagctg a             1851
```

```
<210> SEQ ID NO 141
<211> LENGTH: 1830
<212> TYPE: DNA
<213> ORGANISM: Artificial Sequence
<220> FEATURE:
<223> OTHER INFORMATION: E317 NT

<400> SEQUENCE: 141
```

```
atgggccccc agctccttgg ctatgtggtc ctttgccttc taggagcagg cccccctggaa     60 gcccaagtga cccagaaccc aagatacctc atcacagtga ctggaaagaa gttaacagtg    120
acttgttctc agaatatgaa ccatgagtat atgtcctggt atcgacaaga cccagggctg    180
ggcttaaggc agatctacta ttcaatgaat gttgaggtga ctgataaggg agatgttcct    240
gaagggtaca aagtctctcg aaaagagaag aggaatttcc ccctgatcct ggagtcgccc    300
agccccaacc agacctctct gtacttctgt gccagcagtt tatggacaag taattcaccc    360
ctccactttg ggaacgggac caggctcact gtgacagagg acctgaaaaa cgtgttccca    420
cccgaggtcg ctgtgtttga gccatcagaa gcagagatct cccacaccca aaaggccaca    480
ctggtgtgcc tggccacagg cttcttcccc gaccacgtgg agctgagctg gtgggtgaat    540
gggaaggagg tgcacagtgg ggtcagcaca gacccgcagc ccctcaagga gcagcccgcc    600
ctcaatgact ccagatactg cctgagcagc cgcctgaggg tctcggccac cttctggcag    660
aacccccgca accacttccg ctgtcaagtc cagttctacg ggctctcgga gaatgacgag    720
tggacccagg atagggccaa acccgtcacc cagatcgtca gcgccgaggc ctgggggtaga    780 gcagactgtg gctttacctc ggtgtcctac cagcaagggg tcctgtctgc caccatcctc    840
tatgagatcc tgctagggaa ggccacccctg tatgctgtgc tggtcagcgc ccttgtgttg    900
atggccatgg tcaagagaaa ggatttccgg cggaacgga gcggaagcgg agctactaac    960
ttcagcctgc tgaagcaggc tggagacgtg gaggagaacc ctggacctat ggcaggcatt   1020
cgagctttat ttatgtactt gtggctgcag ctggactggg tgagcagagg agagagtgtg   1080
gggctgcatc ttcctaccct gagtgtccag gagggtgaca actctattat caactgtgct   1140
tattcaaaca gcgcctcaga ctacttcatt tggtacaagc aagaatctgg aaaaggtcct   1200
caattcatta tagacattcg ttcaaatatg gacaaaggc aaggccaaag agtcaccgtt   1260
ttattgaata agacagtgaa acatctctct ctgcaaattg cagctactca acctggagac   1320
tcagctgtct acttttgtgc agagacccca gggggttacc agaaagttac ctttggaact   1380
ggaacaaagc tccaagtcat cccaaatatc cagaaccctg accctgccgt gtaccagctg   1440
agagactcta aatccagtga caagtctgtc tgcctattca ccgattttga ttctcaaaca   1500
aatgtgtcac aaagtaagga ttctgatgtg tatatcacag acaaaactgt gctagacatg   1560
aggtctatgg acttcaagag caacagtgct gtggcctgga gcaacaaatc tgactttgca   1620
tgtgcaaacg ccttcaacaa cagcattatt ccagaagaca ccttcttccc cagcccagaa   1680
agttcctgtg atgtcaagct ggtcgagaaa agctttgaaa cagatacgaa cctaaacttt   1740
caaaacctgt cagtgattgg gttccgaatc ctcctcctga aagtggccgg gtttaatctg   1800
```

-continued

```
ctcatgacgc tgcggctgtg gtccagctga                                    1830

<210> SEQ ID NO 142
<211> LENGTH: 1830
<212> TYPE: DNA
<213> ORGANISM: Artificial Sequence
<220> FEATURE:
<223> OTHER INFORMATION: E318 NT

<400> SEQUENCE: 142
atggactcct ggaccttctg ctgtgtgtcc ctttgcatcc tggtagcgaa gcatacagat        60
gctggagtta tccagtcacc ccgccatgag gtgacagaga tgggacaaga agtgactctg       120
agatgtaaac caatttcagg ccacaactcc cttttctggt acagacagac catgatgcgg       180
ggactggagt tgctcattta ctttaacaac aacgttccga tagatgattc agggatgccc       240
gaggatcgat tctcagctaa gatgcctaat gcatcattct ccactctgaa gatccagccc       300
tcagaaccca gggactcagc tgtgtacttc tgtgccagca gtttgggggc agggcattta       360
tggggctaca ccttcggttc ggggaccagg ttaaccgttg tagaggacct gaaaaacgtg       420
ttcccacccg aggtcgctgt gtttgagcca tcagaagcag agatctccca cacccaaaag       480
gccacactgg tgtgcctggc cacaggcttc ttccccgacc acgtggagct gagctggtgg       540
gtgaatggga aggaggtgca cagtggggtc agcacagacc cgcagcccct caaggagcag       600
cccgccctca tgactccag atactgcctg agcagccgcc tgagggtctc ggccaccttc       660
tggcagaacc cccgcaacca cttccgctgt caagtccagt tctacgggct ctcggagaat       720
gacgagtgga cccaggatag ggccaaaccc gtcacccaga tcgtcagcgc cgaggcctgg       780
ggtagagcag actgtggctt tacctcggtg tcctaccagc aagggtcct gtctgccacc        840 atcctctatg agatcctgct agggaaggcc accctgtatg ctgtgctggt cagcgccctt       900
gtgttgatgg ccatggtcaa gagaaaggat ttccggcgga acggagcgg aagcggagct        960 actaacttca gcctgctgaa gcaggctgga gacgtggagg agaaccctgg acctatgaca      1020
tccattcgag ctgtatttat attcctgtgg ctgcagctgg acttggtgaa tggagagaat      1080
gtggagcagc atccttcaac cctgagtgtc caggagggag acagcgctgt tatcaagtgt      1140
acttattcag acagtgcctc aaactacttc ccttggtata gcaagaact tggaaaaaga       1200 cctcagctta ttatagacat tcgttcaaat gtgggcgaaa agaaagacca acgaattgct      1260
gttacattga acaagacagc caaacatttc tccctgcaca tcacagagac ccaacctgaa      1320
gactcggctg tctacttctg tgcagcttcg aacagagatg acaagatcat ctttggaaaa      1380
gggacacgac ttcatattct ccccaatatc cagaaccctg accctgccgt gtaccagctg      1440
agagactcta atccagtga caagtctgtc tgcctattca ccgatttga ttctcaaaca        1500 aatgtgtcac aaagtaagga ttctgatgtg tatatcacag acaaaactgt gctagacatg      1560
aggtctatgg acttcaagag caacagtgct gtggcctgga gcaacaaatc tgactttgca      1620
tgtgcaaacg ccttcaacaa cagcattatt ccagaagaca ccttcttccc cagcccagaa      1680
agttcctgtg atgtcaagct ggtcgagaaa agctttgaaa cagatacgaa cctaaacttt      1740
caaaacctgt cagtgattgg gttccgaatc ctcctcctga agtggccgg gtttaatctg       1800 ctcatgacgc tgcggctgtg gtccagctga                                      1830

<210> SEQ ID NO 143
<211> LENGTH: 1830
<212> TYPE: DNA
```

-continued

```
<213> ORGANISM: Artificial Sequence
<220> FEATURE:
<223> OTHER INFORMATION: E320 NT

<400> SEQUENCE: 143
atgggcacca ggctcctctg ctgggtggtc ctgggtttcc tagggacaga tcacacaggt      60
gctggagtct cccagtcccc taggtacaaa gtcgcaaaga gaggacagga tgtagctctc     120
aggtgtgatc caatttcggg tcatgtatcc cttttttggt accaacaggc cctggggcag     180
gggccagagt ttctgactta tttccagaat gaagctcaac tagacaaatc ggggctgccc     240
agtgatcgct tctttgcaga aaggcctgag ggatccgtct ccactctgaa gatccagcgc     300
acacagcagg aggactccgc cgtgtatctc tgtgccagca gggaaggggt ggggctctac     360
gagcagtact cgggccgggg caccaggctc acggtcacag aggacctgaa aaacgtgttc     420
ccacccgagg tcgctgtgtt tgagccatca gaagcagaga tctcccacac ccaaaaggcc     480
acactggtgt gcctggccac aggcttcttc cccgaccacg tggagctgag ctggtgggtg     540
aatgggaagg aggtgcacag tggggtcagc acagacccgc agcccctcaa ggagcagccc     600
gccctcaatg actccagata ctgcctgagc agccgcctga gggtctcggc caccttctgg     660 cagaacccc gcaaccactt ccgctgtcaa gtccagttct acgggctctc ggagaatgac     720
gagtggaccc aggataggc caaacccgtc acccagatcg tcagcgccga ggcctggggt     780
agagcagact gtggctttac ctcggtgtcc taccagcaag gggtcctgtc tgccaccatc     840
ctctatgaga tcctgctagg gaaggccacc ctgtatgctg tgctggtcag cgcccttgtg     900
ttgatggcca tggtcaagag aaaggatttc cggcggaaac ggagcggaag cggagctact     960
aacttcagcc tgctgaagca ggctggagac gtggaggaga accctggacc tatgaagaag    1020
ctactagcaa tgattctgtg gcttcaacta gaccggttaa gtggagagct gaaagtggaa    1080
caaaaccctc tgttcctgag catgcaggag ggaaaaaact ataccatcta ctgcaattat    1140
tcaaccactt cagacagact gtattggtac aggcaggatc ctgggaaaag tctggaatct    1200
ctgtttgtgt tgctatcaaa tggagcagtg aagcaggagg gacgattaat ggcctcactt    1260
gataccaaag cccgtctcag caccctccac atcacagctg ccgtgcatga cctctctgcc    1320
acctacttct gtgccgtgga cataggtacg gaatatggaa acaagctggt ctttggcgca    1380
ggaaccattc tgagagtcaa gtcctatatc cagaaccctg accctgccgt gtaccagctg    1440
agagactcta atccagtga caagtctgtc tgcctattca ccgattttga ttctcaaaca    1500
aatgtgtcac aaagtaagga ttctgatgtg tatatcacag acaaaactgt gctagacatg    1560
aggtctatgg acttcaagag caacagtgct gtggcctgga gcaacaaatc tgactttgca    1620
tgtgcaaacg ccttcaacaa cagcattatt ccagaagaca ccttcttccc cagcccagaa    1680
agttcctgtg atgtcaagct ggtcgagaaa agctttgaaa cagatacgaa cctaaacttt    1740
caaaacctgt cagtgattgg gttccgaatc ctcctcctga aagtggccgg gtttaatctg    1800
ctcatgacgc tgcggctgtg gtccagctga                                     1830
```

```
<210> SEQ ID NO 144
<211> LENGTH: 23
<212> TYPE: DNA
<213> ORGANISM: Artificial Sequence
<220> FEATURE:
<223> OTHER INFORMATION: Primer

<400> SEQUENCE: 144
tcaggcagta tctggagtca ttg                                               23
```

<210> SEQ ID NO 145
<211> LENGTH: 20
<212> TYPE: DNA
<213> ORGANISM: Artificial Sequence
<220> FEATURE:
<223> OTHER INFORMATION: Primer

<400> SEQUENCE: 145
gcacctcctt cccattcacc                                                                          20

<210> SEQ ID NO 146
<211> LENGTH: 22
<212> TYPE: DNA
<213> ORGANISM: Artificial Sequence
<220> FEATURE:
<223> OTHER INFORMATION: Primer

<400> SEQUENCE: 146
gcttctgatg gctcaaacac ag                                                                       22

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
atggatacct ggctcgtatg c                                                                        21

<210> SEQ ID NO 148
<211> LENGTH: 18
<212> TYPE: DNA
<213> ORGANISM: Artificial Sequence
<220> FEATURE:
<223> OTHER INFORMATION: Primer

<400> SEQUENCE: 148
atgggctgca ggctcctc                                                                            18

<210> SEQ ID NO 149
<211> LENGTH: 18
<212> TYPE: DNA
<213> ORGANISM: Artificial Sequence
<220> FEATURE:
<223> OTHER INFORMATION: Primer

<400> SEQUENCE: 149
atgggctgca ggctgctc                                                                            18

<210> SEQ ID NO 150
<211> LENGTH: 19
<212> TYPE: DNA
<213> ORGANISM: Artificial Sequence
<220> FEATURE:
<223> OTHER INFORMATION: Primer

<400> SEQUENCE: 150
atgggctcca ggctgctct                                                                           19

<210> SEQ ID NO 151
<211> LENGTH: 14
<212> TYPE: DNA
<213> ORGANISM: Artificial Sequence
<220> FEATURE:

-continued

<223> OTHER INFORMATION: Primer

<400> SEQUENCE: 151
atgggccccg ggct                                                   14

<210> SEQ ID NO 152
<211> LENGTH: 17
<212> TYPE: DNA
<213> ORGANISM: Artificial Sequence
<220> FEATURE:
<223> OTHER INFORMATION: Primer

<400> SEQUENCE: 152
atgggccctg ggctcct                                                17

<210> SEQ ID NO 153
<211> LENGTH: 19
<212> TYPE: DNA
<213> ORGANISM: Artificial Sequence
<220> FEATURE:
<223> OTHER INFORMATION: Primer

<400> SEQUENCE: 153
atgggaccca ggctcctct                                              19

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
atgagcatcg ggctcctgtg                                             20

<210> SEQ ID NO 155
<211> LENGTH: 18
<212> TYPE: DNA
<213> ORGANISM: Artificial Sequence
<220> FEATURE:
<223> OTHER INFORMATION: Primer

<400> SEQUENCE: 155
atgagcctcg ggctcctg                                               18

<210> SEQ ID NO 156
<211> LENGTH: 21
<212> TYPE: DNA
<213> ORGANISM: Artificial Sequence
<220> FEATURE:
<223> OTHER INFORMATION: Primer

<400> SEQUENCE: 156
atgagaatca ggctcctgtg c                                           21

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
atgagcatcg gcctcctgtg                                             20

-continued

```
<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
atgagcatca gcctcctgtg                                               20

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
atgggcacaa ggctcctctg                                               20

<210> SEQ ID NO 160
<211> LENGTH: 18
<212> TYPE: DNA
<213> ORGANISM: Artificial Sequence
<220> FEATURE:
<223> OTHER INFORMATION: Primer

<400> SEQUENCE: 160
atgggcacca ggctcctc                                                 18

<210> SEQ ID NO 161
<211> LENGTH: 21
<212> TYPE: DNA
<213> ORGANISM: Artificial Sequence
<220> FEATURE:
<223> OTHER INFORMATION: Primer

<400> SEQUENCE: 161
atgggcacca gtctcctatg c                                             21

<210> SEQ ID NO 162
<211> LENGTH: 23
<212> TYPE: DNA
<213> ORGANISM: Artificial Sequence
<220> FEATURE:
<223> OTHER INFORMATION: Primer

<400> SEQUENCE: 162
atgggtacca gtctcctatg ctg                                           23

<210> SEQ ID NO 163
<211> LENGTH: 18
<212> TYPE: DNA
<213> ORGANISM: Artificial Sequence
<220> FEATURE:
<223> OTHER INFORMATION: Primer

<400> SEQUENCE: 163
atgggcacca gcctcctc                                                 18

<210> SEQ ID NO 164
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 164
atgggcttca ggctcctctg                                                  20

<210> SEQ ID NO 165
<211> LENGTH: 21
<212> TYPE: DNA
<213> ORGANISM: Artificial Sequence
<220> FEATURE:
<223> OTHER INFORMATION: Primer

<400> SEQUENCE: 165
atgggcacga ggctcttctt c                                                 21

<210> SEQ ID NO 166
<211> LENGTH: 21
<212> TYPE: DNA
<213> ORGANISM: Artificial Sequence
<220> FEATURE:
<223> OTHER INFORMATION: Primer

<400> SEQUENCE: 166
atgggcacca ggctcttctt c                                                 21

<210> SEQ ID NO 167
<211> LENGTH: 21
<212> TYPE: DNA
<213> ORGANISM: Artificial Sequence
<220> FEATURE:
<223> OTHER INFORMATION: Primer

<400> SEQUENCE: 167
atgggcacaa ggttgttctt c                                                 21

<210> SEQ ID NO 168
<211> LENGTH: 21
<212> TYPE: DNA
<213> ORGANISM: Artificial Sequence
<220> FEATURE:
<223> OTHER INFORMATION: Primer

<400> SEQUENCE: 168
atgagcacca ggcttctctg c                                                 21

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
atgggtacca ggctcctctg                                                  20

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
atggactcct ggaccttctg ct                                               22

<210> SEQ ID NO 171
<211> LENGTH: 20
```

-continued

```
<212> TYPE: DNA
<213> ORGANISM: Artificial Sequence
<220> FEATURE:
<223> OTHER INFORMATION: Primer

<400> SEQUENCE: 171
atggactcct ggaccctctg                                                20

<210> SEQ ID NO 172
<211> LENGTH: 18
<212> TYPE: DNA
<213> ORGANISM: Artificial Sequence
<220> FEATURE:
<223> OTHER INFORMATION: Primer

<400> SEQUENCE: 172
atggccacca ggctcctc                                                  18

<210> SEQ ID NO 173
<211> LENGTH: 22
<212> TYPE: DNA
<213> ORGANISM: Artificial Sequence
<220> FEATURE:
<223> OTHER INFORMATION: Primer

<400> SEQUENCE: 173
atgcttagtc ctgacctgcc tg                                             22

<210> SEQ ID NO 174
<211> LENGTH: 22
<212> TYPE: DNA
<213> ORGANISM: Artificial Sequence
<220> FEATURE:
<223> OTHER INFORMATION: Primer

<400> SEQUENCE: 174
atggtttcca ggcttctcag tt                                             22

<210> SEQ ID NO 175
<211> LENGTH: 19
<212> TYPE: DNA
<213> ORGANISM: Artificial Sequence
<220> FEATURE:
<223> OTHER INFORMATION: Primer

<400> SEQUENCE: 175
atgggtcctg ggcttctcc                                                 19

<210> SEQ ID NO 176
<211> LENGTH: 22
<212> TYPE: DNA
<213> ORGANISM: Artificial Sequence
<220> FEATURE:
<223> OTHER INFORMATION: Primer

<400> SEQUENCE: 176
atgagcccaa tattcacctg ca                                             22

<210> SEQ ID NO 177
<211> LENGTH: 22
<212> TYPE: DNA
<213> ORGANISM: Artificial Sequence
<220> FEATURE:
<223> OTHER INFORMATION: Primer

<400> SEQUENCE: 177
```

-continued

```
atggatatct ggctcctctg ct                                      22

<210> SEQ ID NO 178
<211> LENGTH: 23
<212> TYPE: DNA
<213> ORGANISM: Artificial Sequence
<220> FEATURE:
<223> OTHER INFORMATION: Primer

<400> SEQUENCE: 178
atggacacca gagtactctg ctg                                     23

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
atgagcaacc aggtgctctg                                         20

<210> SEQ ID NO 180
<211> LENGTH: 19
<212> TYPE: DNA
<213> ORGANISM: Artificial Sequence
<220> FEATURE:
<223> OTHER INFORMATION: Primer

<400> SEQUENCE: 180
atgctgctgc ttctgctgc                                          19

<210> SEQ ID NO 181
<211> LENGTH: 24
<212> TYPE: DNA
<213> ORGANISM: Artificial Sequence
<220> FEATURE:
<223> OTHER INFORMATION: Primer

<400> SEQUENCE: 181
atgactatca ggctcctctg ctac                                    24

<210> SEQ ID NO 182
<211> LENGTH: 16
<212> TYPE: DNA
<213> ORGANISM: Artificial Sequence
<220> FEATURE:
<223> OTHER INFORMATION: Primer

<400> SEQUENCE: 182
atgggccccc agctcc                                             16

<210> SEQ ID NO 183
<211> LENGTH: 22
<212> TYPE: DNA
<213> ORGANISM: Artificial Sequence
<220> FEATURE:
<223> OTHER INFORMATION: Primer

<400> SEQUENCE: 183
atgggaatca ggctcctctg tc                                      22

<210> SEQ ID NO 184
<211> LENGTH: 24
<212> TYPE: DNA
<213> ORGANISM: Artificial Sequence
```

-continued

```
<220> FEATURE:
<223> OTHER INFORMATION: Primer

<400> SEQUENCE: 184
atgctgagtc ttctgctcct tctc                                          24

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185
atgctctgct ctctccttgc                                               20

<210> SEQ ID NO 186
<211> LENGTH: 22
<212> TYPE: DNA
<213> ORGANISM: Artificial Sequence
<220> FEATURE:
<223> OTHER INFORMATION: Primer

<400> SEQUENCE: 186
tcactctgaa gatccggtcc ac                                            22

<210> SEQ ID NO 187
<211> LENGTH: 22
<212> TYPE: DNA
<213> ORGANISM: Artificial Sequence
<220> FEATURE:
<223> OTHER INFORMATION: Primer

<400> SEQUENCE: 187
cttcacatca attccctgga gc                                            22

<210> SEQ ID NO 188
<211> LENGTH: 19
<212> TYPE: DNA
<213> ORGANISM: Artificial Sequence
<220> FEATURE:
<223> OTHER INFORMATION: Primer

<400> SEQUENCE: 188
cacctgaatg ccccaacag                                                19

<210> SEQ ID NO 189
<211> LENGTH: 21
<212> TYPE: DNA
<213> ORGANISM: Artificial Sequence
<220> FEATURE:
<223> OTHER INFORMATION: Primer

<400> SEQUENCE: 189
agtcgcttct cacctgaatg c                                             21

<210> SEQ ID NO 190
<211> LENGTH: 24
<212> TYPE: DNA
<213> ORGANISM: Artificial Sequence
<220> FEATURE:
<223> OTHER INFORMATION: Primer

<400> SEQUENCE: 190
gagatgaatg tgagcacctt ggag                                          24
```

-continued

```
<210> SEQ ID NO 191
<211> LENGTH: 24
<212> TYPE: DNA
<213> ORGANISM: Artificial Sequence
<220> FEATURE:
<223> OTHER INFORMATION: Primer

<400> SEQUENCE: 191
gagatgaatg tgagtgcctt ggag                                          24

<210> SEQ ID NO 192
<211> LENGTH: 22
<212> TYPE: DNA
<213> ORGANISM: Artificial Sequence
<220> FEATURE:
<223> OTHER INFORMATION: Primer

<400> SEQUENCE: 192
gctctgagct gaatgtgaac gc                                            22

<210> SEQ ID NO 193
<211> LENGTH: 22
<212> TYPE: DNA
<213> ORGANISM: Artificial Sequence
<220> FEATURE:
<223> OTHER INFORMATION: Primer

<400> SEQUENCE: 193
gaagtcccca atggctacaa tg                                            22

<210> SEQ ID NO 194
<211> LENGTH: 21
<212> TYPE: DNA
<213> ORGANISM: Artificial Sequence
<220> FEATURE:
<223> OTHER INFORMATION: Primer

<400> SEQUENCE: 194
aggtccctga tggctacaat g                                             21

<210> SEQ ID NO 195
<211> LENGTH: 20
<212> TYPE: DNA
<213> ORGANISM: Artificial Sequence
<220> FEATURE:
<223> OTHER INFORMATION: Primer

<400> SEQUENCE: 195
tggcgtctgc tgtaccctct                                               20

<210> SEQ ID NO 196
<211> LENGTH: 20
<212> TYPE: DNA
<213> ORGANISM: Artificial Sequence
<220> FEATURE:
<223> OTHER INFORMATION: Primer

<400> SEQUENCE: 196
acagaggatt tcccgctcag                                               20

<210> SEQ ID NO 197
<211> LENGTH: 20
<212> TYPE: DNA
<213> ORGANISM: Artificial Sequence
<220> FEATURE:
<223> OTHER INFORMATION: Primer
```

```
<400> SEQUENCE: 197
cccctcaagc tggagtcagc                                            20

<210> SEQ ID NO 198
<211> LENGTH: 23
<212> TYPE: DNA
<213> ORGANISM: Artificial Sequence
<220> FEATURE:
<223> OTHER INFORMATION: Primer

<400> SEQUENCE: 198
acacagagga tttcccactc agg                                        23

<210> SEQ ID NO 199
<211> LENGTH: 22
<212> TYPE: DNA
<213> ORGANISM: Artificial Sequence
<220> FEATURE:
<223> OTHER INFORMATION: Primer

<400> SEQUENCE: 199
ttctctgcac agaggtctga gg                                         22

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
gctgcccagt gatcgcttct                                            20

<210> SEQ ID NO 201
<211> LENGTH: 22
<212> TYPE: DNA
<213> ORGANISM: Artificial Sequence
<220> FEATURE:
<223> OTHER INFORMATION: Primer

<400> SEQUENCE: 201
actctgaaga tccagcgcac ag                                         22

<210> SEQ ID NO 202
<211> LENGTH: 23
<212> TYPE: DNA
<213> ORGANISM: Artificial Sequence
<220> FEATURE:
<223> OTHER INFORMATION: Primer

<400> SEQUENCE: 202
cgtctccact ctgaagatcc agc                                        23

<210> SEQ ID NO 203
<211> LENGTH: 20
<212> TYPE: DNA
<213> ORGANISM: Artificial Sequence
<220> FEATURE:
<223> OTHER INFORMATION: Primer

<400> SEQUENCE: 203
ggcctgaggg atccatctcc                                            20

<210> SEQ ID NO 204
```

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 204
ggctgctcag tgatcggttc                                                    20

<210> SEQ ID NO 205
<211> LENGTH: 22
<212> TYPE: DNA
<213> ORGANISM: Artificial Sequence
<220> FEATURE:
<223> OTHER INFORMATION: Primer

<400> SEQUENCE: 205
gaacgattct ccgcacaaca gt                                                 22

<210> SEQ ID NO 206
<211> LENGTH: 24
<212> TYPE: DNA
<213> ORGANISM: Artificial Sequence
<220> FEATURE:
<223> OTHER INFORMATION: Primer

<400> SEQUENCE: 206
acaaaggaga agtctcagat ggct                                               24

<210> SEQ ID NO 207
<211> LENGTH: 22
<212> TYPE: DNA
<213> ORGANISM: Artificial Sequence
<220> FEATURE:
<223> OTHER INFORMATION: Primer

<400> SEQUENCE: 207
ccctcactct ggagtcagct ac                                                 22

<210> SEQ ID NO 208
<211> LENGTH: 21
<212> TYPE: DNA
<213> ORGANISM: Artificial Sequence
<220> FEATURE:
<223> OTHER INFORMATION: Primer

<400> SEQUENCE: 208
cctcactctg gagtccgcta c                                                  21

<210> SEQ ID NO 209
<211> LENGTH: 24
<212> TYPE: DNA
<213> ORGANISM: Artificial Sequence
<220> FEATURE:
<223> OTHER INFORMATION: Primer

<400> SEQUENCE: 209
gcagagaggc tcaaaggagt agac                                               24

<210> SEQ ID NO 210
<211> LENGTH: 20
<212> TYPE: DNA
<213> ORGANISM: Artificial Sequence
<220> FEATURE:
<223> OTHER INFORMATION: Primer

<400> SEQUENCE: 210
```

-continued atccagccct cagaacccag                                        20

<210> SEQ ID NO 211
<211> LENGTH: 25
<212> TYPE: DNA
<213> ORGANISM: Artificial Sequence
<220> FEATURE:
<223> OTHER INFORMATION: Primer

<400> SEQUENCE: 211
atcattctga actgaacatg agctc                                  25

<210> SEQ ID NO 212
<211> LENGTH: 25
<212> TYPE: DNA
<213> ORGANISM: Artificial Sequence
<220> FEATURE:
<223> OTHER INFORMATION: Primer

<400> SEQUENCE: 212
tggagggacg tattctactc tgaag                                  25

<210> SEQ ID NO 213
<211> LENGTH: 24
<212> TYPE: DNA
<213> ORGANISM: Artificial Sequence
<220> FEATURE:
<223> OTHER INFORMATION: Primer

<400> SEQUENCE: 213
gacacccctg ataacttcca atcc                                   24

<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214
tgcctcccaa attcaccctg                                        20

<210> SEQ ID NO 215
<211> LENGTH: 17
<212> TYPE: DNA
<213> ORGANISM: Artificial Sequence
<220> FEATURE:
<223> OTHER INFORMATION: Primer

<400> SEQUENCE: 215
catcccgcag agccgag                                           17

<210> SEQ ID NO 216
<211> LENGTH: 21
<212> TYPE: DNA
<213> ORGANISM: Artificial Sequence
<220> FEATURE:
<223> OTHER INFORMATION: Primer

<400> SEQUENCE: 216
gcaggtagtg cgaggagatt c                                      21

<210> SEQ ID NO 217
<211> LENGTH: 20
<212> TYPE: DNA

-continued

```
<213> ORGANISM: Artificial Sequence
<220> FEATURE:
<223> OTHER INFORMATION: Primer

<400> SEQUENCE: 217
ctgtgacatc ggcccaaaag                                                      20

<210> SEQ ID NO 218
<211> LENGTH: 20
<212> TYPE: DNA
<213> ORGANISM: Artificial Sequence
<220> FEATURE:
<223> OTHER INFORMATION: Primer

<400> SEQUENCE: 218
acagtgacca gtgcccatcc                                                      20

<210> SEQ ID NO 219
<211> LENGTH: 19
<212> TYPE: DNA
<213> ORGANISM: Artificial Sequence
<220> FEATURE:
<223> OTHER INFORMATION: Primer

<400> SEQUENCE: 219
caatgcccca agaacgcac                                                       19

<210> SEQ ID NO 220
<211> LENGTH: 21
<212> TYPE: DNA
<213> ORGANISM: Artificial Sequence
<220> FEATURE:
<223> OTHER INFORMATION: Primer

<400> SEQUENCE: 220
tagagtctgc catccccaac c                                                    21

<210> SEQ ID NO 221
<211> LENGTH: 21
<212> TYPE: DNA
<213> ORGANISM: Artificial Sequence
<220> FEATURE:
<223> OTHER INFORMATION: Primer

<400> SEQUENCE: 221
gacggagcat tttcccctga c                                                    21

<210> SEQ ID NO 222
<211> LENGTH: 20
<212> TYPE: DNA
<213> ORGANISM: Artificial Sequence
<220> FEATURE:
<223> OTHER INFORMATION: Primer

<400> SEQUENCE: 222
gccagcacca accagacatc                                                      20

<210> SEQ ID NO 223
<211> LENGTH: 20
<212> TYPE: DNA
<213> ORGANISM: Artificial Sequence
<220> FEATURE:
<223> OTHER INFORMATION: Primer

<400> SEQUENCE: 223
ctgatcctgg agtcgcccag                                                      20
```

<210> SEQ ID NO 224
<211> LENGTH: 20
<212> TYPE: DNA
<213> ORGANISM: Artificial Sequence
<220> FEATURE:
<223> OTHER INFORMATION: Primer

<400> SEQUENCE: 224
atcagccgcc caaacctaac                                               20

<210> SEQ ID NO 225
<211> LENGTH: 24
<212> TYPE: DNA
<213> ORGANISM: Artificial Sequence
<220> FEATURE:
<223> OTHER INFORMATION: Primer

<400> SEQUENCE: 225
cggcagttca tcctgagttc taag                                         24

<210> SEQ ID NO 226
<211> LENGTH: 20
<212> TYPE: DNA
<213> ORGANISM: Artificial Sequence
<220> FEATURE:
<223> OTHER INFORMATION: Primer

<400> SEQUENCE: 226
cgaccagctt gacatcacag                                              20

<210> SEQ ID NO 227
<211> LENGTH: 25
<212> TYPE: DNA
<213> ORGANISM: Artificial Sequence
<220> FEATURE:
<223> OTHER INFORMATION: Primer

<400> SEQUENCE: 227
gttgctcttg aagtccatag acctc                                        25

<210> SEQ ID NO 228
<211> LENGTH: 20
<212> TYPE: DNA
<213> ORGANISM: Artificial Sequence
<220> FEATURE:
<223> OTHER INFORMATION: Primer

<400> SEQUENCE: 228
cagggtcagg gttctggata                                              20

<210> SEQ ID NO 229
<211> LENGTH: 22
<212> TYPE: DNA
<213> ORGANISM: Artificial Sequence
<220> FEATURE:
<223> OTHER INFORMATION: Primer

<400> SEQUENCE: 229
atgtggggag ctttccttct ct                                           22

<210> SEQ ID NO 230
<211> LENGTH: 25
<212> TYPE: DNA
<213> ORGANISM: Artificial Sequence
<220> FEATURE:

-continued

```
<223> OTHER INFORMATION: Primer

<400> SEQUENCE: 230
atgtggggag ttttccttct ttatg                                                          25

<210> SEQ ID NO 231
<211> LENGTH: 21
<212> TYPE: DNA
<213> ORGANISM: Artificial Sequence
<220> FEATURE:
<223> OTHER INFORMATION: Primer

<400> SEQUENCE: 231
atggctttgc agagcactct g                                                              21

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
atggcctctg cacccatctc                                                                20

<210> SEQ ID NO 233
<211> LENGTH: 20
<212> TYPE: DNA
<213> ORGANISM: Artificial Sequence
<220> FEATURE:
<223> OTHER INFORMATION: Primer

<400> SEQUENCE: 233
atgaggcaag tggcgagagt                                                                20

<210> SEQ ID NO 234
<211> LENGTH: 24
<212> TYPE: DNA
<213> ORGANISM: Artificial Sequence
<220> FEATURE:
<223> OTHER INFORMATION: Primer

<400> SEQUENCE: 234
atgaagacat ttgctggatt ttcg                                                           24

<210> SEQ ID NO 235
<211> LENGTH: 22
<212> TYPE: DNA
<213> ORGANISM: Artificial Sequence
<220> FEATURE:
<223> OTHER INFORMATION: Primer

<400> SEQUENCE: 235
atggagtcat tcctgggagg tg                                                             22

<210> SEQ ID NO 236
<211> LENGTH: 22
<212> TYPE: DNA
<213> ORGANISM: Artificial Sequence
<220> FEATURE:
<223> OTHER INFORMATION: Primer

<400> SEQUENCE: 236
atggagaaga tgcggagacc tg                                                             22
```

-continued

```
<210> SEQ ID NO 237
<211> LENGTH: 22
<212> TYPE: DNA
<213> ORGANISM: Artificial Sequence
<220> FEATURE:
<223> OTHER INFORMATION: Primer

<400> SEQUENCE: 237
atgctcctgt tgctcatacc ag                                          22

<210> SEQ ID NO 238
<211> LENGTH: 19
<212> TYPE: DNA
<213> ORGANISM: Artificial Sequence
<220> FEATURE:
<223> OTHER INFORMATION: Primer

<400> SEQUENCE: 238
atgctcctgc tgctcgtcc                                              19

<210> SEQ ID NO 239
<211> LENGTH: 21
<212> TYPE: DNA
<213> ORGANISM: Artificial Sequence
<220> FEATURE:
<223> OTHER INFORMATION: Primer

<400> SEQUENCE: 239
atgctcctgg agcttatccc a                                           21

<210> SEQ ID NO 240
<211> LENGTH: 24
<212> TYPE: DNA
<213> ORGANISM: Artificial Sequence
<220> FEATURE:
<223> OTHER INFORMATION: Primer

<400> SEQUENCE: 240
atgctcttag tggtcattct gctg                                        24

<210> SEQ ID NO 241
<211> LENGTH: 23
<212> TYPE: DNA
<213> ORGANISM: Artificial Sequence
<220> FEATURE:
<223> OTHER INFORMATION: Primer

<400> SEQUENCE: 241
atgaattctt ctccaggacc agc                                         23

<210> SEQ ID NO 242
<211> LENGTH: 28
<212> TYPE: DNA
<213> ORGANISM: Artificial Sequence
<220> FEATURE:
<223> OTHER INFORMATION: Primer

<400> SEQUENCE: 242
atgaactatt ctccaggctt agtatctc                                    28

<210> SEQ ID NO 243
<211> LENGTH: 24
<212> TYPE: DNA
<213> ORGANISM: Artificial Sequence
<220> FEATURE:
<223> OTHER INFORMATION: Primer
```

<400> SEQUENCE: 243
atgaaaaagc atctgacgac cttc                                                  24

<210> SEQ ID NO 244
<211> LENGTH: 27
<212> TYPE: DNA
<213> ORGANISM: Artificial Sequence
<220> FEATURE:
<223> OTHER INFORMATION: Primer

<400> SEQUENCE: 244
atgatatcct tgagagtttt actggtg                                              27

<210> SEQ ID NO 245
<211> LENGTH: 30
<212> TYPE: DNA
<213> ORGANISM: Artificial Sequence
<220> FEATURE:
<223> OTHER INFORMATION: Primer

<400> SEQUENCE: 245
atgaaatcct tgagagtttt actagtgatc                                          30

<210> SEQ ID NO 246
<211> LENGTH: 28
<212> TYPE: DNA
<213> ORGANISM: Artificial Sequence
<220> FEATURE:
<223> OTHER INFORMATION: Primer

<400> SEQUENCE: 246
atgatgaaat ccttgagagt tttactgg                                            28

<210> SEQ ID NO 247
<211> LENGTH: 26
<212> TYPE: DNA
<213> ORGANISM: Artificial Sequence
<220> FEATURE:
<223> OTHER INFORMATION: Primer

<400> SEQUENCE: 247
atgacatcca ttcgagctgt atttat                                              26

<210> SEQ ID NO 248
<211> LENGTH: 19
<212> TYPE: DNA
<213> ORGANISM: Artificial Sequence
<220> FEATURE:
<223> OTHER INFORMATION: Primer

<400> SEQUENCE: 248
atggcaggca ttcgagctt                                                      19

<210> SEQ ID NO 249
<211> LENGTH: 24
<212> TYPE: DNA
<213> ORGANISM: Artificial Sequence
<220> FEATURE:
<223> OTHER INFORMATION: Primer

<400> SEQUENCE: 249
atgtcacttt ctagcctgct gaag                                                24

<210> SEQ ID NO 250
<211> LENGTH: 22

```
<212> TYPE: DNA
<213> ORGANISM: Artificial Sequence
<220> FEATURE:
<223> OTHER INFORMATION: Primer

<400> SEQUENCE: 250
atgaagccca ccctcatctc ag                                                         22

<210> SEQ ID NO 251
<211> LENGTH: 23
<212> TYPE: DNA
<213> ORGANISM: Artificial Sequence
<220> FEATURE:
<223> OTHER INFORMATION: Primer

<400> SEQUENCE: 251
atggaaactc tcctgggagt gtc                                                        23

<210> SEQ ID NO 252
<211> LENGTH: 22
<212> TYPE: DNA
<213> ORGANISM: Artificial Sequence
<220> FEATURE:
<223> OTHER INFORMATION: Primer

<400> SEQUENCE: 252
atgctgtctg cttcctgctc ag                                                         22

<210> SEQ ID NO 253
<211> LENGTH: 19
<212> TYPE: DNA
<213> ORGANISM: Artificial Sequence
<220> FEATURE:
<223> OTHER INFORMATION: Primer

<400> SEQUENCE: 253
atgctgactg ccagcctgt                                                             19

<210> SEQ ID NO 254
<211> LENGTH: 23
<212> TYPE: DNA
<213> ORGANISM: Artificial Sequence
<220> FEATURE:
<223> OTHER INFORMATION: Primer

<400> SEQUENCE: 254
atggagaaaa tgttggagtg tgc                                                        23

<210> SEQ ID NO 255
<211> LENGTH: 20
<212> TYPE: DNA
<213> ORGANISM: Artificial Sequence
<220> FEATURE:
<223> OTHER INFORMATION: Primer

<400> SEQUENCE: 255
atggagaccc tcttgggcct                                                            20

<210> SEQ ID NO 256
<211> LENGTH: 24
<212> TYPE: DNA
<213> ORGANISM: Artificial Sequence
<220> FEATURE:
<223> OTHER INFORMATION: Primer

<400> SEQUENCE: 256
```

-continued

```
atgaagagga tattgggagc tctg                                    24

<210> SEQ ID NO 257
<211> LENGTH: 25
<212> TYPE: DNA
<213> ORGANISM: Artificial Sequence
<220> FEATURE:
<223> OTHER INFORMATION: Primer

<400> SEQUENCE: 257
atggacaaga tcttaggagc atcat                                   25

<210> SEQ ID NO 258
<211> LENGTH: 20
<212> TYPE: DNA
<213> ORGANISM: Artificial Sequence
<220> FEATURE:
<223> OTHER INFORMATION: Primer

<400> SEQUENCE: 258
atgctgttct ccagcctgct                                         20

<210> SEQ ID NO 259
<211> LENGTH: 22
<212> TYPE: DNA
<213> ORGANISM: Artificial Sequence
<220> FEATURE:
<223> OTHER INFORMATION: Primer

<400> SEQUENCE: 259
atggagaaga tcctttggc ag                                       22

<210> SEQ ID NO 260
<211> LENGTH: 25
<212> TYPE: DNA
<213> ORGANISM: Artificial Sequence
<220> FEATURE:
<223> OTHER INFORMATION: Primer

<400> SEQUENCE: 260
atgctactca tcacatcaat gttgg                                   25

<210> SEQ ID NO 261
<211> LENGTH: 23
<212> TYPE: DNA
<213> ORGANISM: Artificial Sequence
<220> FEATURE:
<223> OTHER INFORMATION: Primer

<400> SEQUENCE: 261
atgaggctgg tggcaagagt aac                                     23

<210> SEQ ID NO 262
<211> LENGTH: 25
<212> TYPE: DNA
<213> ORGANISM: Artificial Sequence
<220> FEATURE:
<223> OTHER INFORMATION: Primer

<400> SEQUENCE: 262
atgaagttgg tgacaagcat tactg                                   25

<210> SEQ ID NO 263
<211> LENGTH: 23
<212> TYPE: DNA
<213> ORGANISM: Artificial Sequence
```

<220> FEATURE:
<223> OTHER INFORMATION: Primer

<400> SEQUENCE: 263
atggtcctga aattctccgt gtc                                                23

<210> SEQ ID NO 264
<211> LENGTH: 17
<212> TYPE: DNA
<213> ORGANISM: Artificial Sequence
<220> FEATURE:
<223> OTHER INFORMATION: Primer

<400> SEQUENCE: 264
atggccatgc tcctggg                                                       17

<210> SEQ ID NO 265
<211> LENGTH: 23
<212> TYPE: DNA
<213> ORGANISM: Artificial Sequence
<220> FEATURE:
<223> OTHER INFORMATION: Primer

<400> SEQUENCE: 265
atggagactc tcctgaaagt gct                                                23

<210> SEQ ID NO 266
<211> LENGTH: 25
<212> TYPE: DNA
<213> ORGANISM: Artificial Sequence
<220> FEATURE:
<223> OTHER INFORMATION: Primer

<400> SEQUENCE: 266
atggagactg ttctgcaagt actcc                                              25

<210> SEQ ID NO 267
<211> LENGTH: 28
<212> TYPE: DNA
<213> ORGANISM: Artificial Sequence
<220> FEATURE:
<223> OTHER INFORMATION: Primer

<400> SEQUENCE: 267
atgctccttg aacatttatt aataatct                                          28

<210> SEQ ID NO 268
<211> LENGTH: 25
<212> TYPE: DNA
<213> ORGANISM: Artificial Sequence
<220> FEATURE:
<223> OTHER INFORMATION: Primer

<400> SEQUENCE: 268
atgatgaagt gtccacaggc tttac                                              25

<210> SEQ ID NO 269
<211> LENGTH: 23
<212> TYPE: DNA
<213> ORGANISM: Artificial Sequence
<220> FEATURE:
<223> OTHER INFORMATION: Primer

<400> SEQUENCE: 269
atgacacgag ttagcttgct gtg                                                23

<210> SEQ ID NO 270
<211> LENGTH: 18
<212> TYPE: DNA
<213> ORGANISM: Artificial Sequence
<220> FEATURE:
<223> OTHER INFORMATION: Primer

<400> SEQUENCE: 270
atggcatgcc ctggcttc                                                            18

<210> SEQ ID NO 271
<211> LENGTH: 27
<212> TYPE: DNA
<213> ORGANISM: Artificial Sequence
<220> FEATURE:
<223> OTHER INFORMATION: Primer

<400> SEQUENCE: 271
atgaagaagc tactagcaat gattctg                                                  27

<210> SEQ ID NO 272
<211> LENGTH: 28
<212> TYPE: DNA
<213> ORGANISM: Artificial Sequence
<220> FEATURE:
<223> OTHER INFORMATION: Primer

<400> SEQUENCE: 272
atgaactcct ctctggactt tctaattc                                                 28

<210> SEQ ID NO 273
<211> LENGTH: 20
<212> TYPE: DNA
<213> ORGANISM: Artificial Sequence
<220> FEATURE:
<223> OTHER INFORMATION: Primer

<400> SEQUENCE: 273
atggtgaaga tccggcaatt                                                          20

<210> SEQ ID NO 274
<211> LENGTH: 26
<212> TYPE: DNA
<213> ORGANISM: Artificial Sequence
<220> FEATURE:
<223> OTHER INFORMATION: Primer

<400> SEQUENCE: 274
tccttagtcg ctctgatagt tatggt                                                   26

<210> SEQ ID NO 275
<211> LENGTH: 27
<212> TYPE: DNA
<213> ORGANISM: Artificial Sequence
<220> FEATURE:
<223> OTHER INFORMATION: Primer

<400> SEQUENCE: 275
tttcttcatt ccttagtcgg tctaaag                                                  27

<210> SEQ ID NO 276
<211> LENGTH: 22
<212> TYPE: DNA
<213> ORGANISM: Artificial Sequence
<220> FEATURE:
<223> OTHER INFORMATION: Primer

<400> SEQUENCE: 276
ctcttcatcg ctgctcatcc tc                                              22

<210> SEQ ID NO 277
<211> LENGTH: 20
<212> TYPE: DNA
<213> ORGANISM: Artificial Sequence
<220> FEATURE:
<223> OTHER INFORMATION: Primer

<400> SEQUENCE: 277
gccaaacctc cttccacctg                                                 20

<210> SEQ ID NO 278
<211> LENGTH: 20
<212> TYPE: DNA
<213> ORGANISM: Artificial Sequence
<220> FEATURE:
<223> OTHER INFORMATION: Primer

<400> SEQUENCE: 278
cctgccgaca gaaagtccag                                                 20

<210> SEQ ID NO 279
<211> LENGTH: 20
<212> TYPE: DNA
<213> ORGANISM: Artificial Sequence
<220> FEATURE:
<223> OTHER INFORMATION: Primer

<400> SEQUENCE: 279
cgcattgcag acacccagac                                                 20

<210> SEQ ID NO 280
<211> LENGTH: 26
<212> TYPE: DNA
<213> ORGANISM: Artificial Sequence
<220> FEATURE:
<223> OTHER INFORMATION: Primer

<400> SEQUENCE: 280
ttgataccac ccttaaacag agtttg                                          26

<210> SEQ ID NO 281
<211> LENGTH: 25
<212> TYPE: DNA
<213> ORGANISM: Artificial Sequence
<220> FEATURE:
<223> OTHER INFORMATION: Primer

<400> SEQUENCE: 281
attactgaag aatggaagca gcttg                                           25

<210> SEQ ID NO 282
<211> LENGTH: 25
<212> TYPE: DNA
<213> ORGANISM: Artificial Sequence
<220> FEATURE:
<223> OTHER INFORMATION: Primer

<400> SEQUENCE: 282
tcctttaatc tgaggaaacc ctctg                                           25

<210> SEQ ID NO 283

-continued

```
<211> LENGTH: 22
<212> TYPE: DNA
<213> ORGANISM: Artificial Sequence
<220> FEATURE:
<223> OTHER INFORMATION: Primer

<400> SEQUENCE: 283
gtgaaacctc cttccacctg ac                                            22

<210> SEQ ID NO 284
<211> LENGTH: 24
<212> TYPE: DNA
<213> ORGANISM: Artificial Sequence
<220> FEATURE:
<223> OTHER INFORMATION: Primer

<400> SEQUENCE: 284
aggctttgag gctgaattta agag                                          24

<210> SEQ ID NO 285
<211> LENGTH: 27
<212> TYPE: DNA
<213> ORGANISM: Artificial Sequence
<220> FEATURE:
<223> OTHER INFORMATION: Primer

<400> SEQUENCE: 285
ggctgaattt aacaagagtc aaacttc                                       27

<210> SEQ ID NO 286
<211> LENGTH: 22
<212> TYPE: DNA
<213> ORGANISM: Artificial Sequence
<220> FEATURE:
<223> OTHER INFORMATION: Primer

<400> SEQUENCE: 286
gagcgaaacc tccttctacc tg                                            22

<210> SEQ ID NO 287
<211> LENGTH: 23
<212> TYPE: DNA
<213> ORGANISM: Artificial Sequence
<220> FEATURE:
<223> OTHER INFORMATION: Primer

<400> SEQUENCE: 287
aaaccacttc tttccacttg gag                                           23

<210> SEQ ID NO 288
<211> LENGTH: 23
<212> TYPE: DNA
<213> ORGANISM: Artificial Sequence
<220> FEATURE:
<223> OTHER INFORMATION: Primer

<400> SEQUENCE: 288
caaagcaaag ctctctgcac atc                                           23

<210> SEQ ID NO 289
<211> LENGTH: 22
<212> TYPE: DNA
<213> ORGANISM: Artificial Sequence
<220> FEATURE:
<223> OTHER INFORMATION: Primer

<400> SEQUENCE: 289
```

-continued cagtgattca gccacctacc tc                                              22

<210> SEQ ID NO 290
<211> LENGTH: 26
<212> TYPE: DNA
<213> ORGANISM: Artificial Sequence
<220> FEATURE:
<223> OTHER INFORMATION: Primer

<400> SEQUENCE: 290
cgaattgctg ttacattgaa caagac                                         26

<210> SEQ ID NO 291
<211> LENGTH: 23
<212> TYPE: DNA
<213> ORGANISM: Artificial Sequence
<220> FEATURE:
<223> OTHER INFORMATION: Primer

<400> SEQUENCE: 291
ttgcagctac tcaacctgga gac                                            23

<210> SEQ ID NO 292
<211> LENGTH: 21
<212> TYPE: DNA
<213> ORGANISM: Artificial Sequence
<220> FEATURE:
<223> OTHER INFORMATION: Primer

<400> SEQUENCE: 292
atccgccaac cttgtcatct c                                              21

<210> SEQ ID NO 293
<211> LENGTH: 21
<212> TYPE: DNA
<213> ORGANISM: Artificial Sequence
<220> FEATURE:
<223> OTHER INFORMATION: Primer

<400> SEQUENCE: 293
aaggcgagac atctttccac c                                              21

<210> SEQ ID NO 294
<211> LENGTH: 26
<212> TYPE: DNA
<213> ORGANISM: Artificial Sequence
<220> FEATURE:
<223> OTHER INFORMATION: Primer

<400> SEQUENCE: 294
agattaagag tcacgcttga cacttc                                         26

<210> SEQ ID NO 295
<211> LENGTH: 26
<212> TYPE: DNA
<213> ORGANISM: Artificial Sequence
<220> FEATURE:
<223> OTHER INFORMATION: Primer

<400> SEQUENCE: 295
gccagtccta tcaagagtga cagttc                                         26

<210> SEQ ID NO 296
<211> LENGTH: 23
<212> TYPE: DNA

<213> ORGANISM: Artificial Sequence
<220> FEATURE:
<223> OTHER INFORMATION: Primer

<400> SEQUENCE: 296
caacttcacc atcacagcct cac                                                 23

<210> SEQ ID NO 297
<211> LENGTH: 22
<212> TYPE: DNA
<213> ORGANISM: Artificial Sequence
<220> FEATURE:
<223> OTHER INFORMATION: Primer

<400> SEQUENCE: 297
cacatcacag cccctaaacc tg                                                  22

<210> SEQ ID NO 298
<211> LENGTH: 22
<212> TYPE: DNA
<213> ORGANISM: Artificial Sequence
<220> FEATURE:
<223> OTHER INFORMATION: Primer

<400> SEQUENCE: 298
tggaagactt aatgcctcgc tg                                                  22

<210> SEQ ID NO 299
<211> LENGTH: 21
<212> TYPE: DNA
<213> ORGANISM: Artificial Sequence
<220> FEATURE:
<223> OTHER INFORMATION: Primer

<400> SEQUENCE: 299
tgtcgctacg gaacgctaca g                                                   21

<210> SEQ ID NO 300
<211> LENGTH: 25
<212> TYPE: DNA
<213> ORGANISM: Artificial Sequence
<220> FEATURE:
<223> OTHER INFORMATION: Primer

<400> SEQUENCE: 300
cttcaataaa agtgccaagc agttc                                               25

<210> SEQ ID NO 301
<211> LENGTH: 25
<212> TYPE: DNA
<213> ORGANISM: Artificial Sequence
<220> FEATURE:
<223> OTHER INFORMATION: Primer

<400> SEQUENCE: 301
aaaaagtggt cgctattctg tcaac                                               25

<210> SEQ ID NO 302
<211> LENGTH: 24
<212> TYPE: DNA
<213> ORGANISM: Artificial Sequence
<220> FEATURE:
<223> OTHER INFORMATION: Primer

<400> SEQUENCE: 302
gaagaaagga cgaataagtg ccac                                                24

```
<210> SEQ ID NO 303
<211> LENGTH: 22
<212> TYPE: DNA
<213> ORGANISM: Artificial Sequence
<220> FEATURE:
<223> OTHER INFORMATION: Primer

<400> SEQUENCE: 303
acatcacagc cacccagact ac                                                 22

<210> SEQ ID NO 304
<211> LENGTH: 24
<212> TYPE: DNA
<213> ORGANISM: Artificial Sequence
<220> FEATURE:
<223> OTHER INFORMATION: Primer

<400> SEQUENCE: 304
cacagaagac agaaagtcca gcac                                               24

<210> SEQ ID NO 305
<211> LENGTH: 23
<212> TYPE: DNA
<213> ORGANISM: Artificial Sequence
<220> FEATURE:
<223> OTHER INFORMATION: Primer

<400> SEQUENCE: 305
gcaatcgctg aagacagaaa gtc                                                23

<210> SEQ ID NO 306
<211> LENGTH: 25
<212> TYPE: DNA
<213> ORGANISM: Artificial Sequence
<220> FEATURE:
<223> OTHER INFORMATION: Primer

<400> SEQUENCE: 306
gaaaggacag ttctctccac atcac                                              25

<210> SEQ ID NO 307
<211> LENGTH: 22
<212> TYPE: DNA
<213> ORGANISM: Artificial Sequence
<220> FEATURE:
<223> OTHER INFORMATION: Primer

<400> SEQUENCE: 307
aaaagtgcca agcacctctc tc                                                 22

<210> SEQ ID NO 308
<211> LENGTH: 22
<212> TYPE: DNA
<213> ORGANISM: Artificial Sequence
<220> FEATURE:
<223> OTHER INFORMATION: Primer

<400> SEQUENCE: 308
gcaaagctcc ctgtacctta cg                                                 22

<210> SEQ ID NO 309
<211> LENGTH: 25
<212> TYPE: DNA
<213> ORGANISM: Artificial Sequence
<220> FEATURE:
```

<223> OTHER INFORMATION: Primer

<400> SEQUENCE: 309
aaagataact gccaagttgg atgag                                25

<210> SEQ ID NO 310
<211> LENGTH: 26
<212> TYPE: DNA
<213> ORGANISM: Artificial Sequence
<220> FEATURE:
<223> OTHER INFORMATION: Primer

<400> SEQUENCE: 310
cttcctgaat atctcagcat ccatac                               26

<210> SEQ ID NO 311
<211> LENGTH: 22
<212> TYPE: DNA
<213> ORGANISM: Artificial Sequence
<220> FEATURE:
<223> OTHER INFORMATION: Primer

<400> SEQUENCE: 311
gcatcctgaa catcacagcc ac                                   22

<210> SEQ ID NO 312
<211> LENGTH: 25
<212> TYPE: DNA
<213> ORGANISM: Artificial Sequence
<220> FEATURE:
<223> OTHER INFORMATION: Primer

<400> SEQUENCE: 312
gaatcgtttc tctgtgaact tccag                                25

<210> SEQ ID NO 313
<211> LENGTH: 21
<212> TYPE: DNA
<213> ORGANISM: Artificial Sequence
<220> FEATURE:
<223> OTHER INFORMATION: Primer

<400> SEQUENCE: 313
tctcagcacc ctccacatca c                                    21

<210> SEQ ID NO 314
<211> LENGTH: 24
<212> TYPE: DNA
<213> ORGANISM: Artificial Sequence
<220> FEATURE:
<223> OTHER INFORMATION: Primer

<400> SEQUENCE: 314
caggtatcag actcagccgt gtac                                 24

<210> SEQ ID NO 315
<211> LENGTH: 25
<212> TYPE: DNA
<213> ORGANISM: Artificial Sequence
<220> FEATURE:
<223> OTHER INFORMATION: Primer

<400> SEQUENCE: 315
gccacaataa acatacagga aaagc                                25

-continued

<210> SEQ ID NO 316
<211> LENGTH: 48
<212> TYPE: DNA
<213> ORGANISM: Artificial Sequence
<220> FEATURE:
<223> OTHER INFORMATION: Primer

<400> SEQUENCE: 316
atttcaggtg tcgtgaagcg gccgcgccac catgagcatc ggcctcct                48

<210> SEQ ID NO 317
<211> LENGTH: 48
<212> TYPE: DNA
<213> ORGANISM: Artificial Sequence
<220> FEATURE:
<223> OTHER INFORMATION: Primer

<400> SEQUENCE: 317
atttcaggtg tcgtgaagcg gccgcgccac catgagcatc ggcctcct                48

<210> SEQ ID NO 318
<211> LENGTH: 48
<212> TYPE: DNA
<213> ORGANISM: Artificial Sequence
<220> FEATURE:
<223> OTHER INFORMATION: Primer

<400> SEQUENCE: 318
atttcaggtg tcgtgaagcg gccgcgccac catgctgctg cttctgct                48

<210> SEQ ID NO 319
<211> LENGTH: 48
<212> TYPE: DNA
<213> ORGANISM: Artificial Sequence
<220> FEATURE:
<223> OTHER INFORMATION: Primer

<400> SEQUENCE: 319
atttcaggtg tcgtgaagcg gccgcgccac catgagcaac caggtgct                48

<210> SEQ ID NO 320
<211> LENGTH: 48
<212> TYPE: DNA
<213> ORGANISM: Artificial Sequence
<220> FEATURE:
<223> OTHER INFORMATION: Primer

<400> SEQUENCE: 320
atttcaggtg tcgtgaagcg gccgcgccac catgggcccc cagctcct                48

<210> SEQ ID NO 321
<211> LENGTH: 49
<212> TYPE: DNA
<213> ORGANISM: Artificial Sequence
<220> FEATURE:
<223> OTHER INFORMATION: Primer

<400> SEQUENCE: 321
atttcaggtg tcgtgaagcg gccgcgccac catgggctgc aggctgctc               49

<210> SEQ ID NO 322
<211> LENGTH: 49
<212> TYPE: DNA
<213> ORGANISM: Artificial Sequence
<220> FEATURE:
<223> OTHER INFORMATION: Primer -continued

```
<400> SEQUENCE: 322
atttcaggtg tcgtgaagcg gccgcgccac catgggctgc aggctgctc              49

<210> SEQ ID NO 323
<211> LENGTH: 48
<212> TYPE: DNA
<213> ORGANISM: Artificial Sequence
<220> FEATURE:
<223> OTHER INFORMATION: Primer

<400> SEQUENCE: 323
atttcaggtg tcgtgaagcg gccgcgccac catgggccct gggctcct               48

<210> SEQ ID NO 324
<211> LENGTH: 54
<212> TYPE: DNA
<213> ORGANISM: Artificial Sequence
<220> FEATURE:
<223> OTHER INFORMATION: Primer

<400> SEQUENCE: 324
atttcaggtg tcgtgaagcg gccgcgccac catggacacc agagtactct gctg         54

<210> SEQ ID NO 325
<211> LENGTH: 47
<212> TYPE: DNA
<213> ORGANISM: Artificial Sequence
<220> FEATURE:
<223> OTHER INFORMATION: Primer

<400> SEQUENCE: 325
atttcaggtg tcgtgaagcg gccgcgccac catgggcccc cagctcc                47

<210> SEQ ID NO 326
<211> LENGTH: 48
<212> TYPE: DNA
<213> ORGANISM: Artificial Sequence
<220> FEATURE:
<223> OTHER INFORMATION: Primer

<400> SEQUENCE: 326
atttcaggtg tcgtgaagcg gccgcgccac catgggccct gggctcct               48

<210> SEQ ID NO 327
<211> LENGTH: 51
<212> TYPE: DNA
<213> ORGANISM: Artificial Sequence
<220> FEATURE:
<223> OTHER INFORMATION: Primer

<400> SEQUENCE: 327
atttcaggtg tcgtgaagcg gccgcgccac catgggcttc aggctcctct g           51

<210> SEQ ID NO 328
<211> LENGTH: 49
<212> TYPE: DNA
<213> ORGANISM: Artificial Sequence
<220> FEATURE:
<223> OTHER INFORMATION: Primer

<400> SEQUENCE: 328
atttcaggtg tcgtgaagcg gccgcgccac catgggctgc aggctgctc              49

<210> SEQ ID NO 329
<211> LENGTH: 49
```

-continued

```
<212> TYPE: DNA
<213> ORGANISM: Artificial Sequence
<220> FEATURE:
<223> OTHER INFORMATION: Primer

<400> SEQUENCE: 329
atttcaggtg tcgtgaagcg gccgcgccac catgggctgc aggctgctc                49

<210> SEQ ID NO 330
<211> LENGTH: 52
<212> TYPE: DNA
<213> ORGANISM: Artificial Sequence
<220> FEATURE:
<223> OTHER INFORMATION: Primer

<400> SEQUENCE: 330
atttcaggtg tcgtgaagcg gccgcgccac catggatacc tggctcgtat gc            52

<210> SEQ ID NO 331
<211> LENGTH: 49
<212> TYPE: DNA
<213> ORGANISM: Artificial Sequence
<220> FEATURE:
<223> OTHER INFORMATION: Primer

<400> SEQUENCE: 331
atttcaggtg tcgtgaagcg gccgcgccac catgggcacc aggctcctc                49

<210> SEQ ID NO 332
<211> LENGTH: 49
<212> TYPE: DNA
<213> ORGANISM: Artificial Sequence
<220> FEATURE:
<223> OTHER INFORMATION: Primer

<400> SEQUENCE: 332
atttcaggtg tcgtgaagcg gccgcgccac catgggctgc aggctgctc                49

<210> SEQ ID NO 333
<211> LENGTH: 49
<212> TYPE: DNA
<213> ORGANISM: Artificial Sequence
<220> FEATURE:
<223> OTHER INFORMATION: Primer

<400> SEQUENCE: 333
atttcaggtg tcgtgaagcg gccgcgccac catgggcacc aggctcctc                49

<210> SEQ ID NO 334
<211> LENGTH: 51
<212> TYPE: DNA
<213> ORGANISM: Artificial Sequence
<220> FEATURE:
<223> OTHER INFORMATION: Primer

<400> SEQUENCE: 334
atttcaggtg tcgtgaagcg gccgcgccac catgagcaac caggtgctct g             51

<210> SEQ ID NO 335
<211> LENGTH: 47
<212> TYPE: DNA
<213> ORGANISM: Artificial Sequence
<220> FEATURE:
<223> OTHER INFORMATION: Primer

<400> SEQUENCE: 335
```

-continued atttcaggtg tcgtgaagcg gccgcgccac catgggcccc cagctcc                    47

<210> SEQ ID NO 336
<211> LENGTH: 46
<212> TYPE: DNA
<213> ORGANISM: Artificial Sequence
<220> FEATURE:
<223> OTHER INFORMATION: Primer

<400> SEQUENCE: 336
atttcaggtg tcgtgaagcg gccgcgccac catggactcc tggacc                     46

<210> SEQ ID NO 337
<211> LENGTH: 49
<212> TYPE: DNA
<213> ORGANISM: Artificial Sequence
<220> FEATURE:
<223> OTHER INFORMATION: Primer

<400> SEQUENCE: 337
atttcaggtg tcgtgaagcg gccgcgccac catgggcacc aggctcctc                  49

<210> SEQ ID NO 338
<211> LENGTH: 81
<212> TYPE: DNA
<213> ORGANISM: Artificial Sequence
<220> FEATURE:
<223> OTHER INFORMATION: Primer

<400> SEQUENCE: 338
tctccagcct gcttcagcag gctgaagtta gtagctccgc ttccgctccg tttccgccgg      60
aaatcctttc tcttgaccat g                                                81

<210> SEQ ID NO 339
<211> LENGTH: 71
<212> TYPE: DNA
<213> ORGANISM: Artificial Sequence
<220> FEATURE:
<223> OTHER INFORMATION: Primer

<400> SEQUENCE: 339
tcagcctgct gaagcaggct ggagacgtgg aggagaaccc tggacctatg gaaactctcc      60
tgggagtgtc t                                                           71

<210> SEQ ID NO 340
<211> LENGTH: 71
<212> TYPE: DNA
<213> ORGANISM: Artificial Sequence
<220> FEATURE:
<223> OTHER INFORMATION: Primer

<400> SEQUENCE: 340
tcagcctgct gaagcaggct ggagacgtgg aggagaaccc tggacctatg gaaactctcc      60
tgggagtgtc t                                                           71

<210> SEQ ID NO 341
<211> LENGTH: 71
<212> TYPE: DNA
<213> ORGANISM: Artificial Sequence
<220> FEATURE:
<223> OTHER INFORMATION: Primer

<400> SEQUENCE: 341
tcagcctgct gaagcaggct ggagacgtgg aggagaaccc tggacctatg gagaagaatc      60

-continued

```
ctttggcagc c                                                              71

<210> SEQ ID NO 342
<211> LENGTH: 71
<212> TYPE: DNA
<213> ORGANISM: Artificial Sequence
<220> FEATURE:
<223> OTHER INFORMATION: Primer

<400> SEQUENCE: 342
tcagcctgct gaagcaggct ggagacgtgg aggagaaccc tggacctatg acatccattc    60
gagctgtatt t                                                              71

<210> SEQ ID NO 343
<211> LENGTH: 71
<212> TYPE: DNA
<213> ORGANISM: Artificial Sequence
<220> FEATURE:
<223> OTHER INFORMATION: Primer

<400> SEQUENCE: 343
tcagcctgct gaagcaggct ggagacgtgg aggagaaccc tggacctatg atgaaatcct    60
tgagagtttt a                                                              71

<210> SEQ ID NO 344
<211> LENGTH: 71
<212> TYPE: DNA
<213> ORGANISM: Artificial Sequence
<220> FEATURE:
<223> OTHER INFORMATION: Primer

<400> SEQUENCE: 344
tcagcctgct gaagcaggct ggagacgtgg aggagaaccc tggacctatg aagaggatat    60
tgggagctct g                                                              71

<210> SEQ ID NO 345
<211> LENGTH: 71
<212> TYPE: DNA
<213> ORGANISM: Artificial Sequence
<220> FEATURE:
<223> OTHER INFORMATION: Primer

<400> SEQUENCE: 345
tcagcctgct gaagcaggct ggagacgtgg aggagaaccc tggacctatg aagaggatat    60
tgggagctct g                                                              71

<210> SEQ ID NO 346
<211> LENGTH: 74
<212> TYPE: DNA
<213> ORGANISM: Artificial Sequence
<220> FEATURE:
<223> OTHER INFORMATION: Primer

<400> SEQUENCE: 346
tcagcctgct gaagcaggct ggagacgtgg aggagaaccc tggacctatg aagaagctac    60
tagcaatgat tctg                                                          74

<210> SEQ ID NO 347
<211> LENGTH: 73
<212> TYPE: DNA
<213> ORGANISM: Artificial Sequence
<220> FEATURE:
```

-continued

<223> OTHER INFORMATION: Primer

<400> SEQUENCE: 347
tcagcctgct gaagcaggct ggagacgtgg aggagaaccc tggacctatg acatccattc      60
gagctgtatt tat                                                         73

<210> SEQ ID NO 348
<211> LENGTH: 73
<212> TYPE: DNA
<213> ORGANISM: Artificial Sequence
<220> FEATURE:
<223> OTHER INFORMATION: Primer

<400> SEQUENCE: 348
tcagcctgct gaagcaggct ggagacgtgg aggagaaccc tggacctatg acatccattc      60
gagctgtatt tat                                                         73

<210> SEQ ID NO 349
<211> LENGTH: 74
<212> TYPE: DNA
<213> ORGANISM: Artificial Sequence
<220> FEATURE:
<223> OTHER INFORMATION: Primer

<400> SEQUENCE: 349
tcagcctgct gaagcaggct ggagacgtgg aggagaaccc tggacctatg aagaagctac      60
tagcaatgat tctg                                                        74

<210> SEQ ID NO 350
<211> LENGTH: 71
<212> TYPE: DNA
<213> ORGANISM: Artificial Sequence
<220> FEATURE:
<223> OTHER INFORMATION: Primer

<400> SEQUENCE: 350
tcagcctgct gaagcaggct ggagacgtgg aggagaaccc tggacctatg aagaggatat      60
tgggagctct g                                                           71

<210> SEQ ID NO 351
<211> LENGTH: 71
<212> TYPE: DNA
<213> ORGANISM: Artificial Sequence
<220> FEATURE:
<223> OTHER INFORMATION: Primer

<400> SEQUENCE: 351
tcagcctgct gaagcaggct ggagacgtgg aggagaaccc tggacctatg aagaggatat      60
tgggagctct g                                                           71

<210> SEQ ID NO 352
<211> LENGTH: 71
<212> TYPE: DNA
<213> ORGANISM: Artificial Sequence
<220> FEATURE:
<223> OTHER INFORMATION: Primer

<400> SEQUENCE: 352
tcagcctgct gaagcaggct ggagacgtgg aggagaaccc tggacctatg aagaggatat      60
tgggagctct g                                                           71

```
<210> SEQ ID NO 353
<211> LENGTH: 74
<212> TYPE: DNA
<213> ORGANISM: Artificial Sequence
<220> FEATURE:
<223> OTHER INFORMATION: Primer

<400> SEQUENCE: 353
tcagcctgct gaagcaggct ggagacgtgg aggagaaccc tggacctatg aagaagctac      60
tagcaatgat tctg                                                        74

<210> SEQ ID NO 354
<211> LENGTH: 66
<212> TYPE: DNA
<213> ORGANISM: Artificial Sequence
<220> FEATURE:
<223> OTHER INFORMATION: Primer

<400> SEQUENCE: 354
tcagcctgct gaagcaggct ggagacgtgg aggagaaccc tggacctatg ctgactgcca      60
gcctgt                                                                 66

<210> SEQ ID NO 355
<211> LENGTH: 71
<212> TYPE: DNA
<213> ORGANISM: Artificial Sequence
<220> FEATURE:
<223> OTHER INFORMATION: Primer

<400> SEQUENCE: 355
tcagcctgct gaagcaggct ggagacgtgg aggagaaccc tggacctatg aagaggatat      60
tgggagctct g                                                           71

<210> SEQ ID NO 356
<211> LENGTH: 67
<212> TYPE: DNA
<213> ORGANISM: Artificial Sequence
<220> FEATURE:
<223> OTHER INFORMATION: Primer

<400> SEQUENCE: 356
tcagcctgct gaagcaggct ggagacgtgg aggagaaccc tggacctatg gagaccctct      60
tgggcct                                                                67

<210> SEQ ID NO 357
<211> LENGTH: 71
<212> TYPE: DNA
<213> ORGANISM: Artificial Sequence
<220> FEATURE:
<223> OTHER INFORMATION: Primer

<400> SEQUENCE: 357
tcagcctgct gaagcaggct ggagacgtgg aggagaaccc tggacctatg tcactttcta      60
gcctgctgaa g                                                           71

<210> SEQ ID NO 358
<211> LENGTH: 66
<212> TYPE: DNA
<213> ORGANISM: Artificial Sequence
<220> FEATURE:
<223> OTHER INFORMATION: Primer

<400> SEQUENCE: 358
```

-continued

```
tcagcctgct gaagcaggct ggagacgtgg aggagaaccc tggacctatg gcaggcattc      60
gagctt                                                                 66

<210> SEQ ID NO 359
<211> LENGTH: 73
<212> TYPE: DNA
<213> ORGANISM: Artificial Sequence
<220> FEATURE:
<223> OTHER INFORMATION: Primer

<400> SEQUENCE: 359
tcagcctgct gaagcaggct ggagacgtgg aggagaaccc tggacctatg acatccattc      60
gagctgtatt tat                                                         73

<210> SEQ ID NO 360
<211> LENGTH: 74
<212> TYPE: DNA
<213> ORGANISM: Artificial Sequence
<220> FEATURE:
<223> OTHER INFORMATION: Primer

<400> SEQUENCE: 360
tcagcctgct gaagcaggct ggagacgtgg aggagaaccc tggacctatg aagaagctac      60
tagcaatgat tctg                                                        74

<210> SEQ ID NO 361
<211> LENGTH: 45
<212> TYPE: DNA
<213> ORGANISM: Artificial Sequence
<220> FEATURE:
<223> OTHER INFORMATION: Primer

<400> SEQUENCE: 361
agggatcctc tagactcgag ctagctcagc tggaccacag ccgca                      45

<210> SEQ ID NO 362
<211> LENGTH: 25
<212> TYPE: DNA
<213> ORGANISM: Artificial Sequence
<220> FEATURE:
<223> OTHER INFORMATION: Primer

<400> SEQUENCE: 362
caccgtctct cagctggtac acggc                                            25

<210> SEQ ID NO 363
<211> LENGTH: 25
<212> TYPE: DNA
<213> ORGANISM: Artificial Sequence
<220> FEATURE:
<223> OTHER INFORMATION: Primer

<400> SEQUENCE: 363
aaacgccgtg taccagctga gagac                                            25

<210> SEQ ID NO 364
<211> LENGTH: 25
<212> TYPE: DNA
<213> ORGANISM: Artificial Sequence
<220> FEATURE:
<223> OTHER INFORMATION: Primer

<400> SEQUENCE: 364
caccgggctc aaacacagcg acctc                                            25
```

-continued

```
<210> SEQ ID NO 365
<211> LENGTH: 25
<212> TYPE: DNA
<213> ORGANISM: Artificial Sequence
<220> FEATURE:
<223> OTHER INFORMATION: Primer

<400> SEQUENCE: 365
aaacgaggtc gctgtgtttg agccc                                          25

<210> SEQ ID NO 366
<211> LENGTH: 21
<212> TYPE: DNA
<213> ORGANISM: Artificial Sequence
<220> FEATURE:
<223> OTHER INFORMATION: Primer

<400> SEQUENCE: 366
atggcctccc tgctcttctt c                                              21
```